United States Patent
Abdou et al.

(10) Patent No.: US 11,179,248 B2
(45) Date of Patent: Nov. 23, 2021

(54) DEVICES AND METHODS FOR SPINAL IMPLANTATION

(71) Applicant: Samy Abdou, San Diego, CA (US)

(72) Inventors: Samy Abdou, San Diego, CA (US);
Brian Bowman, Carlsbad, CA (US);
Colin Murphy, San Diego, CA (US)

(73) Assignee: Samy Abdou, San Diego, CA (US)

( * ) Notice: Subject to any disclaimer, the term of this patent is extended or adjusted under 35 U.S.C. 154(b) by 18 days.

(21) Appl. No.: 16/590,300

(22) Filed: Oct. 1, 2019

(65) Prior Publication Data

US 2020/0100914 A1    Apr. 2, 2020

Related U.S. Application Data

(60) Provisional application No. 62/766,127, filed on Oct. 2, 2018, provisional application No. 62/766,123, filed on Oct. 2, 2018.

(51) Int. Cl.
*A61F 2/46* (2006.01)
*A61F 2/44* (2006.01)
*A61F 2/30* (2006.01)

(52) U.S. Cl.
CPC .......... *A61F 2/4611* (2013.01); *A61F 2/4425* (2013.01); *A61F 2/4603* (2013.01);
(Continued)

(58) Field of Classification Search
CPC .... A61F 2/4611; A61F 2/4425; A61F 2/4603; A61F 2002/4615
See application file for complete search history.

(56) References Cited

U.S. PATENT DOCUMENTS

| | | |
|---|---|---|
| 167,625 A | 9/1875 | Stanford |
| 203,512 A | 5/1878 | Van Viele |

(Continued)

FOREIGN PATENT DOCUMENTS

| | | |
|---|---|---|
| DE | 3114872 A1 | 10/1982 |
| DE | 3741493 A1 | 6/1989 |

(Continued)

OTHER PUBLICATIONS

Abstract for French Patent Publication FR2781359, Published Jan. 28, 2000, entitled: "Osteosynthesis Frame for Spinal Surgery has Rod with Clamps to Hold Cross Bars with Anchor Screws". Accession No. 9867555 (Derwent Information Ltd.).

(Continued)

*Primary Examiner* — Brian A Dukert
(74) *Attorney, Agent, or Firm* — Gazdzinski & Associates, PC

(57) ABSTRACT

Methods and apparatus for providing correction of one or more maladies or conditions of the spinal column of a living being. In one embodiment, the apparatus includes an implant delivery instrument and an implant for use therewith. In one variant, the implant delivery instrument includes a non-detachable distraction member for distraction of the disc space and a track for slidable delivery of an implant to the distracted disc space. In another variant, the implant delivery instrument includes a detachable distraction member for distraction of the disc space and a track for slidable delivery of an implant to the distracted disc space. In the latter variant, the distraction member is co-implanted in the disc space with the implant.

20 Claims, 43 Drawing Sheets

(52) U.S. Cl.
CPC .............. *A61F 2002/30153* (2013.01); *A61F 2002/30263* (2013.01); *A61F 2002/4615* (2013.01)

(56) References Cited

U.S. PATENT DOCUMENTS

| | | | |
|---|---|---|---|
| 203,624 A | 5/1878 | King |
| 229,347 A | 6/1880 | Wheeler |
| 267,269 A | 11/1882 | Smith |
| 824,983 A | 7/1906 | Farrington |
| 944,725 A | 12/1909 | Ferguson, Jr. |
| 1,015,890 A | 1/1912 | Hyde |
| 1,156,440 A | 10/1915 | Smith |
| 1,213,599 A | 1/1917 | Dow |
| 1,785,709 A | 12/1930 | Bonifacio et al. |
| 2,248,054 A | 7/1941 | Becker |
| 2,329,398 A | 9/1943 | Duffy |
| 2,370,407 A | 2/1945 | McCartney |
| 2,574,352 A | 11/1951 | Senter |
| 2,677,369 A | 5/1954 | Knowles |
| 2,774,350 A | 12/1956 | Cleveland, Jr. et al. |
| 3,025,853 A | 3/1962 | Mason |
| 3,037,596 A | 6/1962 | Fordyce |
| 3,072,423 A | 1/1963 | Charlton |
| 3,073,584 A | 1/1963 | Troeger et al. |
| 3,090,386 A | 5/1963 | Babcock et al. |
| 3,236,141 A | 2/1966 | Smith |
| 3,242,922 A | 3/1966 | Thomas |
| 3,260,412 A | 7/1966 | Larkin |
| 3,277,555 A | 10/1966 | Kutash |
| 3,374,786 A | 3/1968 | Callender, Jr. et al. |
| 3,383,769 A | 5/1968 | Davis |
| 3,384,077 A | 5/1968 | Gauthier |
| 3,426,364 A | 2/1969 | Lumb et al. |
| 3,604,487 A | 9/1971 | Gilbert |
| 3,648,691 A | 3/1972 | Lumb et al. |
| 3,659,595 A | 5/1972 | Haboush |
| 3,695,259 A | 10/1972 | Yost et al. |
| 3,708,883 A | 1/1973 | Flander et al. |
| 3,741,205 A | 6/1973 | Markolf et al. |
| 3,749,088 A | 7/1973 | Kohlmann et al. |
| 3,791,380 A | 2/1974 | Dawidowski et al. |
| 3,795,981 A | 3/1974 | Franklin et al. |
| 3,805,219 A | 4/1974 | Bright et al. |
| 3,825,992 A | 7/1974 | Troeger et al. |
| 3,858,578 A | 1/1975 | Milo |
| 3,865,105 A | 2/1975 | Lode |
| 3,867,728 A | 2/1975 | Stubstad et al. |
| 3,892,232 A | 7/1975 | Neufeld |
| 3,965,890 A | 6/1976 | Gauthier |
| 4,009,712 A | 3/1977 | Burstein et al. |
| 4,037,592 A | 7/1977 | Kronner |
| 4,047,524 A | 9/1977 | Hall |
| 4,074,542 A | 2/1978 | Hankosky et al. |
| 4,135,506 A | 1/1979 | Ulrich |
| 4,143,883 A | 3/1979 | Paynter |
| 4,165,746 A | 8/1979 | Burgin |
| 4,175,555 A | 11/1979 | Herbert |
| 4,237,875 A | 12/1980 | Termanini |
| 4,254,763 A | 3/1981 | McCready et al. |
| 4,289,123 A | 9/1981 | Dunn |
| 4,309,777 A | 1/1982 | Patil |
| 4,349,921 A | 9/1982 | Kuntz et al. |
| 4,399,813 A | 8/1983 | Barber |
| 4,409,974 A | 10/1983 | Freedland |
| 4,432,358 A | 2/1984 | Fixel |
| 4,448,181 A | 5/1984 | Ishikawa et al. |
| 4,448,191 A | 5/1984 | Rodnyansky, I et al. |
| 4,488,543 A | 12/1984 | Tornier |
| 4,493,317 A | 1/1985 | Klaue |
| 4,494,535 A | 1/1985 | Haig |
| 4,503,848 A | 3/1985 | Caspar et al. |
| 4,545,374 A | 10/1985 | Jacobson et al. |
| 4,554,914 A | 11/1985 | Kapp et al. |
| 4,561,432 A | 12/1985 | Mazor |
| 4,569,662 A | 2/1986 | Dragan |
| 4,570,618 A | 2/1986 | Wu |
| 4,580,563 A | 4/1986 | Gross |
| 4,604,995 A | 8/1986 | Stephens et al. |
| 4,611,581 A | 9/1986 | Steffee |
| 4,611,582 A | 9/1986 | Duff |
| 4,612,920 A | 9/1986 | Lower |
| 4,632,101 A | 12/1986 | Freedland |
| 4,636,217 A | 1/1987 | Ogilvie et al. |
| 4,653,481 A | 3/1987 | Howland et al. |
| 4,655,462 A | 4/1987 | Balsells |
| 4,655,629 A | 4/1987 | Flaherty |
| 4,655,778 A | 4/1987 | Koeneman |
| 4,664,305 A | 5/1987 | Blake, III et al. |
| 4,697,582 A | 10/1987 | William |
| 4,699,076 A | 10/1987 | Curtis et al. |
| 4,702,230 A | 10/1987 | Pelta |
| 4,711,232 A | 12/1987 | Fischer et al. |
| 4,714,469 A | 12/1987 | Kenna |
| 4,722,331 A | 2/1988 | Fox |
| 4,747,394 A | 5/1988 | Watanabe |
| 4,747,395 A | 5/1988 | Brief |
| 4,756,711 A | 7/1988 | Mai et al. |
| 4,759,766 A | 7/1988 | Buettner-Janz et al. |
| 4,759,769 A | 7/1988 | Hedman et al. |
| 4,773,402 A | 9/1988 | Asher et al. |
| 4,787,908 A | 11/1988 | Wyss et al. |
| 4,790,303 A | 12/1988 | Steffee |
| 4,791,918 A | 12/1988 | Von Hasselbach |
| 4,794,918 A | 1/1989 | Wolter |
| 4,820,305 A | 4/1989 | Harms et al. |
| 4,834,757 A | 5/1989 | Brantigan |
| 4,867,404 A | 9/1989 | Harrington et al. |
| 4,874,389 A | 10/1989 | Downey |
| 4,877,020 A | 10/1989 | Vich |
| 4,881,525 A | 11/1989 | Williams |
| 4,887,595 A | 12/1989 | Heinig et al. |
| 4,898,156 A | 2/1990 | Gatturna et al. |
| 4,899,761 A | 2/1990 | Brown et al. |
| 4,903,692 A | 2/1990 | Reese |
| 4,904,110 A | 2/1990 | Klein |
| 4,907,577 A | 3/1990 | Wu |
| 4,911,718 A | 3/1990 | Lee et al. |
| 4,913,134 A | 4/1990 | Luque |
| 4,932,975 A | 6/1990 | Main et al. |
| 4,934,352 A | 6/1990 | Sullivan, Jr. |
| 4,938,769 A | 7/1990 | Shaw |
| 4,944,757 A | 7/1990 | Martinez et al. |
| 4,946,378 A | 8/1990 | Hirayama et al. |
| 4,946,468 A | 8/1990 | Li |
| 4,949,707 A | 8/1990 | LeVahn et al. |
| 4,955,908 A | 9/1990 | Frey et al. |
| 4,957,495 A | 9/1990 | Kluger |
| 4,957,497 A | 9/1990 | Hoogland et al. |
| 4,961,740 A | 10/1990 | Ray et al. |
| 4,963,152 A | 10/1990 | Hofmann et al. |
| 4,964,403 A | 10/1990 | Karas et al. |
| 4,969,886 A | 11/1990 | Cziffer et al. |
| 4,969,887 A | 11/1990 | Sodhi |
| 4,973,332 A | 11/1990 | Kummer |
| 4,997,123 A | 3/1991 | Backus et al. |
| 4,997,432 A | 3/1991 | Keller |
| 5,002,550 A | 3/1991 | Li |
| 5,002,576 A | 3/1991 | Fuhrmann et al. |
| 5,007,880 A | 4/1991 | Walker |
| 5,007,910 A | 4/1991 | Anapliotis et al. |
| 5,011,484 A | 4/1991 | Breard |
| 5,015,247 A | 5/1991 | Michelson |
| 5,026,373 A | 6/1991 | Ray et al. |
| 5,052,711 A | 10/1991 | Pirkey et al. |
| 5,055,104 A | 10/1991 | Ray |
| 5,061,271 A | 10/1991 | Van Zile |
| 5,071,437 A | 12/1991 | Steffee |
| 5,084,049 A | 1/1992 | Asher et al. |
| 5,087,266 A | 2/1992 | Connell et al. |
| 5,092,866 A | 3/1992 | Breard et al. |
| 5,092,893 A | 3/1992 | Smith |
| 5,098,435 A | 3/1992 | Stednitz et al. |
| 5,116,336 A | 5/1992 | Frigg |

(56) References Cited

U.S. PATENT DOCUMENTS

| | | |
|---|---|---|
| 5,122,130 A | 6/1992 | Keller |
| 5,122,131 A | 6/1992 | Tsou |
| 5,127,914 A | 7/1992 | Calderale et al. |
| 5,129,899 A | 7/1992 | Small et al. |
| 5,131,904 A | 7/1992 | Markoll |
| 5,133,717 A | 7/1992 | Chopin |
| 5,147,360 A | 9/1992 | Dubousset |
| 5,147,361 A | 9/1992 | Ojima et al. |
| 5,152,303 A | 10/1992 | Allen |
| 5,167,662 A | 12/1992 | Hayes et al. |
| 5,176,680 A | 1/1993 | Vignaud et al. |
| 5,180,381 A | 1/1993 | Aust et al. |
| 5,180,393 A | 1/1993 | Commarmond |
| 5,192,327 A | 3/1993 | Brantigan |
| 5,207,679 A | 5/1993 | Li |
| 5,222,954 A | 6/1993 | Baker et al. |
| 5,226,766 A | 7/1993 | Lasner |
| 5,234,431 A | 8/1993 | Keller |
| 5,234,432 A | 8/1993 | Brown |
| 5,234,447 A | 8/1993 | Kaster et al. |
| 5,236,460 A | 8/1993 | Barber |
| 5,242,444 A | 9/1993 | MacMillan |
| 5,242,445 A | 9/1993 | Ashman |
| 5,246,442 A | 9/1993 | Ashman et al. |
| 5,246,458 A | 9/1993 | Graham |
| 5,250,055 A | 10/1993 | Moore et al. |
| 5,252,016 A | 10/1993 | Schmid et al. |
| 5,254,118 A | 10/1993 | Mirkovic |
| 5,258,031 A | 11/1993 | Salib et al. |
| 5,261,907 A | 11/1993 | Vignaud et al. |
| 5,261,909 A | 11/1993 | Sutterlin et al. |
| 5,261,910 A | 11/1993 | Warden et al. |
| 5,261,911 A | 11/1993 | Carl |
| 5,261,914 A | 11/1993 | Warren |
| 5,275,600 A | 1/1994 | Allard et al. |
| 5,275,601 A | 1/1994 | Gogolewski et al. |
| 5,281,222 A | 1/1994 | Allard et al. |
| 5,282,801 A | 2/1994 | Sherman |
| 5,282,862 A | 2/1994 | Baker et al. |
| 5,290,312 A | 3/1994 | Kojimoto et al. |
| 5,300,074 A | 4/1994 | Frigg |
| 5,304,178 A | 4/1994 | Stahurski |
| 5,306,307 A | 4/1994 | Senter et al. |
| 5,312,405 A | 5/1994 | Korotko et al. |
| 5,324,290 A | 6/1994 | Zdeblick et al. |
| 5,324,292 A | 6/1994 | Meyers |
| 5,330,468 A | 7/1994 | Burkhart |
| 5,330,473 A | 7/1994 | Howland |
| 5,334,205 A | 8/1994 | Cain |
| 5,335,418 A | 8/1994 | Krivec |
| 5,336,225 A | 8/1994 | Zang |
| 5,336,226 A | 8/1994 | McDaniel et al. |
| 5,342,394 A | 8/1994 | Matsuno et al. |
| 5,344,421 A | 9/1994 | Crook |
| 5,344,422 A | 9/1994 | Frigg |
| 5,346,493 A | 9/1994 | Stahurski et al. |
| 5,350,380 A | 9/1994 | Goble et al. |
| 5,352,226 A | 10/1994 | Lin |
| 5,352,231 A | 10/1994 | Brumfield et al. |
| 5,354,292 A | 10/1994 | Braeuer et al. |
| 5,356,410 A | 10/1994 | Pennig |
| 5,358,289 A | 10/1994 | Banker et al. |
| 5,360,429 A | 11/1994 | Jeanson et al. |
| 5,360,431 A | 11/1994 | Puno et al. |
| 5,361,766 A | 11/1994 | Nichols et al. |
| 5,364,399 A | 11/1994 | Lowery et al. |
| 5,366,455 A | 11/1994 | Dove et al. |
| 5,370,697 A | 12/1994 | Baumgartner |
| 5,372,599 A | 12/1994 | Martins |
| 5,374,267 A | 12/1994 | Siegal |
| 5,375,823 A | 12/1994 | Navas |
| 5,380,324 A | 1/1995 | Mueller et al. |
| 5,385,583 A | 1/1995 | Cotrel |
| 5,387,176 A | 2/1995 | Markoll |
| 5,387,213 A | 2/1995 | Breard et al. |
| 5,395,371 A | 3/1995 | Miller et al. |
| 5,397,363 A | 3/1995 | Gelbard |
| 5,397,364 A | 3/1995 | Kozak et al. |
| 5,403,316 A | 4/1995 | Ashman |
| 5,413,576 A | 5/1995 | Rivard |
| 5,415,661 A | 5/1995 | Holmes |
| 5,417,712 A | 5/1995 | Whittaker et al. |
| 5,423,816 A | 6/1995 | Lin, I |
| 5,423,818 A | 6/1995 | Van Hoeck et al. |
| 5,423,819 A | 6/1995 | Small et al. |
| 5,423,826 A | 6/1995 | Coates et al. |
| 5,425,772 A | 6/1995 | Brantigan |
| 5,425,773 A | 6/1995 | Boyd et al. |
| 5,427,418 A | 6/1995 | Watts |
| 5,429,639 A | 7/1995 | Judet |
| 5,431,658 A | 7/1995 | Moskovich |
| 5,437,669 A | 8/1995 | Yuan et al. |
| 5,437,670 A | 8/1995 | Sherman et al. |
| 5,437,672 A | 8/1995 | Alleyne |
| 5,437,674 A | 8/1995 | Worcel et al. |
| 5,439,339 A | 8/1995 | Batchelor |
| 5,439,463 A | 8/1995 | Lin |
| 5,443,467 A | 8/1995 | Biedermann et al. |
| 5,443,514 A | 8/1995 | Steffee |
| 5,449,257 A | 9/1995 | Giannuzzi |
| 5,453,073 A | 9/1995 | Markoll |
| 5,456,714 A | 10/1995 | Owen |
| 5,458,638 A | 10/1995 | Kuslich et al. |
| 5,466,237 A | 11/1995 | Byrd, III et al. |
| 5,468,241 A | 11/1995 | Metz-Stavenhagen et al. |
| 5,472,452 A | 12/1995 | Trott |
| 5,474,551 A | 12/1995 | Finn et al. |
| 5,474,555 A | 12/1995 | Puno et al. |
| 5,476,462 A | 12/1995 | Allard et al. |
| 5,476,464 A | 12/1995 | Metz-Stavenhagen et al. |
| 5,478,342 A | 12/1995 | Kohrs |
| 5,480,401 A | 1/1996 | Navas |
| 5,484,437 A | 1/1996 | Michelson |
| 5,484,440 A | 1/1996 | Allard |
| 5,486,174 A | 1/1996 | Fournet-Fayard et al. |
| 5,486,176 A | 1/1996 | Hildebrand et al. |
| 5,487,742 A | 1/1996 | Cotrel |
| 5,489,307 A | 2/1996 | Kuslich et al. |
| 5,489,308 A | 2/1996 | Kuslich et al. |
| 5,490,750 A | 2/1996 | Gundy |
| 5,496,318 A | 3/1996 | Howland et al. |
| 5,496,321 A | 3/1996 | Puno et al. |
| 5,499,892 A | 3/1996 | Reed |
| 5,505,731 A | 4/1996 | Tornier |
| 5,507,745 A | 4/1996 | Logroscino et al. |
| 5,507,754 A | 4/1996 | Green et al. |
| 5,507,816 A | 4/1996 | Bullivant |
| 5,512,038 A | 4/1996 | O'Neal et al. |
| 5,514,180 A | 5/1996 | Heggeness et al. |
| 5,520,690 A | 5/1996 | Errico et al. |
| 5,522,899 A | 6/1996 | Michelson |
| 5,527,314 A | 6/1996 | Brumfield et al. |
| 5,531,747 A | 7/1996 | Ray |
| 5,531,751 A | 7/1996 | Schultheiss et al. |
| 5,534,001 A | 7/1996 | Schlapfer et al. |
| 5,534,002 A | 7/1996 | Brumfield et al. |
| 5,534,027 A | 7/1996 | Hodorek |
| 5,540,688 A | 7/1996 | Navas |
| 5,545,163 A | 8/1996 | Miller et al. |
| 5,545,164 A | 8/1996 | Howland |
| 5,545,165 A | 8/1996 | Harms et al. |
| 5,545,179 A | 8/1996 | Williamson, IV |
| 5,549,607 A | 8/1996 | Olson et al. |
| 5,549,612 A | 8/1996 | Yapp et al. |
| 5,554,157 A | 9/1996 | Errico et al. |
| 5,556,431 A | 9/1996 | Buettner-Janz |
| 5,558,674 A | 9/1996 | Heggeness et al. |
| 5,562,660 A | 10/1996 | Grob |
| 5,562,661 A | 10/1996 | Yoshimi et al. |
| 5,562,662 A | 10/1996 | Brumfield et al. |
| 5,562,663 A | 10/1996 | Wisnewski et al. |
| 5,562,737 A | 10/1996 | Graf |
| 5,562,738 A | 10/1996 | Boyd et al. |
| 5,569,247 A | 10/1996 | Morrison |

(56) References Cited

U.S. PATENT DOCUMENTS

| | | |
|---|---|---|
| 5,569,248 A | 10/1996 | Mathews |
| 5,569,250 A | 10/1996 | Sarver et al. |
| 5,569,251 A | 10/1996 | Baker et al. |
| 5,569,252 A | 10/1996 | Justin et al. |
| 5,575,792 A | 11/1996 | Errico et al. |
| 5,578,033 A | 11/1996 | Errico et al. |
| 5,578,034 A | 11/1996 | Estes |
| 5,582,612 A | 12/1996 | Lin |
| 5,584,833 A | 12/1996 | Fournet-Fayard et al. |
| 5,584,834 A | 12/1996 | Errico et al. |
| 5,586,984 A | 12/1996 | Errico et al. |
| 5,591,166 A | 1/1997 | Bernhardt et al. |
| 5,599,279 A | 2/1997 | Slotman et al. |
| 5,601,553 A | 2/1997 | Trebing et al. |
| 5,603,714 A | 2/1997 | Kaneda et al. |
| 5,607,304 A | 3/1997 | Bailey et al. |
| 5,607,425 A | 3/1997 | Rogozinski |
| 5,607,426 A | 3/1997 | Ralph et al. |
| 5,607,428 A | 3/1997 | Lin |
| 5,609,593 A | 3/1997 | Errico et al. |
| 5,609,594 A | 3/1997 | Errico et al. |
| 5,609,634 A | 3/1997 | Voydeville |
| 5,609,635 A | 3/1997 | Michelson |
| 5,609,636 A | 3/1997 | Kohrs et al. |
| 5,609,637 A | 3/1997 | Biedermann et al. |
| 5,611,800 A | 3/1997 | Davis et al. |
| 5,616,142 A | 4/1997 | Yuan et al. |
| 5,620,169 A | 4/1997 | Payne |
| 5,620,443 A | 4/1997 | Gertzbein et al. |
| 5,628,740 A | 5/1997 | Mullane |
| 5,630,817 A | 5/1997 | Rokegem et al. |
| 5,641,256 A | 6/1997 | Gundy |
| 5,643,260 A | 7/1997 | Doherty |
| 5,643,261 A | 7/1997 | Schaefer et al. |
| 5,643,262 A | 7/1997 | Metz-Stavenhagen et al. |
| 5,643,321 A | 7/1997 | McDevitt |
| 5,645,544 A | 7/1997 | Tai et al. |
| 5,645,599 A | 7/1997 | Samani |
| 5,647,873 A | 7/1997 | Errico et al. |
| 5,649,931 A | 7/1997 | Bryant et al. |
| 5,653,763 A | 8/1997 | Errico et al. |
| 5,662,652 A | 9/1997 | Schaefer et al. |
| 5,662,653 A | 9/1997 | Songer et al. |
| 5,665,049 A | 9/1997 | Markoll |
| 5,667,513 A | 9/1997 | Torrie et al. |
| 5,669,868 A | 9/1997 | Markoll |
| 5,669,909 A | 9/1997 | Zdeblick et al. |
| 5,669,911 A | 9/1997 | Errico et al. |
| 5,669,912 A | 9/1997 | Spetzler |
| 5,672,175 A | 9/1997 | Martin |
| 5,672,176 A | 9/1997 | Biedermann et al. |
| 5,674,294 A | 10/1997 | Bainville et al. |
| 5,674,296 A | 10/1997 | Bryan et al. |
| 5,676,666 A | 10/1997 | Oxland et al. |
| 5,676,697 A | 10/1997 | McDonald |
| 5,676,701 A | 10/1997 | Yuan et al. |
| 5,676,703 A | 10/1997 | Gelbard |
| 5,681,311 A | 10/1997 | Foley et al. |
| 5,681,312 A | 10/1997 | Yuan et al. |
| 5,681,313 A | 10/1997 | Diez |
| 5,681,319 A | 10/1997 | Biedermann et al. |
| 5,683,390 A | 11/1997 | Metz-Stavenhagen et al. |
| 5,683,391 A | 11/1997 | Boyd |
| 5,683,392 A | 11/1997 | Richelsoph et al. |
| 5,683,394 A | 11/1997 | Rinner |
| 5,683,464 A | 11/1997 | Wagner et al. |
| 5,688,275 A | 11/1997 | Koros et al. |
| 5,690,630 A | 11/1997 | Errico et al. |
| 5,697,929 A | 12/1997 | Mellinger |
| 5,702,451 A | 12/1997 | Biedermann et al. |
| 5,704,936 A | 1/1998 | Mazel |
| 5,707,372 A | 1/1998 | Errico et al. |
| 5,709,686 A | 1/1998 | Talos et al. |
| 5,711,709 A | 1/1998 | McCoy |
| 5,713,672 A | 2/1998 | Lu |
| 5,713,898 A | 2/1998 | Stuecker et al. |
| 5,713,899 A | 2/1998 | Marnay et al. |
| 5,713,900 A | 2/1998 | Benzel et al. |
| 5,713,904 A | 2/1998 | Errico et al. |
| 5,716,356 A | 2/1998 | Biedermann et al. |
| 5,716,357 A | 2/1998 | Rogozinski |
| 5,720,751 A | 2/1998 | Jackson |
| 5,722,976 A | 3/1998 | Brown |
| 5,722,977 A | 3/1998 | Wilhelmy |
| 5,723,013 A | 3/1998 | Jeanson et al. |
| 5,725,527 A | 3/1998 | Biedermann et al. |
| 5,725,528 A | 3/1998 | Errico et al. |
| 5,725,582 A | 3/1998 | Bevan et al. |
| 5,728,046 A | 3/1998 | Mayer et al. |
| 5,728,098 A | 3/1998 | Sherman et al. |
| 5,733,284 A | 3/1998 | Martin |
| 5,733,285 A | 3/1998 | Errico et al. |
| 5,733,286 A | 3/1998 | Errico et al. |
| 5,733,290 A | 3/1998 | McCue et al. |
| 5,735,853 A | 4/1998 | Olerud |
| 5,738,685 A | 4/1998 | Halm et al. |
| 5,741,254 A | 4/1998 | Henry et al. |
| 5,741,261 A | 4/1998 | Moskovitz et al. |
| 5,746,743 A | 5/1998 | Greenberg |
| 5,749,916 A | 5/1998 | Richelsoph |
| 5,749,968 A | 5/1998 | Melanson et al. |
| 5,752,957 A | 5/1998 | Ralph et al. |
| 5,755,660 A | 5/1998 | Tyagi |
| 5,755,732 A | 5/1998 | Green et al. |
| 5,766,252 A | 6/1998 | Henry et al. |
| 5,772,583 A | 6/1998 | Wright et al. |
| 5,776,135 A | 7/1998 | Errico et al. |
| 5,776,199 A | 7/1998 | Michelson |
| 5,782,830 A | 7/1998 | Farris |
| 5,782,832 A | 7/1998 | Larsen et al. |
| 5,782,833 A | 7/1998 | Haider |
| 5,782,919 A | 7/1998 | Zdeblick et al. |
| 5,792,044 A | 8/1998 | Foley et al. |
| 5,795,289 A | 8/1998 | Wyttenbach |
| 5,795,291 A | 8/1998 | Koros et al. |
| 5,795,584 A | 8/1998 | Totakura et al. |
| 5,797,911 A | 8/1998 | Sherman et al. |
| 5,800,433 A | 9/1998 | Benzel et al. |
| 5,800,435 A | 9/1998 | Errico et al. |
| 5,800,547 A | 9/1998 | Schaefer et al. |
| 5,807,403 A | 9/1998 | Beyar et al. |
| 5,810,818 A | 9/1998 | Errico et al. |
| 5,810,819 A | 9/1998 | Errico et al. |
| 5,817,094 A | 10/1998 | Errico et al. |
| 5,833,418 A | 11/1998 | Shoji |
| 5,836,948 A | 11/1998 | Zucherman et al. |
| 5,842,966 A | 12/1998 | Markoll |
| 5,846,192 A | 12/1998 | Teixido |
| 5,860,977 A | 1/1999 | Zucherman et al. |
| 5,863,293 A | 1/1999 | Richelsoph |
| 5,865,848 A | 2/1999 | Baker |
| 5,873,878 A | 2/1999 | Harms et al. |
| 5,876,402 A | 3/1999 | Errico et al. |
| 5,876,404 A | 3/1999 | Zucherman et al. |
| 5,879,350 A | 3/1999 | Sherman et al. |
| 5,879,351 A | 3/1999 | Viart |
| 5,882,298 A | 3/1999 | Sharratt |
| 5,882,350 A | 3/1999 | Ralph et al. |
| 5,882,351 A | 3/1999 | Fox |
| 5,884,702 A | 3/1999 | Yokley et al. |
| 5,885,286 A | 3/1999 | Sherman et al. |
| 5,888,197 A | 3/1999 | Mulac et al. |
| 5,888,222 A | 3/1999 | Coates et al. |
| 5,888,224 A | 3/1999 | Beckers et al. |
| 5,888,226 A | 3/1999 | Rogozinski |
| 5,890,271 A | 4/1999 | Bromley et al. |
| 5,891,145 A | 4/1999 | Morrison et al. |
| 5,893,831 A | 4/1999 | Koros et al. |
| 5,899,425 A | 5/1999 | Corey Jr. et al. |
| 5,899,904 A | 5/1999 | Errico et al. |
| 5,899,905 A | 5/1999 | Errico et al. |
| 5,902,231 A | 5/1999 | Foley et al. |
| 5,902,233 A | 5/1999 | Farley et al. |
| 5,902,304 A | 5/1999 | Walker et al. |

(56) References Cited

U.S. PATENT DOCUMENTS

| | | |
|---|---|---|
| 5,904,683 A | 5/1999 | Pohndorf et al. |
| RE36,221 E | 6/1999 | Breard et al. |
| 5,908,382 A | 6/1999 | Koros et al. |
| 5,910,141 A | 6/1999 | Morrison et al. |
| 5,928,139 A | 7/1999 | Koros et al. |
| 5,928,231 A | 7/1999 | Klein et al. |
| 5,928,233 A | 7/1999 | Apfelbaum, I et al. |
| 5,931,777 A | 8/1999 | Sava |
| 5,938,663 A | 8/1999 | Petreto |
| 5,941,885 A | 8/1999 | Jackson |
| 5,944,465 A | 8/1999 | Janitzki |
| 5,944,658 A | 8/1999 | Koros et al. |
| 5,947,967 A | 9/1999 | Barker |
| 5,947,970 A | 9/1999 | Schmelzeisen et al. |
| 5,951,553 A | 9/1999 | Betz et al. |
| 5,951,558 A | 9/1999 | Fiz |
| 5,954,722 A | 9/1999 | Bono |
| 5,954,725 A | 9/1999 | Sherman et al. |
| 5,961,516 A | 10/1999 | Graf |
| 5,961,517 A | 10/1999 | Biedermann et al. |
| 5,961,518 A | 10/1999 | Errico et al. |
| 5,964,760 A | 10/1999 | Richelsoph |
| 5,964,762 A | 10/1999 | Biedermann et al. |
| 5,964,763 A | 10/1999 | Incavo et al. |
| 5,967,970 A | 10/1999 | Cowan et al. |
| 5,967,972 A | 10/1999 | Santilli et al. |
| 5,971,987 A | 10/1999 | Huxel et al. |
| 5,976,135 A | 11/1999 | Sherman et al. |
| 5,976,140 A | 11/1999 | Haas |
| 5,976,146 A | 11/1999 | Ogawa et al. |
| 5,976,186 A | 11/1999 | Bao et al. |
| 5,980,522 A | 11/1999 | Koros et al. |
| 5,984,865 A | 11/1999 | Farley et al. |
| 5,984,923 A | 11/1999 | Breard |
| 5,984,967 A | 11/1999 | Zdeblick et al. |
| 5,993,385 A | 11/1999 | Johnston et al. |
| 5,993,449 A | 11/1999 | Schlapfer et al. |
| 5,997,539 A | 12/1999 | Errico et al. |
| 6,001,098 A | 12/1999 | Metz-Stavenhagen et al. |
| 6,001,130 A | 12/1999 | Bryan et al. |
| 6,004,326 A | 12/1999 | Castro et al. |
| 6,004,349 A | 12/1999 | Jackson |
| 6,010,503 A | 1/2000 | Richelsoph et al. |
| 6,010,692 A | 1/2000 | Goldberg et al. |
| 6,016,727 A | 1/2000 | Morgan |
| 6,017,342 A | 1/2000 | Rinner |
| 6,017,344 A | 1/2000 | Errico et al. |
| 6,019,759 A | 2/2000 | Rogozinski |
| 6,019,792 A | 2/2000 | Cauthen |
| 6,022,350 A | 2/2000 | Ganem |
| 6,022,376 A | 2/2000 | Assell et al. |
| 6,030,388 A | 2/2000 | Yoshimi et al. |
| 6,033,170 A | 3/2000 | Gold |
| 6,033,406 A | 3/2000 | Mathews |
| 6,033,436 A | 3/2000 | Steinke et al. |
| 6,039,740 A | 3/2000 | Olerud |
| 6,039,761 A | 3/2000 | Li et al. |
| D422,705 S | 4/2000 | Koros et al. |
| 6,045,555 A | 4/2000 | Smith et al. |
| 6,045,579 A | 4/2000 | Hochshuler et al. |
| 6,048,302 A | 4/2000 | Markoll |
| 6,048,342 A | 4/2000 | Zucherman et al. |
| 6,048,343 A | 4/2000 | Mathis et al. |
| 6,050,997 A | 4/2000 | Mullane |
| 6,053,917 A | 4/2000 | Sherman et al. |
| 6,059,785 A | 5/2000 | Schavan et al. |
| 6,059,786 A | 5/2000 | Jackson |
| 6,063,089 A | 5/2000 | Errico et al. |
| 6,063,090 A | 5/2000 | Schlaepfer |
| 6,066,174 A | 5/2000 | Farris |
| 6,066,175 A | 5/2000 | Henderson et al. |
| 6,068,630 A | 5/2000 | Zucherman et al. |
| 6,071,310 A | 6/2000 | Picha et al. |
| 6,074,343 A | 6/2000 | Nathanson et al. |
| 6,074,390 A | 6/2000 | Zucherman et al. |
| 6,074,391 A | 6/2000 | Metz-Stavenhagen et al. |
| 6,077,262 A | 6/2000 | Schlaepfer et al. |
| 6,080,193 A | 6/2000 | Hochshuler et al. |
| 6,083,224 A | 7/2000 | Gertzbein et al. |
| 6,083,225 A | 7/2000 | Winslow et al. |
| 6,083,624 A | 7/2000 | Hiura |
| 6,086,588 A | 7/2000 | Ameil et al. |
| 6,086,589 A | 7/2000 | Kuslich et al. |
| 6,086,613 A | 7/2000 | Camino et al. |
| 6,090,110 A | 7/2000 | Metz-Stavenhagen |
| 6,090,111 A | 7/2000 | Nichols |
| 6,090,113 A | 7/2000 | Le et al. |
| 6,093,205 A | 7/2000 | McLeod et al. |
| 6,096,060 A | 8/2000 | Fitts et al. |
| 6,099,528 A | 8/2000 | Saurat |
| 6,099,531 A | 8/2000 | Bonutti |
| 6,102,912 A | 8/2000 | Cazin et al. |
| 6,102,913 A | 8/2000 | Jackson |
| 6,110,172 A | 8/2000 | Jackson |
| 6,110,173 A | 8/2000 | Thomas, Jr. |
| 6,111,164 A | 8/2000 | Rainey et al. |
| 6,113,599 A | 9/2000 | Landsberger |
| 6,113,601 A | 9/2000 | Tatar |
| 6,113,638 A | 9/2000 | Williams et al. |
| 6,117,135 A | 9/2000 | Schlaepfer |
| 6,117,137 A | 9/2000 | Halm et al. |
| 6,119,631 A | 9/2000 | Markoll |
| 6,120,502 A | 9/2000 | Michelson |
| 6,123,706 A | 9/2000 | Lange |
| 6,123,707 A | 9/2000 | Wagner |
| 6,126,689 A | 10/2000 | Brett |
| 6,132,370 A | 10/2000 | Furnish et al. |
| 6,132,430 A | 10/2000 | Wagner |
| 6,132,431 A | 10/2000 | Nilsson et al. |
| 6,132,432 A | 10/2000 | Richelsoph |
| 6,132,434 A | 10/2000 | Sherman et al. |
| 6,132,464 A | 10/2000 | Martin |
| 6,136,000 A | 10/2000 | Louis et al. |
| 6,136,002 A | 10/2000 | Shih et al. |
| 6,139,316 A | 10/2000 | Sachdeva et al. |
| 6,139,493 A | 10/2000 | Koros et al. |
| 6,139,549 A | 10/2000 | Keller |
| 6,143,032 A | 11/2000 | Schafer et al. |
| 6,146,044 A | 11/2000 | Calvet |
| 6,146,383 A | 11/2000 | Studer et al. |
| 6,146,422 A | 11/2000 | Lawson |
| 6,149,650 A | 11/2000 | Michelson |
| 6,152,927 A | 11/2000 | Farris et al. |
| 6,156,037 A | 12/2000 | Lehuec et al. |
| 6,159,210 A | 12/2000 | Voor |
| 6,159,211 A | 12/2000 | Boriani et al. |
| 6,159,215 A | 12/2000 | Urbahns et al. |
| 6,159,244 A | 12/2000 | Suddaby |
| 6,162,252 A | 12/2000 | Kuras et al. |
| 6,174,311 B1 | 1/2001 | Branch et al. |
| 6,176,882 B1 | 1/2001 | Biedermann et al. |
| 6,179,838 B1 | 1/2001 | Fiz |
| 6,179,873 B1 | 1/2001 | Zientek |
| 6,179,874 B1 | 1/2001 | Cauthen |
| 6,183,472 B1 | 2/2001 | Lutz |
| 6,183,473 B1 | 2/2001 | Ashman |
| 6,186,005 B1 | 2/2001 | Leidl |
| 6,186,718 B1 | 2/2001 | Fogard |
| 6,187,005 B1 | 2/2001 | Brace et al. |
| 6,193,720 B1 | 2/2001 | Yuan et al. |
| 6,193,721 B1 | 2/2001 | Michelson |
| 6,193,757 B1 | 2/2001 | Foley et al. |
| 6,197,033 B1 | 3/2001 | Haid, Jr. et al. |
| 6,200,322 B1 | 3/2001 | Branch et al. |
| 6,206,826 B1 | 3/2001 | Mathews et al. |
| 6,206,879 B1 | 3/2001 | Marnay et al. |
| 6,206,922 B1 | 3/2001 | Zdeblick et al. |
| 6,206,923 B1 | 3/2001 | Boyd et al. |
| D440,311 S | 4/2001 | Michelson |
| 6,210,376 B1 | 4/2001 | Grayson |
| 6,210,412 B1 | 4/2001 | Michelson |
| 6,210,413 B1 | 4/2001 | Justis et al. |
| 6,214,005 B1 | 4/2001 | Benzel et al. |
| 6,214,012 B1 | 4/2001 | Karpman et al. |

(56) References Cited

U.S. PATENT DOCUMENTS

| | | |
|---|---|---|
| 6,221,077 B1 | 4/2001 | Rinner et al. |
| RE37,161 E | 5/2001 | Michelson et al. |
| 6,224,545 B1 | 5/2001 | Cocchia et al. |
| 6,224,595 B1 | 5/2001 | Michelson |
| 6,224,596 B1 | 5/2001 | Jackson |
| 6,224,598 B1 | 5/2001 | Jackson |
| 6,224,602 B1 | 5/2001 | Hayes |
| 6,224,607 B1 | 5/2001 | Michelson |
| 6,226,548 B1 | 5/2001 | Foley et al. |
| 6,228,022 B1 | 5/2001 | Friesem et al. |
| 6,228,085 B1 | 5/2001 | Theken et al. |
| 6,231,575 B1 | 5/2001 | Krag |
| 6,234,705 B1 | 5/2001 | Troxell |
| 6,235,028 B1 | 5/2001 | Brumfield et al. |
| 6,235,034 B1 | 5/2001 | Bray |
| 6,235,726 B1 | 5/2001 | Burns et al. |
| 6,238,396 B1 | 5/2001 | Lombardo |
| 6,241,729 B1 | 6/2001 | Estes et al. |
| 6,241,730 B1 | 6/2001 | Alby |
| 6,241,769 B1 | 6/2001 | Nicholson et al. |
| 6,241,770 B1 | 6/2001 | Michelson |
| 6,245,072 B1 | 6/2001 | Zdeblick et al. |
| 6,245,108 B1 | 6/2001 | Biscup |
| 6,248,104 B1 | 6/2001 | Chopin et al. |
| 6,248,105 B1 | 6/2001 | Schlaepfer et al. |
| 6,248,106 B1 | 6/2001 | Ferree |
| 6,248,107 B1 | 6/2001 | Foley et al. |
| 6,248,110 B1 | 6/2001 | Reiley et al. |
| 6,250,984 B1 | 6/2001 | Jin et al. |
| 6,251,112 B1 | 6/2001 | Jackson |
| 6,251,140 B1 | 6/2001 | Marino et al. |
| 6,254,146 B1 | 7/2001 | Church |
| 6,254,602 B1 | 7/2001 | Justis |
| 6,254,603 B1 | 7/2001 | Gertzbein et al. |
| 6,258,089 B1 | 7/2001 | Campbell et al. |
| 6,258,125 B1 | 7/2001 | Paul et al. |
| 6,261,287 B1 | 7/2001 | Metz-Stavenhagen |
| 6,261,291 B1 | 7/2001 | Talaber et al. |
| 6,264,656 B1 | 7/2001 | Michelson |
| 6,267,764 B1 | 7/2001 | Elberg |
| 6,267,765 B1 | 7/2001 | Taylor et al. |
| 6,270,498 B1 | 8/2001 | Michelson |
| 6,273,888 B1 | 8/2001 | Justis |
| 6,273,889 B1 | 8/2001 | Richelsoph |
| 6,277,122 B1 | 8/2001 | McGahan et al. |
| 6,277,149 B1 | 8/2001 | Boyle et al. |
| 6,280,442 B1 | 8/2001 | Barker et al. |
| 6,280,445 B1 | 8/2001 | Morrison et al. |
| D448,081 S | 9/2001 | Koros et al. |
| 6,283,967 B1 | 9/2001 | Troxell et al. |
| 6,287,308 B1 | 9/2001 | Betz et al. |
| 6,287,309 B1 | 9/2001 | Baccelli et al. |
| 6,287,311 B1 | 9/2001 | Sherman et al. |
| 6,290,703 B1 | 9/2001 | Ganem |
| 6,293,949 B1 | 9/2001 | Justis et al. |
| 6,294,202 B1 | 9/2001 | Burns et al. |
| D449,692 S | 10/2001 | Michelson |
| 6,296,642 B1 | 10/2001 | Morrison et al. |
| 6,296,643 B1 | 10/2001 | Hopf et al. |
| 6,296,664 B1 | 10/2001 | Middleton |
| 6,299,613 B1 | 10/2001 | Ogilvie et al. |
| 6,302,843 B1 | 10/2001 | Lees et al. |
| 6,302,888 B1 | 10/2001 | Mellinger et al. |
| 6,302,914 B1 | 10/2001 | Michelson |
| 6,304,178 B1 | 10/2001 | Hayashida |
| 6,306,136 B1 | 10/2001 | Baccelli |
| 6,306,137 B2 | 10/2001 | Troxell |
| 6,306,170 B2 | 10/2001 | Ray |
| 6,309,391 B1 | 10/2001 | Crandall et al. |
| 6,312,431 B1 | 11/2001 | Asfora |
| 6,315,564 B1 | 11/2001 | Levisman |
| 6,315,779 B1 | 11/2001 | Morrison et al. |
| 6,317,957 B1 | 11/2001 | Gregor et al. |
| 6,319,002 B1 | 11/2001 | Pond |
| 6,319,257 B1 | 11/2001 | Carignan et al. |
| 6,322,500 B1 | 11/2001 | Sikora et al. |
| RE37,479 E | 12/2001 | Kuslich |
| 6,331,179 B1 | 12/2001 | Freid et al. |
| 6,332,882 B1 | 12/2001 | Zucherman et al. |
| 6,340,345 B1 | 1/2002 | Lees et al. |
| 6,342,074 B1 | 1/2002 | Simpson |
| 6,344,057 B1 | 2/2002 | Rabbe et al. |
| 6,348,058 B1 | 2/2002 | Melkent et al. |
| 6,348,071 B1 | 2/2002 | Steffee et al. |
| 6,350,283 B1 | 2/2002 | Michelson |
| 6,355,038 B1 | 3/2002 | Pisharodi |
| 6,355,039 B1 | 3/2002 | Troussel et al. |
| 6,355,040 B1 | 3/2002 | Richelsoph et al. |
| 6,360,750 B1 | 3/2002 | Gerber et al. |
| 6,361,258 B1 | 3/2002 | Heesch |
| RE37,665 E | 4/2002 | Ralph |
| 6,364,880 B1 | 4/2002 | Michelson |
| 6,364,881 B1 | 4/2002 | Apgar et al. |
| 6,364,883 B1 | 4/2002 | Santilli |
| 6,368,320 B1 | 4/2002 | Le Couedic et al. |
| 6,368,321 B1 | 4/2002 | Jackson |
| 6,368,350 B1 | 4/2002 | Erickson et al. |
| 6,371,957 B1 | 4/2002 | Amrein et al. |
| 6,371,987 B1 | 4/2002 | Weiland et al. |
| 6,371,988 B1 | 4/2002 | Pafford et al. |
| 6,375,655 B1 | 4/2002 | Zdeblick et al. |
| 6,375,681 B1 | 4/2002 | Truscott |
| 6,379,355 B1 | 4/2002 | Zucherman et al. |
| 6,379,357 B1 | 4/2002 | Bernstein et al. |
| 6,387,130 B1 | 5/2002 | Stone et al. |
| 6,389,391 B1 | 5/2002 | Terauchi |
| 6,395,031 B1 | 5/2002 | Foley et al. |
| 6,395,035 B2 | 5/2002 | Bresina et al. |
| 6,398,783 B1 | 6/2002 | Michelson |
| 6,402,749 B1 | 6/2002 | Ashman |
| 6,402,750 B1 | 6/2002 | Atkinson et al. |
| 6,402,751 B1 | 6/2002 | Van Hoeck et al. |
| 6,402,752 B2 | 6/2002 | Schaffler-Wachter et al. |
| 6,402,756 B1 | 6/2002 | Ralph et al. |
| 6,402,757 B1 | 6/2002 | Moore, III et al. |
| 6,402,785 B1 | 6/2002 | Zdeblick et al. |
| 6,406,478 B1 | 6/2002 | Kuo |
| 6,409,765 B1 | 6/2002 | Bianchi et al. |
| 6,412,999 B1 | 7/2002 | Pierpont |
| 6,413,258 B1 | 7/2002 | Bernhardt, Jr. |
| 6,413,259 B1 | 7/2002 | Lyons et al. |
| 6,413,278 B1 | 7/2002 | Marchosky |
| 6,416,465 B2 | 7/2002 | Brau |
| 6,416,515 B1 | 7/2002 | Wagner |
| 6,419,676 B1 | 7/2002 | Zucherman et al. |
| 6,419,677 B2 | 7/2002 | Zucherman et al. |
| 6,419,703 B1 | 7/2002 | Fallin et al. |
| 6,419,704 B1 | 7/2002 | Ferree |
| 6,419,706 B1 | 7/2002 | Graf |
| 6,423,063 B1 | 7/2002 | Bonutti |
| 6,423,095 B1 | 7/2002 | Van Hoeck et al. |
| 6,428,542 B1 | 8/2002 | Michelson |
| 6,428,576 B1 | 8/2002 | Haldimann |
| 6,432,108 B1 | 8/2002 | Burgess et al. |
| 6,432,140 B1 | 8/2002 | Lin |
| 6,440,133 B1 | 8/2002 | Beale et al. |
| 6,440,137 B1 | 8/2002 | Horvath et al. |
| 6,440,139 B2 | 8/2002 | Michelson |
| 6,440,168 B1 | 8/2002 | Cauthen |
| 6,440,169 B1 | 8/2002 | Elberg et al. |
| 6,440,170 B1 | 8/2002 | Jackson |
| 6,443,956 B1 | 9/2002 | Ray |
| 6,443,989 B1 | 9/2002 | Jackson |
| 6,447,440 B1 | 9/2002 | Markoll |
| 6,447,443 B1 | 9/2002 | Keogh et al. |
| 6,447,547 B1 | 9/2002 | Michelson |
| 6,447,548 B1 | 9/2002 | Ralph et al. |
| 6,451,019 B1 | 9/2002 | Zucherman et al. |
| 6,451,020 B1 | 9/2002 | Zucherman et al. |
| 6,451,021 B1 | 9/2002 | Ralph et al. |
| 6,454,769 B2 | 9/2002 | Wagner et al. |
| 6,454,771 B1 | 9/2002 | Michelson |
| 6,454,773 B1 | 9/2002 | Sherman et al. |
| 6,458,159 B1 | 10/2002 | Thalgott |

(56) References Cited

U.S. PATENT DOCUMENTS

| | | |
|---|---|---|
| 6,461,358 B1 | 10/2002 | Faccioli et al. |
| 6,461,359 B1 | 10/2002 | Tribus et al. |
| 6,468,310 B1 | 10/2002 | Ralph et al. |
| 6,471,703 B1 | 10/2002 | Ashman |
| 6,471,704 B2 | 10/2002 | Gertzbein et al. |
| 6,471,705 B1 | 10/2002 | Biedermann et al. |
| 6,471,724 B2 | 10/2002 | Zdeblick et al. |
| 6,475,218 B2 | 11/2002 | Gournay et al. |
| 6,478,796 B2 | 11/2002 | Zucherman et al. |
| 6,478,798 B1 | 11/2002 | Howland |
| 6,478,800 B1 | 11/2002 | Fraser et al. |
| 6,478,801 B1 | 11/2002 | Ralph et al. |
| 6,482,234 B1 | 11/2002 | Weber et al. |
| 6,485,491 B1 | 11/2002 | Farris et al. |
| 6,485,492 B1 | 11/2002 | Halm et al. |
| 6,485,494 B1 | 11/2002 | Haider |
| 6,485,517 B1 | 11/2002 | Michelson |
| 6,485,518 B1 | 11/2002 | Cornwall et al. |
| 6,488,681 B2 | 12/2002 | Martin et al. |
| 6,497,726 B1 | 12/2002 | Carter et al. |
| 6,500,205 B1 | 12/2002 | Michelson |
| 6,503,250 B2 | 1/2003 | Paul |
| 6,508,818 B2 | 1/2003 | Steiner et al. |
| 6,508,839 B1 | 1/2003 | Lambrecht et al. |
| 6,511,484 B2 | 1/2003 | Torode et al. |
| 6,514,256 B2 | 2/2003 | Zucherman et al. |
| 6,514,260 B1 | 2/2003 | Zdeblick et al. |
| 6,517,580 B1 | 2/2003 | Ramadan et al. |
| 6,520,962 B1 | 2/2003 | Taylor et al. |
| 6,520,967 B1 | 2/2003 | Cauthen |
| 6,520,996 B1 | 2/2003 | Manasas et al. |
| 6,521,223 B1 | 2/2003 | Calias et al. |
| 6,524,233 B2 | 2/2003 | Markoll |
| 6,524,238 B2 | 2/2003 | Velikaris et al. |
| 6,524,312 B2 | 2/2003 | Landry et al. |
| 6,524,315 B2 | 2/2003 | Selvitelli et al. |
| 6,527,773 B1 | 3/2003 | Lin et al. |
| 6,527,803 B1 | 3/2003 | Crozet et al. |
| 6,527,804 B1 | 3/2003 | Gauchet et al. |
| 6,527,806 B2 | 3/2003 | Ralph et al. |
| 6,530,929 B1 | 3/2003 | Justis et al. |
| 6,531,146 B2 | 3/2003 | Calhoun et al. |
| 6,533,786 B1 | 3/2003 | Needham et al. |
| 6,537,276 B2 | 3/2003 | Metz-Stavenhagen |
| 6,537,279 B1 | 3/2003 | Michelson |
| 6,538,262 B1 | 3/2003 | Crespi et al. |
| 6,539,826 B2 | 4/2003 | Oesterle et al. |
| 6,540,749 B2 | 4/2003 | Schaefer et al. |
| 6,540,785 B1 | 4/2003 | Gill et al. |
| 6,547,790 B2 | 4/2003 | Harkey, III et al. |
| 6,547,795 B2 | 4/2003 | Schneiderman |
| 6,551,242 B1 | 4/2003 | Furnish et al. |
| 6,551,320 B2 | 4/2003 | Lieberman |
| 6,551,322 B1 | 4/2003 | Lieberman |
| 6,551,323 B2 | 4/2003 | Doubler et al. |
| 6,554,831 B1 | 4/2003 | Rivard et al. |
| 6,554,832 B2 | 4/2003 | Shluzas |
| 6,554,834 B1 | 4/2003 | Crozet et al. |
| 6,554,863 B2 | 4/2003 | Paul et al. |
| 6,558,386 B1 | 5/2003 | Cragg |
| 6,558,387 B2 | 5/2003 | Errico et al. |
| 6,558,390 B2 | 5/2003 | Cragg |
| 6,558,423 B1 | 5/2003 | Michelson |
| 6,558,424 B2 | 5/2003 | Thalgott |
| 6,562,038 B1 | 5/2003 | Morrison |
| 6,562,040 B1 | 5/2003 | Wagner |
| 6,562,046 B2 | 5/2003 | Sasso |
| 6,562,074 B2 | 5/2003 | Gerbec et al. |
| 6,565,565 B1 | 5/2003 | Yuan et al. |
| 6,565,567 B1 | 5/2003 | Haider |
| 6,565,571 B1 | 5/2003 | Jackowski et al. |
| 6,565,605 B2 | 5/2003 | Goble et al. |
| 6,569,168 B2 | 5/2003 | Lin |
| 6,572,618 B1 | 6/2003 | Morrison |
| 6,575,899 B1 | 6/2003 | Foley et al. |
| 6,575,981 B1 | 6/2003 | Boyd et al. |
| 6,576,016 B1 | 6/2003 | Hochshuler et al. |
| 6,579,291 B1 | 6/2003 | Keith et al. |
| 6,579,319 B2 | 6/2003 | Goble et al. |
| 6,582,431 B1 | 6/2003 | Ray |
| 6,582,433 B2 | 6/2003 | Yun |
| 6,582,436 B2 | 6/2003 | Schlapfer et al. |
| 6,582,466 B1 | 6/2003 | Gauchet |
| 6,585,740 B2 | 7/2003 | Schlapfer et al. |
| 6,589,243 B1 | 7/2003 | Viart et al. |
| 6,592,585 B2 | 7/2003 | Lee et al. |
| 6,592,624 B1 | 7/2003 | Fraser et al. |
| 6,595,992 B1 | 7/2003 | Wagner et al. |
| 6,595,993 B2 | 7/2003 | Donno et al. |
| 6,595,995 B2 | 7/2003 | Zdeblick et al. |
| 6,599,240 B2 | 7/2003 | Puchovsky et al. |
| 6,599,290 B2 | 7/2003 | Bailey et al. |
| 6,599,292 B1 | 7/2003 | Ray |
| 6,599,294 B2 | 7/2003 | Fuss et al. |
| 6,599,295 B1 | 7/2003 | Tornier et al. |
| 6,599,320 B1 | 7/2003 | Kuslich et al. |
| 6,599,321 B2 | 7/2003 | Hyde, Jr. |
| 6,602,254 B2 | 8/2003 | Gertzbein et al. |
| 6,602,255 B1 | 8/2003 | Campbell et al. |
| 6,602,256 B1 | 8/2003 | Hayes |
| 6,602,257 B1 | 8/2003 | Thramann |
| 6,605,089 B1 | 8/2003 | Michelson |
| 6,607,530 B1 | 8/2003 | Carl et al. |
| 6,607,558 B2 | 8/2003 | Kuras |
| 6,610,063 B2 | 8/2003 | Kumar et al. |
| 6,610,089 B1 | 8/2003 | Liu et al. |
| 6,610,093 B1 | 8/2003 | Pisharodi |
| 6,613,050 B1 | 9/2003 | Wagner et al. |
| 6,613,089 B1 | 9/2003 | Estes et al. |
| 6,613,091 B1 | 9/2003 | Zdeblick et al. |
| 6,613,278 B1 | 9/2003 | Mills et al. |
| 6,616,664 B2 | 9/2003 | Walulik et al. |
| 6,616,665 B2 | 9/2003 | Grafton et al. |
| 6,616,667 B1 | 9/2003 | Steiger et al. |
| 6,616,669 B2 | 9/2003 | Ogilvie et al. |
| 6,616,695 B1 | 9/2003 | Crozet et al. |
| 6,620,163 B1 | 9/2003 | Michelson |
| 6,622,344 B1 | 9/2003 | Lu |
| 6,623,485 B2 | 9/2003 | Doubler et al. |
| 6,626,347 B2 | 9/2003 | Ng |
| 6,626,904 B1 | 9/2003 | Jammet et al. |
| 6,626,906 B1 | 9/2003 | Young |
| 6,626,907 B2 | 9/2003 | Campbell et al. |
| 6,626,908 B2 | 9/2003 | Cooper et al. |
| 6,635,059 B2 | 10/2003 | Randall et al. |
| 6,635,060 B2 | 10/2003 | Hanson et al. |
| 6,635,086 B2 | 10/2003 | Lin |
| 6,635,087 B2 | 10/2003 | Angelucci et al. |
| 6,638,276 B2 | 10/2003 | Sharkey et al. |
| 6,638,310 B2 | 10/2003 | Lin et al. |
| 6,641,583 B2 | 11/2003 | Shluzas et al. |
| 6,641,585 B2 | 11/2003 | Sato et al. |
| 6,641,586 B2 | 11/2003 | Varieur |
| 6,641,614 B1 | 11/2003 | Wagner et al. |
| 6,645,206 B1 | 11/2003 | Zdeblick et al. |
| 6,645,207 B2 | 11/2003 | Dixon et al. |
| 6,645,208 B2 | 11/2003 | Apfelbaum, I et al. |
| 6,645,249 B2 | 11/2003 | Ralph et al. |
| 6,648,885 B1 | 11/2003 | Friesem |
| 6,648,887 B2 | 11/2003 | Ashman |
| 6,648,888 B1 | 11/2003 | Shluzas |
| 6,648,891 B2 | 11/2003 | Kim |
| 6,648,894 B2 | 11/2003 | Abdelgany et al. |
| 6,648,895 B2 | 11/2003 | Burkus et al. |
| 6,648,917 B2 | 11/2003 | Gerbec et al. |
| 6,652,525 B1 | 11/2003 | Assaker et al. |
| 6,652,526 B1 | 11/2003 | Arafiles |
| 6,652,533 B2 | 11/2003 | O'Neil |
| 6,652,584 B2 | 11/2003 | Michelson |
| 6,652,586 B2 | 11/2003 | Hunter et al. |
| 6,652,765 B1 | 11/2003 | Beaty |
| 6,652,818 B1 | 11/2003 | Mills et al. |
| 6,656,179 B1 | 12/2003 | Schaefer et al. |
| 6,656,181 B2 | 12/2003 | Dixon et al. |

(56) References Cited

U.S. PATENT DOCUMENTS

| | | |
|---|---|---|
| 6,656,224 B2 | 12/2003 | Middleton |
| 6,660,004 B2 | 12/2003 | Barker et al. |
| 6,660,006 B2 | 12/2003 | Markworth et al. |
| 6,663,631 B2 | 12/2003 | Kuntz |
| 6,663,632 B1 | 12/2003 | Frigg |
| 6,663,635 B2 | 12/2003 | Frigg et al. |
| 6,663,642 B2 | 12/2003 | Beyar et al. |
| 6,665,555 B2 | 12/2003 | Henderson et al. |
| 6,666,612 B2 | 12/2003 | Lorigny et al. |
| 6,666,866 B2 | 12/2003 | Martz et al. |
| 6,666,867 B2 | 12/2003 | Ralph et al. |
| 6,666,890 B2 | 12/2003 | Michelson |
| 6,666,891 B2 | 12/2003 | Boehm et al. |
| 6,668,688 B2 | 12/2003 | Zhao et al. |
| 6,669,700 B1 | 12/2003 | Farris et al. |
| 6,669,730 B2 | 12/2003 | Ralph et al. |
| 6,673,073 B1 | 1/2004 | Schaefer |
| 6,673,113 B2 | 1/2004 | Ralph et al. |
| 6,673,362 B2 | 1/2004 | Calhoun et al. |
| 6,675,805 B1 | 1/2004 | Graether |
| 6,676,661 B1 | 1/2004 | Martin et al. |
| 6,676,703 B2 | 1/2004 | Biscup |
| 6,679,833 B2 | 1/2004 | Smith et al. |
| 6,679,883 B2 | 1/2004 | Hawkes et al. |
| 6,679,887 B2 | 1/2004 | Nicholson et al. |
| 6,679,915 B1 | 1/2004 | Cauthen |
| 6,682,529 B1 | 1/2004 | Stahurski |
| 6,682,530 B2 | 1/2004 | Dixon et al. |
| 6,682,533 B1 | 1/2004 | Dinsdale et al. |
| 6,682,562 B2 | 1/2004 | Viart et al. |
| 6,683,690 B1 | 1/2004 | Tobias |
| 6,685,705 B1 | 2/2004 | Taylor |
| 6,689,133 B2 | 2/2004 | Morrison et al. |
| 6,689,134 B2 | 2/2004 | Ralph et al. |
| 6,692,495 B1 | 2/2004 | Zacouto |
| 6,695,842 B2 | 2/2004 | Zucherman et al. |
| 6,695,843 B2 | 2/2004 | Biedermann et al. |
| 6,695,846 B2 | 2/2004 | Richelsoph et al. |
| 6,695,851 B2 | 2/2004 | Zdeblick et al. |
| 6,699,246 B2 | 3/2004 | Zucherman et al. |
| 6,699,247 B2 | 3/2004 | Zucherman et al. |
| 6,699,249 B2 | 3/2004 | Schlaepfer et al. |
| 6,702,814 B2 | 3/2004 | Walulik et al. |
| 6,706,045 B2 | 3/2004 | Lin et al. |
| 6,706,067 B2 | 3/2004 | Shimp et al. |
| 6,706,068 B2 | 3/2004 | Ferree |
| 6,706,070 B1 | 3/2004 | Wagner et al. |
| 6,706,922 B2 | 3/2004 | Wolff et al. |
| 6,709,389 B2 | 3/2004 | Farascioni |
| 6,709,458 B2 | 3/2004 | Michelson |
| 6,709,461 B2 | 3/2004 | O'Neil et al. |
| 6,712,795 B1 | 3/2004 | Cohen |
| 6,712,818 B1 | 3/2004 | Michelson |
| 6,712,819 B2 | 3/2004 | Zucherman et al. |
| 6,712,852 B1 | 3/2004 | Chung et al. |
| 6,716,212 B1 | 4/2004 | Pickens |
| 6,716,213 B2 | 4/2004 | Shitoto |
| 6,716,214 B1 | 4/2004 | Jackson |
| 6,716,247 B2 | 4/2004 | Michelson |
| 6,719,794 B2 | 4/2004 | Gerber et al. |
| 6,719,795 B1 | 4/2004 | Cornwall et al. |
| 6,723,043 B2 | 4/2004 | Kleeman et al. |
| 6,723,096 B1 | 4/2004 | Dorchak et al. |
| 6,723,100 B2 | 4/2004 | Biedermann et al. |
| 6,723,126 B1 | 4/2004 | Berry |
| 6,723,127 B2 | 4/2004 | Ralph et al. |
| 6,723,128 B2 | 4/2004 | Uk |
| 6,726,685 B2 | 4/2004 | To et al. |
| 6,726,687 B2 | 4/2004 | Jackson |
| 6,726,720 B2 | 4/2004 | Ross et al. |
| 6,730,093 B2 | 5/2004 | Saint |
| 6,730,126 B2 | 5/2004 | Boehm, Jr. et al. |
| 6,730,127 B2 | 5/2004 | Michelson |
| 6,733,444 B2 | 5/2004 | Phillips |
| 6,733,496 B2 | 5/2004 | Sharkey et al. |
| 6,733,502 B2 | 5/2004 | Altarac et al. |
| 6,733,531 B1 | 5/2004 | Trieu |
| 6,733,534 B2 | 5/2004 | Sherman |
| 6,733,535 B2 | 5/2004 | Michelson |
| 6,736,816 B2 | 5/2004 | Ritland |
| 6,736,817 B2 | 5/2004 | Troxell et al. |
| 6,736,820 B2 | 5/2004 | Biedermann et al. |
| 6,739,068 B1 | 5/2004 | Rinner |
| 6,740,086 B2 | 5/2004 | Richelsoph |
| 6,740,087 B2 | 5/2004 | Knox |
| 6,740,090 B1 | 5/2004 | Cragg et al. |
| 6,740,118 B2 | 5/2004 | Eisermann et al. |
| 6,743,231 B1 | 6/2004 | Gray et al. |
| 6,743,255 B2 | 6/2004 | Ferree |
| 6,743,256 B2 | 6/2004 | Mason |
| 6,743,257 B2 | 6/2004 | Castro |
| 6,746,449 B2 | 6/2004 | Jones et al. |
| 6,746,454 B2 | 6/2004 | Winterbottom et al. |
| 6,749,613 B1 | 6/2004 | Conchy et al. |
| 6,749,614 B2 | 6/2004 | Teitelbaum et al. |
| 6,749,635 B1 | 6/2004 | Bryan |
| 6,749,636 B2 | 6/2004 | Michelson |
| 6,752,832 B2 | 6/2004 | Neumann |
| 6,755,829 B1 | 6/2004 | Bono et al. |
| 6,755,830 B2 | 6/2004 | Minfelde et al. |
| 6,755,833 B1 | 6/2004 | Paul et al. |
| 6,755,835 B2 | 6/2004 | Schultheiss et al. |
| 6,755,836 B1 | 6/2004 | Lewis |
| 6,755,841 B2 | 6/2004 | Fraser et al. |
| 6,758,861 B2 | 7/2004 | Ralph et al. |
| 6,761,719 B2 | 7/2004 | Justis et al. |
| 6,761,720 B1 | 7/2004 | Senegas |
| 6,761,721 B2 | 7/2004 | Burgess et al. |
| 6,761,723 B2 | 7/2004 | Buttermann et al. |
| 6,761,738 B1 | 7/2004 | Boyd |
| 6,764,515 B2 | 7/2004 | Ralph et al. |
| 6,767,351 B2 | 7/2004 | Orbay et al. |
| 6,767,367 B1 | 7/2004 | Michelson |
| 6,770,074 B2 | 8/2004 | Michelson |
| 6,770,075 B2 | 8/2004 | Howland |
| 6,770,096 B2 | 8/2004 | Bolger et al. |
| 6,778,861 B1 | 8/2004 | Liebrecht et al. |
| 6,780,186 B2 | 8/2004 | Errico et al. |
| 6,780,192 B2 | 8/2004 | McKay et al. |
| 6,783,527 B2 | 8/2004 | Drewry et al. |
| 6,783,547 B2 | 8/2004 | Castro |
| 6,790,209 B2 | 9/2004 | Beale et al. |
| 6,790,210 B1 | 9/2004 | Cragg et al. |
| 6,793,658 B2 | 9/2004 | Lehuec et al. |
| 6,802,844 B2 | 10/2004 | Ferree |
| 6,805,697 B1 | 10/2004 | Helm et al. |
| 6,805,713 B1 | 10/2004 | Carter et al. |
| 6,805,714 B2 | 10/2004 | Sutcliffe |
| 6,808,493 B1 | 10/2004 | Bookwalter et al. |
| 6,808,537 B2 | 10/2004 | Michelson |
| 6,811,567 B2 | 11/2004 | Reiley |
| 6,814,737 B2 | 11/2004 | Cauthen |
| 6,821,277 B2 | 11/2004 | Teitelbaum |
| 6,824,565 B2 | 11/2004 | Muhanna et al. |
| 6,827,719 B2 | 12/2004 | Ralph et al. |
| 6,827,722 B1 | 12/2004 | Schoenefeld |
| 6,830,570 B1 | 12/2004 | Frey et al. |
| 6,830,571 B2 | 12/2004 | Lenke et al. |
| 6,830,589 B2 | 12/2004 | Erickson |
| 6,832,997 B2 | 12/2004 | Uchida et al. |
| 6,832,999 B2 | 12/2004 | Ueyama et al. |
| 6,835,196 B2 | 12/2004 | Biedermann et al. |
| 6,835,206 B2 | 12/2004 | Jackson |
| 6,837,884 B2 | 1/2005 | Woloszko |
| 6,837,889 B2 | 1/2005 | Shluzas |
| 6,840,940 B2 | 1/2005 | Ralph et al. |
| 6,843,791 B2 | 1/2005 | Serhan |
| 6,849,076 B2 | 2/2005 | Blunn et al. |
| 6,849,093 B2 | 2/2005 | Michelson |
| 6,852,127 B2 | 2/2005 | Varga et al. |
| 6,852,128 B2 | 2/2005 | Lange |
| 6,852,129 B2 | 2/2005 | Gerbec et al. |
| 6,855,147 B2 | 2/2005 | Harrington et al. |
| 6,857,343 B1 | 2/2005 | Easterbrooks et al. |

(56) References Cited

U.S. PATENT DOCUMENTS

| | | |
|---|---|---|
| 6,858,030 B2 | 2/2005 | Martin et al. |
| 6,858,031 B2 | 2/2005 | Morrison et al. |
| 6,860,850 B2 | 3/2005 | Phillips et al. |
| 6,863,673 B2 | 3/2005 | Gerbec et al. |
| 6,869,398 B2 | 3/2005 | Obenchain et al. |
| 6,869,432 B2 | 3/2005 | Schlapfer et al. |
| 6,869,433 B2 | 3/2005 | Glascott |
| 6,872,208 B1 | 3/2005 | McBride et al. |
| 6,875,211 B2 | 4/2005 | Nichols et al. |
| 6,881,228 B2 | 4/2005 | Zdeblick et al. |
| 6,884,241 B2 | 4/2005 | Bertranou et al. |
| 6,884,242 B2 | 4/2005 | Lehuec et al. |
| 6,884,243 B2 | 4/2005 | Sellers |
| 6,885,243 B2 | 4/2005 | Burstein et al. |
| D505,205 S | 5/2005 | Freid |
| 6,887,242 B2 | 5/2005 | Doubler et al. |
| 6,890,355 B2 | 5/2005 | Michelson |
| 6,893,444 B2 | 5/2005 | Orbay |
| 6,896,675 B2 | 5/2005 | Leung et al. |
| 6,896,676 B2 | 5/2005 | Zubok et al. |
| 6,896,677 B1 | 5/2005 | Lin |
| 6,896,680 B2 | 5/2005 | Michelson |
| 6,899,714 B2 | 5/2005 | Vaughan |
| 6,899,716 B2 | 5/2005 | Cragg |
| 6,902,566 B2 | 6/2005 | Zucherman et al. |
| 6,902,580 B2 | 6/2005 | Fallin et al. |
| 6,911,045 B2 | 6/2005 | Shimp |
| 6,916,320 B2 | 7/2005 | Michelson |
| 6,916,340 B2 | 7/2005 | Metzger et al. |
| 6,918,910 B2 | 7/2005 | Smith et al. |
| 6,918,911 B2 | 7/2005 | Biedermann et al. |
| 6,921,403 B2 | 7/2005 | Cragg et al. |
| 6,923,811 B1 | 8/2005 | Carl et al. |
| 6,923,830 B2 | 8/2005 | Michelson |
| 6,926,658 B2 | 8/2005 | Farnan |
| 6,926,737 B2 | 8/2005 | Jackson |
| 6,929,606 B2 | 8/2005 | Ritland |
| 6,929,640 B1 | 8/2005 | Underwood et al. |
| 6,932,817 B2 | 8/2005 | Baynham et al. |
| 6,932,820 B2 | 8/2005 | Osman |
| 6,936,071 B1 | 8/2005 | Marnay et al. |
| 6,945,933 B2 | 9/2005 | Branch et al. |
| 6,945,972 B2 | 9/2005 | Frigg et al. |
| 6,945,973 B2 | 9/2005 | Bray |
| 6,945,975 B2 | 9/2005 | Dalton |
| 6,947,967 B2 | 9/2005 | Ferris et al. |
| 6,949,100 B1 | 9/2005 | Venturini |
| 6,949,105 B2 | 9/2005 | Bryan et al. |
| 6,951,538 B2 | 10/2005 | Ritland |
| 6,951,561 B2 | 10/2005 | Warren et al. |
| 6,953,462 B2 | 10/2005 | Lieberman |
| 6,953,477 B2 | 10/2005 | Berry |
| 6,955,677 B2 | 10/2005 | Dahners |
| 6,958,065 B2 | 10/2005 | Ueyama et al. |
| 6,964,664 B2 | 11/2005 | Freid et al. |
| 6,964,665 B2 | 11/2005 | Thomas et al. |
| 6,964,666 B2 | 11/2005 | Jackson |
| 6,964,667 B2 | 11/2005 | Shaolian et al. |
| 6,964,687 B1 | 11/2005 | Bernard et al. |
| 6,966,910 B2 | 11/2005 | Ritland |
| 6,966,929 B2 | 11/2005 | Mitchell |
| 6,972,019 B2 | 12/2005 | Michelson |
| 6,972,035 B2 | 12/2005 | Michelson |
| 6,974,460 B2 | 12/2005 | Carbone et al. |
| 6,979,334 B2 | 12/2005 | Dalton |
| 6,980,862 B2 | 12/2005 | Fredricks et al. |
| 6,981,973 B2 | 1/2006 | McKinley |
| 6,981,975 B2 | 1/2006 | Michelson |
| 6,984,234 B2 | 1/2006 | Bray |
| 6,984,245 B2 | 1/2006 | McGahan et al. |
| 6,986,771 B2 | 1/2006 | Paul et al. |
| 6,986,772 B2 | 1/2006 | Michelson |
| 6,989,011 B2 | 1/2006 | Paul et al. |
| 6,989,044 B2 | 1/2006 | Zhang et al. |
| 6,991,632 B2 | 1/2006 | Ritland |
| 6,991,654 B2 | 1/2006 | Foley |
| 6,994,688 B2 | 2/2006 | Brauckman et al. |
| 6,997,929 B2 | 2/2006 | Manzi et al. |
| 6,997,941 B2 | 2/2006 | Sharkey et al. |
| 7,001,385 B2 | 2/2006 | Bonutti |
| 7,001,432 B2 | 2/2006 | Keller et al. |
| 7,004,947 B2 | 2/2006 | Shluzas et al. |
| RE39,035 E | 3/2006 | Finn et al. |
| 7,008,422 B2 | 3/2006 | Foley et al. |
| 7,008,424 B2 | 3/2006 | Teitelbaum |
| 7,008,426 B2 | 3/2006 | Paul |
| 7,008,453 B1 | 3/2006 | Michelson |
| 7,011,619 B1 | 3/2006 | Lewis et al. |
| 7,011,658 B2 | 3/2006 | Young |
| 7,011,660 B2 | 3/2006 | Sherman et al. |
| 7,014,608 B2 | 3/2006 | Larson et al. |
| 7,014,633 B2 | 3/2006 | Cragg |
| 7,018,378 B2 | 3/2006 | Biedermann et al. |
| 7,018,379 B2 | 3/2006 | Drewry et al. |
| 7,018,412 B2 | 3/2006 | Ferreira et al. |
| 7,018,415 B1 | 3/2006 | Mckay |
| 7,018,416 B2 | 3/2006 | Hanson et al. |
| 7,022,122 B2 | 4/2006 | Amrein et al. |
| 7,025,716 B1 | 4/2006 | Meloul et al. |
| 7,025,787 B2 | 4/2006 | Bryan et al. |
| 7,029,472 B1 | 4/2006 | Fortin |
| 7,029,475 B2 | 4/2006 | Panjabi |
| 7,033,362 B2 | 4/2006 | McGahan et al. |
| RE39,089 E | 5/2006 | Ralph et al. |
| 7,037,339 B2 | 5/2006 | Houfburg |
| 7,041,135 B2 | 5/2006 | Michelson |
| 7,041,136 B2 | 5/2006 | Goble et al. |
| 7,044,971 B2 | 5/2006 | Suddaby |
| 7,048,736 B2 | 5/2006 | Robinson et al. |
| 7,052,497 B2 | 5/2006 | Sherman et al. |
| 7,056,321 B2 | 6/2006 | Pagliuca et al. |
| 7,056,344 B2 | 6/2006 | Huppert et al. |
| 7,060,066 B2 | 6/2006 | Zhao et al. |
| 7,060,097 B2 | 6/2006 | Fraser et al. |
| 7,063,702 B2 | 6/2006 | Michelson |
| 7,066,062 B2 | 6/2006 | Flesher |
| 7,066,937 B2 | 6/2006 | Shluzas |
| 7,066,961 B2 | 6/2006 | Michelson |
| 7,070,598 B2 | 7/2006 | Lim et al. |
| 7,074,237 B2 | 7/2006 | Goble et al. |
| 7,081,116 B1 | 7/2006 | Carly |
| 7,083,621 B2 | 8/2006 | Shaolian et al. |
| 7,083,622 B2 | 8/2006 | Simonson |
| 7,083,625 B2 | 8/2006 | Berry |
| 7,083,649 B2 | 8/2006 | Zucherman et al. |
| 7,087,057 B2 | 8/2006 | Konieczynski et al. |
| 7,087,058 B2 | 8/2006 | Cragg |
| 7,087,083 B2 | 8/2006 | Pasquet et al. |
| 7,090,674 B2 | 8/2006 | Doubler et al. |
| 7,090,679 B2 | 8/2006 | Saint-Martin et al. |
| 7,090,680 B2 | 8/2006 | Bonati et al. |
| 7,094,242 B2 | 8/2006 | Ralph et al. |
| 7,094,258 B2 | 8/2006 | Lambrecht et al. |
| 7,097,648 B1 | 8/2006 | Globerman et al. |
| 7,101,375 B2 | 9/2006 | Zucherman et al. |
| 7,101,399 B2 | 9/2006 | Errico et al. |
| 7,105,024 B2 | 9/2006 | Richelsoph |
| 7,108,698 B2 | 9/2006 | Robbins et al. |
| 7,112,206 B2 | 9/2006 | Michelson |
| 7,118,576 B2 | 10/2006 | Gitis et al. |
| 7,118,579 B2 | 10/2006 | Michelson |
| 7,118,580 B1 | 10/2006 | Beyersdorff et al. |
| 7,118,598 B2 | 10/2006 | Michelson |
| 7,121,755 B2 | 10/2006 | Schlapfer et al. |
| 7,122,629 B2 | 10/2006 | Bejanin et al. |
| 7,125,410 B2 | 10/2006 | Freudiger |
| 7,125,425 B2 | 10/2006 | Simonton et al. |
| 7,125,426 B2 | 10/2006 | Moumene et al. |
| 7,128,743 B2 | 10/2006 | Metz-Stavenhagen |
| 7,128,760 B2 | 10/2006 | Michelson |
| 7,128,761 B2 | 10/2006 | Kuras et al. |
| 7,137,985 B2 | 11/2006 | Jahng |
| 7,137,986 B2 | 11/2006 | Troxell et al. |
| 7,141,051 B2 | 11/2006 | Janowski et al. |

(56) References Cited

U.S. PATENT DOCUMENTS

| | | | |
|---|---|---|---|
| 7,144,396 B2 | 12/2006 | Shluzas |
| 7,144,397 B2 | 12/2006 | Lambrecht et al. |
| 7,147,599 B2 | 12/2006 | Phillips et al. |
| 7,150,714 B2 | 12/2006 | Myles |
| 7,153,281 B2 | 12/2006 | Holmes |
| 7,153,325 B2 | 12/2006 | Kim et al. |
| 7,156,806 B2 | 1/2007 | Dobrovolny |
| 7,160,300 B2 | 1/2007 | Jackson |
| 7,163,538 B2 | 1/2007 | Altarac et al. |
| 7,163,539 B2 | 1/2007 | Abdelgany et al. |
| 7,163,558 B2 | 1/2007 | Senegas et al. |
| 7,163,561 B2 | 1/2007 | Michelson |
| 7,166,073 B2 | 1/2007 | Ritland |
| 7,166,107 B2 | 1/2007 | Anderson |
| 7,166,108 B2 | 1/2007 | Mazda et al. |
| 7,166,121 B2 | 1/2007 | Reiley et al. |
| 7,169,183 B2 | 1/2007 | Liu et al. |
| 7,179,261 B2 | 2/2007 | Sicvol et al. |
| 7,182,729 B2 | 2/2007 | Abdelgany et al. |
| 7,186,255 B2 | 3/2007 | Baynham et al. |
| 7,188,626 B2 | 3/2007 | Foley et al. |
| 7,198,644 B2 | 4/2007 | Schultz et al. |
| 7,201,751 B2 | 4/2007 | Zucherman et al. |
| 7,204,851 B2 | 4/2007 | Trieu et al. |
| 7,204,852 B2 | 4/2007 | Marnay et al. |
| 7,204,853 B2 | 4/2007 | Gordon et al. |
| 7,207,949 B2 | 4/2007 | Miles et al. |
| 7,207,991 B2 | 4/2007 | Michelson |
| 7,207,992 B2 | 4/2007 | Ritland |
| 7,211,085 B2 | 5/2007 | Michelson |
| 7,211,086 B2 | 5/2007 | Biedermann et al. |
| 7,211,087 B2 | 5/2007 | Young |
| 7,211,112 B2 | 5/2007 | Baynham et al. |
| 7,214,186 B2 | 5/2007 | Ritland |
| 7,214,227 B2 | 5/2007 | Colleran et al. |
| 7,217,291 B2 | 5/2007 | Zucherman et al. |
| 7,223,268 B2 | 5/2007 | Biedermann |
| 7,223,289 B2 | 5/2007 | Trieu et al. |
| 7,227,477 B2 | 6/2007 | Ye |
| 7,229,441 B2 | 6/2007 | Trieu et al. |
| 7,232,441 B2 | 6/2007 | Altarac et al. |
| 7,232,463 B2 | 6/2007 | Falahee |
| 7,232,464 B2 | 6/2007 | Mathieu et al. |
| 7,235,048 B2 | 6/2007 | Rein et al. |
| 7,235,105 B2 | 6/2007 | Jackson |
| 7,241,297 B2 | 7/2007 | Shaolian et al. |
| 7,250,052 B2 | 7/2007 | Landry et al. |
| 7,252,673 B2 | 8/2007 | Lim |
| 7,264,621 B2 | 9/2007 | Coates et al. |
| 7,270,665 B2 | 9/2007 | Morrison et al. |
| 7,273,496 B2 | 9/2007 | Mitchell |
| 7,276,081 B1 | 10/2007 | Coates et al. |
| 7,276,082 B2 | 10/2007 | Zdeblick et al. |
| 7,282,063 B2 | 10/2007 | Cohen et al. |
| 7,282,064 B2 | 10/2007 | Chin |
| 7,282,065 B2 | 10/2007 | Kirschman |
| 7,285,121 B2 | 10/2007 | Braun et al. |
| 7,291,149 B1 | 11/2007 | Michelson |
| 7,291,151 B2 | 11/2007 | Alvarez |
| 7,291,152 B2 | 11/2007 | Abdou |
| 7,291,153 B2 | 11/2007 | Glascott |
| 7,294,128 B2 | 11/2007 | Alleyne et al. |
| 7,294,129 B2 | 11/2007 | Hawkins et al. |
| 7,300,441 B2 | 11/2007 | Haid et al. |
| 7,303,563 B2 | 12/2007 | Poyner et al. |
| 7,306,603 B2 | 12/2007 | Boehm, Jr. et al. |
| 7,306,604 B2 | 12/2007 | Carli |
| 7,306,606 B2 | 12/2007 | Sasing |
| 7,306,628 B2 | 12/2007 | Zucherman et al. |
| 7,309,338 B2 | 12/2007 | Cragg |
| 7,311,734 B2 | 12/2007 | Van Hoeck et al. |
| 7,314,467 B2 | 1/2008 | Howland |
| 7,316,684 B1 | 1/2008 | Baccelli et al. |
| 7,316,714 B2 | 1/2008 | Gordon et al. |
| 7,318,817 B2 | 1/2008 | Hamada |
| 7,318,840 B2 | 1/2008 | McKay |
| 7,322,979 B2 | 1/2008 | Crandall et al. |
| 7,326,216 B2 | 2/2008 | Bertagnoli et al. |
| 7,329,258 B2 | 2/2008 | Studer |
| 7,331,961 B2 | 2/2008 | Abdou |
| 7,331,995 B2 | 2/2008 | Eisermann et al. |
| 7,335,201 B2 | 2/2008 | Doubler et al. |
| 7,335,202 B2 | 2/2008 | Matthis et al. |
| 7,335,203 B2 | 2/2008 | Winslow et al. |
| 7,338,490 B2 | 3/2008 | Ogilvie et al. |
| 7,338,491 B2 | 3/2008 | Baker et al. |
| 7,338,527 B2 | 3/2008 | Blatt et al. |
| 7,341,587 B2 | 3/2008 | Molz, IV et al. |
| 7,347,874 B2 | 3/2008 | Disilvestro |
| 7,361,179 B2 | 4/2008 | Rousseau et al. |
| 7,361,196 B2 | 4/2008 | Fallin et al. |
| 7,374,534 B2 | 5/2008 | Dalton |
| 7,377,921 B2 | 5/2008 | Studer et al. |
| 7,377,942 B2 | 5/2008 | Berry |
| 7,396,328 B2 | 7/2008 | Penenberg |
| 7,396,360 B2 | 7/2008 | Lieberman |
| 7,410,501 B2 | 8/2008 | Michelson |
| 7,419,505 B2 | 9/2008 | Fleischmann et al. |
| 7,431,735 B2 | 10/2008 | Liu et al. |
| 7,435,262 B2 | 10/2008 | Michelson |
| 7,442,209 B2 | 10/2008 | Michelson |
| 7,445,635 B2 | 11/2008 | Fallin et al. |
| 7,445,637 B2 | 11/2008 | Taylor |
| 7,455,639 B2 | 11/2008 | Ritland |
| 7,455,685 B2 | 11/2008 | Justis |
| 7,465,306 B2 | 12/2008 | Pond, Jr. et al. |
| 7,473,223 B2 | 1/2009 | Fetzer |
| 7,473,276 B2 | 1/2009 | Aebi et al. |
| 7,476,228 B2 | 1/2009 | Abdou |
| 7,476,238 B2 | 1/2009 | Panjabi |
| 7,479,160 B2 | 1/2009 | Branch et al. |
| 7,485,132 B1 | 2/2009 | McBride et al. |
| 7,491,205 B1 | 2/2009 | Michelson |
| 7,491,208 B2 | 2/2009 | Pond, Jr. et al. |
| 7,494,508 B2 | 2/2009 | Zeegers |
| 7,497,859 B2 | 3/2009 | Zucherman et al. |
| 7,503,918 B2 | 3/2009 | Baccelli et al. |
| 7,503,933 B2 | 3/2009 | Michelson |
| 7,520,888 B2 | 4/2009 | Trieu |
| 7,527,640 B2 | 5/2009 | Ziolo et al. |
| 7,534,265 B1 | 5/2009 | Boyd et al. |
| 7,537,565 B2 | 5/2009 | Bass |
| 7,537,616 B1 | 5/2009 | Branch et al. |
| 7,540,882 B2 | 6/2009 | Michelson |
| 7,547,308 B2 | 6/2009 | Bertagnoli et al. |
| 7,547,325 B2 | 6/2009 | Biedermann et al. |
| 7,556,639 B2 | 7/2009 | Rothman et al. |
| 7,559,930 B2 | 7/2009 | Allard et al. |
| 7,559,942 B2 | 7/2009 | Paul et al. |
| 7,563,274 B2 | 7/2009 | Justis et al. |
| 7,563,283 B2 | 7/2009 | Kwak |
| 7,566,345 B1 | 7/2009 | Fallin et al. |
| 7,569,014 B2 | 8/2009 | Bass et al. |
| 7,572,276 B2 | 8/2009 | Lim et al. |
| 7,575,580 B2 | 8/2009 | Lim et al. |
| 7,575,587 B2 | 8/2009 | Rezach et al. |
| 7,578,820 B2 | 8/2009 | Moore et al. |
| 7,578,849 B2 | 8/2009 | Trieu |
| 7,582,058 B1 | 9/2009 | Miles et al. |
| 7,582,107 B2 | 9/2009 | Trail et al. |
| 7,585,316 B2 | 9/2009 | Trieu |
| 7,588,537 B2 | 9/2009 | Bass |
| 7,588,579 B2 | 9/2009 | Mommaerts |
| 7,588,589 B2 | 9/2009 | Falahee |
| 7,588,593 B2 | 9/2009 | Aferzon |
| 7,591,839 B2 | 9/2009 | Biedermann et al. |
| 7,591,851 B2 | 9/2009 | Winslow et al. |
| 7,594,919 B2 | 9/2009 | Peterman |
| 7,594,931 B2 | 9/2009 | Louis et al. |
| 7,594,932 B2 | 9/2009 | Aferzon et al. |
| 7,597,694 B2 | 10/2009 | Lim et al. |
| 7,601,166 B2 | 10/2009 | Biedermann et al. |
| 7,601,170 B2 | 10/2009 | Winslow et al. |
| 7,604,643 B2 | 10/2009 | Ciccone et al. |

(56) References Cited

U.S. PATENT DOCUMENTS

| | | | |
|---|---|---|---|
| 7,604,654 | B2 | 10/2009 | Fallin et al. |
| 7,611,518 | B2 | 11/2009 | Walder et al. |
| 7,618,423 | B1 | 11/2009 | Valentine et al. |
| 7,618,443 | B2 | 11/2009 | Abdou |
| 7,618,455 | B2 | 11/2009 | Goble et al. |
| 7,618,456 | B2 | 11/2009 | Mathieu et al. |
| 7,621,912 | B2 | 11/2009 | Harms et al. |
| 7,621,939 | B2 | 11/2009 | Zucherman et al. |
| 7,621,940 | B2 | 11/2009 | Harms et al. |
| 7,621,942 | B2 | 11/2009 | Piehl |
| 7,621,953 | B2 | 11/2009 | Braddock, Jr. et al. |
| 7,621,955 | B2 | 11/2009 | Goble et al. |
| 7,621,957 | B2 | 11/2009 | Errico et al. |
| 7,625,379 | B2 | 12/2009 | Puno et al. |
| 7,625,380 | B2 * | 12/2009 | Drewry .............. A61F 2/447 606/99 |
| 7,625,393 | B2 | 12/2009 | Fallin et al. |
| 7,625,396 | B2 | 12/2009 | Jackson |
| 7,628,799 | B2 | 12/2009 | Richelsoph et al. |
| 7,632,292 | B2 | 12/2009 | Sengupta et al. |
| 7,635,366 | B2 | 12/2009 | Abdou |
| 7,635,371 | B2 | 12/2009 | McGahan et al. |
| 7,641,673 | B2 | 1/2010 | Le et al. |
| 7,641,690 | B2 | 1/2010 | Abdou |
| 7,641,693 | B2 | 1/2010 | Gutlin et al. |
| 7,645,281 | B2 | 1/2010 | Marik |
| 7,651,515 | B2 | 1/2010 | Mack et al. |
| 7,654,954 | B1 | 2/2010 | Phillips et al. |
| 7,655,026 | B2 | 2/2010 | Justis et al. |
| 7,655,027 | B2 | 2/2010 | Michelson |
| 7,655,028 | B2 | 2/2010 | Kirschman |
| 7,655,042 | B2 | 2/2010 | Foley et al. |
| 7,658,739 | B2 | 2/2010 | Shluzas |
| 7,658,752 | B2 | 2/2010 | Labrom et al. |
| 7,658,766 | B2 | 2/2010 | Melkent et al. |
| 7,682,375 | B2 | 3/2010 | Ritland |
| 7,682,396 | B2 | 3/2010 | Beaurain et al. |
| 7,686,809 | B2 | 3/2010 | Triplett et al. |
| 7,691,057 | B2 | 4/2010 | Miles et al. |
| 7,691,129 | B2 | 4/2010 | Felix |
| 7,695,496 | B2 | 4/2010 | Labrom et al. |
| 7,695,498 | B2 | 4/2010 | Ritland |
| 7,695,514 | B2 | 4/2010 | Kwak |
| 7,695,516 | B2 | 4/2010 | Zeegers |
| 7,695,517 | B2 | 4/2010 | Benzel et al. |
| 7,704,271 | B2 | 4/2010 | Abdou |
| 7,708,743 | B2 | 5/2010 | Anderson et al. |
| 7,708,765 | B2 | 5/2010 | Carl et al. |
| 7,722,618 | B2 | 5/2010 | Estes et al. |
| 7,727,233 | B2 | 6/2010 | Blackwell et al. |
| 7,727,280 | B2 | 6/2010 | McLuen |
| 7,738,968 | B2 | 6/2010 | Bleich |
| 7,744,635 | B2 | 6/2010 | Sweeney et al. |
| 7,749,231 | B2 | 7/2010 | Bonvallet et al. |
| 7,749,251 | B2 | 7/2010 | Obenchain et al. |
| 7,749,252 | B2 | 7/2010 | Zucherman et al. |
| 7,749,269 | B2 | 7/2010 | Peterman et al. |
| 7,749,270 | B2 | 7/2010 | Peterman |
| 7,749,274 | B2 | 7/2010 | Razian |
| 7,753,844 | B2 | 7/2010 | Sharratt et al. |
| 7,753,937 | B2 | 7/2010 | Chervitz et al. |
| 7,753,938 | B2 | 7/2010 | Aschmann et al. |
| 7,753,958 | B2 | 7/2010 | Gordon et al. |
| 7,758,274 | B2 | 7/2010 | Paul |
| 7,758,501 | B2 | 7/2010 | Frasier et al. |
| 7,758,644 | B2 | 7/2010 | Trieu et al. |
| 7,758,645 | B2 | 7/2010 | Studer et al. |
| 7,758,648 | B2 | 7/2010 | Castleman et al. |
| 7,763,074 | B2 | 7/2010 | Altarac et al. |
| 7,763,078 | B2 | 7/2010 | Peterman et al. |
| 7,766,918 | B2 | 8/2010 | Allard et al. |
| 7,771,432 | B2 | 8/2010 | Schwab et al. |
| 7,771,473 | B2 | 8/2010 | Thramann |
| 7,771,475 | B2 | 8/2010 | Michelson |
| 7,776,049 | B1 | 8/2010 | Curran et al. |
| 7,776,067 | B2 | 8/2010 | Jackson |
| 7,776,090 | B2 | 8/2010 | Winslow et al. |
| 7,780,670 | B2 | 8/2010 | Bonutti |
| 7,780,732 | B2 | 8/2010 | Abernathie et al. |
| 7,789,914 | B2 | 9/2010 | Michelson |
| 7,794,501 | B2 | 9/2010 | Edie et al. |
| 7,799,053 | B2 | 9/2010 | Haid, Jr. et al. |
| 7,799,081 | B2 | 9/2010 | McKinley |
| 7,806,911 | B2 | 10/2010 | Peckham |
| 7,806,913 | B2 | 10/2010 | Fanger et al. |
| 7,811,326 | B2 | 10/2010 | Braddock, Jr. et al. |
| 7,815,683 | B2 | 10/2010 | Melkent et al. |
| 7,819,801 | B2 | 10/2010 | Miles et al. |
| 7,819,903 | B2 | 10/2010 | Fraser et al. |
| 7,824,445 | B2 | 11/2010 | Biro et al. |
| 7,828,807 | B2 | 11/2010 | Lehuec et al. |
| 7,828,847 | B2 | 11/2010 | Abdou |
| 7,837,688 | B2 | 11/2010 | Boyer, II et al. |
| 7,837,714 | B2 | 11/2010 | Drewry et al. |
| 7,837,732 | B2 | 11/2010 | Zucherman et al. |
| 7,837,734 | B2 | 11/2010 | Zucherman et al. |
| 7,842,074 | B2 | 11/2010 | Abdou |
| 7,846,186 | B2 | 12/2010 | Taylor |
| 7,846,207 | B2 | 12/2010 | Lechmann et al. |
| 7,850,608 | B2 | 12/2010 | Hamada |
| 7,850,731 | B2 | 12/2010 | Brittan et al. |
| 7,850,732 | B2 | 12/2010 | Heinz |
| 7,850,733 | B2 | 12/2010 | Baynham et al. |
| 7,854,752 | B2 | 12/2010 | Colleran et al. |
| 7,857,818 | B2 | 12/2010 | Trieu et al. |
| 7,857,833 | B2 | 12/2010 | Abdou |
| 7,871,426 | B2 | 1/2011 | Chin et al. |
| 7,875,034 | B2 | 1/2011 | Josse et al. |
| 7,875,076 | B2 | 1/2011 | Mathieu et al. |
| 7,875,078 | B2 | 1/2011 | Wysocki et al. |
| 7,879,074 | B2 | 2/2011 | Kwak et al. |
| 7,883,532 | B2 | 2/2011 | Biscup et al. |
| 7,883,542 | B2 | 2/2011 | Zipnick, I et al. |
| 7,887,591 | B2 | 2/2011 | Aebi et al. |
| 7,892,173 | B2 | 2/2011 | Miles et al. |
| 7,892,261 | B2 | 2/2011 | Bonutti |
| 7,892,286 | B2 | 2/2011 | Michelson |
| 7,901,409 | B2 | 3/2011 | Canaveral et al. |
| 7,901,458 | B2 | 3/2011 | Deridder et al. |
| 7,905,840 | B2 | 3/2011 | Pimenta et al. |
| 7,905,886 | B1 | 3/2011 | Curran et al. |
| 7,909,829 | B2 | 3/2011 | Patel et al. |
| 7,909,848 | B2 | 3/2011 | Patel et al. |
| 7,909,870 | B2 | 3/2011 | Kraus |
| 7,909,871 | B2 | 3/2011 | Abdou |
| 7,914,558 | B2 | 3/2011 | Landry et al. |
| 7,918,792 | B2 | 4/2011 | Drzyzga et al. |
| 7,922,658 | B2 | 4/2011 | Cohen et al. |
| 7,922,745 | B2 | 4/2011 | Hestad et al. |
| 7,922,750 | B2 | 4/2011 | Trautwein et al. |
| 7,927,337 | B2 | 4/2011 | Keller |
| 7,931,589 | B2 | 4/2011 | Cohen et al. |
| 7,931,674 | B2 | 4/2011 | Zucherman et al. |
| 7,935,134 | B2 | 5/2011 | Reglos et al. |
| 7,935,147 | B2 | 5/2011 | Wales |
| 7,935,149 | B2 | 5/2011 | Michelson |
| 7,938,848 | B2 | 5/2011 | Sweeney |
| 7,946,982 | B2 | 5/2011 | Hamada |
| 7,951,198 | B2 | 5/2011 | Sucec et al. |
| 7,955,390 | B2 | 6/2011 | Fallin et al. |
| 7,955,392 | B2 | 6/2011 | Dewey et al. |
| 7,959,564 | B2 | 6/2011 | Ritland |
| 7,959,677 | B2 | 6/2011 | Landry et al. |
| 7,972,363 | B2 | 7/2011 | Moskowitz et al. |
| 7,976,566 | B2 | 7/2011 | Michelson |
| 7,981,031 | B2 | 7/2011 | Frasier et al. |
| 7,985,258 | B2 | 7/2011 | Zdeblick et al. |
| 7,988,699 | B2 | 8/2011 | Martz et al. |
| 8,002,802 | B2 | 8/2011 | Abdou |
| 8,002,833 | B2 | 8/2011 | Fabris et al. |
| 8,002,842 | B2 | 8/2011 | Ronk |
| 8,012,207 | B2 | 9/2011 | Kim |
| 8,021,393 | B2 | 9/2011 | Seifert et al. |
| 8,021,401 | B2 | 9/2011 | Carl et al. |

(56) References Cited

U.S. PATENT DOCUMENTS

| | | |
|---|---|---|
| 8,021,429 B2 | 9/2011 | Viker |
| 8,025,680 B2 | 9/2011 | Hayes et al. |
| 8,025,697 B2 | 9/2011 | McClellan, III et al. |
| 8,034,109 B2 | 10/2011 | Zwirkoski |
| 8,034,110 B2 | 10/2011 | Garner et al. |
| 8,038,716 B2 | 10/2011 | Duggal et al. |
| 8,043,334 B2 | 10/2011 | Fisher et al. |
| 8,043,343 B2 | 10/2011 | Miller et al. |
| 8,043,376 B2 | 10/2011 | Falahee |
| 8,043,380 B1 | 10/2011 | Park et al. |
| 8,048,120 B1 | 11/2011 | Fallin et al. |
| 8,062,299 B2 | 11/2011 | McGahan et al. |
| 8,062,336 B2 | 11/2011 | Triplett et al. |
| 8,062,337 B2 | 11/2011 | Bruneau et al. |
| 8,066,710 B2 | 11/2011 | Estes et al. |
| 8,066,714 B2 | 11/2011 | Shipp et al. |
| 8,066,741 B2 | 11/2011 | Fallin et al. |
| 8,066,742 B2 | 11/2011 | Anderson et al. |
| 8,066,749 B2 | 11/2011 | Winslow et al. |
| 8,070,749 B2 | 12/2011 | Stern |
| 8,070,816 B2 | 12/2011 | Taylor |
| 8,075,593 B2 | 12/2011 | Hess |
| 8,075,618 B2 | 12/2011 | Trieu et al. |
| 8,075,621 B2 | 12/2011 | Michelson |
| 8,080,046 B2 | 12/2011 | Suddaby |
| 8,083,798 B2 | 12/2011 | Allard et al. |
| 8,097,018 B2 | 1/2012 | Malandain et al. |
| 8,100,828 B2 | 1/2012 | Frey et al. |
| 8,105,358 B2 | 1/2012 | Phan |
| 8,114,131 B2 | 2/2012 | Kohm et al. |
| 8,123,807 B2 | 2/2012 | Kim |
| 8,128,659 B2 | 3/2012 | Ginsberg et al. |
| 8,128,664 B2 | 3/2012 | Pasquet |
| 8,137,284 B2 | 3/2012 | Miles et al. |
| 8,142,479 B2 | 3/2012 | Hess |
| 8,157,840 B2 | 4/2012 | Zucherman et al. |
| 8,163,026 B2 | 4/2012 | Gray |
| 8,167,887 B2 | 5/2012 | McLean |
| 8,167,908 B2 | 5/2012 | Ely et al. |
| 8,167,915 B2 | 5/2012 | Ferree et al. |
| 8,167,946 B2 | 5/2012 | Michelson |
| 8,167,949 B2 | 5/2012 | Tyber et al. |
| 8,172,855 B2 | 5/2012 | Abdou |
| 8,182,423 B2 | 5/2012 | Miles et al. |
| 8,192,358 B2 | 6/2012 | Leahy |
| 8,197,514 B2 | 6/2012 | Maas et al. |
| 8,197,522 B2 | 6/2012 | Park et al. |
| 8,206,420 B2 | 6/2012 | Patel et al. |
| 8,216,312 B2 | 7/2012 | Gray |
| 8,226,690 B2 | 7/2012 | Altarac et al. |
| 8,231,623 B1 | 7/2012 | Jordan |
| 8,241,330 B2 | 8/2012 | Lamborne et al. |
| 8,241,359 B2 | 8/2012 | Davis et al. |
| 8,241,362 B2 | 8/2012 | Voorhies |
| 8,251,997 B2 | 8/2012 | Michelson |
| 8,268,004 B2 | 9/2012 | Castleman et al. |
| 8,277,489 B2 | 10/2012 | Saidha et al. |
| 8,287,569 B1 | 10/2012 | Powell |
| 8,303,629 B1 | 11/2012 | Abdou |
| 8,303,660 B1 | 11/2012 | Abdou |
| 8,308,804 B2 | 11/2012 | Krueger |
| 8,343,046 B2 | 1/2013 | Miles et al. |
| 8,343,190 B1 | 1/2013 | Mueller et al. |
| 8,349,012 B2 | 1/2013 | McKay |
| 8,353,826 B2 | 1/2013 | Weiman et al. |
| 8,361,108 B2 | 1/2013 | Gold et al. |
| 8,382,801 B2 | 2/2013 | Lamborne et al. |
| 8,388,660 B1 | 3/2013 | Abdou |
| 8,388,687 B2 | 3/2013 | Gimbel et al. |
| 8,397,522 B2 | 3/2013 | Springer et al. |
| 8,403,959 B2 | 3/2013 | Doellinger |
| 8,419,738 B2 | 4/2013 | Smisson, III et al. |
| 8,419,772 B2 | 4/2013 | Thompson et al. |
| 8,425,602 B2 | 4/2013 | Guyer et al. |
| 8,435,268 B2 | 5/2013 | Thompson et al. |
| 8,435,269 B2 | 5/2013 | Woolley et al. |
| 8,439,953 B2 | 5/2013 | Mitchell et al. |
| 8,454,621 B2 | 6/2013 | Deridder et al. |
| 8,454,661 B2 | 6/2013 | Rathbun et al. |
| 8,454,694 B2 | 6/2013 | Armstrong et al. |
| 8,465,547 B2 | 6/2013 | Melkent et al. |
| RE44,380 E | 7/2013 | de la Torre et al. |
| 8,475,497 B2 | 7/2013 | Grizzard |
| 8,480,712 B1 | 7/2013 | Samuel et al. |
| 8,480,747 B2 | 7/2013 | Melkent et al. |
| 8,486,147 B2 | 7/2013 | de Villiers et al. |
| 8,491,471 B2 | 7/2013 | Deshmukh et al. |
| 8,506,629 B2 | 8/2013 | Weiland |
| 8,512,343 B2 | 8/2013 | Dziedzic et al. |
| 8,529,611 B2 | 9/2013 | Champagne et al. |
| 8,562,650 B2 | 10/2013 | Dace |
| 8,574,267 B2 | 11/2013 | Linares |
| 8,603,143 B2 | 12/2013 | Robinson |
| 8,623,088 B1 | 1/2014 | Tohmeh et al. |
| 8,636,655 B1 | 1/2014 | Childs |
| 8,636,772 B2 | 1/2014 | Schmierer et al. |
| 8,657,855 B2 | 2/2014 | Zhang |
| 8,663,331 B2 | 3/2014 | McClellan, III et al. |
| 8,685,065 B1 | 4/2014 | Taber et al. |
| 8,685,093 B2 | 4/2014 | Anderson et al. |
| 8,690,917 B2 | 4/2014 | Suh et al. |
| 8,690,950 B2 | 4/2014 | Refai et al. |
| 8,696,709 B2 | 4/2014 | Dinville et al. |
| 8,702,756 B2 | 4/2014 | Reimels |
| 8,721,686 B2 | 5/2014 | Gordon et al. |
| 8,721,689 B2 | 5/2014 | Butler et al. |
| 8,771,318 B2 | 7/2014 | Triplett et al. |
| 8,771,360 B2 | 7/2014 | Jimenez et al. |
| 8,795,335 B1 | 8/2014 | Abdou et al. |
| 8,795,375 B2 | 8/2014 | Malberg, I |
| 8,827,900 B1 | 9/2014 | Pimenta |
| 8,828,055 B2 | 9/2014 | Blain et al. |
| 8,828,056 B2 | 9/2014 | Buss et al. |
| 8,828,061 B2 | 9/2014 | Scrantz et al. |
| 8,845,728 B1 | 9/2014 | Abdou |
| 8,876,904 B2 | 11/2014 | Pimenta et al. |
| 8,900,137 B1 | 12/2014 | Lovell et al. |
| 8,906,092 B2 | 12/2014 | Abdou |
| 8,911,441 B2 | 12/2014 | Dace et al. |
| 8,940,019 B2 | 1/2015 | Gordon et al. |
| 8,940,051 B2 | 1/2015 | Gimbel et al. |
| 8,940,052 B2 | 1/2015 | Lechmann et al. |
| 8,956,415 B2 | 2/2015 | Cowan |
| 8,974,381 B1 | 3/2015 | Lovell et al. |
| 8,998,905 B2 | 4/2015 | Marik et al. |
| 9,005,248 B2 | 4/2015 | Taber et al. |
| 9,011,538 B2 | 4/2015 | Allard et al. |
| 9,044,280 B1 | 6/2015 | Arambula et al. |
| 9,113,853 B1 | 8/2015 | Casey et al. |
| 9,135,059 B2 | 9/2015 | Ballard et al. |
| 9,179,903 B2 | 11/2015 | Cianfrani et al. |
| 9,198,767 B2 | 12/2015 | Abdou |
| 9,211,147 B2 | 12/2015 | Gordon et al. |
| 9,247,968 B2 | 2/2016 | Taber et al. |
| 9,265,526 B1 | 2/2016 | Abdou |
| 9,308,099 B2 | 4/2016 | Triplett et al. |
| 9,320,506 B2 | 4/2016 | Bertagnoli et al. |
| 9,345,464 B2 | 5/2016 | Abdou et al. |
| 9,364,338 B2 | 6/2016 | Malberg, I |
| 9,408,596 B2 | 8/2016 | Blain |
| 9,408,717 B2 | 8/2016 | Perrow et al. |
| 9,445,918 B1 | 9/2016 | Lin et al. |
| 9,451,940 B2 | 9/2016 | Spann |
| 9,486,328 B2 | 11/2016 | Jimenez et al. |
| 9,622,795 B2 | 4/2017 | Reitblat et al. |
| 9,655,505 B1 | 5/2017 | Gharib et al. |
| 9,687,356 B1 | 6/2017 | Spangler et al. |
| 9,687,357 B2 | 6/2017 | Bannigan et al. |
| 9,730,737 B2 | 8/2017 | Baynham et al. |
| 9,730,802 B1 | 8/2017 | Harvey |
| 9,795,367 B1 | 10/2017 | Lee et al. |
| 9,795,370 B2 | 10/2017 | O'Connell et al. |
| RE46,647 E | 12/2017 | Messerli et al. |
| 9,867,714 B1 | 1/2018 | Abdou |

(56) References Cited

U.S. PATENT DOCUMENTS

| | | |
|---|---|---|
| 9,901,458 B1 | 2/2018 | Abdou |
| 10,166,018 B2 | 1/2019 | Hunt et al. |
| 10,426,450 B2 | 10/2019 | Vogel et al. |
| 10,548,740 B1 | 2/2020 | Abdou |
| 2001/0001129 A1 | 5/2001 | McKay et al. |
| 2001/0012938 A1 | 8/2001 | Zucherman et al. |
| 2001/0021850 A1 | 9/2001 | Zucherman et al. |
| 2001/0031965 A1 | 10/2001 | Zucherman et al. |
| 2001/0039452 A1 | 11/2001 | Zucherman et al. |
| 2001/0047172 A1 | 11/2001 | Foley et al. |
| 2001/0053914 A1 | 12/2001 | Landry et al. |
| 2001/0056219 A1 | 12/2001 | Brauckman et al. |
| 2002/0016595 A1 | 2/2002 | Michelson |
| 2002/0019626 A1 | 2/2002 | Sharkey et al. |
| 2002/0019637 A1 | 2/2002 | Frey et al. |
| 2002/0026101 A1 | 2/2002 | Bookwalter et al. |
| 2002/0032484 A1 | 3/2002 | Hyde |
| 2002/0045899 A1 | 4/2002 | Errico et al. |
| 2002/0045904 A1 | 4/2002 | Fuss et al. |
| 2002/0045945 A1 | 4/2002 | Liu et al. |
| 2002/0049394 A1 | 4/2002 | Roy et al. |
| 2002/0049444 A1 | 4/2002 | Knox |
| 2002/0049446 A1 | 4/2002 | Harkey |
| 2002/0055738 A1 | 5/2002 | Lieberman |
| 2002/0055741 A1 | 5/2002 | Schlapfer et al. |
| 2002/0058944 A1 | 5/2002 | Michelson |
| 2002/0065558 A1 | 5/2002 | Varga et al. |
| 2002/0077530 A1 | 6/2002 | Velikaris et al. |
| 2002/0082602 A1 | 6/2002 | Biedermann et al. |
| 2002/0082700 A1 | 6/2002 | Bianchi et al. |
| 2002/0099386 A1 | 7/2002 | Beger et al. |
| 2002/0111628 A1 | 8/2002 | Ralph et al. |
| 2002/0120268 A1 | 8/2002 | Berger |
| 2002/0128713 A1 | 9/2002 | Ferree |
| 2002/0138146 A1 | 9/2002 | Jackson |
| 2002/0143328 A1 | 10/2002 | Shluzas et al. |
| 2002/0143332 A1 | 10/2002 | Lin et al. |
| 2002/0143341 A1 | 10/2002 | Biedermann et al. |
| 2002/0147449 A1 | 10/2002 | Yun |
| 2002/0161368 A1 | 10/2002 | Foley et al. |
| 2002/0165550 A1 | 11/2002 | Frey et al. |
| 2002/0165612 A1 | 11/2002 | Gerber et al. |
| 2002/0169450 A1 | 11/2002 | Lange |
| 2002/0169453 A1 | 11/2002 | Berger |
| 2002/0183748 A1 | 12/2002 | Martin et al. |
| 2002/0183755 A1 | 12/2002 | Michelson |
| 2002/0183761 A1 | 12/2002 | Johnson et al. |
| 2002/0183848 A1 | 12/2002 | Ray et al. |
| 2002/0188296 A1 | 12/2002 | Michelson |
| 2003/0000350 A1 | 1/2003 | Zhao et al. |
| 2003/0004572 A1 | 1/2003 | Goble et al. |
| 2003/0014068 A1 | 1/2003 | Bonutti et al. |
| 2003/0014123 A1 | 1/2003 | Copf et al. |
| 2003/0018389 A1 | 1/2003 | Castro et al. |
| 2003/0023240 A1 | 1/2003 | Amrein et al. |
| 2003/0023243 A1 | 1/2003 | Biedermann et al. |
| 2003/0023305 A1 | 1/2003 | McKay |
| 2003/0023306 A1 | 1/2003 | Liu et al. |
| 2003/0023308 A1 | 1/2003 | Leroux et al. |
| 2003/0028251 A1 | 2/2003 | Mathews |
| 2003/0040746 A1 | 2/2003 | Mitchell et al. |
| 2003/0040798 A1 | 2/2003 | Michelson |
| 2003/0045878 A1 | 3/2003 | Petit et al. |
| 2003/0045935 A1 | 3/2003 | Angelucci et al. |
| 2003/0055430 A1 | 3/2003 | Kim |
| 2003/0060826 A1 | 3/2003 | Foley et al. |
| 2003/0065330 A1 | 4/2003 | Zucherman et al. |
| 2003/0065395 A1 | 4/2003 | Ralph et al. |
| 2003/0065396 A1 | 4/2003 | Michelson |
| 2003/0073997 A1 | 4/2003 | Doubler et al. |
| 2003/0074001 A1 | 4/2003 | Apfelbaum, I |
| 2003/0074005 A1 | 4/2003 | Roth et al. |
| 2003/0078583 A1 | 4/2003 | Biedermann et al. |
| 2003/0078662 A1 | 4/2003 | Ralph et al. |
| 2003/0078664 A1 | 4/2003 | Ralph et al. |
| 2003/0083747 A1 | 5/2003 | Winterbottom et al. |
| 2003/0088251 A1 | 5/2003 | Braun et al. |
| 2003/0093153 A1 | 5/2003 | Banick et al. |
| 2003/0094812 A1 | 5/2003 | Balsells |
| 2003/0100896 A1 | 5/2003 | Biedermann et al. |
| 2003/0105460 A1 | 6/2003 | Crandall et al. |
| 2003/0109880 A1 | 6/2003 | Shirado et al. |
| 2003/0114852 A1 | 6/2003 | Biedermann et al. |
| 2003/0125741 A1 | 7/2003 | Biedermann et al. |
| 2003/0125742 A1 | 7/2003 | Yuan et al. |
| 2003/0139813 A1 | 7/2003 | Messerli et al. |
| 2003/0149341 A1 | 8/2003 | Clifton |
| 2003/0149431 A1 | 8/2003 | Varieur |
| 2003/0149432 A1 | 8/2003 | Frigg et al. |
| 2003/0149484 A1 | 8/2003 | Michelson |
| 2003/0153911 A1 | 8/2003 | Shluzas |
| 2003/0153913 A1 | 8/2003 | Altarac et al. |
| 2003/0163133 A1 | 8/2003 | Altarac et al. |
| 2003/0163199 A1 | 8/2003 | Boehm et al. |
| 2003/0167058 A1 | 9/2003 | Shluzas |
| 2003/0171749 A1 | 9/2003 | Le et al. |
| 2003/0171751 A1 | 9/2003 | Ritland |
| 2003/0176862 A1 | 9/2003 | Taylor et al. |
| 2003/0176864 A1 | 9/2003 | Ueyama et al. |
| 2003/0176923 A1 | 9/2003 | Keller et al. |
| 2003/0181975 A1 | 9/2003 | Ishii et al. |
| 2003/0187436 A1 | 10/2003 | Bolger et al. |
| 2003/0187510 A1 | 10/2003 | Hyde |
| 2003/0191470 A1 | 10/2003 | Ritland |
| 2003/0195518 A1 | 10/2003 | Cragg |
| 2003/0195633 A1 | 10/2003 | Hyde |
| 2003/0199873 A1 | 10/2003 | Richelsoph |
| 2003/0199981 A1 | 10/2003 | Ferree |
| 2003/0208202 A1 | 11/2003 | Falahee |
| 2003/0208203 A1 | 11/2003 | Lim et al. |
| 2003/0208204 A1 | 11/2003 | Bailey et al. |
| 2003/0208273 A1 | 11/2003 | Eisermann et al. |
| 2003/0212398 A1 | 11/2003 | Jackson |
| 2003/0216735 A1 | 11/2003 | Altarac et al. |
| 2003/0216736 A1 | 11/2003 | Robinson et al. |
| 2003/0216737 A1 | 11/2003 | Biscup |
| 2003/0217809 A1 | 11/2003 | Morishige |
| 2003/0220642 A1 | 11/2003 | Freudiger |
| 2003/0220643 A1 | 11/2003 | Ferree |
| 2003/0225408 A1 | 12/2003 | Nichols et al. |
| 2003/0229347 A1 | 12/2003 | Sherman et al. |
| 2003/0233136 A1 | 12/2003 | Williams, I et al. |
| 2003/0236472 A1 | 12/2003 | Van et al. |
| 2003/0236572 A1 | 12/2003 | Bertram |
| 2004/0002708 A1 | 1/2004 | Ritland |
| 2004/0006342 A1 | 1/2004 | Altarac et al. |
| 2004/0006391 A1 | 1/2004 | Reiley |
| 2004/0010253 A1 | 1/2004 | Morrison |
| 2004/0012938 A1 | 1/2004 | Sylvester et al. |
| 2004/0018228 A1 | 1/2004 | Fischell et al. |
| 2004/0019263 A1 | 1/2004 | Jutras et al. |
| 2004/0030338 A1 | 2/2004 | Paul |
| 2004/0030346 A1 | 2/2004 | Frey et al. |
| 2004/0039387 A1 | 2/2004 | Gause et al. |
| 2004/0044412 A1 | 3/2004 | Lambrecht et al. |
| 2004/0049189 A1 | 3/2004 | Le Couedic et al. |
| 2004/0049190 A1 | 3/2004 | Biedermann et al. |
| 2004/0049271 A1 | 3/2004 | Biedermann et al. |
| 2004/0049280 A1 | 3/2004 | Cauthen |
| 2004/0054412 A1 | 3/2004 | Gerbec et al. |
| 2004/0059318 A1 | 3/2004 | Zhang et al. |
| 2004/0068261 A1 | 4/2004 | Fourcault et al. |
| 2004/0068318 A1 | 4/2004 | Coates et al. |
| 2004/0073215 A1 | 4/2004 | Carli |
| 2004/0073216 A1 | 4/2004 | Lieberman |
| 2004/0078079 A1 | 4/2004 | Foley |
| 2004/0078082 A1 | 4/2004 | Lange |
| 2004/0087947 A1 | 5/2004 | Lim et al. |
| 2004/0087948 A1 | 5/2004 | Suddaby |
| 2004/0087949 A1 | 5/2004 | Bono et al. |
| 2004/0087952 A1 | 5/2004 | Borgstrom et al. |
| 2004/0092930 A1 | 5/2004 | Petit et al. |
| 2004/0092933 A1 | 5/2004 | Shaolian et al. |
| 2004/0092934 A1 | 5/2004 | Howland |

(56) References Cited

U.S. PATENT DOCUMENTS

| | | |
|---|---|---|
| 2004/0093083 A1 | 5/2004 | Branch et al. |
| 2004/0097933 A1 | 5/2004 | Lourdel et al. |
| 2004/0097935 A1 | 5/2004 | Richelsoph et al. |
| 2004/0097940 A1 | 5/2004 | Paul |
| 2004/0098129 A1 | 5/2004 | Lin |
| 2004/0102780 A1 | 5/2004 | West |
| 2004/0106927 A1 | 6/2004 | Ruffner et al. |
| 2004/0106995 A1 | 6/2004 | Le Couedic et al. |
| 2004/0106996 A1 | 6/2004 | Liu et al. |
| 2004/0111136 A1 | 6/2004 | Sharkey et al. |
| 2004/0111141 A1 | 6/2004 | Brabec et al. |
| 2004/0116929 A1 | 6/2004 | Barker et al. |
| 2004/0116965 A1 | 6/2004 | Falkenberg |
| 2004/0122518 A1 | 6/2004 | Rhoda |
| 2004/0127963 A1 | 7/2004 | Uchida et al. |
| 2004/0127990 A1 | 7/2004 | Bartish et al. |
| 2004/0127994 A1 | 7/2004 | Kast et al. |
| 2004/0133207 A1 | 7/2004 | Abdou |
| 2004/0138662 A1 | 7/2004 | Landry et al. |
| 2004/0138671 A1 | 7/2004 | Zander et al. |
| 2004/0143264 A1 | 7/2004 | McAfee |
| 2004/0143265 A1 | 7/2004 | Landry et al. |
| 2004/0143270 A1 | 7/2004 | Zucherman et al. |
| 2004/0143332 A1 | 7/2004 | Krueger et al. |
| 2004/0147928 A1 | 7/2004 | Landry et al. |
| 2004/0147929 A1 | 7/2004 | Biedermann et al. |
| 2004/0153065 A1 | 8/2004 | Lim |
| 2004/0153070 A1 | 8/2004 | Barker et al. |
| 2004/0158247 A1 | 8/2004 | Sitiso et al. |
| 2004/0158254 A1 | 8/2004 | Eisermann |
| 2004/0162558 A1 | 8/2004 | Hegde et al. |
| 2004/0162560 A1 | 8/2004 | Raynor et al. |
| 2004/0167520 A1 | 8/2004 | Zucherman et al. |
| 2004/0167625 A1 | 8/2004 | Beyar et al. |
| 2004/0167626 A1 | 8/2004 | Geremakis et al. |
| 2004/0172022 A1 | 9/2004 | Landry et al. |
| 2004/0172025 A1 | 9/2004 | Drewry et al. |
| 2004/0172134 A1 | 9/2004 | Berry |
| 2004/0176766 A1 | 9/2004 | Shluzas |
| 2004/0181226 A1 | 9/2004 | Michelson |
| 2004/0181285 A1 | 9/2004 | Simonson |
| 2004/0186473 A1 | 9/2004 | Cournoyer et al. |
| 2004/0186572 A1 | 9/2004 | Lange et al. |
| 2004/0193151 A1 | 9/2004 | To et al. |
| 2004/0193159 A1 | 9/2004 | Zucherman et al. |
| 2004/0195089 A1 | 10/2004 | O'Brien |
| 2004/0204712 A1 | 10/2004 | Kolb et al. |
| 2004/0204713 A1 | 10/2004 | Abdou |
| 2004/0210216 A1 | 10/2004 | Farris et al. |
| 2004/0215190 A1 | 10/2004 | Nguyen et al. |
| 2004/0220567 A1 | 11/2004 | Eisermann et al. |
| 2004/0220670 A1 | 11/2004 | Eisermann et al. |
| 2004/0220671 A1 | 11/2004 | Ralph et al. |
| 2004/0225289 A1 | 11/2004 | Biedermann et al. |
| 2004/0225291 A1 | 11/2004 | Schwammberger et al. |
| 2004/0225364 A1 | 11/2004 | Richelsoph et al. |
| 2004/0225365 A1 | 11/2004 | Eisermann et al. |
| 2004/0225366 A1 | 11/2004 | Eisermann et al. |
| 2004/0230309 A1 | 11/2004 | Dimauro et al. |
| 2004/0236327 A1 | 11/2004 | Paul et al. |
| 2004/0236328 A1 | 11/2004 | Paul et al. |
| 2004/0236329 A1 | 11/2004 | Panjabi |
| 2004/0236330 A1 | 11/2004 | Purcell et al. |
| 2004/0236333 A1 | 11/2004 | Lin |
| 2004/0236425 A1 | 11/2004 | Huang |
| 2004/0243240 A1 | 12/2004 | Beaurain et al. |
| 2004/0249377 A1 | 12/2004 | Kaes et al. |
| 2004/0249379 A1 | 12/2004 | Winslow et al. |
| 2004/0249380 A1 | 12/2004 | Glascott |
| 2004/0249461 A1 | 12/2004 | Ferree |
| 2004/0254574 A1 | 12/2004 | Morrison et al. |
| 2004/0254575 A1 | 12/2004 | Obenchain et al. |
| 2004/0260283 A1 | 12/2004 | Wu et al. |
| 2004/0260291 A1 | 12/2004 | Jensen |
| 2004/0267264 A1 | 12/2004 | Konieczynski et al. |
| 2004/0267369 A1 | 12/2004 | Lyons et al. |
| 2005/0004573 A1 | 1/2005 | Abdou |
| 2005/0010227 A1 | 1/2005 | Paul |
| 2005/0010291 A1 | 1/2005 | Stinson et al. |
| 2005/0010301 A1 | 1/2005 | Disilvestro et al. |
| 2005/0012506 A1 | 1/2005 | Yudahira |
| 2005/0015149 A1 | 1/2005 | Michelson |
| 2005/0021029 A1 | 1/2005 | Trieu et al. |
| 2005/0021031 A1 | 1/2005 | Foley et al. |
| 2005/0021040 A1 | 1/2005 | Bertagnoli |
| 2005/0021041 A1 | 1/2005 | Michelson |
| 2005/0027296 A1 | 2/2005 | Thramann et al. |
| 2005/0027360 A1 | 2/2005 | Webb et al. |
| 2005/0033296 A1 | 2/2005 | Bono et al. |
| 2005/0033298 A1 | 2/2005 | Hawkes et al. |
| 2005/0033431 A1 | 2/2005 | Gordon et al. |
| 2005/0033432 A1 | 2/2005 | Gordon et al. |
| 2005/0033434 A1 | 2/2005 | Berry |
| 2005/0038432 A1 | 2/2005 | Shaolian et al. |
| 2005/0038511 A1 | 2/2005 | Martz et al. |
| 2005/0043800 A1 | 2/2005 | Paul et al. |
| 2005/0043802 A1 | 2/2005 | Eisermann et al. |
| 2005/0049705 A1 | 3/2005 | Hale et al. |
| 2005/0049708 A1 | 3/2005 | Atkinson et al. |
| 2005/0055026 A1 | 3/2005 | Biedermann et al. |
| 2005/0055031 A1 | 3/2005 | Lim |
| 2005/0065514 A1 | 3/2005 | Studer |
| 2005/0065515 A1 | 3/2005 | Jahng |
| 2005/0065516 A1 | 3/2005 | Jahng |
| 2005/0065517 A1 | 3/2005 | Chin |
| 2005/0069701 A1 | 3/2005 | Watanabe et al. |
| 2005/0070899 A1 | 3/2005 | Doubler et al. |
| 2005/0070901 A1 | 3/2005 | David |
| 2005/0071007 A1 | 3/2005 | Malek |
| 2005/0075636 A1 | 4/2005 | Gotzen |
| 2005/0080320 A1 | 4/2005 | Lee et al. |
| 2005/0080415 A1 | 4/2005 | Keyer et al. |
| 2005/0085812 A1 | 4/2005 | Sherman et al. |
| 2005/0085813 A1 | 4/2005 | Spitler et al. |
| 2005/0085815 A1 | 4/2005 | Harms et al. |
| 2005/0085816 A1 | 4/2005 | Michelson |
| 2005/0085909 A1 | 4/2005 | Eisermann |
| 2005/0096652 A1 | 5/2005 | Burton |
| 2005/0096653 A1 | 5/2005 | Doubler et al. |
| 2005/0096654 A1 | 5/2005 | Lin |
| 2005/0096745 A1 | 5/2005 | Andre et al. |
| 2005/0107788 A1 | 5/2005 | Beaurain et al. |
| 2005/0113830 A1 | 5/2005 | Rezach et al. |
| 2005/0113833 A1 | 5/2005 | Davison |
| 2005/0113927 A1 | 5/2005 | Malek |
| 2005/0113928 A1 | 5/2005 | Cragg et al. |
| 2005/0119663 A1 | 6/2005 | Keyer et al. |
| 2005/0119747 A1 | 6/2005 | Fabris et al. |
| 2005/0119748 A1 | 6/2005 | Reiley et al. |
| 2005/0124991 A1 | 6/2005 | Jahng |
| 2005/0125061 A1 | 6/2005 | Zucherman et al. |
| 2005/0125066 A1 | 6/2005 | McAfee |
| 2005/0126576 A1 | 6/2005 | Ferree |
| 2005/0131404 A1 | 6/2005 | Mazda et al. |
| 2005/0131406 A1 | 6/2005 | Reiley et al. |
| 2005/0131407 A1 | 6/2005 | Sicvol et al. |
| 2005/0131409 A1 | 6/2005 | Chervitz et al. |
| 2005/0131413 A1 | 6/2005 | O'Driscoll et al. |
| 2005/0131420 A1 | 6/2005 | Techiera et al. |
| 2005/0131421 A1 | 6/2005 | Anderson et al. |
| 2005/0137597 A1 | 6/2005 | Butler et al. |
| 2005/0137604 A1 | 6/2005 | Assell et al. |
| 2005/0143737 A1 | 6/2005 | Pafford et al. |
| 2005/0143822 A1 | 6/2005 | Paul |
| 2005/0143823 A1 | 6/2005 | Boyd et al. |
| 2005/0149020 A1 | 7/2005 | Jahng |
| 2005/0149023 A1 | 7/2005 | Ritland |
| 2005/0149035 A1 | 7/2005 | Pimenta et al. |
| 2005/0149188 A1 | 7/2005 | Cook et al. |
| 2005/0149196 A1 | 7/2005 | Zucherman et al. |
| 2005/0154389 A1 | 7/2005 | Selover et al. |
| 2005/0154390 A1 | 7/2005 | Biedermann et al. |
| 2005/0154391 A1 | 7/2005 | Doherty et al. |
| 2005/0154461 A1 | 7/2005 | Humphreys et al. |

(56) References Cited

U.S. PATENT DOCUMENTS

| | | |
|---|---|---|
| 2005/0159750 A1 | 7/2005 | Doherty |
| 2005/0159756 A1 | 7/2005 | Ray |
| 2005/0159813 A1 | 7/2005 | Molz, IV |
| 2005/0159815 A1 | 7/2005 | Kamimura et al. |
| 2005/0165396 A1 | 7/2005 | Fortin et al. |
| 2005/0165398 A1 | 7/2005 | Reiley |
| 2005/0165400 A1 | 7/2005 | Fernandez |
| 2005/0165487 A1 | 7/2005 | Muhanna et al. |
| 2005/0171540 A1 | 8/2005 | Lim et al. |
| 2005/0171541 A1 | 8/2005 | Boehm et al. |
| 2005/0171543 A1 | 8/2005 | Timm et al. |
| 2005/0171608 A1 | 8/2005 | Peterman et al. |
| 2005/0171609 A1 | 8/2005 | Humphreys et al. |
| 2005/0171610 A1 | 8/2005 | Humphreys et al. |
| 2005/0177156 A1 | 8/2005 | Timm et al. |
| 2005/0177157 A1 | 8/2005 | Jahng |
| 2005/0177163 A1 | 8/2005 | Abdou et al. |
| 2005/0177164 A1 | 8/2005 | Walters et al. |
| 2005/0177166 A1 | 8/2005 | Timm et al. |
| 2005/0177167 A1 | 8/2005 | Muckter |
| 2005/0177209 A1 | 8/2005 | Leung et al. |
| 2005/0177210 A1 | 8/2005 | Leung et al. |
| 2005/0177211 A1 | 8/2005 | Leung et al. |
| 2005/0177240 A1 | 8/2005 | Blain |
| 2005/0182401 A1 | 8/2005 | Timm et al. |
| 2005/0182404 A1 | 8/2005 | Lauryssen et al. |
| 2005/0187548 A1 | 8/2005 | Butler et al. |
| 2005/0187555 A1 | 8/2005 | Biedermann et al. |
| 2005/0187628 A1 | 8/2005 | Michelson |
| 2005/0192571 A1 | 9/2005 | Abdelgany |
| 2005/0192577 A1 | 9/2005 | Mosca et al. |
| 2005/0192580 A1 | 9/2005 | Dalton |
| 2005/0192589 A1 | 9/2005 | Raymond et al. |
| 2005/0192671 A1 | 9/2005 | Bao et al. |
| 2005/0197660 A1 | 9/2005 | Haid, Jr. et al. |
| 2005/0197702 A1 | 9/2005 | Coppes et al. |
| 2005/0203511 A1 | 9/2005 | Wilson-MacDonald et al. |
| 2005/0203512 A1 | 9/2005 | Hawkins et al. |
| 2005/0203513 A1 | 9/2005 | Jahng et al. |
| 2005/0203514 A1 | 9/2005 | Jahng et al. |
| 2005/0203516 A1 | 9/2005 | Biedermann et al. |
| 2005/0203517 A1 | 9/2005 | Jahng et al. |
| 2005/0203518 A1 | 9/2005 | Biedermann et al. |
| 2005/0203519 A1 | 9/2005 | Harms et al. |
| 2005/0203533 A1 | 9/2005 | Ferguson et al. |
| 2005/0203604 A1 | 9/2005 | Brabec et al. |
| 2005/0203624 A1 | 9/2005 | Serhan et al. |
| 2005/0209694 A1 | 9/2005 | Loeb |
| 2005/0215999 A1 | 9/2005 | Birkmeyer et al. |
| 2005/0216001 A1 | 9/2005 | David |
| 2005/0216003 A1 | 9/2005 | Biedermann et al. |
| 2005/0216083 A1 | 9/2005 | Michelson |
| 2005/0222682 A1 | 10/2005 | Link et al. |
| 2005/0222683 A1 | 10/2005 | Berry |
| 2005/0228376 A1 | 10/2005 | Boomer et al. |
| 2005/0228377 A1 | 10/2005 | Chao et al. |
| 2005/0228395 A1 | 10/2005 | Auxepaules et al. |
| 2005/0228400 A1 | 10/2005 | Chao et al. |
| 2005/0228501 A1 | 10/2005 | Miller et al. |
| 2005/0234449 A1 | 10/2005 | Aferzon |
| 2005/0234450 A1 | 10/2005 | Barker |
| 2005/0234451 A1 | 10/2005 | Markworth |
| 2005/0234452 A1 | 10/2005 | Malandain |
| 2005/0234453 A1 | 10/2005 | Shaolian et al. |
| 2005/0234454 A1 | 10/2005 | Chin |
| 2005/0234456 A1 | 10/2005 | Malandain |
| 2005/0234555 A1 | 10/2005 | Sutton et al. |
| 2005/0240181 A1 | 10/2005 | Boomer et al. |
| 2005/0240183 A1 | 10/2005 | Vaughan |
| 2005/0240265 A1 | 10/2005 | Kuiper et al. |
| 2005/0240273 A1 | 10/2005 | Khandkar et al. |
| 2005/0245928 A1 | 11/2005 | Colleran et al. |
| 2005/0245930 A1 | 11/2005 | Timm et al. |
| 2005/0251137 A1 | 11/2005 | Ball |
| 2005/0251139 A1 | 11/2005 | Roh |
| 2005/0251140 A1 | 11/2005 | Shaolian et al. |
| 2005/0251141 A1 | 11/2005 | Frigg et al. |
| 2005/0251258 A1 | 11/2005 | Jackson |
| 2005/0256576 A1 | 11/2005 | Moskowitz et al. |
| 2005/0256578 A1 | 11/2005 | Blatt et al. |
| 2005/0260058 A1 | 11/2005 | Cassagne, III |
| 2005/0261685 A1 | 11/2005 | Fortin et al. |
| 2005/0261687 A1 | 11/2005 | Garamszegi et al. |
| 2005/0261768 A1 | 11/2005 | Trieu |
| 2005/0267470 A1 | 12/2005 | McBride |
| 2005/0267471 A1 | 12/2005 | Biedermann et al. |
| 2005/0267474 A1 | 12/2005 | Dalton |
| 2005/0267477 A1 | 12/2005 | Jackson |
| 2005/0267579 A1 | 12/2005 | Reiley et al. |
| 2005/0267580 A1 | 12/2005 | Suddaby |
| 2005/0273099 A1 | 12/2005 | Baccelli et al. |
| 2005/0273101 A1 | 12/2005 | Schumacher |
| 2005/0273120 A1 | 12/2005 | Abdou et al. |
| 2005/0273171 A1 | 12/2005 | Gordon et al. |
| 2005/0277919 A1 | 12/2005 | Slivka et al. |
| 2005/0277921 A1 | 12/2005 | Eisermann et al. |
| 2005/0277922 A1 | 12/2005 | Trieu et al. |
| 2005/0277923 A1 | 12/2005 | Sweeney |
| 2005/0277924 A1 | 12/2005 | Roychowdhury |
| 2005/0277925 A1 | 12/2005 | Mujwid |
| 2005/0277927 A1 | 12/2005 | Guenther et al. |
| 2005/0277928 A1 | 12/2005 | Boschert |
| 2005/0277931 A1 | 12/2005 | Sweeney et al. |
| 2005/0277934 A1 | 12/2005 | Vardiman |
| 2005/0278026 A1 | 12/2005 | Gordon et al. |
| 2005/0283152 A1 | 12/2005 | Lindemann et al. |
| 2005/0283153 A1 | 12/2005 | Poyner et al. |
| 2005/0283157 A1 | 12/2005 | Coates et al. |
| 2005/0283236 A1 | 12/2005 | Razian |
| 2005/0283238 A1 | 12/2005 | Reiley |
| 2005/0283241 A1 | 12/2005 | Keller et al. |
| 2005/0283244 A1 | 12/2005 | Gordon et al. |
| 2005/0283245 A1 | 12/2005 | Gordon et al. |
| 2005/0288669 A1 | 12/2005 | Abdou et al. |
| 2005/0288670 A1 | 12/2005 | Panjabi et al. |
| 2005/0288671 A1 | 12/2005 | Yuan et al. |
| 2005/0288672 A1 | 12/2005 | Ferree |
| 2005/0288673 A1 | 12/2005 | An et al. |
| 2006/0004357 A1 | 1/2006 | Lee et al. |
| 2006/0004359 A1 | 1/2006 | Kramer et al. |
| 2006/0004360 A1 | 1/2006 | Kramer et al. |
| 2006/0004363 A1 | 1/2006 | Brockmeyer et al. |
| 2006/0004367 A1 | 1/2006 | Alamin et al. |
| 2006/0004453 A1 | 1/2006 | Bartish et al. |
| 2006/0009767 A1 | 1/2006 | Kiester |
| 2006/0009768 A1 | 1/2006 | Ritland |
| 2006/0009769 A1 | 1/2006 | Lieberman |
| 2006/0009770 A1 | 1/2006 | Speirs et al. |
| 2006/0009775 A1 | 1/2006 | Dec et al. |
| 2006/0009780 A1 | 1/2006 | Foley et al. |
| 2006/0009846 A1 | 1/2006 | Trieu et al. |
| 2006/0015099 A1 | 1/2006 | Cannon et al. |
| 2006/0015104 A1 | 1/2006 | Dalton |
| 2006/0015181 A1 | 1/2006 | Elberg |
| 2006/0015183 A1 | 1/2006 | Gilbert et al. |
| 2006/0020342 A1 | 1/2006 | Ferree et al. |
| 2006/0024614 A1 | 2/2006 | Williamson |
| 2006/0025767 A1 | 2/2006 | Khalili |
| 2006/0025768 A1 | 2/2006 | Iott et al. |
| 2006/0025770 A1 | 2/2006 | Schlapfer et al. |
| 2006/0030839 A1 | 2/2006 | Park et al. |
| 2006/0030850 A1 | 2/2006 | Keegan et al. |
| 2006/0030943 A1 | 2/2006 | Peterman |
| 2006/0036240 A1 | 2/2006 | Colleran et al. |
| 2006/0036242 A1 | 2/2006 | Nilsson et al. |
| 2006/0036244 A1 | 2/2006 | Spitler et al. |
| 2006/0036246 A1 | 2/2006 | Carl et al. |
| 2006/0036250 A1 | 2/2006 | Lange et al. |
| 2006/0036252 A1 | 2/2006 | Baynham et al. |
| 2006/0036254 A1 | 2/2006 | Lim |
| 2006/0036255 A1 | 2/2006 | Pond, Jr. et al. |
| 2006/0036256 A1 | 2/2006 | Carl et al. |
| 2006/0036258 A1 | 2/2006 | Zucherman et al. |
| 2006/0036259 A1 | 2/2006 | Carl et al. |

(56) References Cited

U.S. PATENT DOCUMENTS

| | | |
|---|---|---|
| 2006/0036260 A1 | 2/2006 | Runco et al. |
| 2006/0036323 A1 | 2/2006 | Carl et al. |
| 2006/0036324 A1 | 2/2006 | Sachs et al. |
| 2006/0041259 A1 | 2/2006 | Paul et al. |
| 2006/0052780 A1 | 3/2006 | Errico et al. |
| 2006/0052783 A1 | 3/2006 | Dant et al. |
| 2006/0052784 A1 | 3/2006 | Dant et al. |
| 2006/0052786 A1 | 3/2006 | Dant et al. |
| 2006/0052870 A1 | 3/2006 | Ferree |
| 2006/0052872 A1 | 3/2006 | Studer et al. |
| 2006/0058788 A1 | 3/2006 | Hammer et al. |
| 2006/0058790 A1 | 3/2006 | Carl et al. |
| 2006/0058791 A1 | 3/2006 | Broman et al. |
| 2006/0058800 A1 | 3/2006 | Ainsworth et al. |
| 2006/0058878 A1 | 3/2006 | Michelson |
| 2006/0064090 A1 | 3/2006 | Park |
| 2006/0064091 A1 | 3/2006 | Ludwig et al. |
| 2006/0064092 A1 | 3/2006 | Howland |
| 2006/0064095 A1 | 3/2006 | Senn et al. |
| 2006/0069315 A1 | 3/2006 | Miles et al. |
| 2006/0069390 A1 | 3/2006 | Frigg et al. |
| 2006/0069436 A1 | 3/2006 | Sutton et al. |
| 2006/0069438 A1 | 3/2006 | Zucherman et al. |
| 2006/0074419 A1 | 4/2006 | Taylor et al. |
| 2006/0074445 A1 | 4/2006 | Gerber et al. |
| 2006/0074488 A1 | 4/2006 | Abdou et al. |
| 2006/0079894 A1 | 4/2006 | Colleran et al. |
| 2006/0079895 A1 | 4/2006 | McLeer |
| 2006/0079896 A1 | 4/2006 | Kwak et al. |
| 2006/0079898 A1 | 4/2006 | Ainsworth et al. |
| 2006/0079899 A1 | 4/2006 | Ritland |
| 2006/0079903 A1 | 4/2006 | Wong |
| 2006/0079905 A1 | 4/2006 | Beyar et al. |
| 2006/0084844 A1 | 4/2006 | Nehls |
| 2006/0084976 A1 | 4/2006 | Borgstrom et al. |
| 2006/0084977 A1 | 4/2006 | Lieberman |
| 2006/0084981 A1 | 4/2006 | Shluzas |
| 2006/0084982 A1 | 4/2006 | Kim |
| 2006/0084983 A1 | 4/2006 | Kim |
| 2006/0084984 A1 | 4/2006 | Kim |
| 2006/0084985 A1 | 4/2006 | Kim |
| 2006/0084986 A1 | 4/2006 | Grinberg et al. |
| 2006/0084987 A1 | 4/2006 | Kim |
| 2006/0084988 A1 | 4/2006 | Kim |
| 2006/0084989 A1 | 4/2006 | Dickinson et al. |
| 2006/0084991 A1 | 4/2006 | Borgstrom et al. |
| 2006/0084993 A1 | 4/2006 | Landry et al. |
| 2006/0084995 A1 | 4/2006 | Biedermann et al. |
| 2006/0085069 A1 | 4/2006 | Kim |
| 2006/0085076 A1 | 4/2006 | Krishna et al. |
| 2006/0088398 A1 | 4/2006 | Lund |
| 2006/0089643 A1 | 4/2006 | Mujwid |
| 2006/0089644 A1 | 4/2006 | Felix |
| 2006/0089646 A1 | 4/2006 | Bonutti |
| 2006/0089647 A1 | 4/2006 | Culbert et al. |
| 2006/0089656 A1 | 4/2006 | Allard et al. |
| 2006/0089718 A1 | 4/2006 | Zucherman et al. |
| 2006/0095037 A1 | 5/2006 | Jones et al. |
| 2006/0106380 A1 | 5/2006 | Colleran et al. |
| 2006/0106381 A1 | 5/2006 | Ferree et al. |
| 2006/0106383 A1 | 5/2006 | Biedermann et al. |
| 2006/0106387 A1 | 5/2006 | Fanger et al. |
| 2006/0106395 A1 | 5/2006 | Link et al. |
| 2006/0106397 A1 | 5/2006 | Lins |
| 2006/0111714 A1 | 5/2006 | Foley |
| 2006/0111715 A1 | 5/2006 | Jackson |
| 2006/0111728 A1 | 5/2006 | Abdou |
| 2006/0116677 A1 | 6/2006 | Burd et al. |
| 2006/0116768 A1 | 6/2006 | Krueger et al. |
| 2006/0122597 A1 | 6/2006 | Jones et al. |
| 2006/0122599 A1 | 6/2006 | Drewry et al. |
| 2006/0122604 A1 | 6/2006 | Gorhan et al. |
| 2006/0122607 A1 | 6/2006 | Kolb |
| 2006/0122625 A1 | 6/2006 | Truckai et al. |
| 2006/0122701 A1 | 6/2006 | Kiester |
| 2006/0129147 A1 | 6/2006 | Biedermann et al. |
| 2006/0129149 A1 | 6/2006 | Iott et al. |
| 2006/0129239 A1 | 6/2006 | Kwak |
| 2006/0129244 A1 | 6/2006 | Ensign |
| 2006/0136060 A1 | 6/2006 | Taylor |
| 2006/0136062 A1 | 6/2006 | Dinello et al. |
| 2006/0142758 A1 | 6/2006 | Petit |
| 2006/0142760 A1 | 6/2006 | McDonnell |
| 2006/0142761 A1 | 6/2006 | Landry et al. |
| 2006/0142858 A1 | 6/2006 | Colleran et al. |
| 2006/0149228 A1 | 7/2006 | Schlapfer et al. |
| 2006/0149229 A1 | 7/2006 | Kwak et al. |
| 2006/0149232 A1 | 7/2006 | Sasing |
| 2006/0149234 A1 | 7/2006 | de Coninck |
| 2006/0149238 A1 | 7/2006 | Sherman et al. |
| 2006/0149240 A1 | 7/2006 | Jackson |
| 2006/0149241 A1 | 7/2006 | Richelsoph et al. |
| 2006/0149244 A1 | 7/2006 | Amrein et al. |
| 2006/0149245 A1 | 7/2006 | Sweeney |
| 2006/0149278 A1 | 7/2006 | Abdou |
| 2006/0149284 A1 | 7/2006 | McCormack et al. |
| 2006/0149385 A1 | 7/2006 | McKay |
| 2006/0155277 A1 | 7/2006 | Metz-Stavenhagen |
| 2006/0155278 A1 | 7/2006 | Warnick |
| 2006/0155284 A1 | 7/2006 | Doherty et al. |
| 2006/0161152 A1 | 7/2006 | Ensign et al. |
| 2006/0161154 A1 | 7/2006 | McAfee |
| 2006/0167454 A1 | 7/2006 | Ludwig et al. |
| 2006/0167455 A1 | 7/2006 | Clement et al. |
| 2006/0173454 A1 | 8/2006 | Spitler et al. |
| 2006/0173456 A1 | 8/2006 | Hawkes et al. |
| 2006/0178746 A1 | 8/2006 | Bartish, Jr. et al. |
| 2006/0184112 A1 | 8/2006 | Horn et al. |
| 2006/0184171 A1 | 8/2006 | Biedermann et al. |
| 2006/0184180 A1 | 8/2006 | Augostino et al. |
| 2006/0184247 A1 | 8/2006 | Edidin et al. |
| 2006/0187562 A1 | 8/2006 | Mounnarat et al. |
| 2006/0189983 A1 | 8/2006 | Fallin et al. |
| 2006/0189984 A1 | 8/2006 | Fallin et al. |
| 2006/0189985 A1 | 8/2006 | Lewis |
| 2006/0189999 A1 | 8/2006 | Zwirkoski |
| 2006/0190082 A1 | 8/2006 | Keller et al. |
| 2006/0190083 A1 | 8/2006 | Arnin et al. |
| 2006/0195089 A1 | 8/2006 | Lehuec et al. |
| 2006/0195090 A1 | 8/2006 | Suddaby |
| 2006/0195093 A1 | 8/2006 | Jahng |
| 2006/0195096 A1 | 8/2006 | Lee et al. |
| 2006/0195098 A1 | 8/2006 | Schumacher |
| 2006/0195102 A1 | 8/2006 | Malandain |
| 2006/0195192 A1 | 8/2006 | Gordon et al. |
| 2006/0200121 A1 | 9/2006 | Mowery |
| 2006/0200128 A1 | 9/2006 | Mueller |
| 2006/0200130 A1 | 9/2006 | Hawkins et al. |
| 2006/0200131 A1 | 9/2006 | Chao et al. |
| 2006/0200132 A1 | 9/2006 | Chao et al. |
| 2006/0200135 A1 | 9/2006 | Sherman et al. |
| 2006/0200138 A1 | 9/2006 | Michelson |
| 2006/0200139 A1 | 9/2006 | Michelson |
| 2006/0200149 A1 | 9/2006 | Hoy et al. |
| 2006/0210494 A1 | 9/2006 | Rabiei et al. |
| 2006/0212033 A1 | 9/2006 | Rothman et al. |
| 2006/0212034 A1 | 9/2006 | Triplett et al. |
| 2006/0217710 A1 | 9/2006 | Abdou |
| 2006/0217712 A1 | 9/2006 | Mueller et al. |
| 2006/0217713 A1 | 9/2006 | Serhan et al. |
| 2006/0217714 A1 | 9/2006 | Serhan et al. |
| 2006/0217716 A1 | 9/2006 | Baker et al. |
| 2006/0217719 A1 | 9/2006 | Albert et al. |
| 2006/0217731 A1 | 9/2006 | Gil et al. |
| 2006/0217809 A1 | 9/2006 | Albert et al. |
| 2006/0224159 A1 | 10/2006 | Anderson |
| 2006/0224241 A1 | 10/2006 | Butler et al. |
| 2006/0229608 A1 | 10/2006 | Foster et al. |
| 2006/0229609 A1 | 10/2006 | Wang |
| 2006/0229610 A1 | 10/2006 | Piehl |
| 2006/0229612 A1 | 10/2006 | Rothman et al. |
| 2006/0229613 A1 | 10/2006 | Timm et al. |
| 2006/0229614 A1 | 10/2006 | Foley et al. |
| 2006/0229615 A1 | 10/2006 | Abdou et al. |

(56) References Cited

U.S. PATENT DOCUMENTS

| | | |
|---|---|---|
| 2006/0229627 A1 | 10/2006 | Hunt et al. |
| 2006/0229629 A1 | 10/2006 | Manzi et al. |
| 2006/0229715 A1 | 10/2006 | Istephanous et al. |
| 2006/0229729 A1 | 10/2006 | Gordon et al. |
| 2006/0235387 A1 | 10/2006 | Peterman |
| 2006/0235389 A1 | 10/2006 | Albert et al. |
| 2006/0235391 A1 | 10/2006 | Sutterlin, III |
| 2006/0235392 A1 | 10/2006 | Hammer et al. |
| 2006/0235393 A1 | 10/2006 | Bono et al. |
| 2006/0235403 A1 | 10/2006 | Blain |
| 2006/0235411 A1 | 10/2006 | Blain et al. |
| 2006/0235414 A1 | 10/2006 | Lim et al. |
| 2006/0235426 A1 | 10/2006 | Lim et al. |
| 2006/0235532 A1 | 10/2006 | Meunier et al. |
| 2006/0241593 A1 | 10/2006 | Sherman et al. |
| 2006/0241595 A1 | 10/2006 | Molz, IV et al. |
| 2006/0241599 A1 | 10/2006 | Konieczynski et al. |
| 2006/0241600 A1 | 10/2006 | Ensign et al. |
| 2006/0241601 A1 | 10/2006 | Trautwein et al. |
| 2006/0241610 A1 | 10/2006 | Lim et al. |
| 2006/0241614 A1 | 10/2006 | Bruneau et al. |
| 2006/0241615 A1 | 10/2006 | Melkent |
| 2006/0241641 A1 | 10/2006 | Albans et al. |
| 2006/0241761 A1 | 10/2006 | Gately |
| 2006/0241769 A1 | 10/2006 | Gordon et al. |
| 2006/0241771 A1 | 10/2006 | Gordon et al. |
| 2006/0247624 A1 | 11/2006 | Banouskou et al. |
| 2006/0247630 A1 | 11/2006 | Iott et al. |
| 2006/0247631 A1 | 11/2006 | Ahn et al. |
| 2006/0247632 A1 | 11/2006 | Winslow et al. |
| 2006/0247633 A1 | 11/2006 | Winslow et al. |
| 2006/0247634 A1 | 11/2006 | Warner et al. |
| 2006/0247635 A1 | 11/2006 | Gordon et al. |
| 2006/0247636 A1 | 11/2006 | Yuan et al. |
| 2006/0247637 A1 | 11/2006 | Colleran et al. |
| 2006/0247640 A1 | 11/2006 | Blackwell et al. |
| 2006/0247655 A1 | 11/2006 | Francis et al. |
| 2006/0247679 A1 | 11/2006 | Peterman |
| 2006/0247772 A1 | 11/2006 | McKay |
| 2006/0247778 A1 | 11/2006 | Ferree et al. |
| 2006/0247779 A1 | 11/2006 | Gordon et al. |
| 2006/0247781 A1 | 11/2006 | Francis |
| 2006/0247782 A1 | 11/2006 | Molz, IV et al. |
| 2006/0253198 A1 | 11/2006 | Myint et al. |
| 2006/0253201 A1 | 11/2006 | McLuen |
| 2006/0264933 A1 | 11/2006 | Baker et al. |
| 2006/0264934 A1 | 11/2006 | Fallin |
| 2006/0264935 A1 | 11/2006 | White |
| 2006/0264936 A1 | 11/2006 | Partin, I et al. |
| 2006/0264937 A1 | 11/2006 | White |
| 2006/0264940 A1 | 11/2006 | Hartmann |
| 2006/0264942 A1 | 11/2006 | Lim et al. |
| 2006/0264962 A1 | 11/2006 | Chin et al. |
| 2006/0265077 A1 | 11/2006 | Zwirkoski |
| 2006/0269940 A1 | 11/2006 | Li et al. |
| 2006/0271046 A1 | 11/2006 | Kwak et al. |
| 2006/0276787 A1 | 12/2006 | Zubok et al. |
| 2006/0276789 A1 | 12/2006 | Jackson |
| 2006/0276791 A1 | 12/2006 | Shluzas |
| 2006/0276792 A1 | 12/2006 | Ensign et al. |
| 2006/0276793 A1 | 12/2006 | Berry |
| 2006/0276803 A1 | 12/2006 | Salerni |
| 2006/0276900 A1 | 12/2006 | Carpenter |
| 2006/0282074 A1 | 12/2006 | Renaud et al. |
| 2006/0282075 A1 | 12/2006 | Labrom et al. |
| 2006/0282076 A1 | 12/2006 | Labrom et al. |
| 2006/0282078 A1 | 12/2006 | Labrom et al. |
| 2006/0282079 A1 | 12/2006 | Labrom et al. |
| 2006/0287583 A1 | 12/2006 | Mangiardi |
| 2006/0293662 A1 | 12/2006 | Boyer, II et al. |
| 2007/0010889 A1 | 1/2007 | Francis |
| 2007/0016218 A1 | 1/2007 | Winslow et al. |
| 2007/0016298 A1 | 1/2007 | Recoules-Arche et al. |
| 2007/0021836 A1 | 1/2007 | Doty |
| 2007/0027542 A1 | 2/2007 | Xu |
| 2007/0032790 A1 | 2/2007 | Aschmann et al. |
| 2007/0039837 A1 | 2/2007 | Hanina et al. |
| 2007/0043356 A1 | 2/2007 | Timm et al. |
| 2007/0043442 A1 | 2/2007 | Abernathie et al. |
| 2007/0049935 A1 | 3/2007 | Edidin et al. |
| 2007/0050030 A1 | 3/2007 | Kim |
| 2007/0050032 A1 | 3/2007 | Gittings et al. |
| 2007/0055236 A1 | 3/2007 | Hudgins et al. |
| 2007/0055377 A1 | 3/2007 | Hanson et al. |
| 2007/0067035 A1 | 3/2007 | Falahee |
| 2007/0073111 A1 | 3/2007 | Bass |
| 2007/0073398 A1 | 3/2007 | Fabian et al. |
| 2007/0083266 A1 | 4/2007 | Lang |
| 2007/0090238 A1 | 4/2007 | Justis |
| 2007/0093817 A1 | 4/2007 | Barrus et al. |
| 2007/0093823 A1 | 4/2007 | Booth et al. |
| 2007/0093825 A1 | 4/2007 | Ferree et al. |
| 2007/0093828 A1 | 4/2007 | Abdou et al. |
| 2007/0093829 A1 | 4/2007 | Abdou |
| 2007/0093901 A1 | 4/2007 | Grotz et al. |
| 2007/0100212 A1 | 5/2007 | Pimenta et al. |
| 2007/0100340 A1 | 5/2007 | Lange et al. |
| 2007/0100341 A1 | 5/2007 | Reglos et al. |
| 2007/0106298 A1 | 5/2007 | Carli et al. |
| 2007/0106383 A1 | 5/2007 | Abdou et al. |
| 2007/0108383 A1 | 5/2007 | Combes et al. |
| 2007/0118121 A1 | 5/2007 | Purcell et al. |
| 2007/0118122 A1 | 5/2007 | Butler et al. |
| 2007/0118123 A1 | 5/2007 | Strausbaugh et al. |
| 2007/0118132 A1 | 5/2007 | Culbert et al. |
| 2007/0123867 A1 | 5/2007 | Kirschman |
| 2007/0123869 A1 | 5/2007 | Chin et al. |
| 2007/0123884 A1 | 5/2007 | Abdou |
| 2007/0129804 A1 | 6/2007 | Bentley et al. |
| 2007/0142916 A1 | 6/2007 | Olson, Jr. et al. |
| 2007/0149978 A1 | 6/2007 | Shezifi et al. |
| 2007/0151116 A1 | 7/2007 | Malandain |
| 2007/0156233 A1 | 7/2007 | Kapadia et al. |
| 2007/0161962 A1 | 7/2007 | Edie et al. |
| 2007/0161992 A1 | 7/2007 | Kwak et al. |
| 2007/0162000 A1 | 7/2007 | Perkins |
| 2007/0162001 A1 | 7/2007 | Chin et al. |
| 2007/0162005 A1 | 7/2007 | Peterson et al. |
| 2007/0162127 A1 | 7/2007 | Peterman et al. |
| 2007/0162133 A1 | 7/2007 | Doubler et al. |
| 2007/0162138 A1 | 7/2007 | Heinz |
| 2007/0167948 A1 | 7/2007 | Abdou |
| 2007/0168036 A1 | 7/2007 | Ainsworth et al. |
| 2007/0173831 A1 | 7/2007 | Abdou |
| 2007/0173842 A1 | 7/2007 | Abdou |
| 2007/0179493 A1 | 8/2007 | Kim |
| 2007/0179500 A1 | 8/2007 | Chin et al. |
| 2007/0179614 A1 | 8/2007 | Heinz et al. |
| 2007/0185367 A1 | 8/2007 | Abdou |
| 2007/0185376 A1 | 8/2007 | Wilson et al. |
| 2007/0185489 A1 | 8/2007 | Abdou |
| 2007/0191834 A1 | 8/2007 | Bruneau et al. |
| 2007/0191861 A1 | 8/2007 | Allard et al. |
| 2007/0191946 A1 | 8/2007 | Heinz et al. |
| 2007/0191951 A1 | 8/2007 | Branch, Jr. et al. |
| 2007/0191958 A1 | 8/2007 | Abdou |
| 2007/0198090 A1 | 8/2007 | Abdou |
| 2007/0208227 A1 | 9/2007 | Smith et al. |
| 2007/0213597 A1 | 9/2007 | Wooster |
| 2007/0213732 A1 | 9/2007 | Khanna et al. |
| 2007/0225724 A1 | 9/2007 | Edmond |
| 2007/0225726 A1 | 9/2007 | Dye et al. |
| 2007/0225807 A1 | 9/2007 | Phan et al. |
| 2007/0225808 A1 | 9/2007 | Warnick |
| 2007/0225812 A1 | 9/2007 | Gill |
| 2007/0233074 A1 | 10/2007 | Anderson et al. |
| 2007/0233077 A1 | 10/2007 | Khalili |
| 2007/0233082 A1 | 10/2007 | Chin et al. |
| 2007/0233083 A1 | 10/2007 | Abdou |
| 2007/0233084 A1 | 10/2007 | Betz et al. |
| 2007/0233088 A1 | 10/2007 | Edmond |
| 2007/0233089 A1 | 10/2007 | Dipoto et al. |
| 2007/0233118 A1 | 10/2007 | McLain |
| 2007/0233129 A1 | 10/2007 | Bertagnoli et al. |

(56) References Cited

U.S. PATENT DOCUMENTS

| | | |
|---|---|---|
| 2007/0233247 A1 | 10/2007 | Schwab |
| 2007/0233251 A1 | 10/2007 | Abdou |
| 2007/0255389 A1 | 11/2007 | Oberti et al. |
| 2007/0255415 A1 | 11/2007 | Edie et al. |
| 2007/0260314 A1 | 11/2007 | Biyani |
| 2007/0270812 A1 | 11/2007 | Peckham |
| 2007/0270813 A1 | 11/2007 | Garamszegi |
| 2007/0270824 A1 | 11/2007 | Lim et al. |
| 2007/0270827 A1 | 11/2007 | Lim et al. |
| 2007/0270838 A1 | 11/2007 | Bruneau et al. |
| 2007/0270840 A1 | 11/2007 | Chin et al. |
| 2007/0270874 A1 | 11/2007 | Anderson |
| 2007/0270963 A1 | 11/2007 | Melkent et al. |
| 2007/0270968 A1 | 11/2007 | Baynham et al. |
| 2007/0274772 A1 | 11/2007 | Tiberghien et al. |
| 2007/0276370 A1 | 11/2007 | Altarac et al. |
| 2007/0282448 A1 | 12/2007 | Abdou |
| 2007/0293949 A1 | 12/2007 | Salerni et al. |
| 2007/0299445 A1 | 12/2007 | Shadduck et al. |
| 2007/0299521 A1 | 12/2007 | Glenn et al. |
| 2008/0009880 A1 | 1/2008 | Warnick et al. |
| 2008/0015580 A1 | 1/2008 | Chao |
| 2008/0015597 A1 | 1/2008 | Whipple |
| 2008/0015698 A1 | 1/2008 | Marino et al. |
| 2008/0021466 A1 | 1/2008 | Shadduck et al. |
| 2008/0021559 A1 | 1/2008 | Thramann |
| 2008/0027432 A1 | 1/2008 | Strauss et al. |
| 2008/0027438 A1 | 1/2008 | Abdou |
| 2008/0027458 A1 | 1/2008 | Aikins et al. |
| 2008/0027544 A1 | 1/2008 | Melkent |
| 2008/0027545 A1 | 1/2008 | Zucherman et al. |
| 2008/0027550 A1 | 1/2008 | Link et al. |
| 2008/0039837 A1 | 2/2008 | Gambale |
| 2008/0039843 A1 | 2/2008 | Abdou |
| 2008/0045963 A1 | 2/2008 | Abdou |
| 2008/0045968 A1 | 2/2008 | Yu et al. |
| 2008/0045983 A1 | 2/2008 | To et al. |
| 2008/0051783 A1 | 2/2008 | Null et al. |
| 2008/0051896 A1 | 2/2008 | Suddaby |
| 2008/0058606 A1 | 3/2008 | Miles et al. |
| 2008/0058810 A1 | 3/2008 | Abdou |
| 2008/0065219 A1 | 3/2008 | Dye |
| 2008/0065222 A1 | 3/2008 | Hamada |
| 2008/0081951 A1 | 4/2008 | Frasier et al. |
| 2008/0086080 A1 | 4/2008 | Mastri et al. |
| 2008/0091211 A1 | 4/2008 | Gately |
| 2008/0108993 A1 | 5/2008 | Bennett et al. |
| 2008/0114401 A1 | 5/2008 | Liu et al. |
| 2008/0114455 A1 | 5/2008 | Lange et al. |
| 2008/0119853 A1 | 5/2008 | Felt et al. |
| 2008/0119935 A1 | 5/2008 | Alvarez |
| 2008/0125813 A1 | 5/2008 | Erickson et al. |
| 2008/0125865 A1 | 5/2008 | Abdelgany |
| 2008/0126813 A1 | 5/2008 | Kawakami |
| 2008/0132951 A1 | 6/2008 | Reiley et al. |
| 2008/0133012 A1 | 6/2008 | McGuckin |
| 2008/0133014 A1 | 6/2008 | Gately et al. |
| 2008/0133016 A1 | 6/2008 | Heinz |
| 2008/0133017 A1 | 6/2008 | Beyar et al. |
| 2008/0139879 A1 | 6/2008 | Olson et al. |
| 2008/0140085 A1 | 6/2008 | Gately et al. |
| 2008/0140125 A1 | 6/2008 | Mitchell et al. |
| 2008/0140204 A1 | 6/2008 | Heinz |
| 2008/0140207 A1 | 6/2008 | Olmos et al. |
| 2008/0147123 A1 | 6/2008 | Schermerhorn |
| 2008/0147190 A1 | 6/2008 | Dewey et al. |
| 2008/0154308 A1 | 6/2008 | Sherman et al. |
| 2008/0154374 A1 | 6/2008 | Labrom |
| 2008/0161818 A1 | 7/2008 | Kloss et al. |
| 2008/0161821 A1 | 7/2008 | Heinz |
| 2008/0161853 A1 | 7/2008 | Arnold et al. |
| 2008/0161856 A1 | 7/2008 | Liu et al. |
| 2008/0167655 A1 | 7/2008 | Wang et al. |
| 2008/0167657 A1 | 7/2008 | Greenhalgh |
| 2008/0177271 A1 | 7/2008 | Yeh |
| 2008/0177298 A1 | 7/2008 | Zucherman et al. |
| 2008/0177306 A1 | 7/2008 | Lamborne et al. |
| 2008/0177312 A1 | 7/2008 | Perez-Cruet et al. |
| 2008/0177326 A1 | 7/2008 | Thompson |
| 2008/0177391 A1 | 7/2008 | Mitchell et al. |
| 2008/0183204 A1 | 7/2008 | Greenhalgh et al. |
| 2008/0183209 A1 | 7/2008 | Robinson et al. |
| 2008/0183211 A1 | 7/2008 | Lamborne et al. |
| 2008/0183218 A1 | 7/2008 | Mueller et al. |
| 2008/0188898 A1 | 8/2008 | Jackson |
| 2008/0188941 A1 | 8/2008 | Grotz |
| 2008/0195152 A1 | 8/2008 | Altarac et al. |
| 2008/0234735 A1 | 9/2008 | Joshi |
| 2008/0243185 A1 | 10/2008 | Felix et al. |
| 2008/0243186 A1 | 10/2008 | Abdou |
| 2008/0243188 A1 | 10/2008 | Walder et al. |
| 2008/0243189 A1 | 10/2008 | Purcell et al. |
| 2008/0243255 A1 | 10/2008 | Butler et al. |
| 2008/0249622 A1 | 10/2008 | Gray |
| 2008/0249628 A1 | 10/2008 | Altarac et al. |
| 2008/0262318 A1 | 10/2008 | Gorek et al. |
| 2008/0262554 A1 | 10/2008 | Hayes et al. |
| 2008/0269904 A1 | 10/2008 | Voorhies |
| 2008/0281346 A1 | 11/2008 | Greenhalgh et al. |
| 2008/0281358 A1 | 11/2008 | Abdou |
| 2008/0281359 A1 | 11/2008 | Abdou |
| 2008/0288073 A1 | 11/2008 | Renganath et al. |
| 2008/0294199 A1 | 11/2008 | Kohm et al. |
| 2008/0294200 A1 | 11/2008 | Kohm et al. |
| 2008/0300598 A1 | 12/2008 | Barreiro et al. |
| 2008/0300601 A1 | 12/2008 | Fabian et al. |
| 2008/0300685 A1 | 12/2008 | Carls et al. |
| 2008/0300686 A1 | 12/2008 | Khoo |
| 2008/0306601 A1 | 12/2008 | Dreyfuss |
| 2008/0312655 A1 | 12/2008 | Kirschman et al. |
| 2008/0312692 A1 | 12/2008 | Brennan et al. |
| 2008/0312741 A1 | 12/2008 | Lee et al. |
| 2008/0312743 A1 | 12/2008 | Vila et al. |
| 2008/0319487 A1 | 12/2008 | Fielding et al. |
| 2008/0319549 A1 | 12/2008 | Greenhalgh et al. |
| 2009/0012566 A1 | 1/2009 | Fauth |
| 2009/0012623 A1 | 1/2009 | Sack et al. |
| 2009/0024166 A1 | 1/2009 | Carl et al. |
| 2009/0024217 A1 | 1/2009 | Levy et al. |
| 2009/0030423 A1 | 1/2009 | Puno |
| 2009/0030457 A1 | 1/2009 | Janowski et al. |
| 2009/0030465 A1 | 1/2009 | Altarac et al. |
| 2009/0030519 A1 | 1/2009 | Falahee |
| 2009/0030520 A1 | 1/2009 | Biedermann et al. |
| 2009/0036746 A1 | 2/2009 | Blackwell et al. |
| 2009/0036927 A1 | 2/2009 | Vestgaarden |
| 2009/0036929 A1 | 2/2009 | Reglos et al. |
| 2009/0036988 A1 | 2/2009 | Peckham |
| 2009/0048668 A1 | 2/2009 | Wilson et al. |
| 2009/0054931 A1 | 2/2009 | Metz-Stavenhagen |
| 2009/0062869 A1 | 3/2009 | Claverie et al. |
| 2009/0062915 A1 | 3/2009 | Kohm et al. |
| 2009/0062918 A1 | 3/2009 | Wang et al. |
| 2009/0062920 A1 | 3/2009 | Tauber |
| 2009/0076333 A1 | 3/2009 | Bjork |
| 2009/0076516 A1 | 3/2009 | Lowry et al. |
| 2009/0076615 A1 | 3/2009 | Duggal et al. |
| 2009/0082808 A1 | 3/2009 | Butler et al. |
| 2009/0082813 A1 | 3/2009 | Long et al. |
| 2009/0093884 A1 | 4/2009 | Bass |
| 2009/0099601 A1 | 4/2009 | Aferzon et al. |
| 2009/0105547 A1 | 4/2009 | Vayser et al. |
| 2009/0105761 A1 | 4/2009 | Robie |
| 2009/0105768 A1 | 4/2009 | Cragg et al. |
| 2009/0105773 A1 | 4/2009 | Lange et al. |
| 2009/0105830 A1 | 4/2009 | Jones et al. |
| 2009/0105831 A1 | 4/2009 | Jones et al. |
| 2009/0118766 A1 | 5/2009 | Park et al. |
| 2009/0118771 A1 | 5/2009 | Gonzalez-Hernandez |
| 2009/0124861 A1 | 5/2009 | Fetzer |
| 2009/0125062 A1 | 5/2009 | Arnin |
| 2009/0125071 A1 | 5/2009 | Skinlo et al. |
| 2009/0132054 A1 | 5/2009 | Zeegers |
| 2009/0143859 A1 | 6/2009 | McClellan, III et al. |

(56) References Cited

U.S. PATENT DOCUMENTS

| | | |
|---|---|---|
| 2009/0149956 A1 | 6/2009 | Greenhalgh et al. |
| 2009/0149959 A1 | 6/2009 | Conner et al. |
| 2009/0157186 A1 | 6/2009 | Magerl |
| 2009/0157188 A1 | 6/2009 | Zeegers |
| 2009/0163920 A1 | 6/2009 | Hochschuler et al. |
| 2009/0163957 A1 | 6/2009 | St. Clair et al. |
| 2009/0163961 A1 | 6/2009 | Kirschman |
| 2009/0164020 A1 | 6/2009 | Janowski et al. |
| 2009/0171394 A1 | 7/2009 | Abdou |
| 2009/0177262 A1 | 7/2009 | Oberti et al. |
| 2009/0182429 A1 | 7/2009 | Humphreys et al. |
| 2009/0182430 A1 | 7/2009 | Tyber et al. |
| 2009/0186333 A1 | 7/2009 | Mills et al. |
| 2009/0187249 A1 | 7/2009 | Osman |
| 2009/0192613 A1 | 7/2009 | Wing et al. |
| 2009/0192615 A1 | 7/2009 | Tyber et al. |
| 2009/0198211 A1 | 8/2009 | Thorne, Jr. et al. |
| 2009/0198277 A1 | 8/2009 | Gordon et al. |
| 2009/0204151 A1 | 8/2009 | Bracken |
| 2009/0204154 A1 | 8/2009 | Kiester |
| 2009/0204218 A1 | 8/2009 | Richelsoph |
| 2009/0204219 A1 | 8/2009 | Beaurain et al. |
| 2009/0210007 A1 | 8/2009 | Levy et al. |
| 2009/0210015 A1 | 8/2009 | Cermak et al. |
| 2009/0210062 A1 | 8/2009 | Thalgott et al. |
| 2009/0216234 A1 | 8/2009 | Farr et al. |
| 2009/0216241 A1 | 8/2009 | Dinville |
| 2009/0222046 A1 | 9/2009 | Gorek |
| 2009/0222092 A1 | 9/2009 | Davis et al. |
| 2009/0222100 A1 | 9/2009 | Cipoletti et al. |
| 2009/0227845 A1 | 9/2009 | Lo et al. |
| 2009/0228045 A1 | 9/2009 | Hayes et al. |
| 2009/0228108 A1 | 9/2009 | Keller |
| 2009/0228110 A1 | 9/2009 | McClintock |
| 2009/0234364 A1 | 9/2009 | Crook |
| 2009/0234455 A1 | 9/2009 | Moskowitz et al. |
| 2009/0240334 A1 | 9/2009 | Richelsoph |
| 2009/0240335 A1 | 9/2009 | Arcenio et al. |
| 2009/0247819 A1 | 10/2009 | Wilson et al. |
| 2009/0248078 A1 | 10/2009 | Dant |
| 2009/0248089 A1 | 10/2009 | Jacofsky et al. |
| 2009/0254125 A1 | 10/2009 | Predick |
| 2009/0259257 A1 | 10/2009 | Prevost |
| 2009/0259316 A1* | 10/2009 | Ginn ................ A61B 17/7062 623/17.16 |
| 2009/0265007 A1 | 10/2009 | Colleran |
| 2009/0270918 A1 | 10/2009 | Attia et al. |
| 2009/0270989 A1 | 10/2009 | Conner et al. |
| 2009/0270990 A1 | 10/2009 | Louis et al. |
| 2009/0276040 A1 | 11/2009 | Rowe et al. |
| 2009/0276049 A1 | 11/2009 | Weiland |
| 2009/0281628 A1 | 11/2009 | Oglaza et al. |
| 2009/0290316 A1 | 11/2009 | Kariya |
| 2009/0292361 A1 | 11/2009 | Lopez |
| 2009/0299478 A1 | 12/2009 | Carls et al. |
| 2009/0326538 A1 | 12/2009 | Sennett et al. |
| 2009/0326581 A1 | 12/2009 | Galley et al. |
| 2009/0326584 A1 | 12/2009 | Slivka et al. |
| 2010/0004664 A1 | 1/2010 | Boyajian et al. |
| 2010/0009929 A1 | 1/2010 | Cheng et al. |
| 2010/0016897 A1 | 1/2010 | Le Couedic et al. |
| 2010/0016906 A1 | 1/2010 | Abdou |
| 2010/0023061 A1 | 1/2010 | Randol et al. |
| 2010/0023064 A1 | 1/2010 | Brunger et al. |
| 2010/0036423 A1 | 2/2010 | Hayes et al. |
| 2010/0036495 A1 | 2/2010 | Daum et al. |
| 2010/0042149 A1 | 2/2010 | Chao et al. |
| 2010/0049324 A1 | 2/2010 | Valdevit et al. |
| 2010/0069929 A1 | 3/2010 | Abdou |
| 2010/0069962 A1 | 3/2010 | Harms et al. |
| 2010/0069965 A1 | 3/2010 | Abdou |
| 2010/0070041 A1 | 3/2010 | Peterman et al. |
| 2010/0076448 A1 | 3/2010 | Abdou |
| 2010/0082109 A1 | 4/2010 | Greenhalgh et al. |
| 2010/0087858 A1 | 4/2010 | Abdou |
| 2010/0087869 A1 | 4/2010 | Abdou |
| 2010/0087878 A1 | 4/2010 | Abdou |
| 2010/0087923 A1 | 4/2010 | Abdou |
| 2010/0094422 A1 | 4/2010 | Hansell et al. |
| 2010/0100137 A1 | 4/2010 | Justis et al. |
| 2010/0106250 A1 | 4/2010 | Abdou |
| 2010/0121384 A1 | 5/2010 | Abdou |
| 2010/0130827 A1 | 5/2010 | Pimenta et al. |
| 2010/0152778 A1 | 6/2010 | Saint Martin |
| 2010/0174315 A1 | 7/2010 | Scodary et al. |
| 2010/0179657 A1 | 7/2010 | Greenhalgh et al. |
| 2010/0185291 A1 | 7/2010 | Jimenez et al. |
| 2010/0191336 A1 | 7/2010 | Greenhalgh |
| 2010/0191337 A1 | 7/2010 | Zamani et al. |
| 2010/0198140 A1 | 8/2010 | Lawson |
| 2010/0204795 A1 | 8/2010 | Greenhalgh |
| 2010/0211101 A1 | 8/2010 | Blackwell et al. |
| 2010/0211176 A1 | 8/2010 | Greenhalgh |
| 2010/0211177 A1 | 8/2010 | Abdou |
| 2010/0217382 A1 | 8/2010 | Chau et al. |
| 2010/0222644 A1 | 9/2010 | Sebastian et al. |
| 2010/0222816 A1 | 9/2010 | Gabelberger et al. |
| 2010/0222884 A1 | 9/2010 | Greenhalgh et al. |
| 2010/0234889 A1 | 9/2010 | Hess |
| 2010/0234952 A1 | 9/2010 | Peterman |
| 2010/0234956 A1 | 9/2010 | Attia et al. |
| 2010/0241168 A1 | 9/2010 | Franck et al. |
| 2010/0249933 A1 | 9/2010 | Trieu |
| 2010/0256759 A1 | 10/2010 | Hansell et al. |
| 2010/0256760 A1 | 10/2010 | Hansell |
| 2010/0262245 A1 | 10/2010 | Alfaro et al. |
| 2010/0262248 A1 | 10/2010 | Sournac et al. |
| 2010/0268281 A1 | 10/2010 | Abdou |
| 2010/0280622 A1 | 11/2010 | McKinley |
| 2010/0286483 A1 | 11/2010 | Bettuchi et al. |
| 2010/0286779 A1 | 11/2010 | Thibodeau |
| 2010/0286780 A1 | 11/2010 | Dryer et al. |
| 2010/0292796 A1 | 11/2010 | Greenhalgh et al. |
| 2010/0305705 A1 | 12/2010 | Butler et al. |
| 2010/0312282 A1 | 12/2010 | Abdou |
| 2010/0312347 A1 | 12/2010 | Arramon et al. |
| 2010/0318128 A1 | 12/2010 | Abdou |
| 2010/0331883 A1 | 12/2010 | Schmitz et al. |
| 2010/0331887 A1 | 12/2010 | Jackson et al. |
| 2010/0331889 A1 | 12/2010 | Abdou |
| 2010/0331981 A1 | 12/2010 | Mohammed |
| 2010/0331985 A1 | 12/2010 | Gordon et al. |
| 2011/0004284 A1 | 1/2011 | Abdou |
| 2011/0009969 A1 | 1/2011 | Puno |
| 2011/0009970 A1 | 1/2011 | Puno |
| 2011/0022090 A1 | 1/2011 | Gordon et al. |
| 2011/0029083 A1 | 2/2011 | Hynes et al. |
| 2011/0029085 A1 | 2/2011 | Hynes et al. |
| 2011/0035011 A1 | 2/2011 | Cain |
| 2011/0046679 A1 | 2/2011 | Chow et al. |
| 2011/0046740 A1 | 2/2011 | Chen et al. |
| 2011/0054531 A1 | 3/2011 | Lamborne et al. |
| 2011/0060366 A1 | 3/2011 | Heim et al. |
| 2011/0066186 A1 | 3/2011 | Boyer, II et al. |
| 2011/0082551 A1 | 4/2011 | Kraus |
| 2011/0082553 A1 | 4/2011 | Abdou |
| 2011/0093074 A1 | 4/2011 | Glerum et al. |
| 2011/0098749 A1 | 4/2011 | Boomer et al. |
| 2011/0106163 A1 | 5/2011 | Hochschuler et al. |
| 2011/0106259 A1 | 5/2011 | Lindenmann et al. |
| 2011/0118552 A1 | 5/2011 | Fischvogt |
| 2011/0125266 A1 | 5/2011 | Rodgers et al. |
| 2011/0130793 A1 | 6/2011 | Woolley et al. |
| 2011/0137353 A1 | 6/2011 | Buttermann |
| 2011/0144692 A1 | 6/2011 | Saladin et al. |
| 2011/0166600 A1 | 7/2011 | Lamborne et al. |
| 2011/0172720 A1 | 7/2011 | Metcalf, Jr. et al. |
| 2011/0172772 A1 | 7/2011 | Abdou |
| 2011/0184471 A1 | 7/2011 | Foley et al. |
| 2011/0190825 A1 | 8/2011 | Thalgott et al. |
| 2011/0196492 A1 | 8/2011 | Lambrecht et al. |
| 2011/0213465 A1 | 9/2011 | Landry et al. |
| 2011/0224496 A1 | 9/2011 | Weiman |
| 2011/0224497 A1 | 9/2011 | Weiman et al. |

(56) References Cited

U.S. PATENT DOCUMENTS

| | | |
|---|---|---|
| 2011/0238181 A1 | 9/2011 | Trieu |
| 2011/0251693 A1 | 10/2011 | Barreiro et al. |
| 2011/0264218 A1 | 10/2011 | Asaad |
| 2011/0264228 A1 | 10/2011 | Johnson et al. |
| 2011/0276099 A1 | 11/2011 | Champagne et al. |
| 2011/0276142 A1 | 11/2011 | Niemiec et al. |
| 2011/0282459 A1 | 11/2011 | McClellan, III et al. |
| 2011/0288588 A1 | 11/2011 | Chin et al. |
| 2011/0288594 A1 | 11/2011 | Woolley et al. |
| 2011/0288644 A1 | 11/2011 | Gray et al. |
| 2011/0288645 A1 | 11/2011 | Braddock, Jr. et al. |
| 2011/0301710 A1 | 12/2011 | Mather et al. |
| 2011/0301712 A1 | 12/2011 | Palmatier et al. |
| 2011/0307011 A1 | 12/2011 | Moskowitz et al. |
| 2011/0307012 A1 | 12/2011 | Mir et al. |
| 2011/0319941 A1 | 12/2011 | Bar et al. |
| 2011/0319995 A1 | 12/2011 | Voellmicke et al. |
| 2012/0010472 A1 | 1/2012 | Spann |
| 2012/0010658 A1 | 1/2012 | Kirschman |
| 2012/0016481 A1 | 1/2012 | Zwirkoski |
| 2012/0029565 A1 | 2/2012 | Seifert et al. |
| 2012/0029639 A1 | 2/2012 | Blackwell et al. |
| 2012/0035424 A1 | 2/2012 | Schulte |
| 2012/0041272 A1 | 2/2012 | Dietze, Jr. et al. |
| 2012/0071980 A1 | 3/2012 | Purcell et al. |
| 2012/0078301 A1 | 3/2012 | Hess |
| 2012/0089184 A1 | 4/2012 | Yeh |
| 2012/0095512 A1 | 4/2012 | Nihalani |
| 2012/0101528 A1 | 4/2012 | Souza et al. |
| 2012/0123546 A1 | 5/2012 | Medina |
| 2012/0136442 A1 | 5/2012 | Kleiner |
| 2012/0150229 A1 | 6/2012 | Hess |
| 2012/0150302 A1 | 6/2012 | Gray |
| 2012/0158060 A1 | 6/2012 | Abrahams et al. |
| 2012/0158140 A1 | 6/2012 | Miller et al. |
| 2012/0158150 A1 | 6/2012 | Siegal |
| 2012/0179260 A1 | 7/2012 | Nottingham |
| 2012/0185045 A1 | 7/2012 | Morris et al. |
| 2012/0190933 A1 | 7/2012 | Kleyman |
| 2012/0191135 A1 | 7/2012 | Abdou |
| 2012/0197297 A1 | 8/2012 | Bootwala et al. |
| 2012/0197401 A1 | 8/2012 | Duncan et al. |
| 2012/0197402 A1 | 8/2012 | Blackwell et al. |
| 2012/0203279 A1 | 8/2012 | Walters et al. |
| 2012/0209271 A1 | 8/2012 | Cohen et al. |
| 2012/0209383 A1 | 8/2012 | Tsuang et al. |
| 2012/0215316 A1 | 8/2012 | Mohr et al. |
| 2012/0221049 A1 | 8/2012 | Blain et al. |
| 2012/0226313 A1 | 9/2012 | Dace |
| 2012/0232592 A1 | 9/2012 | Massoudi |
| 2012/0232658 A1 | 9/2012 | Morgenstern et al. |
| 2012/0238825 A1 | 9/2012 | Smith |
| 2012/0245425 A1 | 9/2012 | Okoniewski |
| 2012/0245431 A1 | 9/2012 | Baudouin et al. |
| 2012/0245432 A1 | 9/2012 | Karpowicz et al. |
| 2012/0245704 A1 | 9/2012 | Childs et al. |
| 2012/0253393 A1 | 10/2012 | Fiorella |
| 2012/0253396 A1 | 10/2012 | Stern et al. |
| 2012/0259416 A1 | 10/2012 | Blackwell et al. |
| 2012/0265021 A1 | 10/2012 | Nottmeier |
| 2012/0271119 A1 | 10/2012 | White |
| 2012/0277864 A1 | 11/2012 | Brodke et al. |
| 2012/0283521 A1 | 11/2012 | Smith et al. |
| 2012/0290017 A1 | 11/2012 | Haidukewych |
| 2012/0290096 A1 | 11/2012 | Messerli |
| 2012/0296171 A1 | 11/2012 | Lovell et al. |
| 2012/0296377 A1 | 11/2012 | Ferree et al. |
| 2013/0018467 A1 | 1/2013 | Suh |
| 2013/0023933 A1 | 1/2013 | Haas |
| 2013/0023937 A1 | 1/2013 | Biedermann et al. |
| 2013/0030467 A1 | 1/2013 | Karas et al. |
| 2013/0030469 A1 | 1/2013 | Karas et al. |
| 2013/0030470 A1 | 1/2013 | Karas et al. |
| 2013/0041471 A1 | 2/2013 | Siegal et al. |
| 2013/0053896 A1 | 2/2013 | Voyadzis |
| 2013/0060284 A1 | 3/2013 | Abdou |
| 2013/0066374 A1 | 3/2013 | Galley et al. |
| 2013/0079883 A1 | 3/2013 | Butler et al. |
| 2013/0090691 A1 | 4/2013 | Zhang et al. |
| 2013/0103088 A1 | 4/2013 | Karahalios et al. |
| 2013/0103089 A1 | 4/2013 | Gordon et al. |
| 2013/0123849 A1 | 5/2013 | Abdou |
| 2013/0123924 A1 | 5/2013 | Butler et al. |
| 2013/0131738 A1 | 5/2013 | Powell et al. |
| 2013/0144339 A1 | 6/2013 | Choi et al. |
| 2013/0144340 A1 | 6/2013 | Sheffer et al. |
| 2013/0144387 A1 | 6/2013 | Walker et al. |
| 2013/0144391 A1 | 6/2013 | Siegal et al. |
| 2013/0150886 A1 | 6/2013 | Altarac et al. |
| 2013/0150970 A1 | 6/2013 | Thaiyananthan |
| 2013/0158359 A1 | 6/2013 | Predick et al. |
| 2013/0165982 A1 | 6/2013 | Ek et al. |
| 2013/0172932 A1 | 7/2013 | Altarac et al. |
| 2013/0172933 A1 | 7/2013 | Altarac et al. |
| 2013/0172934 A1 | 7/2013 | Walker et al. |
| 2013/0184752 A1 | 7/2013 | Binder |
| 2013/0184758 A1 | 7/2013 | Karim |
| 2013/0190573 A1 | 7/2013 | Smith |
| 2013/0190575 A1 | 7/2013 | Mast et al. |
| 2013/0197647 A1 | 8/2013 | Wolters et al. |
| 2013/0204091 A1 | 8/2013 | Menendez et al. |
| 2013/0218166 A1 | 8/2013 | Elmore |
| 2013/0226240 A1 | 8/2013 | Abdou |
| 2013/0245383 A1 | 9/2013 | Friedrich et al. |
| 2013/0253585 A1 | 9/2013 | Garcia et al. |
| 2013/0253586 A1 | 9/2013 | Rathbun et al. |
| 2013/0261401 A1 | 10/2013 | Hawkins et al. |
| 2013/0261666 A1 | 10/2013 | Gundanna |
| 2013/0274883 A1 | 10/2013 | McLuen et al. |
| 2013/0274884 A1 | 10/2013 | Matsumoto et al. |
| 2013/0296939 A1 | 11/2013 | Perkins |
| 2013/0296940 A1 | 11/2013 | Northcutt et al. |
| 2013/0310942 A1 | 11/2013 | Abdou |
| 2013/0325128 A1 | 12/2013 | Perloff et al. |
| 2014/0005484 A1 | 1/2014 | Charles |
| 2014/0031874 A1 | 1/2014 | Kucharzyk et al. |
| 2014/0058512 A1 | 2/2014 | Petersheim |
| 2014/0058513 A1 | 2/2014 | Gahman et al. |
| 2014/0081331 A1 | 3/2014 | Zappacosta et al. |
| 2014/0107783 A1 | 4/2014 | Abdou |
| 2014/0114137 A1 | 4/2014 | Reglos et al. |
| 2014/0114138 A1 | 4/2014 | Fedorov et al. |
| 2014/0114139 A1 | 4/2014 | Ziolo et al. |
| 2014/0135584 A1 | 5/2014 | Lee et al. |
| 2014/0148652 A1 | 5/2014 | Weiman |
| 2014/0148856 A1 | 5/2014 | Ibarra et al. |
| 2014/0155939 A1 | 6/2014 | Sugawara |
| 2014/0172002 A1 | 6/2014 | Predick |
| 2014/0172105 A1 | 6/2014 | Frasier et al. |
| 2014/0172107 A1 | 6/2014 | Thirugnanasambandam et al. |
| 2014/0188223 A1 | 7/2014 | Jensen et al. |
| 2014/0188233 A1 | 7/2014 | Mutchler et al. |
| 2014/0249631 A1 | 9/2014 | Weiman |
| 2014/0257466 A1 | 9/2014 | Board et al. |
| 2014/0277143 A1 | 9/2014 | Zappacosta |
| 2014/0277486 A1* | 9/2014 | Abdou ............... A61F 2/4465 623/17.16 |
| 2014/0277490 A1 | 9/2014 | Perloff et al. |
| 2014/0277499 A1 | 9/2014 | Ainsworth et al. |
| 2014/0277502 A1 | 9/2014 | Schiffman et al. |
| 2014/0288480 A1 | 9/2014 | Zimmerman et al. |
| 2014/0309741 A1 | 10/2014 | Ganter et al. |
| 2014/0336471 A1 | 11/2014 | Pfabe et al. |
| 2014/0343608 A1 | 11/2014 | Whiton et al. |
| 2014/0343678 A1 | 11/2014 | Suddaby et al. |
| 2014/0350347 A1 | 11/2014 | Karpowicz et al. |
| 2014/0379032 A1 | 12/2014 | Hennard |
| 2014/0379086 A1 | 12/2014 | Elahinia et al. |
| 2015/0018829 A1 | 1/2015 | Woodburn, Sr. et al. |
| 2015/0057755 A1 | 2/2015 | Suddaby et al. |
| 2015/0080973 A1* | 3/2015 | Eastlack ............... A61B 17/025 606/86 A |
| 2015/0094814 A1 | 4/2015 | Emerick et al. |
| 2015/0190242 A1 | 7/2015 | Blain et al. |

(56) References Cited

U.S. PATENT DOCUMENTS

| | | |
|---|---|---|
| 2015/0202053 A1 | 7/2015 | Willis et al. |
| 2015/0257894 A1 | 9/2015 | Levy et al. |
| 2015/0305785 A1 | 10/2015 | Taber et al. |
| 2015/0313585 A1 | 11/2015 | Abidin et al. |
| 2015/0313650 A1 | 11/2015 | Taber et al. |
| 2015/0351738 A1 | 12/2015 | Perrow |
| 2015/0351925 A1 | 12/2015 | Emerick et al. |
| 2015/0359640 A1 | 12/2015 | Taber et al. |
| 2016/0000419 A1 | 1/2016 | Weisshaupt et al. |
| 2016/0030030 A1 | 2/2016 | Bass |
| 2016/0045333 A1 | 2/2016 | Baynham |
| 2016/0081681 A1 | 3/2016 | Waugh et al. |
| 2016/0089247 A1 | 3/2016 | Nichols et al. |
| 2016/0103689 A1 | 4/2016 | Sanghi et al. |
| 2016/0143747 A1 | 5/2016 | Agarwal et al. |
| 2016/0199195 A1 | 7/2016 | Hauck et al. |
| 2016/0213443 A1 | 7/2016 | Lueck et al. |
| 2016/0270772 A1 | 9/2016 | Beale et al. |
| 2016/0287236 A1 | 10/2016 | Garcia-Bengochea et al. |
| 2016/0310294 A1 | 10/2016 | McConnell et al. |
| 2016/0317323 A1 | 11/2016 | Cho et al. |
| 2016/0317324 A1 | 11/2016 | Cho et al. |
| 2016/0354210 A1 | 12/2016 | Tran |
| 2016/0361177 A1 | 12/2016 | Biedermann et al. |
| 2017/0007226 A1 | 1/2017 | Fehling |
| 2017/0014117 A1 | 1/2017 | Capote |
| 2017/0042527 A1 | 2/2017 | Farley et al. |
| 2017/0056194 A1 | 3/2017 | Biedermann et al. |
| 2017/0065269 A1 | 3/2017 | Thommen et al. |
| 2017/0112635 A1 | 4/2017 | Ty et al. |
| 2017/0143325 A1 | 5/2017 | Lynn et al. |
| 2017/0172759 A1 | 6/2017 | Kukkar et al. |
| 2017/0172760 A1 | 6/2017 | Loebl et al. |
| 2017/0231613 A1 | 8/2017 | Casey et al. |
| 2017/0245997 A1* | 8/2017 | Trischler ............ A61F 2/30771 |
| 2017/0340451 A1 | 11/2017 | McCormack et al. |
| 2018/0021149 A1 | 1/2018 | Boehm et al. |
| 2018/0085105 A1 | 3/2018 | Kim |
| 2018/0206834 A1 | 7/2018 | Villamil et al. |
| 2018/0235724 A1 | 8/2018 | Nowatschin et al. |
| 2018/0249992 A1 | 9/2018 | Truckey |
| 2018/0256363 A1 | 9/2018 | Moon |
| 2018/0289506 A1 | 10/2018 | Kim et al. |
| 2018/0303624 A1 | 10/2018 | Shoshtaev |
| 2018/0310927 A1 | 11/2018 | Garcia-Bengochea et al. |
| 2018/0333061 A1 | 11/2018 | Pracyk et al. |
| 2018/0344481 A1 | 12/2018 | Garcia-Bengochea |
| 2018/0360621 A1 | 12/2018 | Moon |
| 2019/0192312 A1 | 6/2019 | Ullrich, Jr. et al. |
| 2019/0209154 A1 | 7/2019 | Richter et al. |
| 2019/0216450 A1 | 7/2019 | Bjork et al. |
| 2019/0216453 A1 | 7/2019 | Predick et al. |
| 2019/0307439 A1 | 10/2019 | Chhit et al. |
| 2019/0321022 A1 | 10/2019 | Karpowicz et al. |
| 2020/0085530 A1 | 3/2020 | Sauer |
| 2020/0113713 A1 | 4/2020 | LaMarca et al. |

FOREIGN PATENT DOCUMENTS

| | | |
|---|---|---|
| DE | 29911422 U1 | 8/1999 |
| DE | 10035182 A1 | 2/2002 |
| DE | 20320454 U1 | 10/2004 |
| DE | 10323363 A1 | 12/2004 |
| EP | 0077159 A1 | 4/1983 |
| EP | 0274713 A1 | 7/1988 |
| EP | 0301489 A1 | 2/1989 |
| EP | 0317972 A1 | 5/1989 |
| EP | 0333990 A2 | 9/1989 |
| EP | 0356112 A1 | 2/1990 |
| EP | 0418387 A1 | 3/1991 |
| EP | 0512529 A1 | 11/1992 |
| EP | 0560141 A1 | 9/1993 |
| EP | 0566810 A1 | 10/1993 |
| EP | 0611116 A1 | 8/1994 |
| EP | 0614649 A1 | 9/1994 |
| EP | 0637439 A1 | 2/1995 |
| EP | 0697200 A1 | 2/1996 |
| EP | 0611116 B1 | 7/1996 |
| EP | 0566810 B1 | 8/1996 |
| EP | 0747025 A1 | 12/1996 |
| EP | 0951879 A2 | 10/1999 |
| EP | 0955021 A1 | 11/1999 |
| EP | 0965313 A1 | 12/1999 |
| EP | 1180348 A2 | 2/2002 |
| EP | 1192910 A2 | 4/2002 |
| EP | 1222903 A1 | 7/2002 |
| EP | 1254640 A2 | 11/2002 |
| EP | 1287795 A1 | 3/2003 |
| EP | 1442715 A2 | 8/2004 |
| EP | 1504733 A1 | 2/2005 |
| EP | 1374808 B1 | 12/2005 |
| EP | 1758511 A2 | 3/2007 |
| EP | 1848352 A2 | 10/2007 |
| EP | 1872731 A1 | 1/2008 |
| EP | 1942816 A2 | 7/2008 |
| EP | 1942838 A2 | 7/2008 |
| EP | 1980222 A1 | 10/2008 |
| EP | 1389978 B1 | 1/2009 |
| EP | 2032086 A2 | 3/2009 |
| EP | 2101691 A2 | 9/2009 |
| EP | 2113228 A1 | 11/2009 |
| EP | 2327375 A1 | 6/2011 |
| EP | 2340788 A1 | 7/2011 |
| EP | 2363080 A1 | 9/2011 |
| EP | 2131790 B1 | 10/2012 |
| EP | 3111896 A1 | 1/2017 |
| FR | 1037262 A | 9/1953 |
| FR | 2124815 A5 | 9/1972 |
| FR | 2632516 A1 | 12/1989 |
| FR | 2659226 A1 | 9/1991 |
| FR | 2703239 A1 | 10/1994 |
| FR | 2703580 A1 | 10/1994 |
| FR | 2723841 A1 | 3/1996 |
| FR | 2724108 A1 | 3/1996 |
| FR | 2730159 A1 | 8/1996 |
| FR | 2733413 A1 | 10/1996 |
| FR | 2747034 A1 | 10/1997 |
| FR | 2781359 A1 | 1/2000 |
| FR | 2787021 A1 | 6/2000 |
| FR | 2788958 A1 | 8/2000 |
| FR | 2806614 A1 | 9/2001 |
| FR | 2808995 A1 | 11/2001 |
| FR | 2813782 A1 | 3/2002 |
| FR | 2824261 A1 | 11/2002 |
| FR | 2827156 A1 | 1/2003 |
| FR | 2831796 A1 | 5/2003 |
| FR | 2846550 A1 | 5/2004 |
| FR | 2856271 A1 | 12/2004 |
| FR | 2861582 A1 | 5/2005 |
| FR | 2865629 A1 | 8/2005 |
| FR | 2879436 A1 | 6/2006 |
| FR | 2880795 A1 | 7/2006 |
| FR | 2887762 A1 | 1/2007 |
| FR | 2891135 A1 | 3/2007 |
| FR | 2893838 A1 | 6/2007 |
| FR | 2897259 A1 | 8/2007 |
| FR | 2902639 A1 | 12/2007 |
| FR | 2916956 A1 | 12/2008 |
| FR | 2930718 A1 | 11/2009 |
| GB | 780652 A | 8/1957 |
| GB | 2178323 A | 2/1987 |
| JP | H02261446 A | 10/1990 |
| JP | H0998983 A | 4/1997 |
| WO | WO-9000037 A1 | 1/1990 |
| WO | WO-9107931 A1 | 6/1991 |
| WO | WO-9301771 A1 | 2/1993 |
| WO | WO-9307823 A1 | 4/1993 |
| WO | WO-9314721 A1 | 8/1993 |
| WO | WO-9404100 A1 | 3/1994 |
| WO | WO-9420048 A1 | 9/1994 |
| WO | WO-9508306 A1 | 3/1995 |
| WO | WO-9510240 A1 | 4/1995 |
| WO | WO-9515133 A1 | 6/1995 |
| WO | WO-9525474 A1 | 9/1995 |

(56) References Cited

FOREIGN PATENT DOCUMENTS

| | | |
|---|---|---|
| WO | WO-9715248 A1 | 5/1997 |
| WO | WO-9723174 A1 | 7/1997 |
| WO | WO-9730666 A2 | 8/1997 |
| WO | WO-9737620 A1 | 10/1997 |
| WO | WO-9801091 A1 | 1/1998 |
| WO | WO-9817209 A2 | 4/1998 |
| WO | WO-9855052 A1 | 12/1998 |
| WO | WO-9900065 A1 | 1/1999 |
| WO | WO-9904718 A1 | 2/1999 |
| WO | WO-9909914 A1 | 3/1999 |
| WO | WO-9921500 A1 | 5/1999 |
| WO | WO-9921502 A1 | 5/1999 |
| WO | WO-9933405 A1 | 7/1999 |
| WO | WO-9938463 A2 | 8/1999 |
| WO | WO-9953871 A1 | 10/1999 |
| WO | WO-9956653 A1 | 11/1999 |
| WO | WO-9956675 A1 | 11/1999 |
| WO | WO-9956676 A1 | 11/1999 |
| WO | WO-9963914 A1 | 12/1999 |
| WO | WO-9965412 A1 | 12/1999 |
| WO | WO-9966864 A1 | 12/1999 |
| WO | WO-0015125 A1 | 3/2000 |
| WO | WO-0018312 A1 | 4/2000 |
| WO | WO-0023015 A1 | 4/2000 |
| WO | WO-0024325 A1 | 5/2000 |
| WO | WO-0024327 A2 | 5/2000 |
| WO | WO-0053127 A1 | 9/2000 |
| WO | WO-0064362 A1 | 11/2000 |
| WO | WO-0072770 A1 | 12/2000 |
| WO | WO-0074606 A1 | 12/2000 |
| WO | WO-0078238 A1 | 12/2000 |
| WO | WO-0101874 A1 | 1/2001 |
| WO | WO-0103592 A1 | 1/2001 |
| WO | WO-0106940 A1 | 2/2001 |
| WO | WO-0119295 A1 | 3/2001 |
| WO | WO-0126566 A1 | 4/2001 |
| WO | WO-0128465 A2 | 4/2001 |
| WO | WO-0141680 A1 | 6/2001 |
| WO | WO-0143620 A2 | 6/2001 |
| WO | WO-0145577 A2 | 6/2001 |
| WO | WO-0160270 A1 | 8/2001 |
| WO | WO-0162191 A2 | 8/2001 |
| WO | WO-0170141 A1 | 9/2001 |
| WO | WO-0187194 A1 | 11/2001 |
| WO | WO-0211633 A2 | 2/2002 |
| WO | WO-0213732 A2 | 2/2002 |
| WO | WO-0228299 A1 | 4/2002 |
| WO | WO-0230307 A2 | 4/2002 |
| WO | WO-02051326 A1 | 7/2002 |
| WO | WO-02058599 A2 | 8/2002 |
| WO | WO-02058600 A2 | 8/2002 |
| WO | WO-02071960 A1 | 9/2002 |
| WO | WO-02076315 A1 | 10/2002 |
| WO | WO-02080788 A1 | 10/2002 |
| WO | WO-02089701 A2 | 11/2002 |
| WO | WO-03005939 A2 | 1/2003 |
| WO | WO-03007829 A1 | 1/2003 |
| WO | WO-03015646 A2 | 2/2003 |
| WO | WO-03024298 A2 | 3/2003 |
| WO | WO-03026522 A2 | 4/2003 |
| WO | WO-03032850 A1 | 4/2003 |
| WO | WO-03032851 A1 | 4/2003 |
| WO | WO-03037200 A2 | 5/2003 |
| WO | WO-03039400 A2 | 5/2003 |
| WO | WO-03045262 A2 | 6/2003 |
| WO | WO-03049629 A1 | 6/2003 |
| WO | WO-03051212 A2 | 6/2003 |
| WO | WO-03059212 A1 | 7/2003 |
| WO | WO-03075803 A1 | 9/2003 |
| WO | WO-03075804 A1 | 9/2003 |
| WO | WO-2004016217 A2 | 2/2004 |
| WO | WO-2004032726 A2 | 4/2004 |
| WO | WO-2004034935 A1 | 4/2004 |
| WO | WO-2004039283 A2 | 5/2004 |
| WO | WO-2004039291 A1 | 5/2004 |
| WO | WO-2004041129 A1 | 5/2004 |
| WO | WO-2004049915 A2 | 6/2004 |
| WO | WO-2004062482 A2 | 7/2004 |
| WO | WO-2004084774 A1 | 10/2004 |
| WO | WO-2004093702 A2 | 11/2004 |
| WO | WO-2004105577 A2 | 12/2004 |
| WO | WO-2005007040 A1 | 1/2005 |
| WO | WO-2005009262 A1 | 2/2005 |
| WO | WO-2005011522 A2 | 2/2005 |
| WO | WO-2005020829 A1 | 3/2005 |
| WO | WO-2005044119 A2 | 5/2005 |
| WO | WO-2005046534 A1 | 5/2005 |
| WO | WO-2005051243 A2 | 6/2005 |
| WO | WO-2005074839 A1 | 8/2005 |
| WO | WO-2005077288 A1 | 8/2005 |
| WO | WO-2005104996 A1 | 11/2005 |
| WO | WO-2005117728 A1 | 12/2005 |
| WO | WO-2005122922 A2 | 12/2005 |
| WO | WO-2006016384 A1 | 2/2006 |
| WO | WO-2006041963 A2 | 4/2006 |
| WO | WO-2006042335 A1 | 4/2006 |
| WO | WO-2006045089 A2 | 4/2006 |
| WO | WO-2006047587 A2 | 5/2006 |
| WO | WO-2006058221 A2 | 6/2006 |
| WO | WO-2006062960 A2 | 6/2006 |
| WO | WO-2006086241 A2 | 8/2006 |
| WO | WO-2006089292 A2 | 8/2006 |
| WO | WO-2006096756 A2 | 9/2006 |
| WO | WO-2006106268 A2 | 10/2006 |
| WO | WO-2006110578 A2 | 10/2006 |
| WO | WO-2006120505 A1 | 11/2006 |
| WO | WO-2006130460 A2 | 12/2006 |
| WO | WO-2006136760 A2 | 12/2006 |
| WO | WO-2007000634 A1 | 1/2007 |
| WO | WO-2007000654 A2 | 1/2007 |
| WO | WO-2007034310 A1 | 3/2007 |
| WO | WO-2007038475 A2 | 4/2007 |
| WO | WO-2007041648 A2 | 4/2007 |
| WO | WO-2007044705 A2 | 4/2007 |
| WO | WO-2007044836 A2 | 4/2007 |
| WO | WO-2007056516 A2 | 5/2007 |
| WO | WO-2007059207 A2 | 5/2007 |
| WO | WO-2007063398 A2 | 6/2007 |
| WO | WO-2007078978 A2 | 7/2007 |
| WO | WO-2007087535 A2 | 8/2007 |
| WO | WO-2007089975 A1 | 8/2007 |
| WO | WO-2007093900 A2 | 8/2007 |
| WO | WO-2007095333 A2 | 8/2007 |
| WO | WO-2007106573 A2 | 9/2007 |
| WO | WO-2007075843 A3 | 12/2007 |
| WO | WO-2007140382 A2 | 12/2007 |
| WO | WO-2008013960 A2 | 1/2008 |
| WO | WO-2008021319 A2 | 2/2008 |
| WO | WO-2008024373 A2 | 2/2008 |
| WO | WO-2008067452 A1 | 6/2008 |
| WO | WO-2008073447 A2 | 6/2008 |
| WO | WO-2008082836 A1 | 7/2008 |
| WO | WO-2008085521 A1 | 7/2008 |
| WO | WO-2008099277 A2 | 8/2008 |
| WO | WO-2008106140 A2 | 9/2008 |
| WO | WO-2008131084 A2 | 10/2008 |
| WO | WO-2008149223 A2 | 12/2008 |
| WO | WO-2009033100 A1 | 3/2009 |
| WO | WO-2009064787 A2 | 5/2009 |
| WO | WO-2009135208 A1 | 11/2009 |
| WO | WO-2009152126 A1 | 12/2009 |
| WO | WO-2010057980 A1 | 5/2010 |
| WO | WO-2013006830 A1 | 1/2013 |

OTHER PUBLICATIONS

Abstract for French Patent Publication FR2856271, Published Dec. 24, 2004, Osteo-Synthesis Vertebral Column Plate, has Connection Head Integrated with Plate and Movable in Three Directions of Space so as to Adapt itself to Connection Rod, and Including Opening to Facilitate Introduction of Rod. Accession No. 14694557, (Derwent Information Ltd.).

(56) References Cited

OTHER PUBLICATIONS

Abstract for German Patent No. DE10035182. (Derwent Information Ltd.), publication date Feb. 7, 2002.
Andersen T., et al., "Pain 5 years After Instrumented and Non-Instrumented Posterolateral Lumbar Spinal Fusion," European Spine Journal, 2003, vol. 12 (4), pp. 393-399.
Asazuma T., et al., "Intersegmental Spinal Flexibility With Lumbosacral Instrumentation. An In Vitro Biomechanical Investigation," Spine (Phila Pa 1976), 1990, vol. 15 (11), pp. 1153-1158.
Balderston R.A., et al., "Technique for Achievement and Maintenance of Reduction for Severe Spondylolisthesis Using Spinous Process Traction Wiring and External Fixation of the Pelvis," Spine (Phila Pa 1976), 1985, vol. 10 (4), pp. 376-382.
Barbre C.J.,, "Devices for Targeting the Needle," Neurosurgery Clinics of North America, 2009, vol. 20 (2), pp. 187-191.
Bendo J.A., et al., "Instrumented Posterior Arthrodesis of the Lumbar Spine in Patients with Diabetes Mellitus," American Journal of Orthopedics (Belle Mead, NJ), 2000, vol. 29 (8), pp. 617-620.
Benz R.J., et al., "Current Techniques of Decompression of the Lumbar Spine," Clinical Orthopaedics and Related Research, 2001, No. 384, pp. 75-81.
BOSTMAN O., et al., "Posterior Spinal Fusion Using Internal Fixation with the Daab Plate," Acta Orthopaedica Scandinavica, 1984, vol. 55 (3), pp. 310-314.
Branch C.L., et al., "Posterior Lumbar Interbody Fusion with the Keystone Graft: Technique and Results," Surgical Neurology, 1987, vol. 27 (5), pp. 449-454.
Bridwell K. H., et al., "Decision Making Regarding Smith-Petersen vs. Pedicle Subtraction Osteotomy vs. Vertebral Column Resection for Spinal Deformity," Spine, 2006, vol. 31(19S), pp. S171-S178.
Chen W.J., et al., "Surgical Treatment of Adjacent Instability After Lumbar Spine Fusion," Spine (Phila Pa 1976), 2001, vol. 26 (22), pp. E519-E524.
Chiba M., et al., "Short-Segment Pedicle Instrumentation. Biomechanical Analysis of Supplemental Hook Fixation," Spine (Phila Pa 1976), 1996, vol. 21 (3), pp. 288-294.
Cobo S.J., et al., "Predictors of Outcome After Decompressive Lumbar Surgery and Instrumented Posterolateral Fusion," European Spine Journal, 2010, vol. 19 (11), pp. 1841-1848.
Collins P., Carbon Multiwall Nanotubes: A High-Performance Conductive Additive for Demanding Plastics Applications, Materials Integrity Management Symposium, Jun. 2004, Retrieved from the Internet URL : (http://hyperioncatalysis.com/PDFs/CMWNT.pdf>).
"Curve, The Ultimate Control and Information Center" from https://www.brainlab.com/surgery-products/overview-platform-products/curve-image-guided-surgery/, 8 pages, downloaded from the Internet Mar. 27, 2014.
Dar G., et al., "The Epiphyses Ring: A Long Forgotten Anatomical Structure with Significant Physiological Function", Spine Anatomy, (PA 1976). May 15, 2011, vol. 36 (11), pp. 850-856.
Dawson E.G., et al., "Intertransverse Process Lumbararthodesis with Autogenous Bone Graft," Clinical Orthopaedics and Related Research, 1981, No. 154, pp. 90-96.
Deguchi M., et al., "Biomechanical Comparison of Spondylolysis Fixation Techniques," Spine (Phila Pa 1976), 1999, vol. 24 (4), pp. 328-333.
Denis, F., "The Three Column Spine and its Significance in the Classification of Acute Thoracolumbar Spinal Injuries," Spine (Phila Pa 1976), 1983, vol. 8 (8), pp. 817-831.
Lorenz M., et al., "A Comparison of Single-Level Fusions with and without Hardware," Spine (Phila Pa 1976), 1991, vol. 16 (8 Suppl), pp. S455-S458.
Lowery G.L., "Orion Anterior Cervical Plate System" in: Spinal Instrumentation—Surgical Techniques, Kim D.H., et al., eds., Thieme Medical Publications (New York), 2005, pp. 116-122.
Luque E.R., "Segmental Spinal Instrumentation of the Lumbar Spine," Clinical Orthopaedics and Related Research, 1986, No. 203, pp. 126-134.

Madan S., et al., "Outcome of Posterior Lumbar Interbody Fusion Versus Posterolateral Fusion for Spondylolytic Spondylolisthesis," Spine (Phila Pa 1976), 2002, vol. 27 (14), pp. 1536-1542.
Madan S.S., et al., "Circumferential and Posterolateral Fusion for Lumbar Disc Disease," Clinical Orthopaedics and Related Research, 2003, No. 409, pp. 114-123.
Marotta N., et al., "A Novel Minimally Invasive Presacral Approach and Instrumentation Technique for Anterior L5-S1 Intervertebral Discectomy and Fusion: Technical Description and Case Presentations," Neurosurgical Focus, 2006, vol. 20 (1), pp. E9.
McInerney J., et al., "Frameless Stereotaxy of the Brain," The Mount Sinai Journal of Medicine, 2000, vol. 67 (4), pp. 300-310.
Moskowitz A., "Transforaminal Lumbar Interbody Fusion," Orthopedic Clinics of North America, 2002, vol. 33 (2), pp. 359-366.
Nardi P., et al., "Aperius PercLID Stand Alone Interspinous System for the Treatment of Degenerative Lumbar Stenosis: Experience on 152 Cases," Journal of Spinal Disorders & Techniques, 2010, vol. 23 (3), pp. 203-207.
Neo M., et al., "Spinous Process Plate Fixation as a Salvage Operation for Failed Anterior Cervical Fusion. Technical Note," Journal of Neurosurgery: Spine, 2006, vol. 4 (1), pp. 78-81.
O'Leary P.F., et al., "Distraction Laminoplasty for Decompression of Lumbar Spinal Stenosis," Clinical Orthopaedics and Related Research, 2001, No. 384, pp. 26-34.
Ozgur B.M., et al., "Extreme Lateral Interbody Fusion (XLIF): A Novel Surgical Technique for Anterior Lumbar Interbody Fusion," Spine Journal, 2006, vol. 6 (4), pp. 435-443.
Polly D.W., et al., "Surgical Treatment for the Painful Motion Segment: Matching Technology with the Indications: Posterior Lumbar Fusion," Spine (Phila Pa 1976), 2005, vol. 30 (16 Suppl), pp. S44-S51.
Qian D., et al., "Mechanics of Carbon Nanotubes," Applied Mechanics Reviews, 2002, vol. 55 (2), pp. 495-533.
Rapoff A.J., et al., "Biomechanical Comparison of Posterior Lumbar Interbody Fusion Cages," Spine (Phila Pa 1976), 1997, vol. 22 (20), pp. 2375-2379.
Rompe J.D., et al., "Degenerative Lumbar Spinal Stenosis. Long-Term Results After Undercutting Decompression Compared with Decompressive Laminectomy Alone or with Instrumented Fusion," Neurosurgical Review, 1999, vol. 22 (2-3), pp. 102-106.
Rousseau M.A., et al., "Predictors of Outcomes After Posterior Decompression and Fusion in Degenerative Spondylolisthesis," European Spine Journal, 2005, vol. 14 (1), pp. 55-60.
Santoni BG., et al., "Cortical Bone Trajectory for Lumbar Pedicle Screws" The Spine Journal, 2009, vol. 9 (5), pp. 366-373.
Sasso R.C., et al., "Translaminar Facet Screw Fixation," World Spine Journal, 2006, vol. 1 (1), pp. 34-39.
Sidhu K.S., et al., "Spinal Instrumentation in the Management of Degenerative Disorders of the Lumbar Spine," Clinical Orthopaedics and Related Research, 1997, No. 335, pp. 39-53.
Smith M.D., et al., "A Biomechanical Analysis of Atlantoaxial Stabilization Methods Using a Bovine Model. C1/C2 Fixation Analysis," Clinical Orthopaedics and Related Research, 1993, No. 290, pp. 285-295.
Stambough J.L., et al., "Instrumented One and Two Level Posterolateral Fusions with Recombinant Human Bone Morphogenetic Protein-2 and Allograft: A Computed Tomography Study," Spine (Phila Pa 1976), 2010, vol. 35 (1), pp. 124-129.
Stambough J.L., "Lumbosacral Instrumented Fusion: Analysis of 124 Consecutive Cases," Journal of Spinal Disorders, 1999, vol. 12 (1), pp. 1-9.
Suzuki Y., "Shape Memory and Super-Elasticity Effects in NiTi Alloys," Titanium-Zirconium, 1982, vol. 30 (4), pp. 185-192.
Swanson K.E., et al., "The Effects of an Interspinous Implant on Intervertebral Disc Pressures," Spine (Phila Pa 1976), 2003, vol. 28 (1), pp. 26-32.
Thomsen K., et al., "1997 Volvo Award Winner in Clinical Studies. The Effect of Pedicle Screw Instrumentation on Functional Outcome and Fusion Rates in Posterolateral Lumbar Spinal Fusion: A Prospective, Randomized Clinical Study," Spine (Phila Pa 1976), 1997, vol. 22 (24), pp. 2813-2822.

(56) References Cited

OTHER PUBLICATIONS

Tseng Y.C., et al., "Monolithic Integration of Carbon Nanotube Devices with Silicon MOS Technology," Nano Letters, 2004, vol. 4 (1), pp. 123-127.

Vamvanij V., et al., "Surgical Treatment of Internal Disc Disruption: An Outcome Study of Four Fusion Techniques," Journal of Spinal Disorders, 1998, vol. 11 (5), pp. 375-382.

Voor M.J., et al., "Biomechanical Evaluation of Posterior and Anterior Lumbar Interbody Fusion Techniques," Journal of Spinal Disorders, 1998, vol. 11 (4), pp. 328-334.

Wang J.C., et al., "Comparison of CD Horizon Spire Spinous Process Plate Stabilization and Pedicle Screw Fixation after Anterior Lumbar Interbody Fusion. Invited Submission from the Joint Section Meeting on Disorders of the Spine and Peripheral Nerves, Mar. 2005," Journal of Neurosurgery: Spine, 2006, vol. 4 (2), pp. 132-136.

Wang J.C., et al., "SPIRE Spinous Process Stabilization Plate: Biomechanical Evaluation of a Novel Technology. Invited Submission from the Joint Section Meeting on Disorders of the Spine and Peripheral Nerves, Mar. 2005," Journal of Neurosurgery: Spine, 2006, vol. 4 (2), pp. 160-164.

Webster T.J., et al., "Increased Osteoblast Adhesion on Nanophase Metals: Ti, Ti6Al4V, and CoCrMo," Biomaterials, 2004, vol. 25 (19), pp. 4731-4739.

Willard, F. H., et al., "The Thoracolumbar Fascia: Anatomy, Function and Clinical Considerations." Journal of Anatomy, 2012, vol. 221(6), pp. 507-536.

Wohns R.N.W., et al., Day Surgery for Anterior Cervical Microdiskectomy: Experience with 75 Cases, Jul. 11, 2002, pp. 1-3.

Wood M.J., et al., "Improving Accuracy and Reducing Radiation Exposure in Minimally Invasive Lumbar Interbody Fusion," Journal of Neurosurgery: Spine, 2010, vol. 12 (5), pp. 533-539.

Yang C.K., et al., "Binding energies and electronic Structures of Adsorbed Titanium Chains on Carbon Nanotubes," Physical Review 66, 2002, 041403-1.

Yerby S., et al., "The Effect of Cutting Flute Design on the Insertion and Pullout Properties of Self-tapping Bone Screws," Jul. 2, 2002, pp. 1-2.

\* cited by examiner

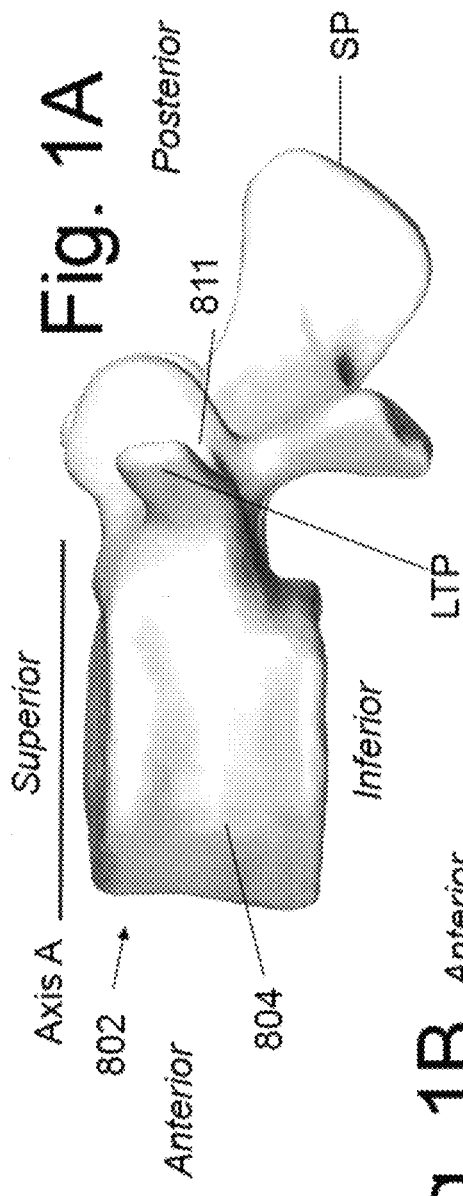
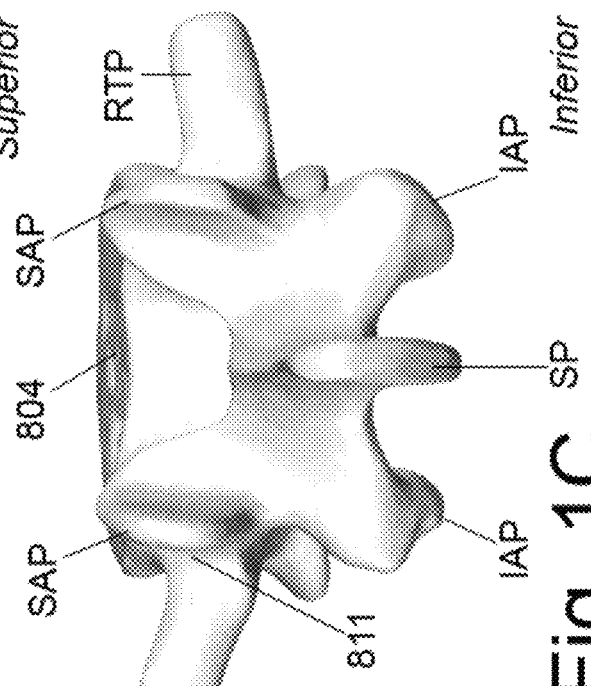
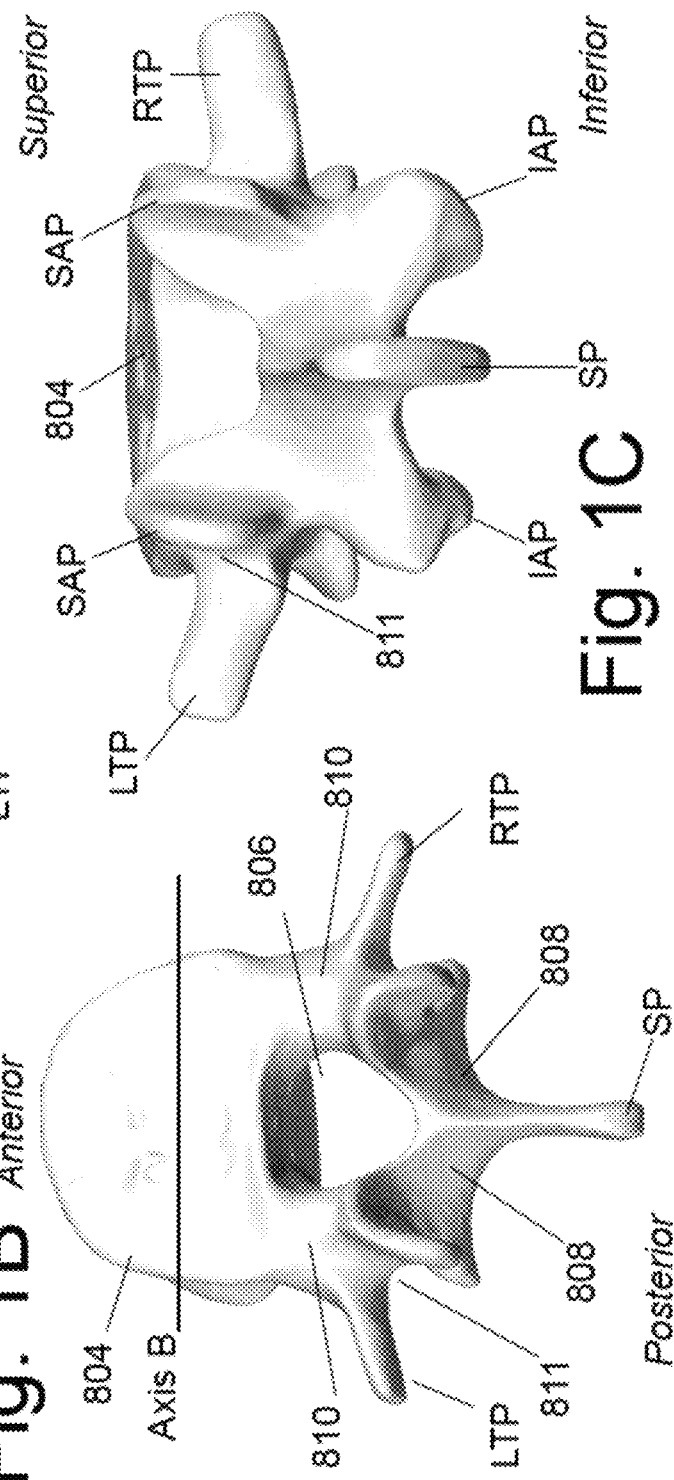

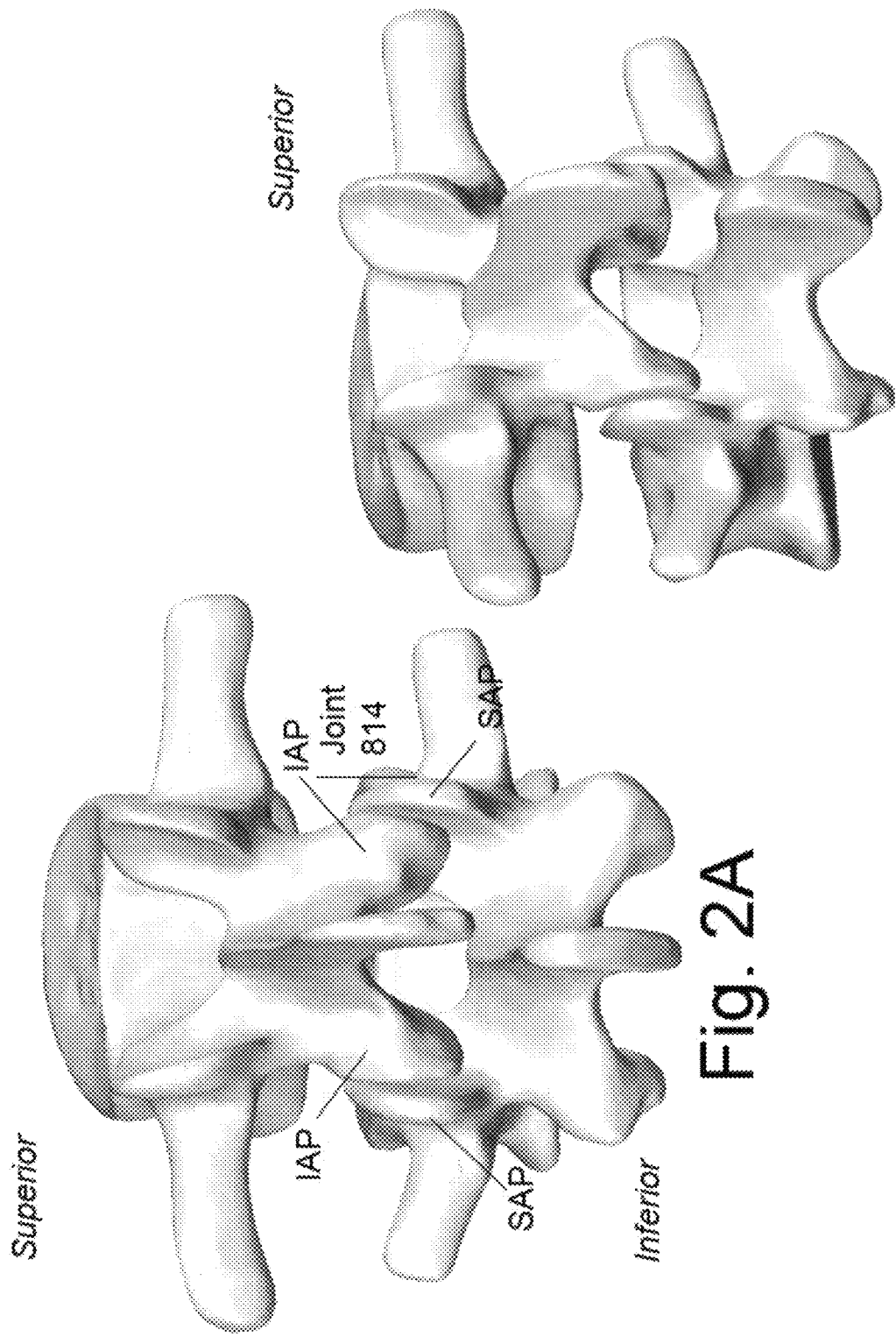

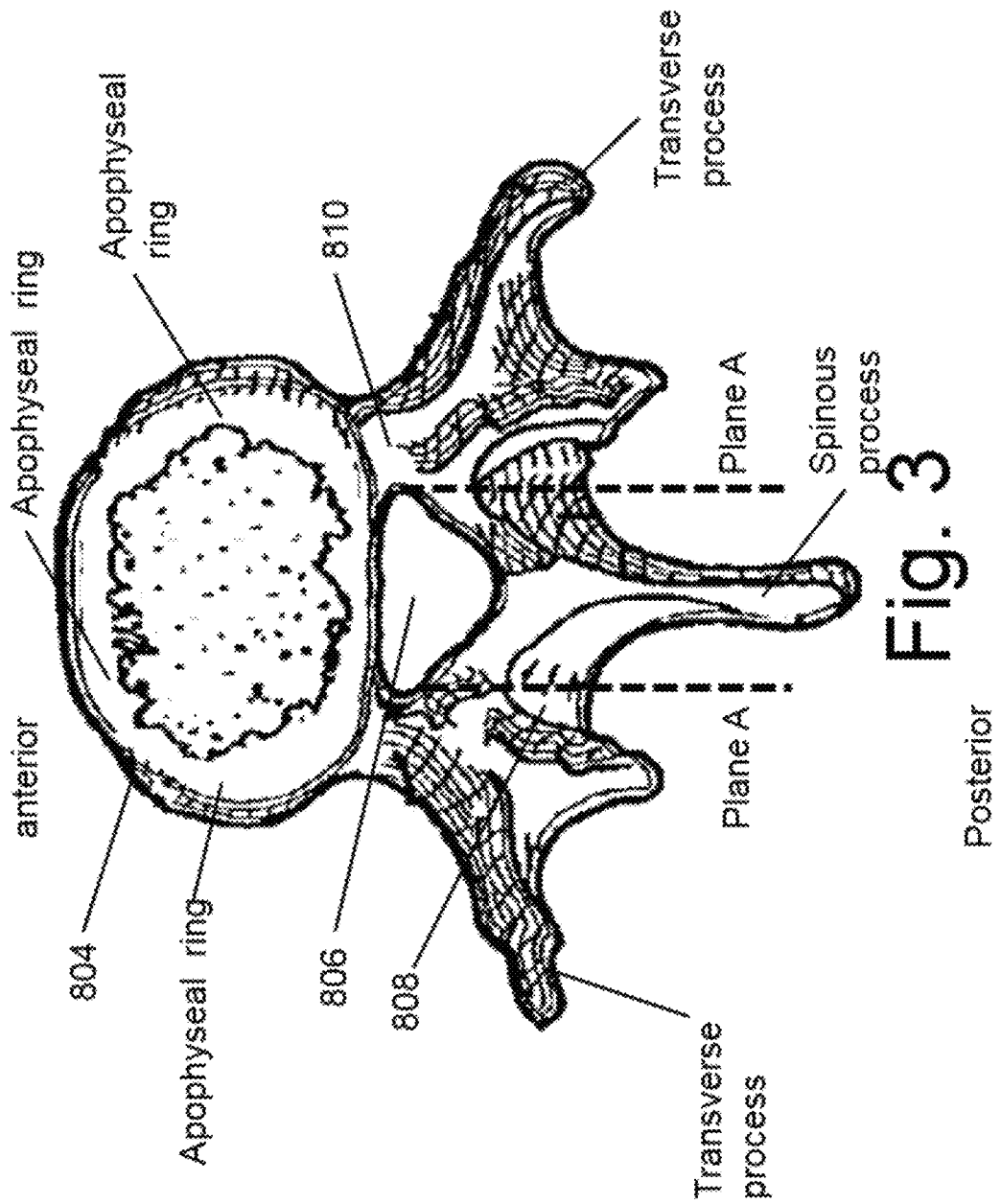

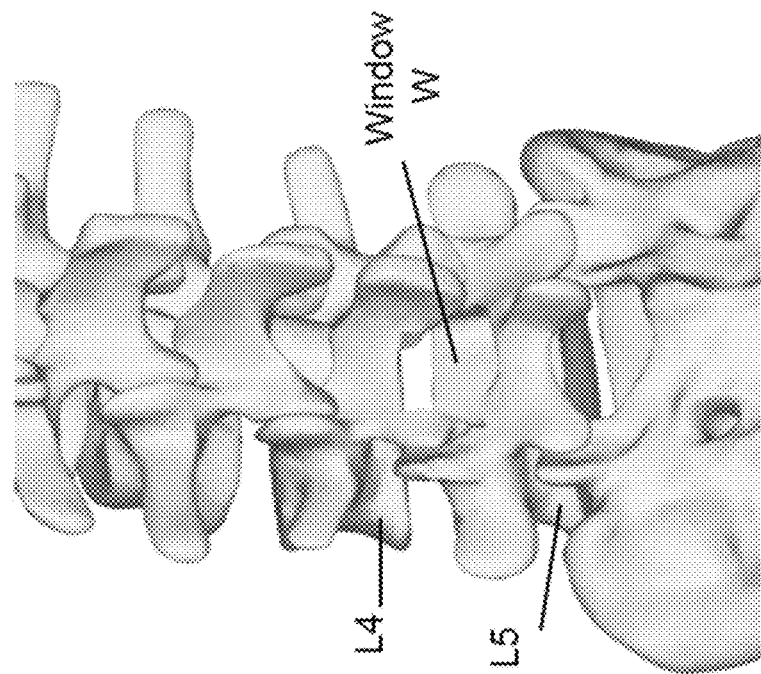
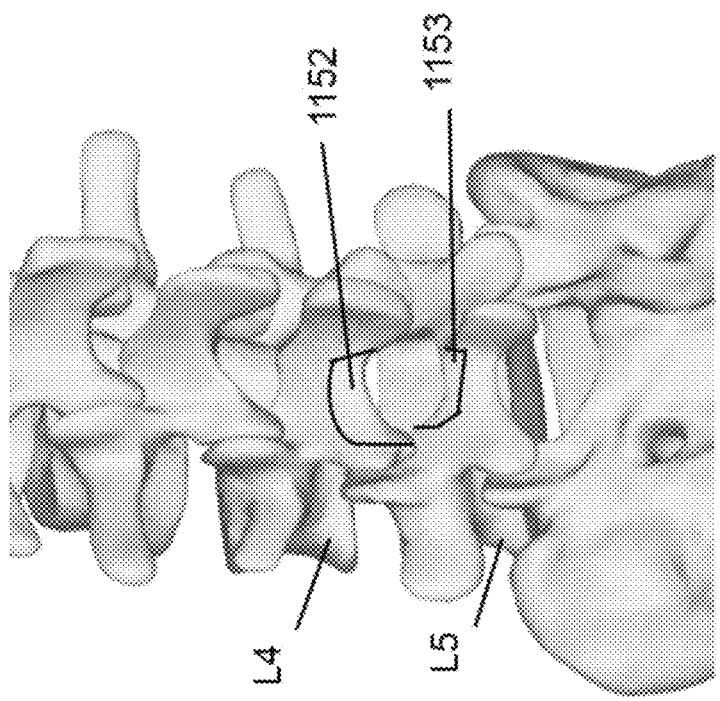

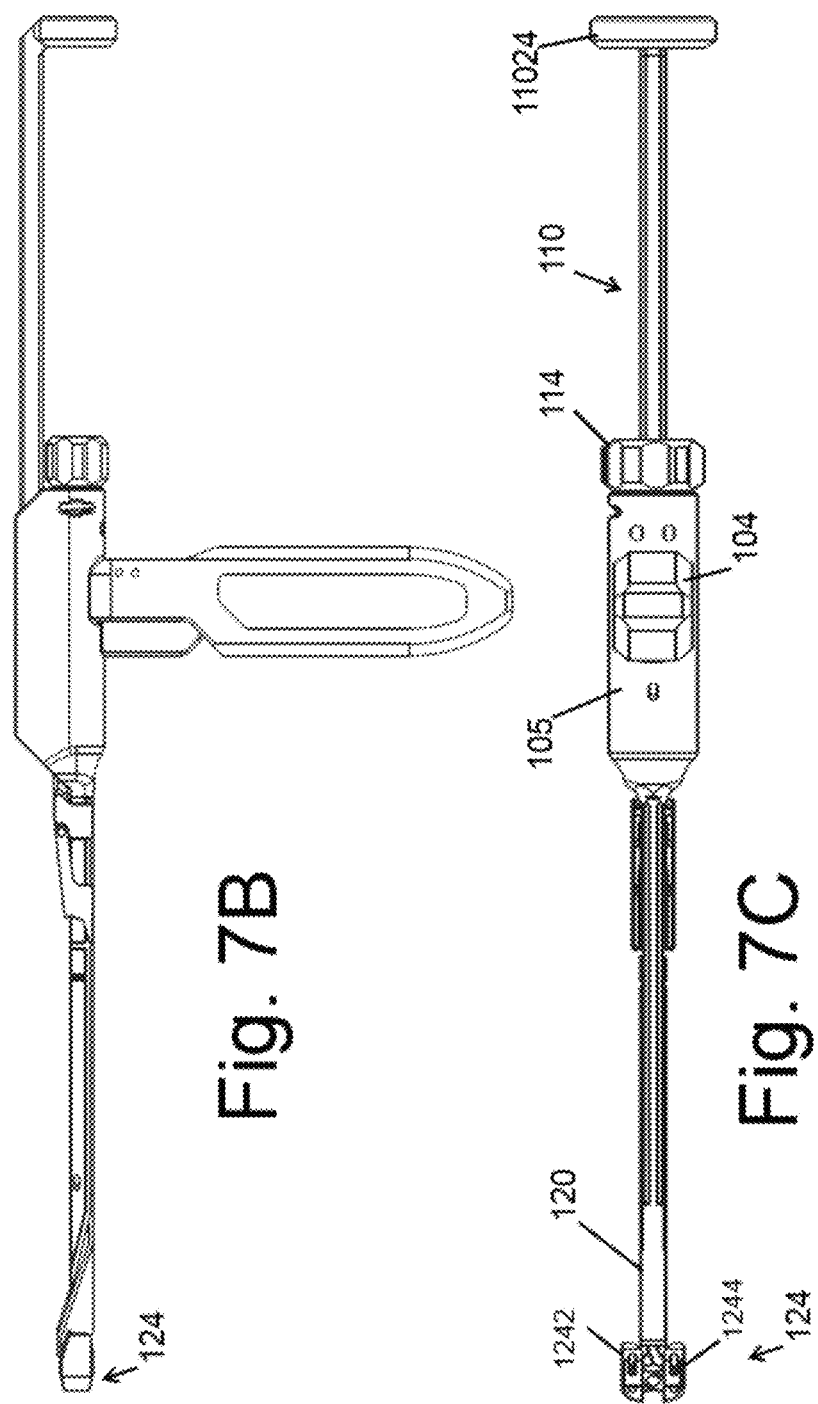

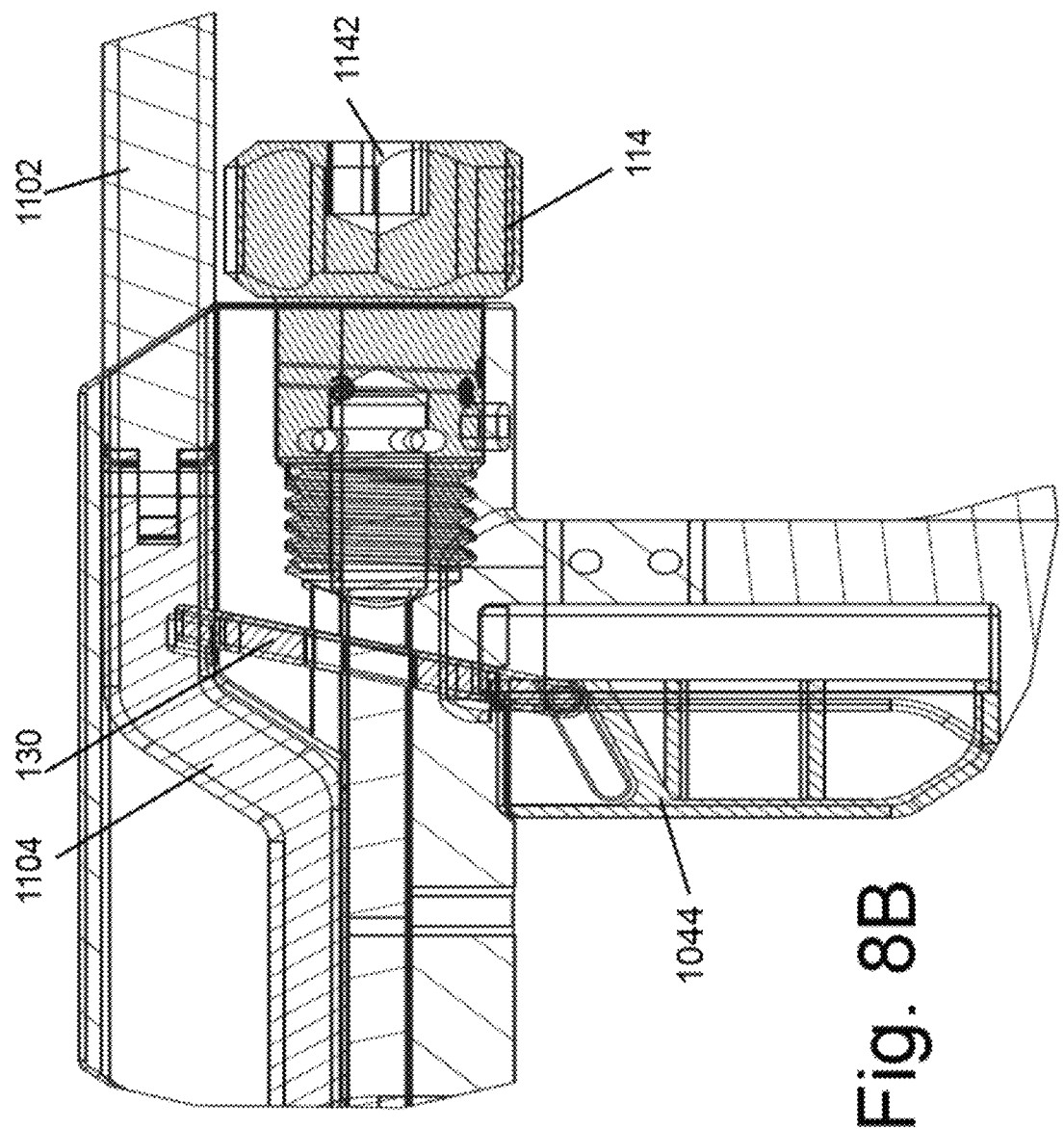

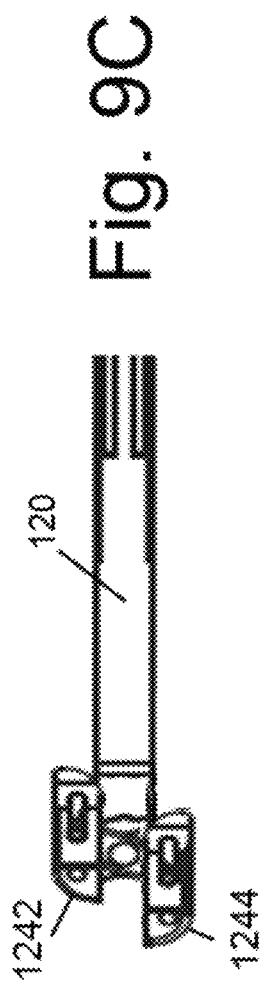
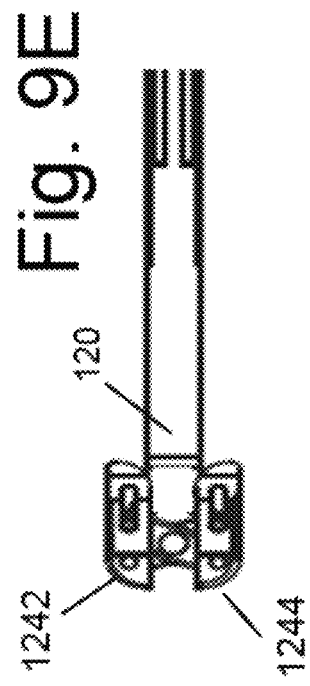
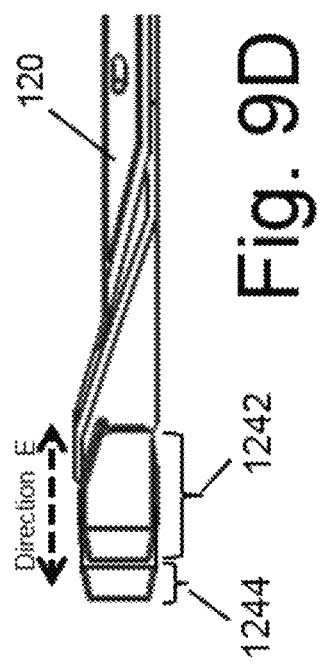
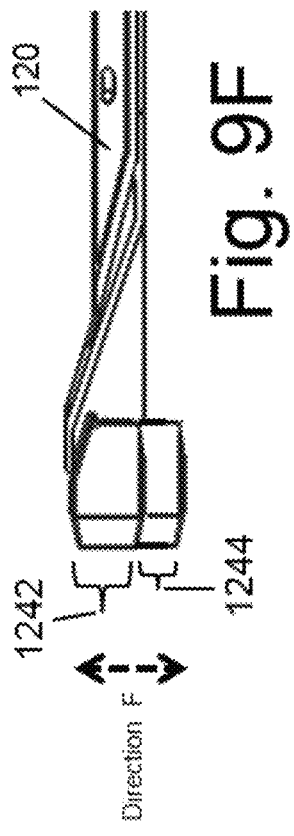

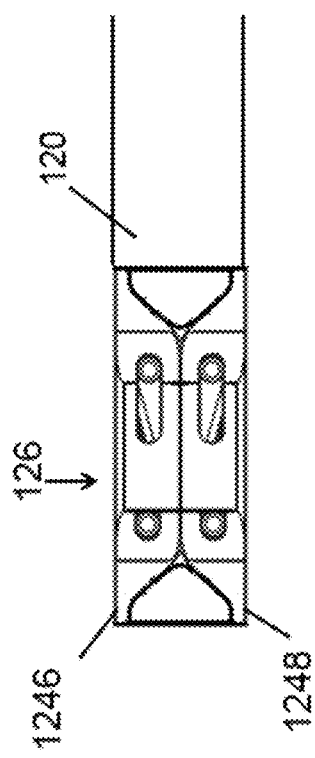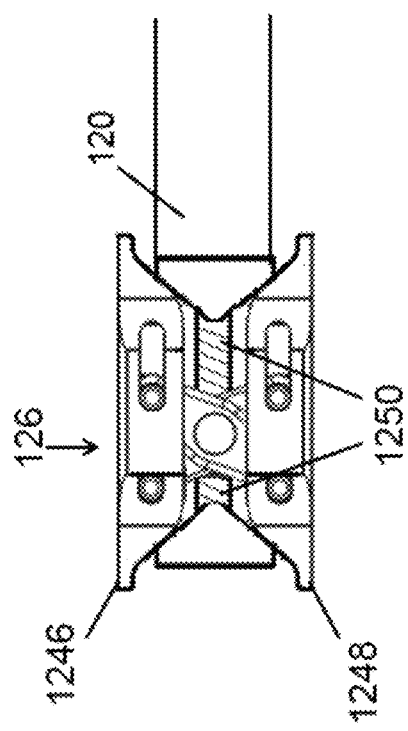

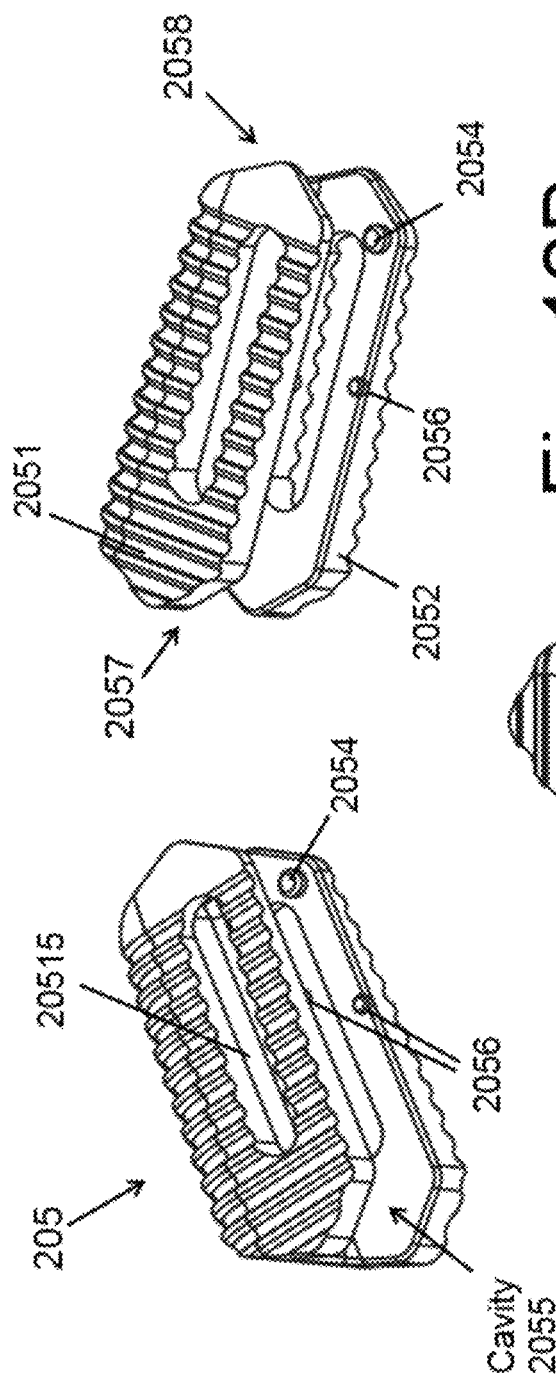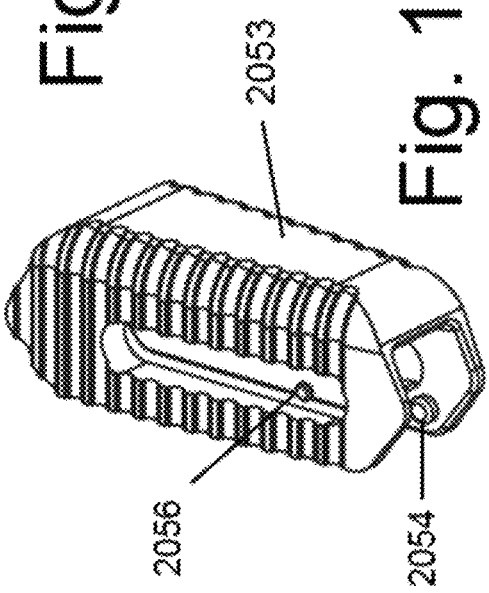
Fig. 12A
Fig. 12B
Fig. 12C

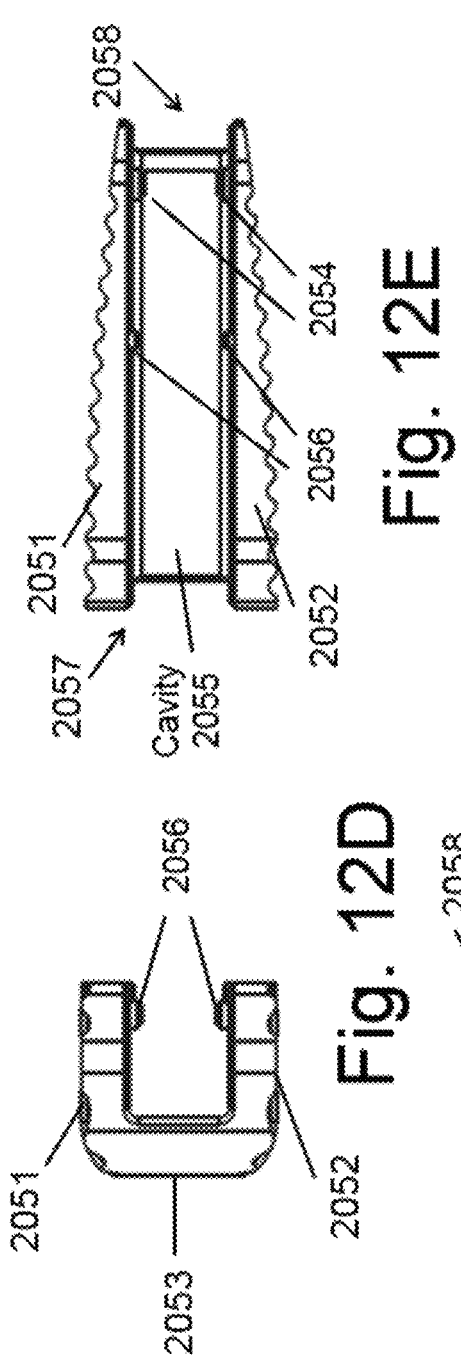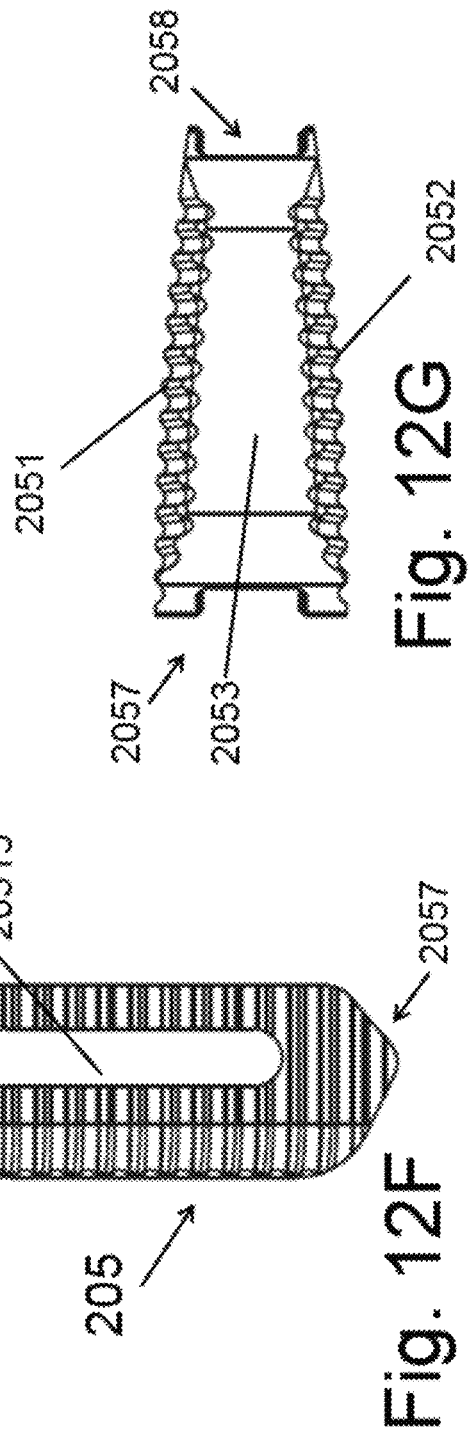

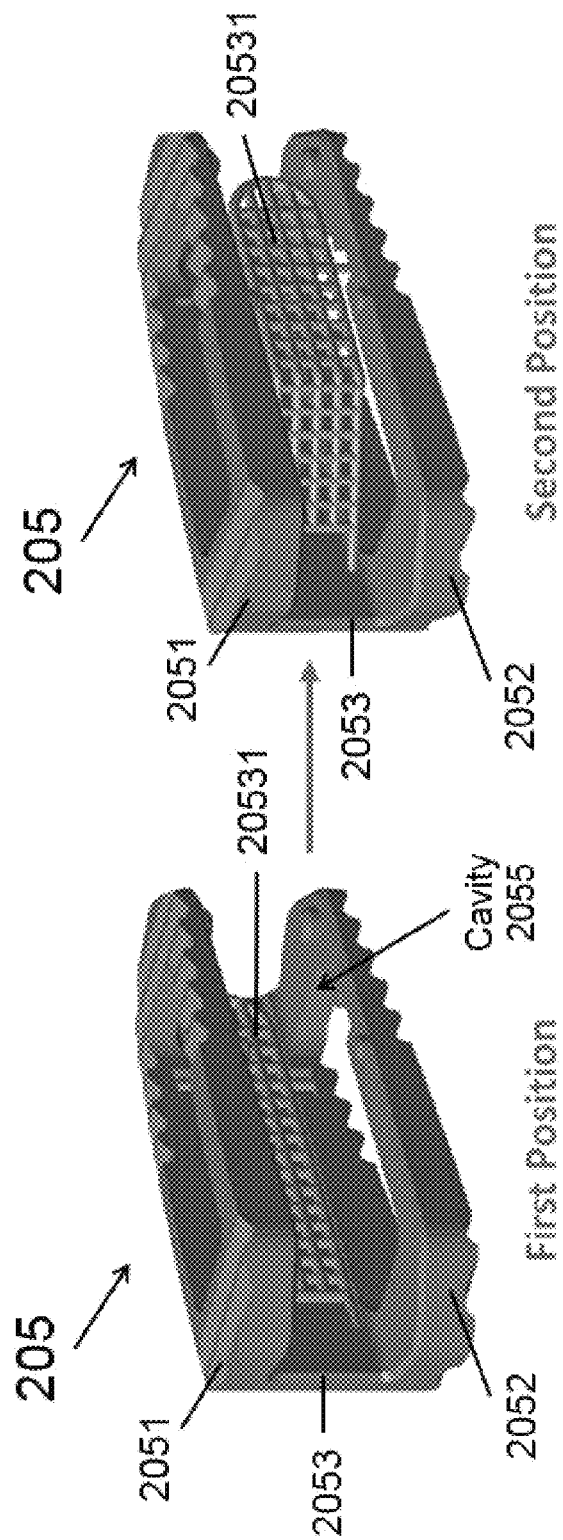

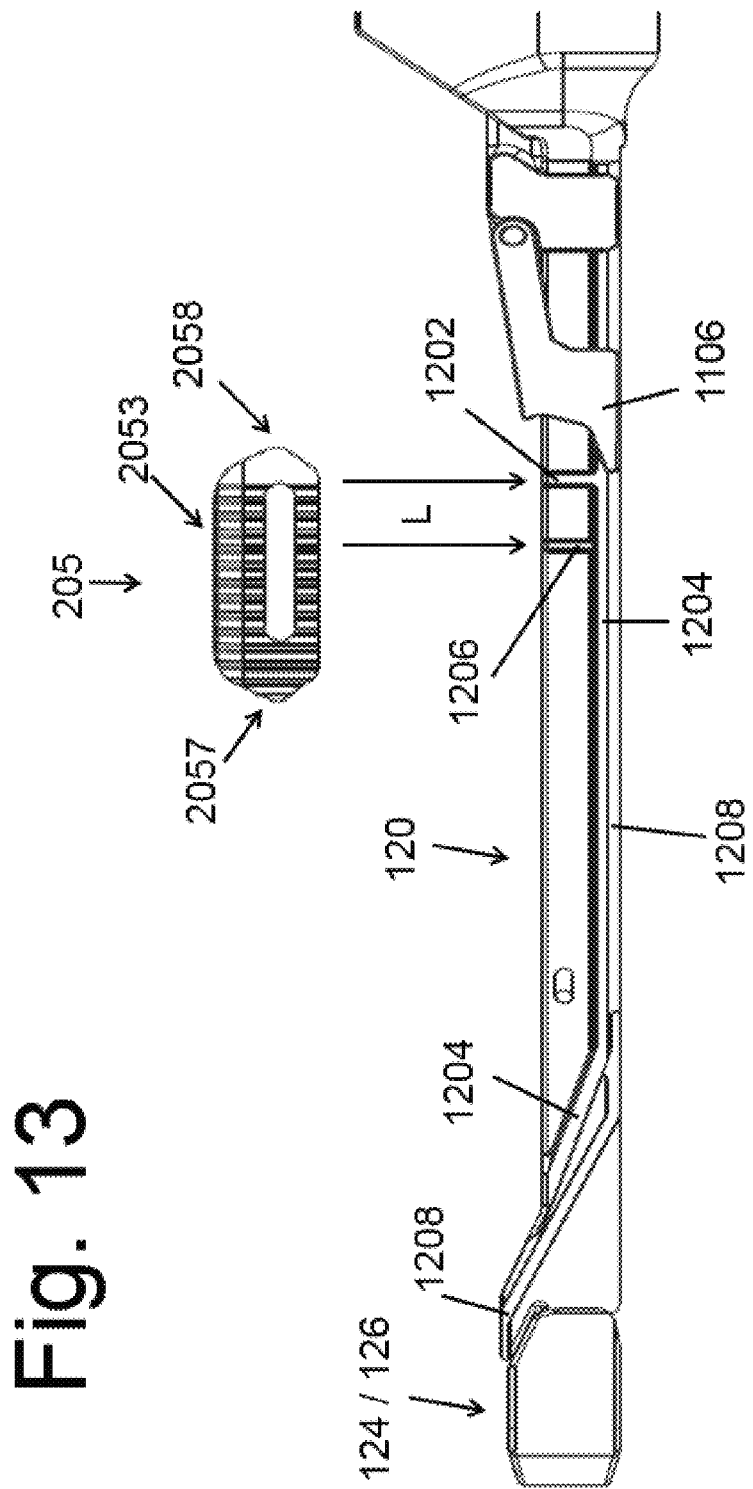

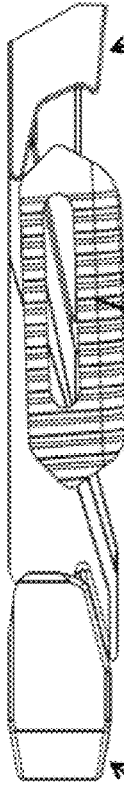
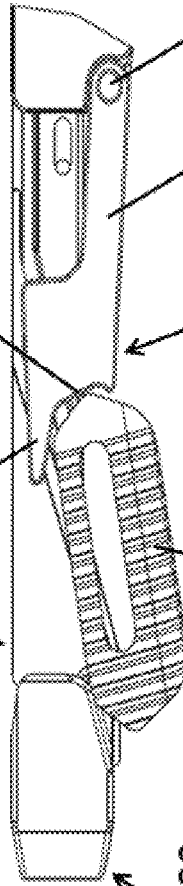
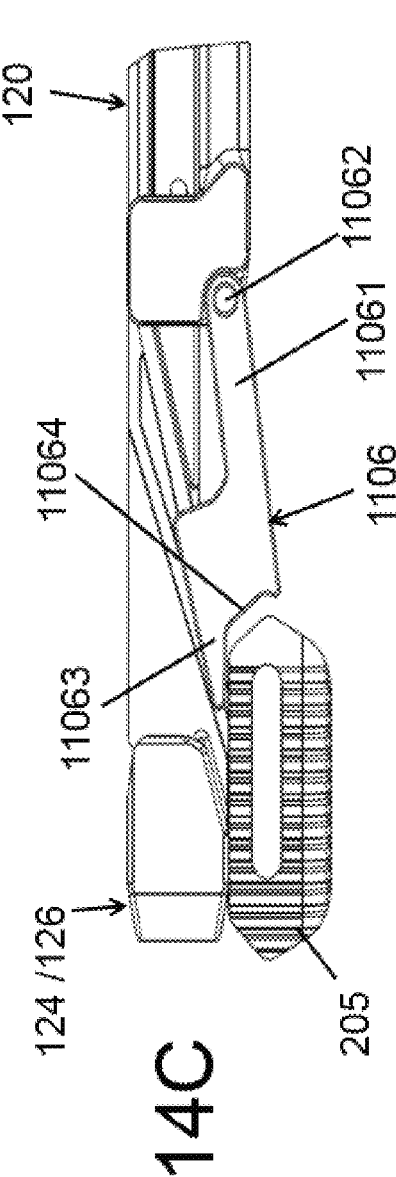
Fig. 14A
Fig. 14B
Fig. 14C

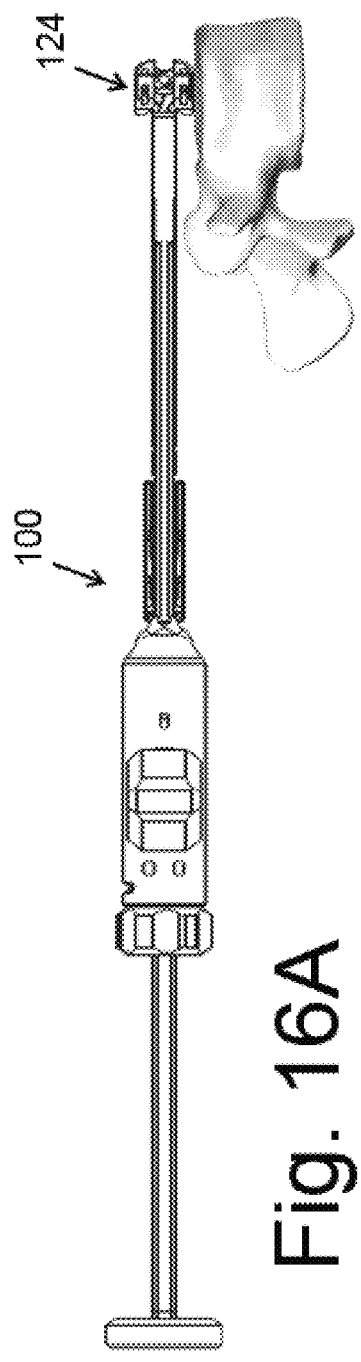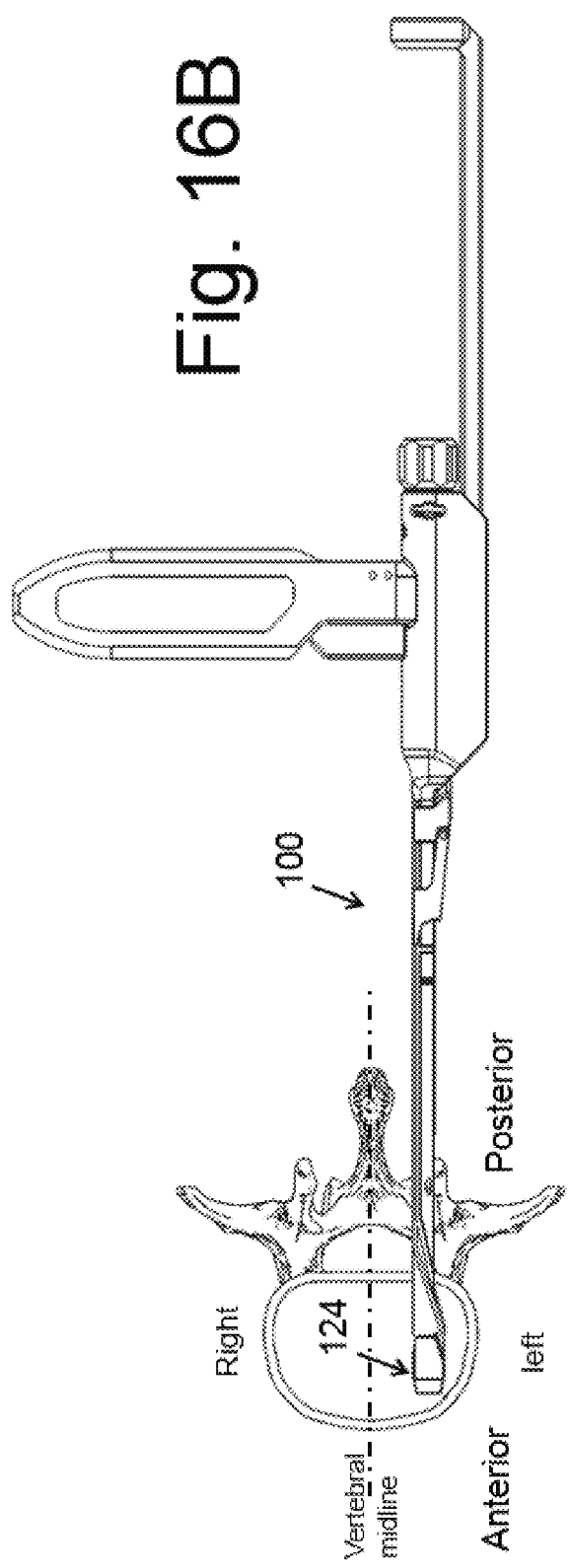

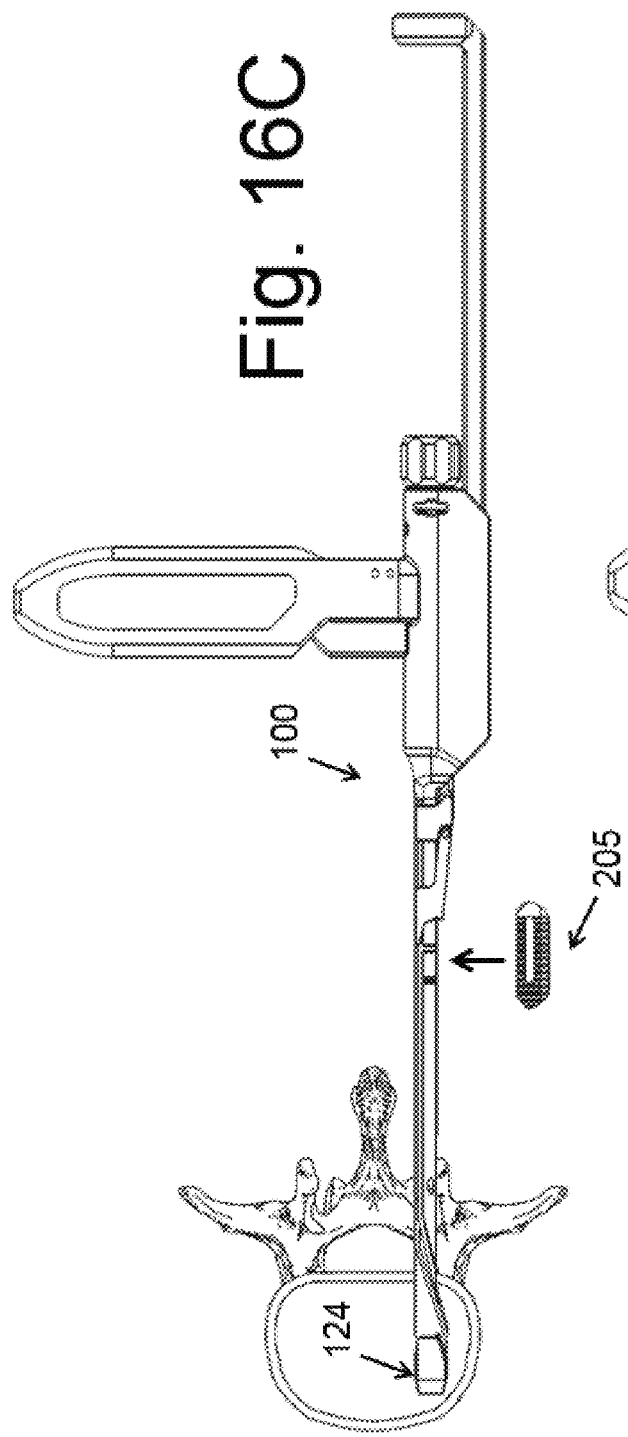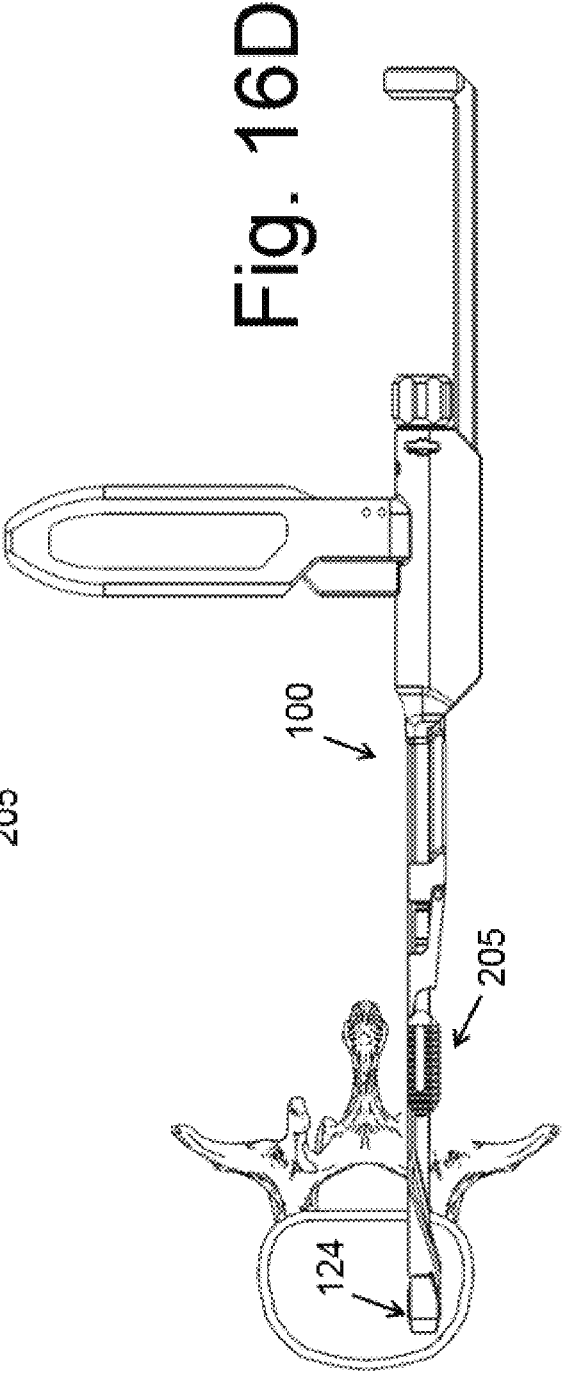

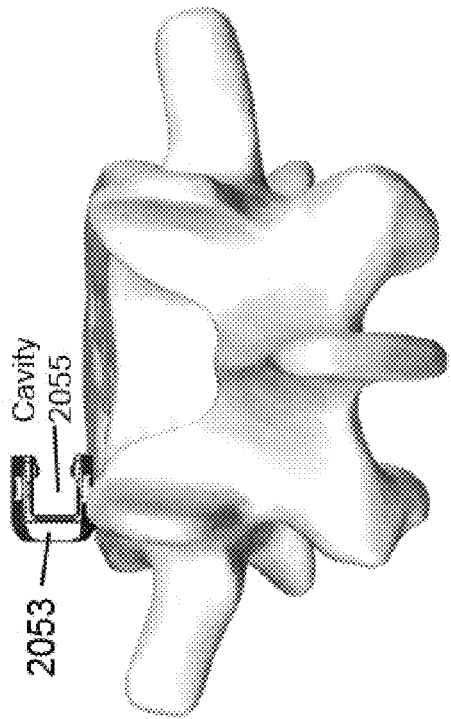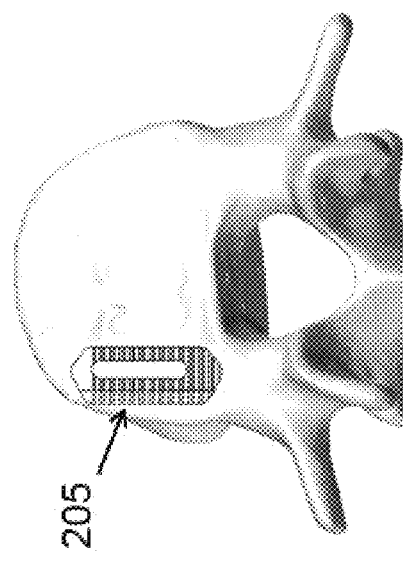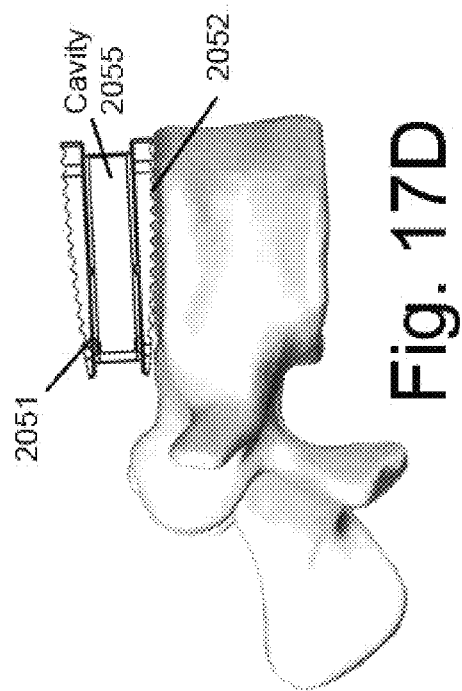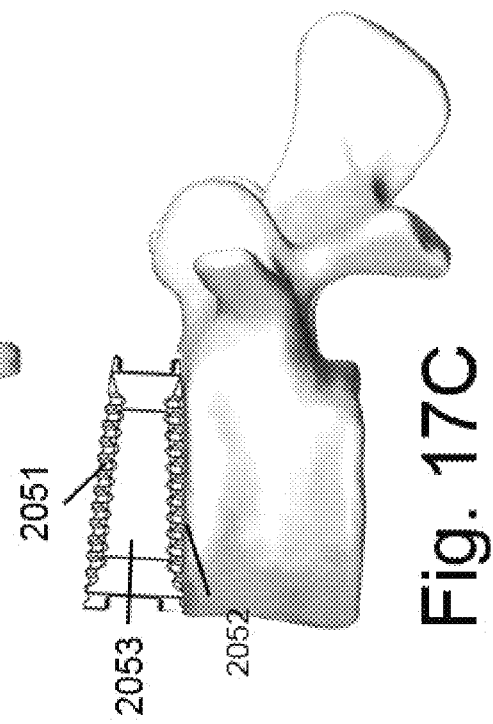

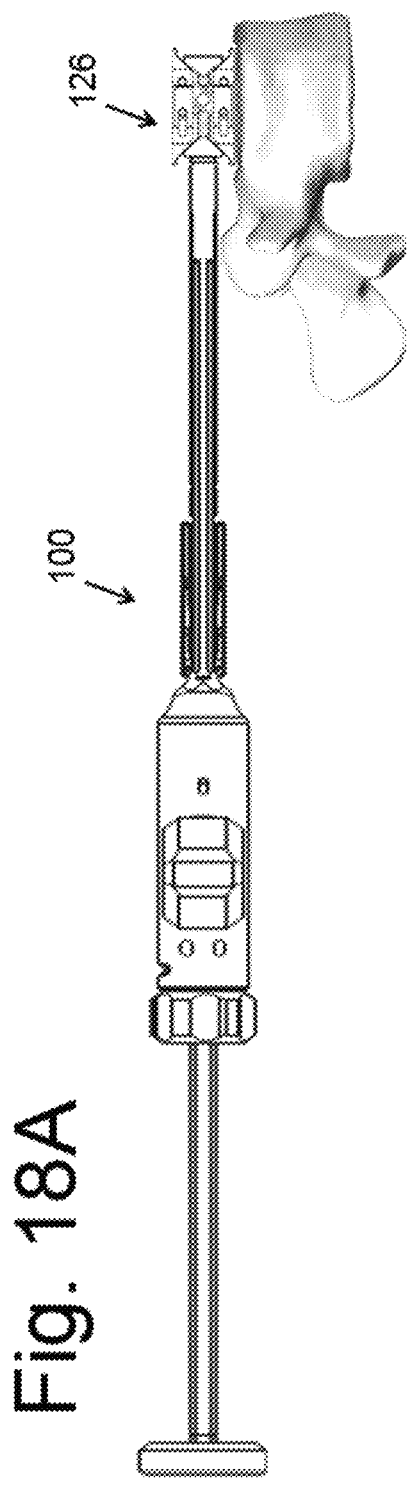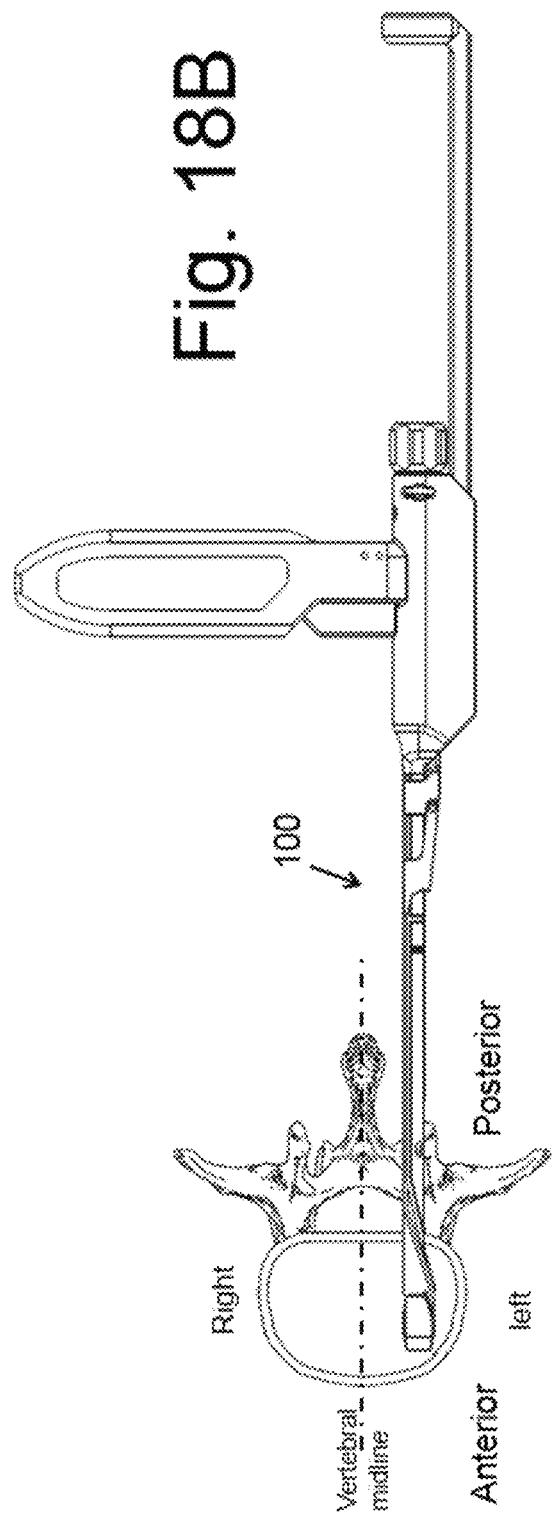

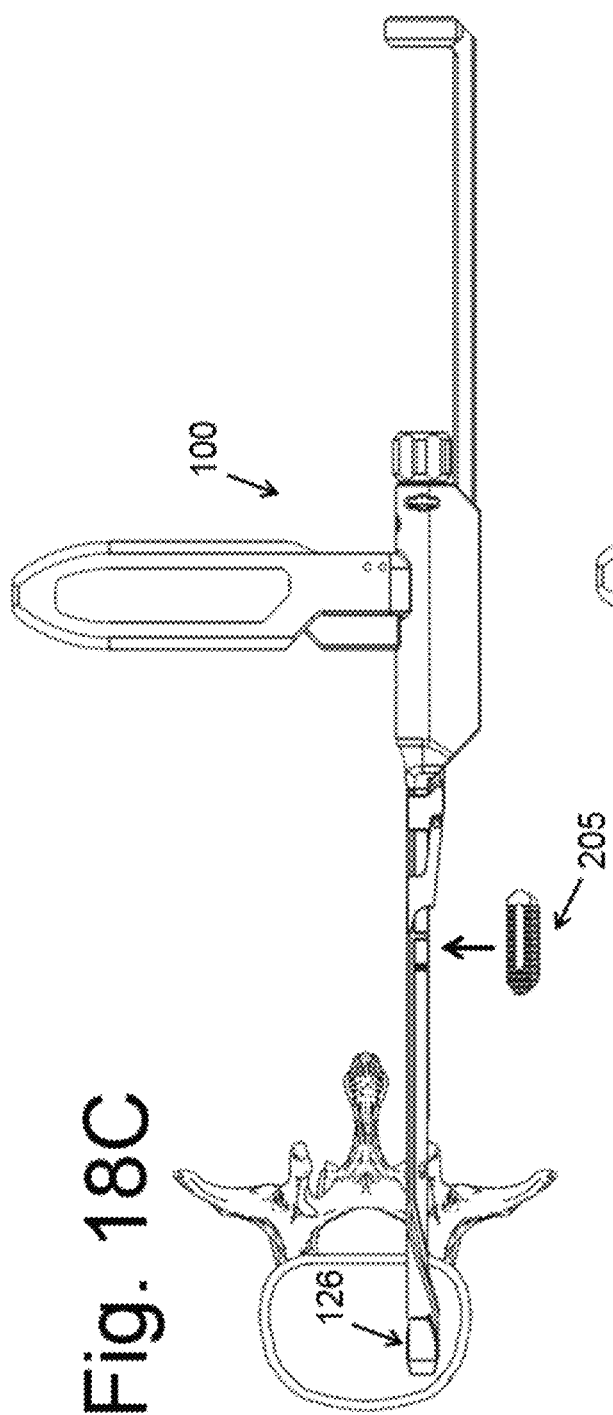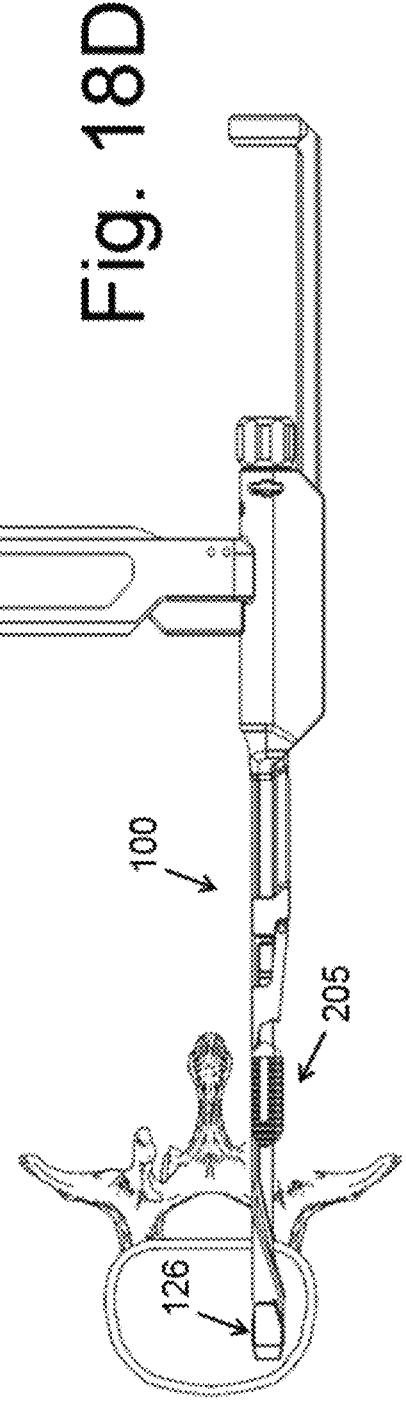

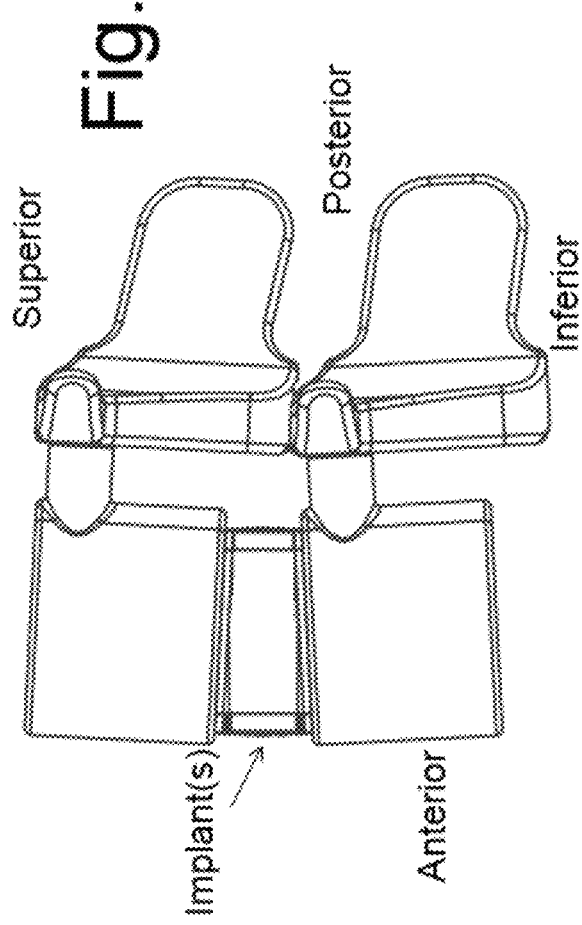
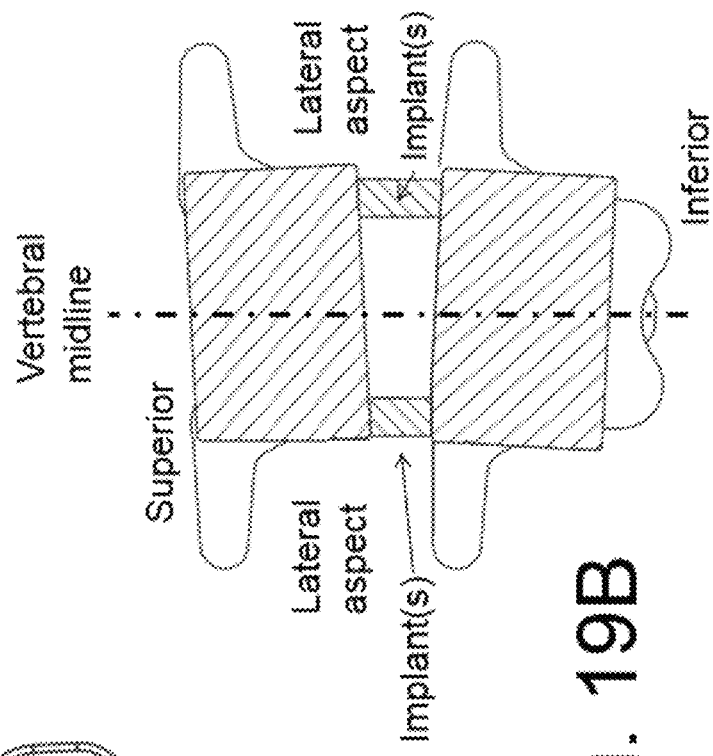
Fig. 19A
Fig. 19B

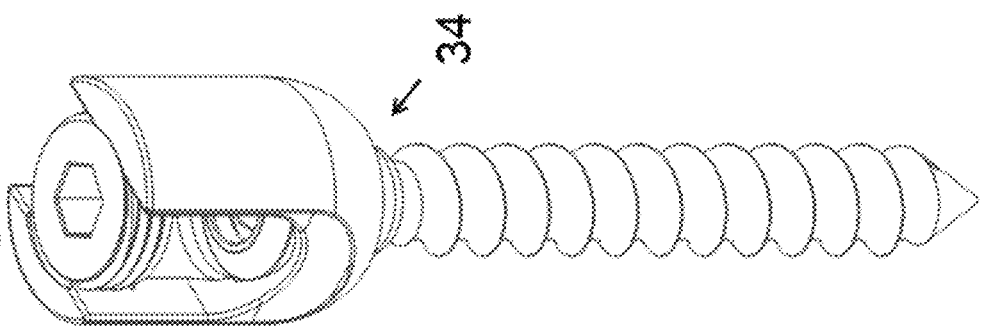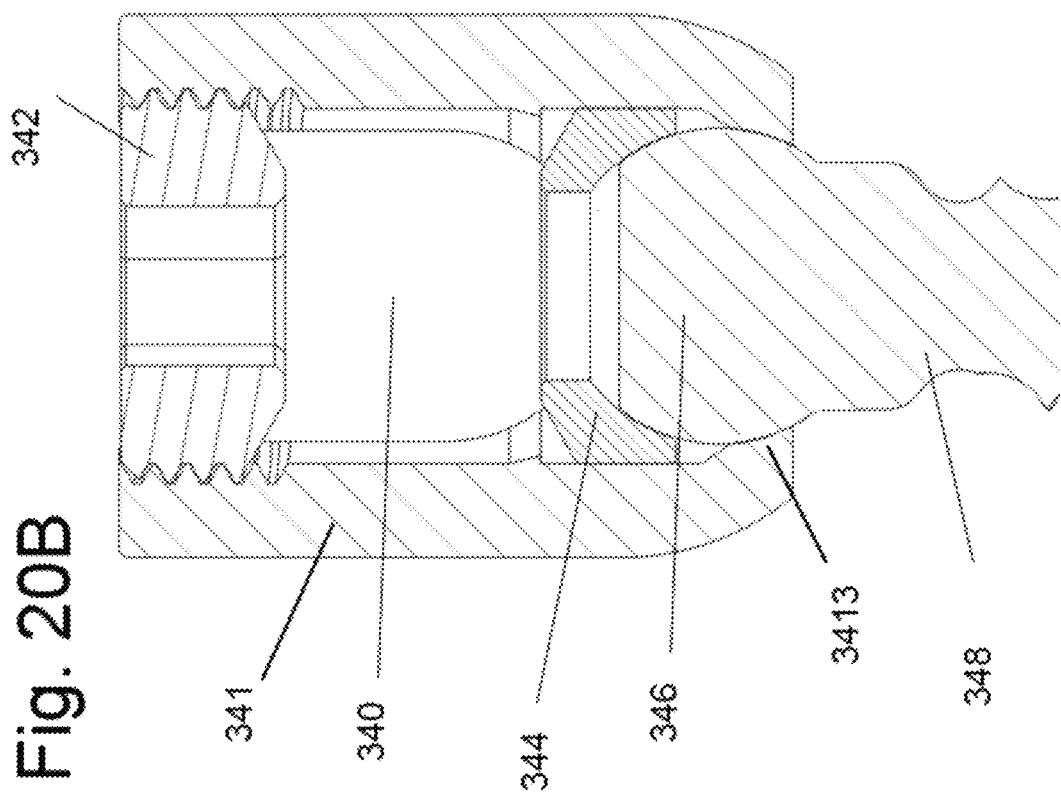

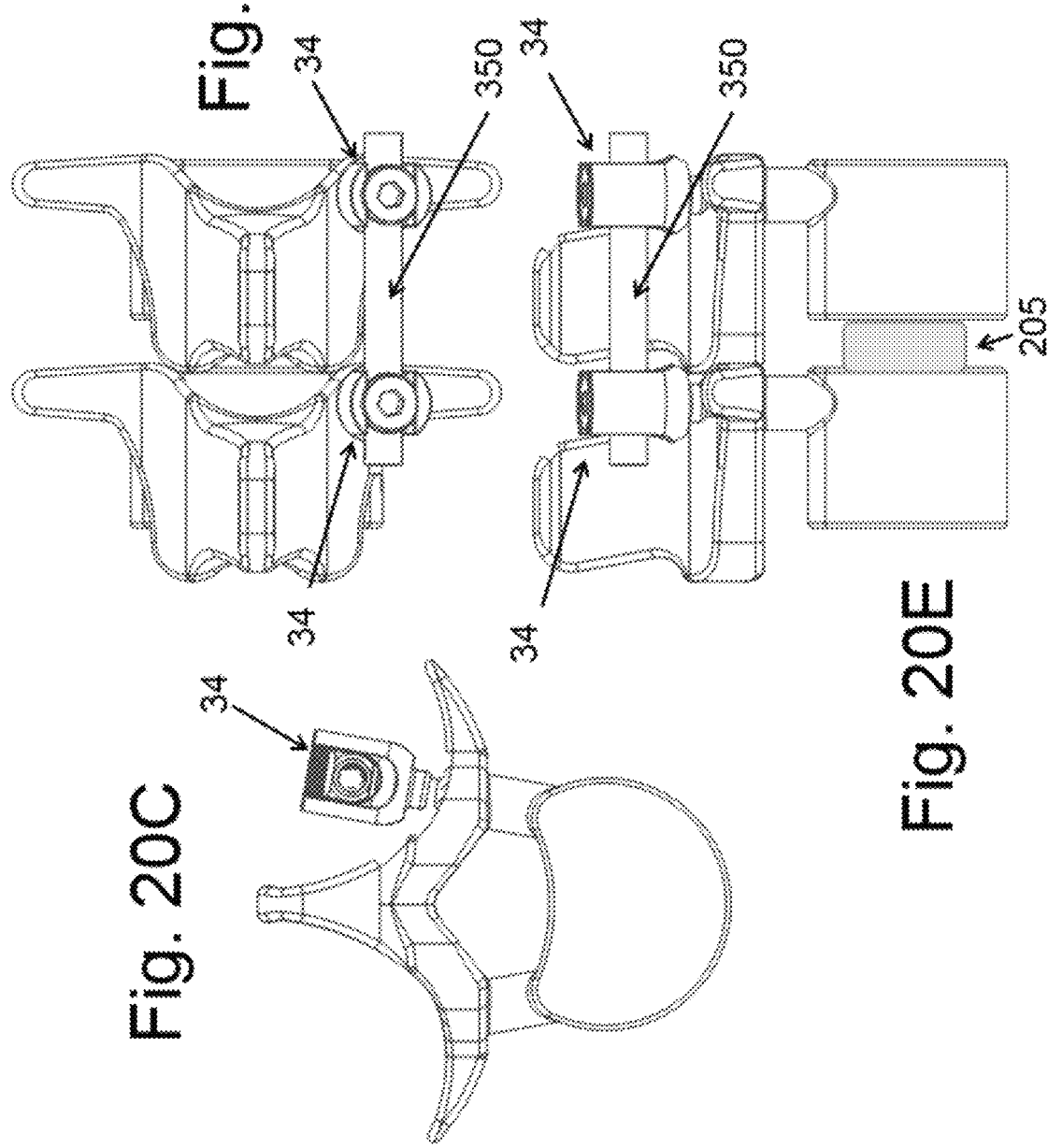

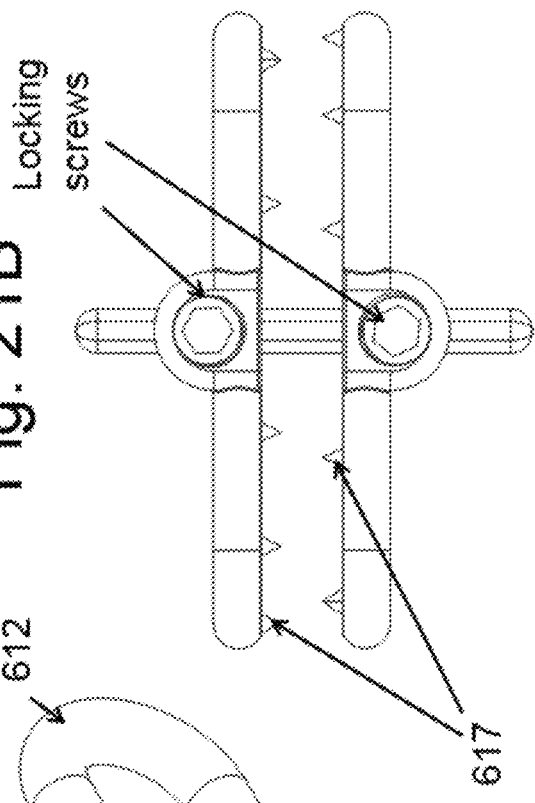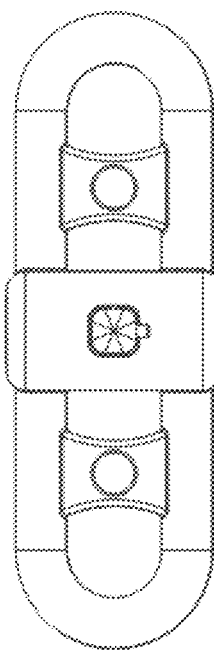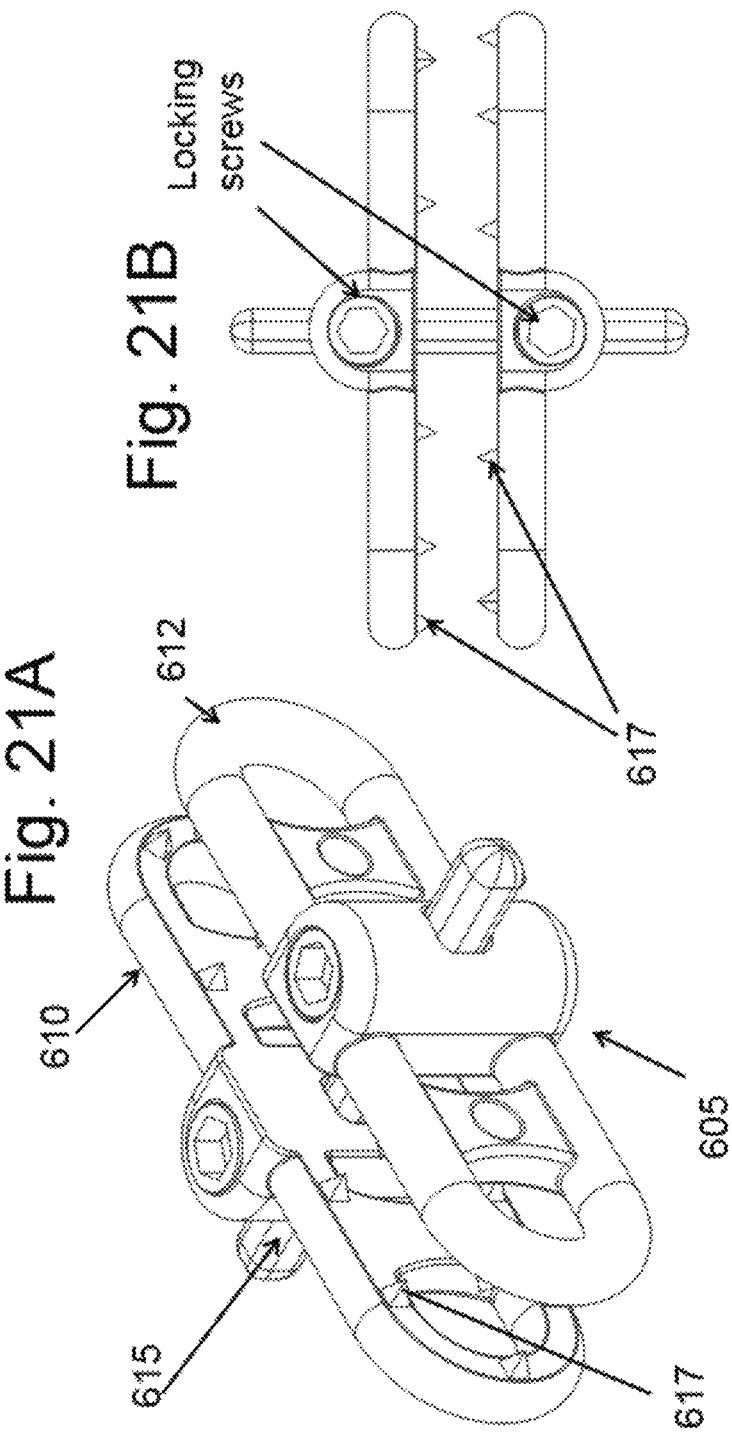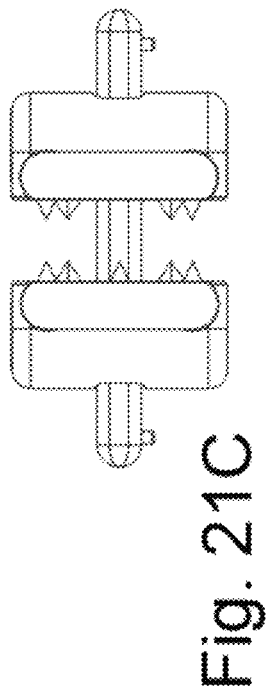

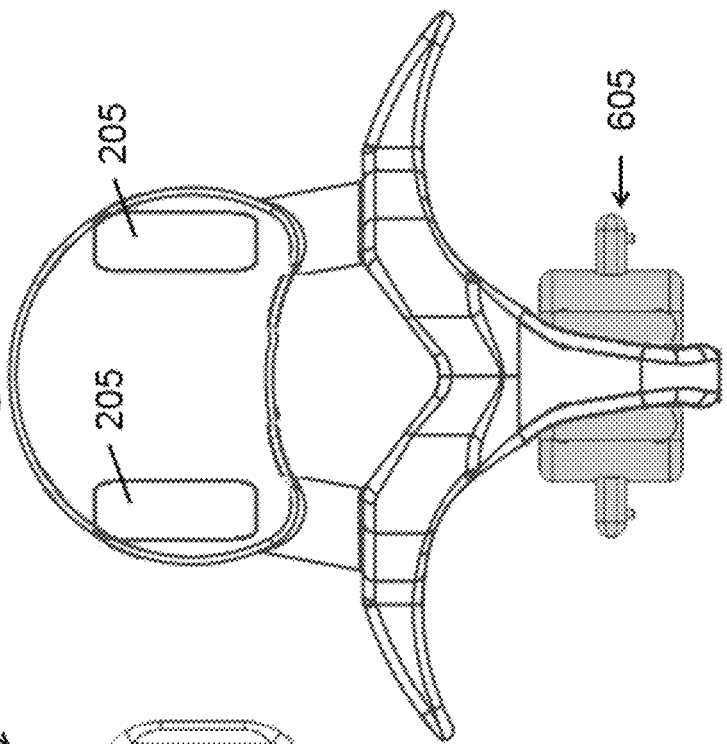
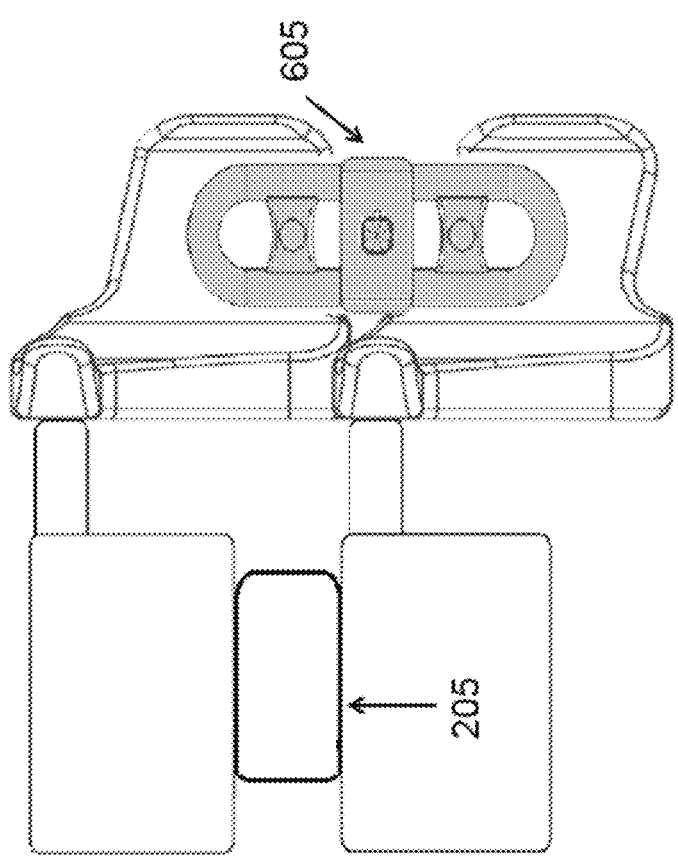
Fig. 21F
Fig. 21E

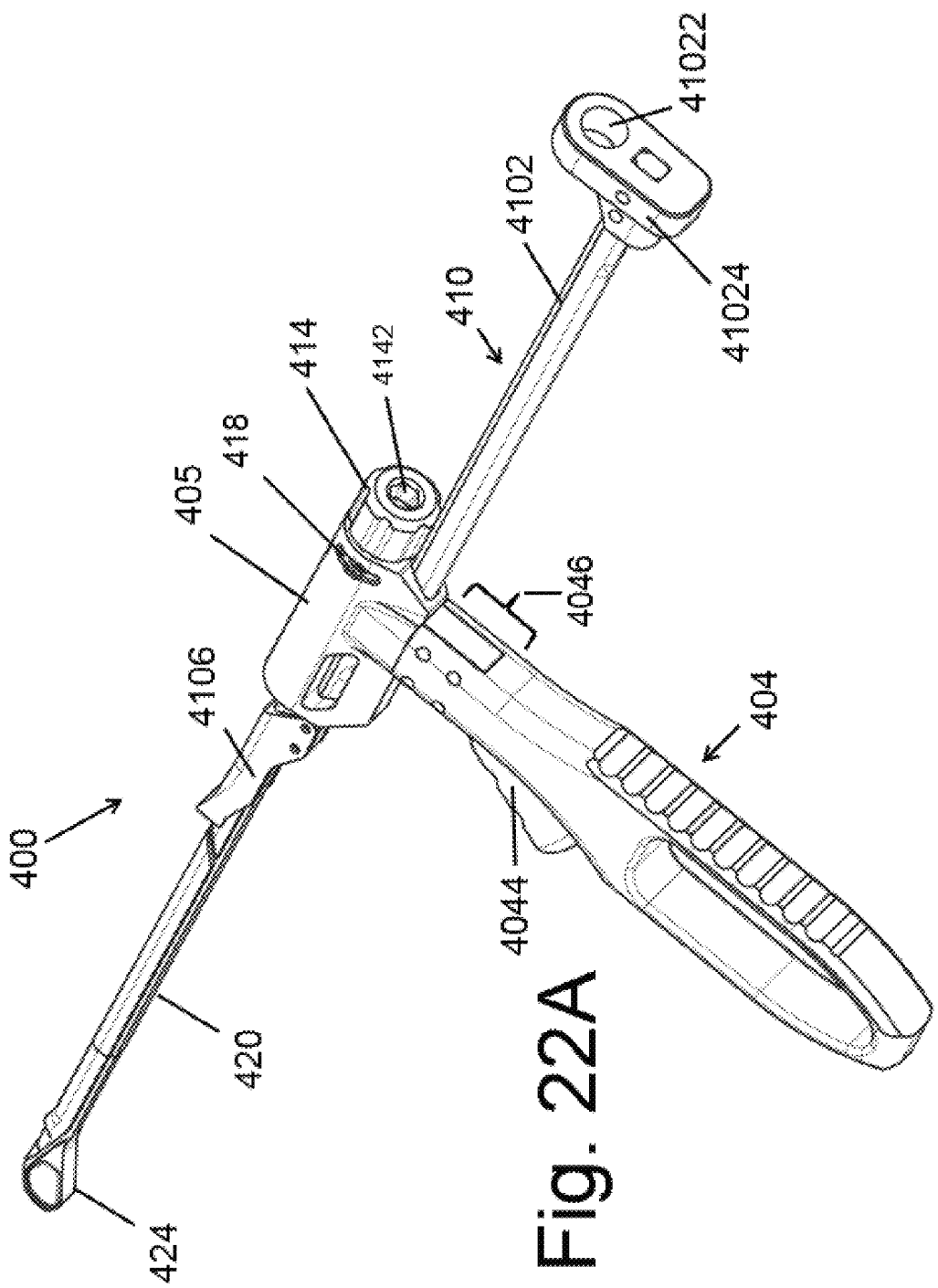

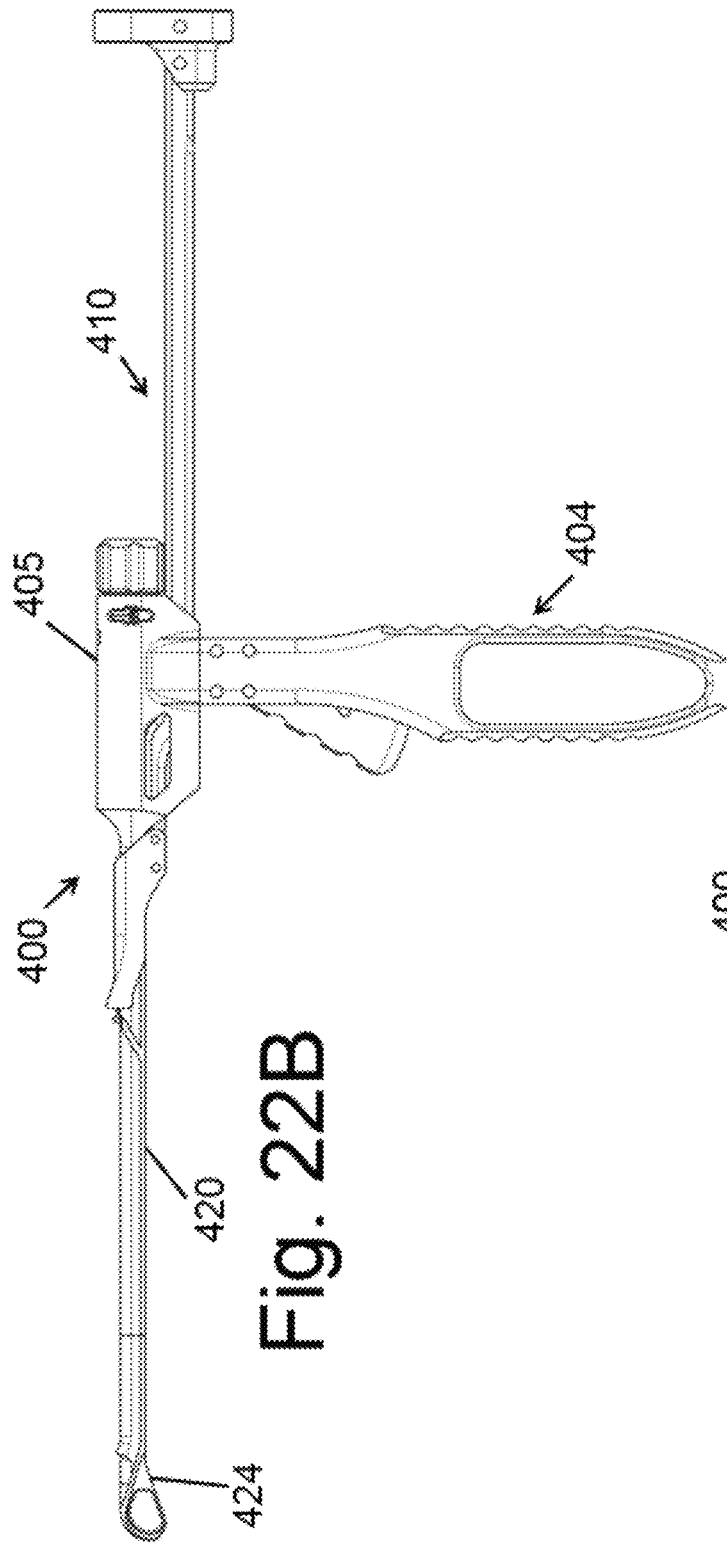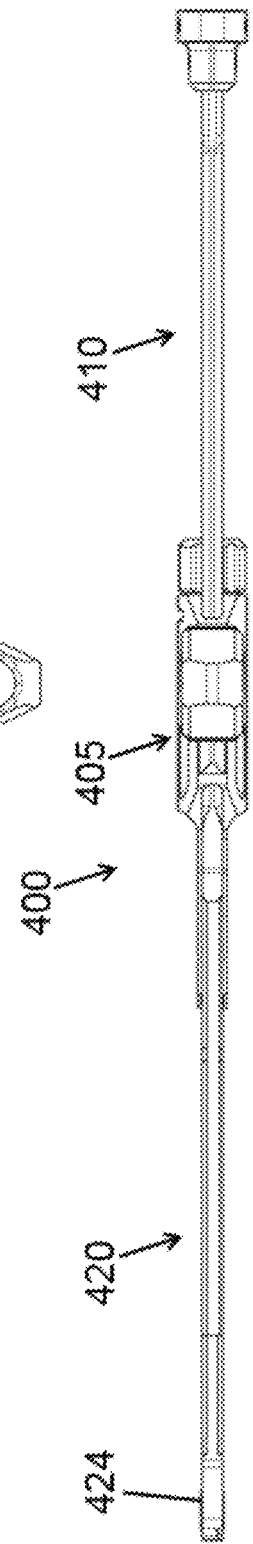

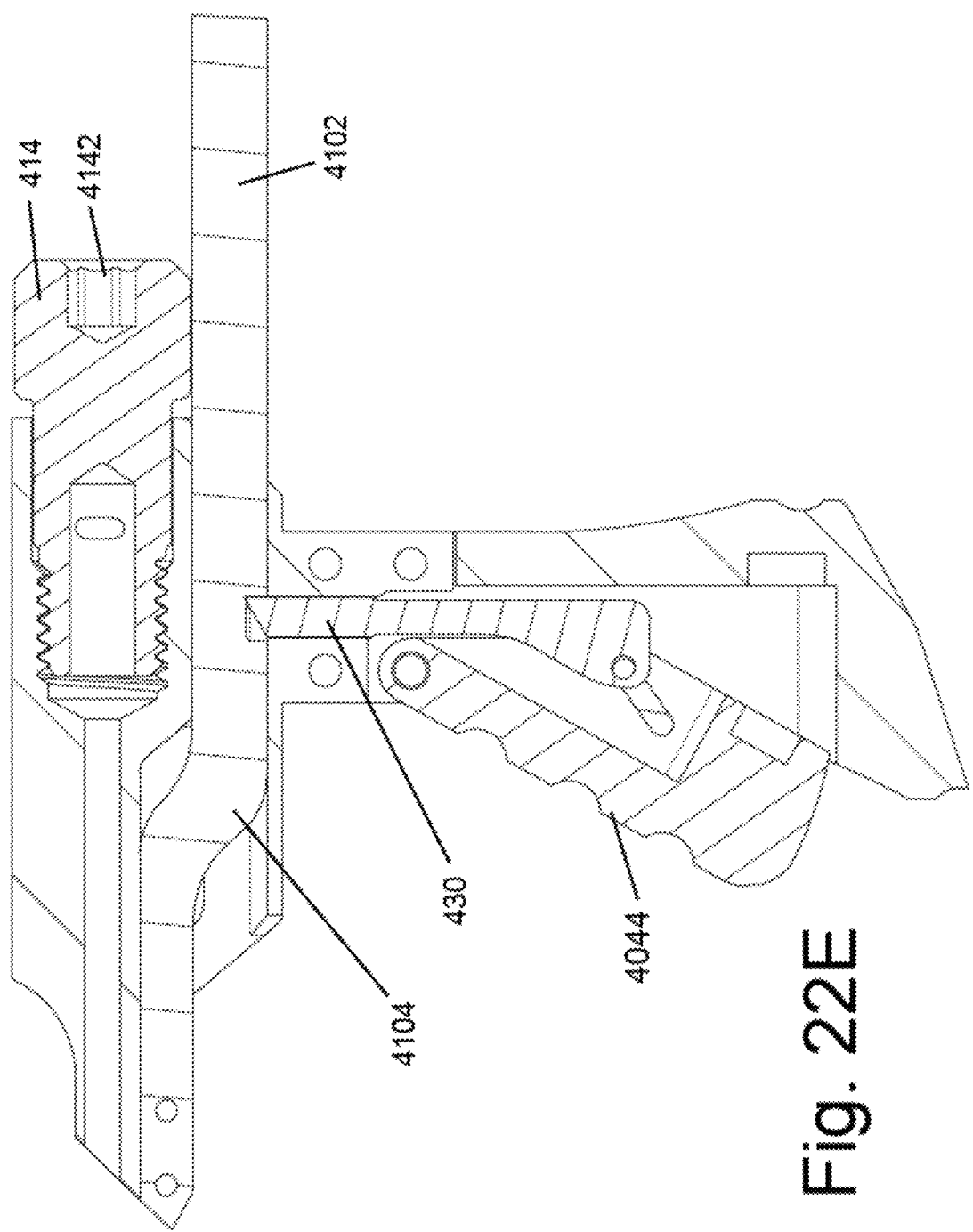

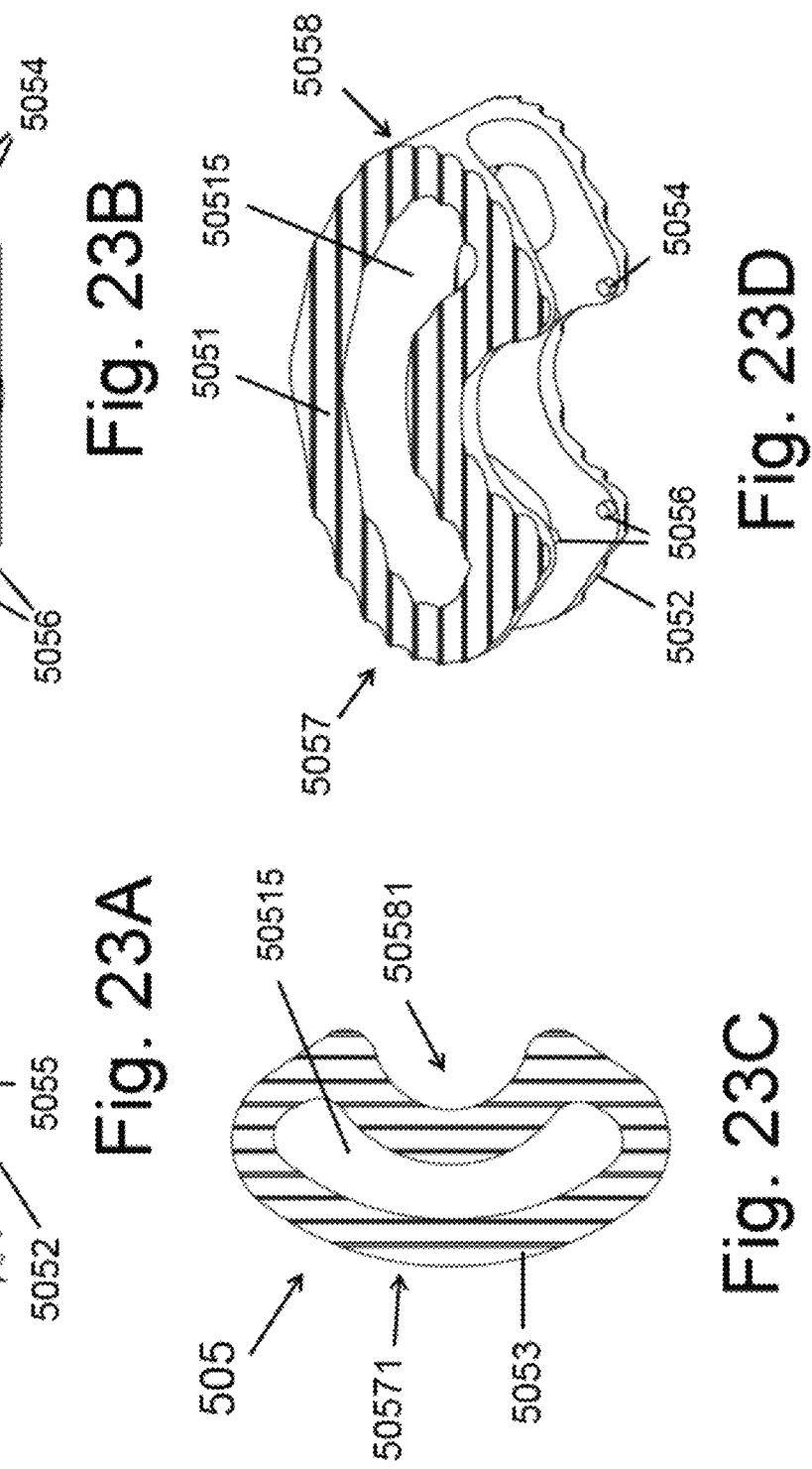

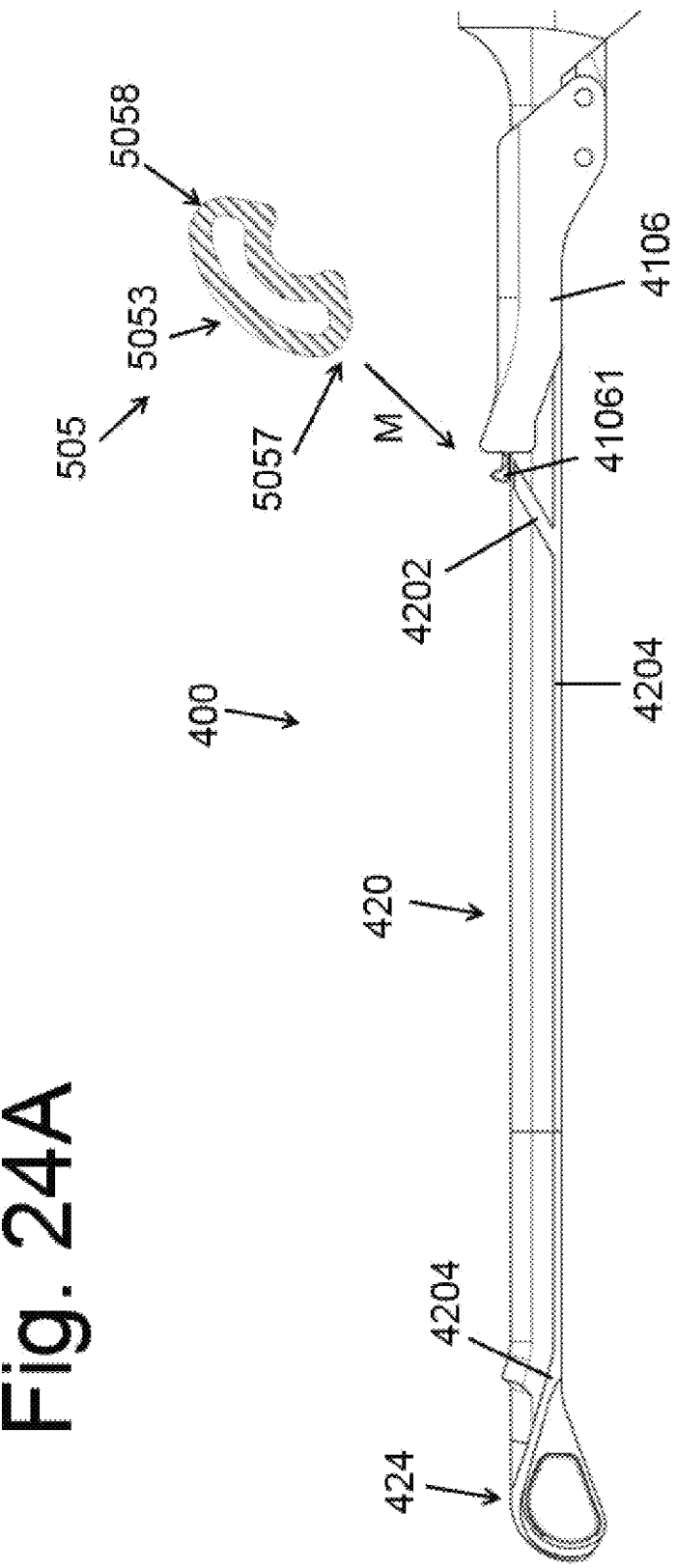

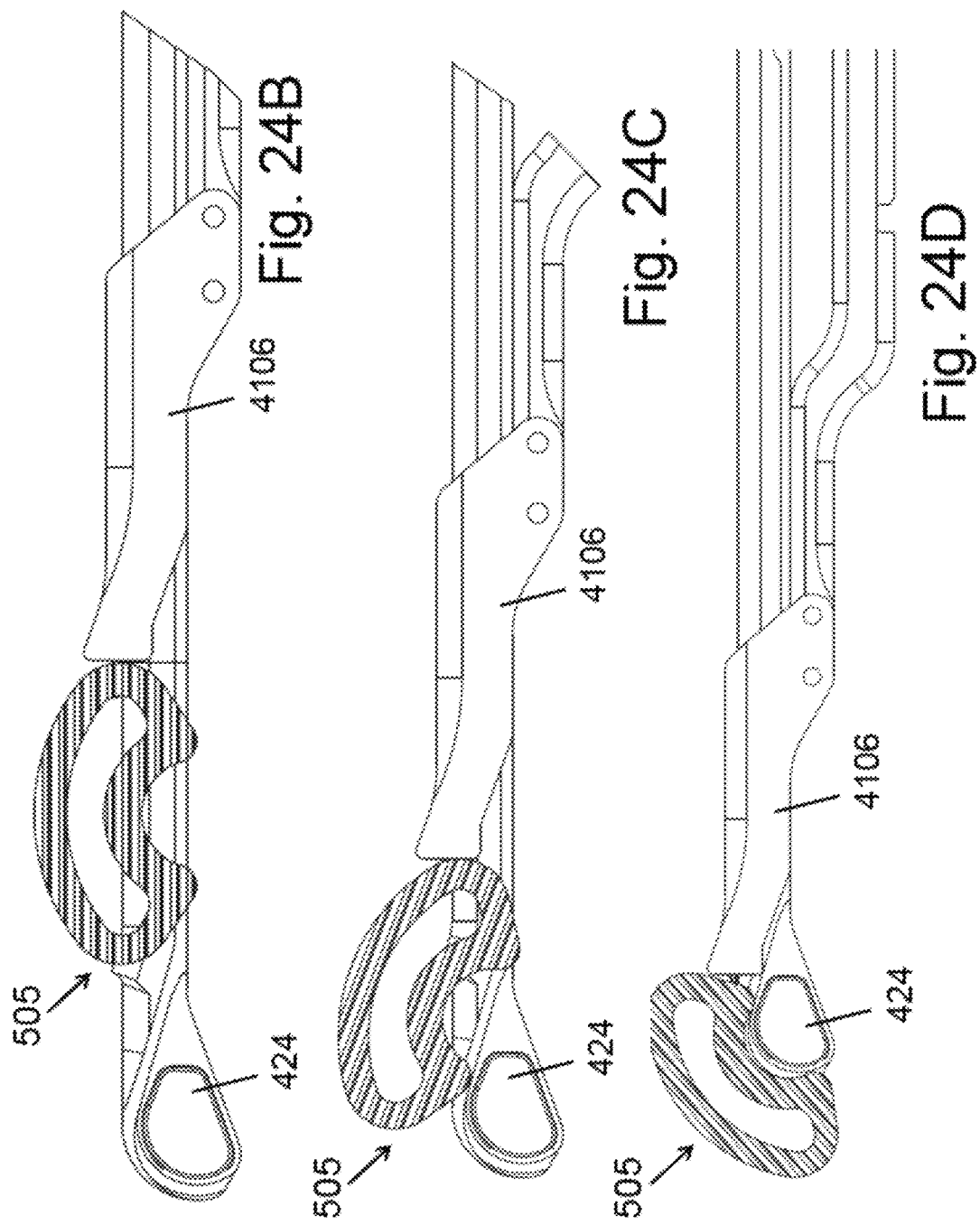

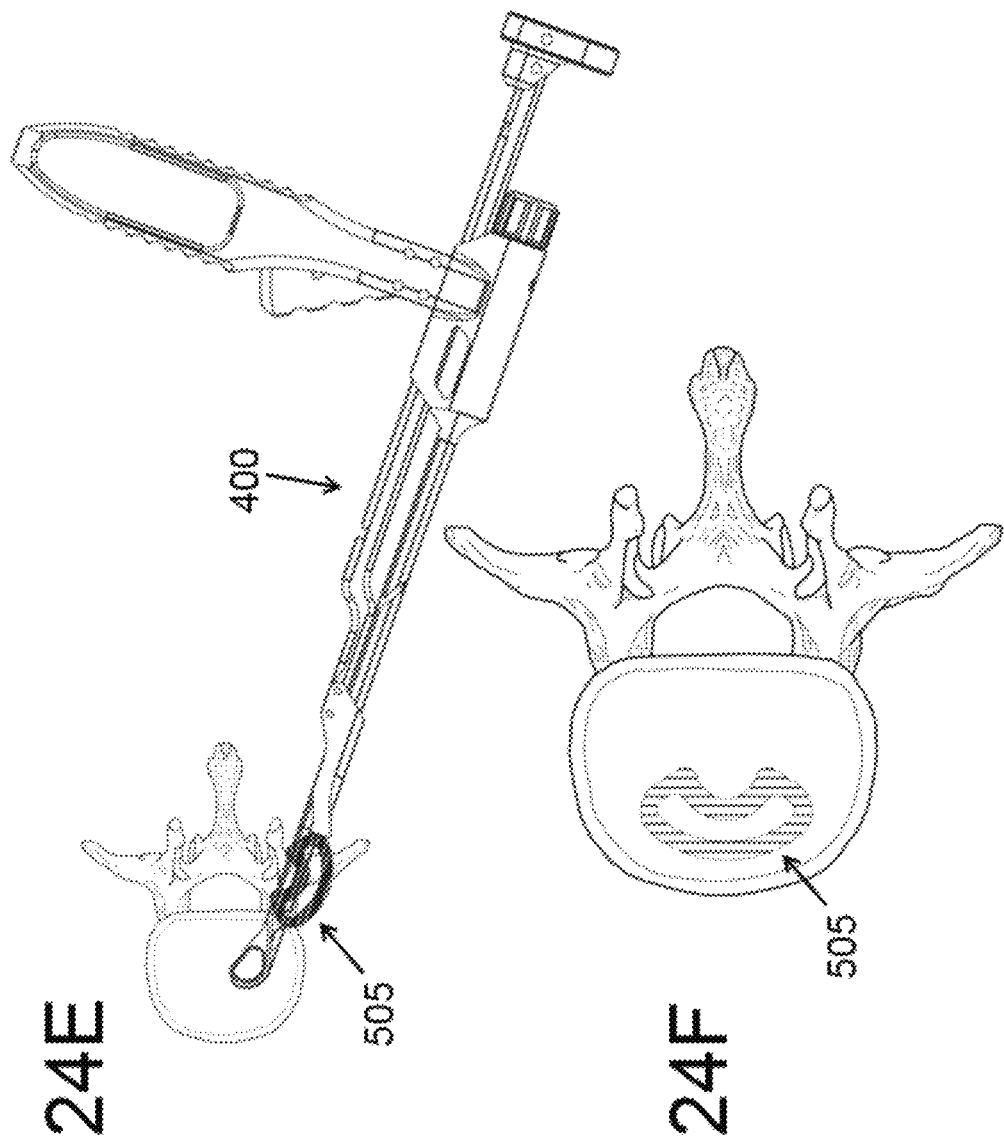

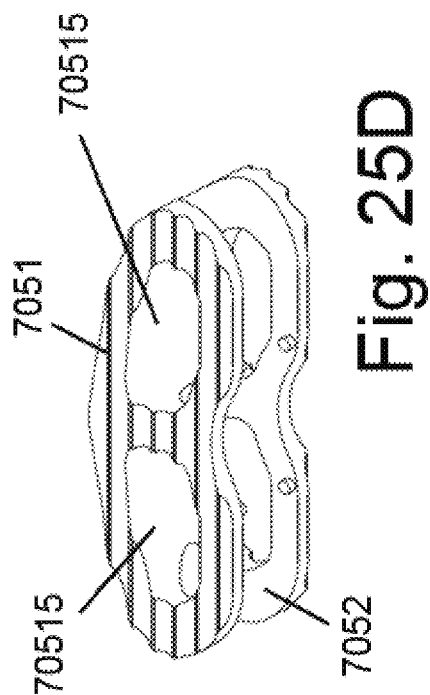
Fig. 25B
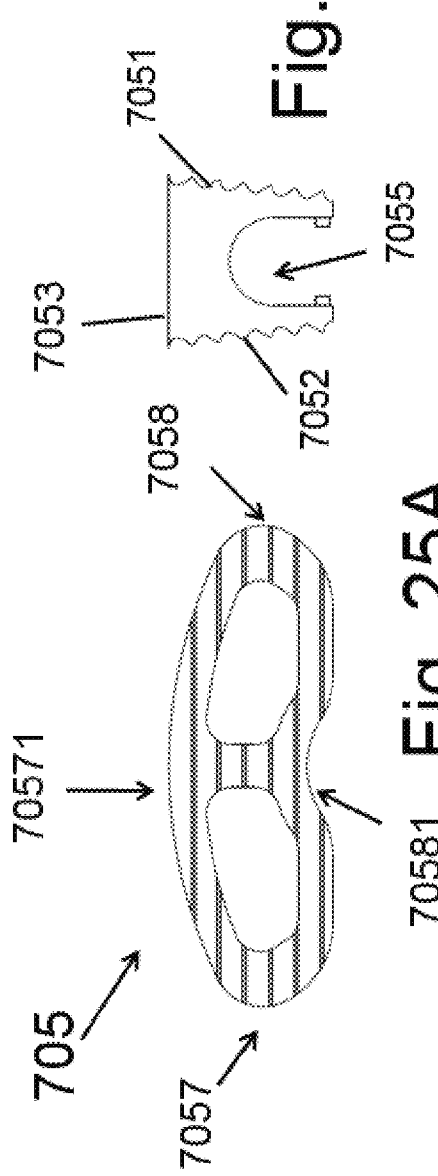
Fig. 25A
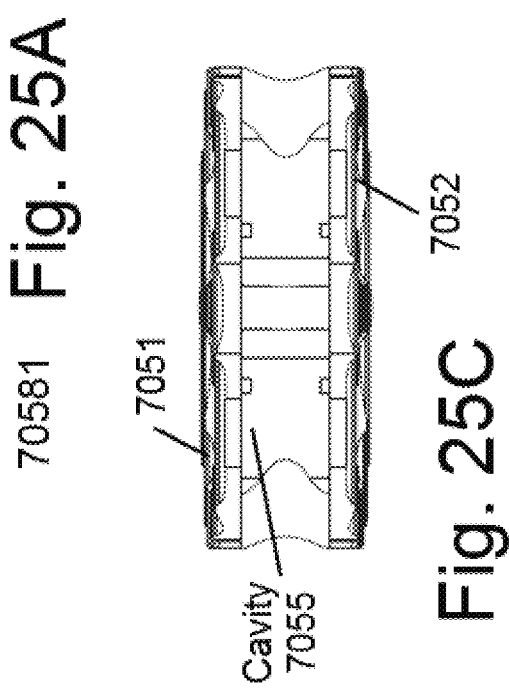
Fig. 25D
Fig. 25C

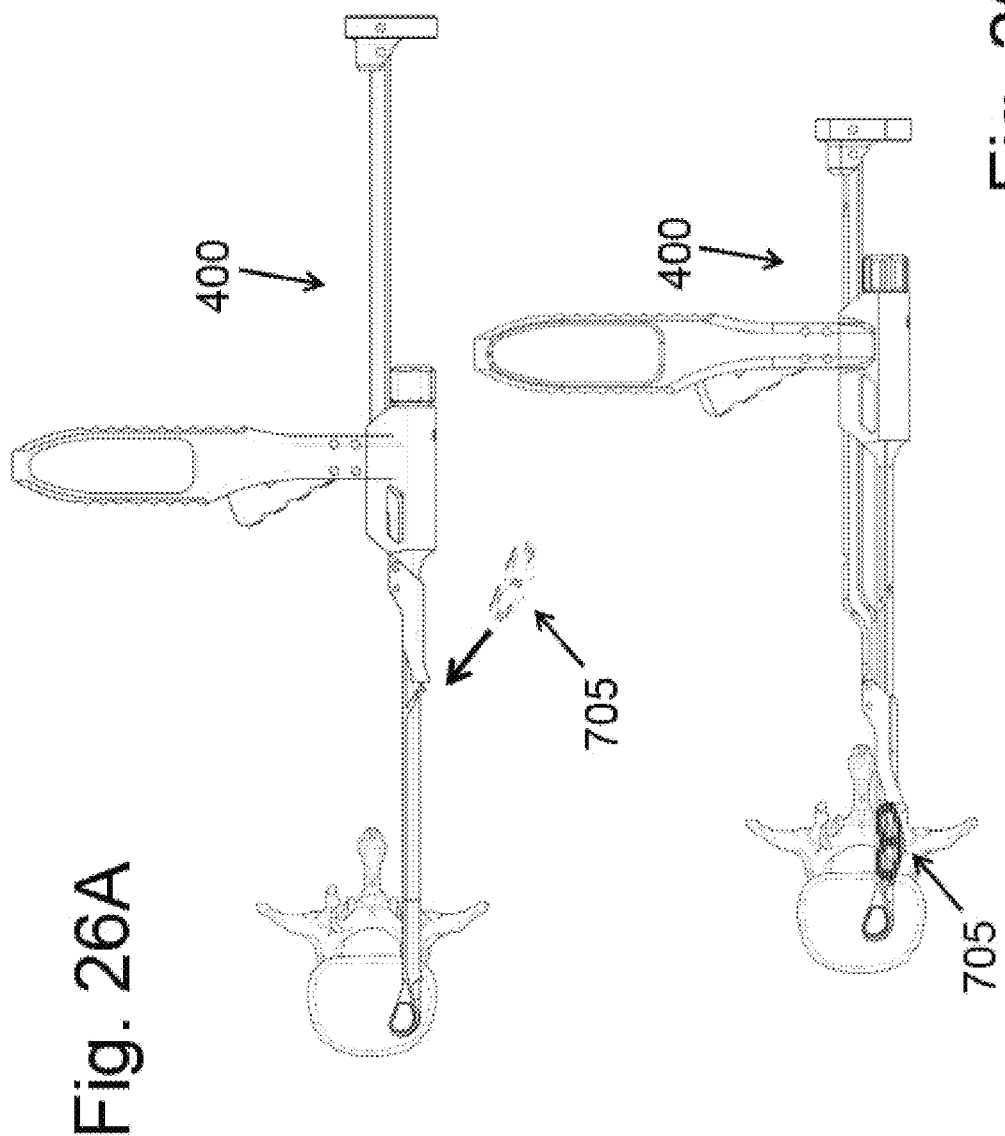

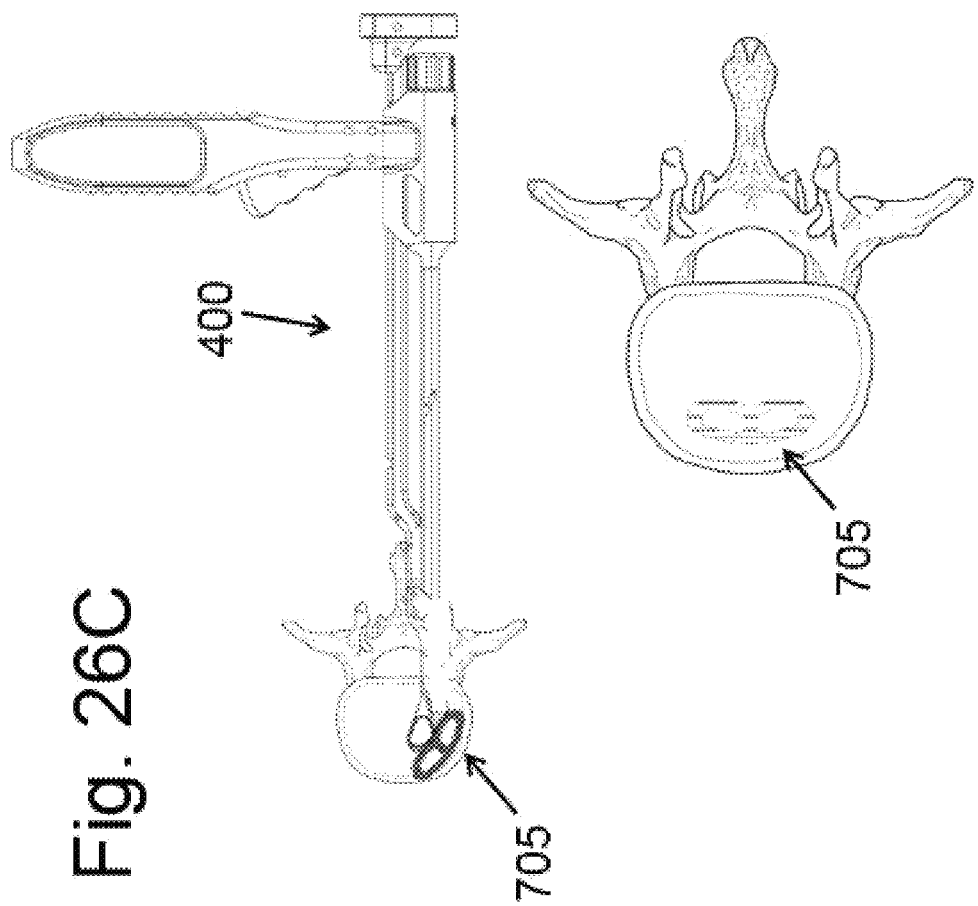

DEVICES AND METHODS FOR SPINAL IMPLANTATION

PRIORITY

This application claims the benefit of and priority to each of co-owned U.S. Provisional Patent Application Ser. No. 62/766,127 entitled "Spinal Implant with Placement Instrument Comprising a Non-detachable Distraction Member," filed Oct. 2, 2018, and U.S. Provisional Patent Application Ser. No. 62/766,123 entitled "Spinal Implant with Placement Instrument Comprising a Detachable Distraction Member," filed Oct. 2, 2018, each of which is incorporated herein by reference in its entirety.

COPYRIGHT

A portion of the disclosure of this patent document contains material that is subject to copyright protection. The copyright owner has no objection to the facsimile reproduction by anyone of the patent document or the patent disclosure, as it appears in the Patent and Trademark Office patent files or records, but otherwise reserves all copyright rights whatsoever.

BACKGROUND

1. Field of the Disclosure

This disclosure relates generally to medical devices, and in one exemplary aspect to bone implants and implantation apparatus and systems, components thereof, and methods of implant placement, which can be used to, inter alia, adjust, align and maintain the spatial relationship(s) of adjacent bones or bony fragments during and/or after surgical reconstruction of skeletal segments.

2. Description of Related Technology

Whether from congenital malformation, degenerative disease, traumatic disruption, infection or neoplastic invasion, alteration in the anatomical alignment between the spinal vertebrae can cause significant pain, deformity, neurological decline and disability. Spinal disease is a major health problem in the industrialized world and the surgical treatment of spinal pathology is an evolving discipline. The traditional surgical treatment of abnormal vertebral motion and/or formation is the complete immobilization and bony fusion of the involved spinal segment and an extensive array of surgical techniques and implantable devices have been formulated to accomplish the treatment objective.

Vertebral fusion may be accomplished by using various approaches to a target spinal segment, such as e.g., anterior, antero-lateral, lateral, posterolateral, or posterior approaches (or variations and/or combinations thereof), each of which may have advantages and disadvantages. Frequently, circumferential fusion of the unstable or diseased portion of the spine with fixation of both the anterior and the posterior aspects thereof is desired. Such fusion typically requires that a patient undergoes a combination of the aforementioned approaches. For example, the anterior and/or the lateral approaches can be used to insert the bone graft into the disc space between the adjacent vertebrae, while the posterior approach is used to place bone screws or similar fasteners that are used to immobilize the vertebral bodies.

However, the combined surgical approaches utilized for circumferential fusion (as well as the multiple tools required for the procedures) can cause additional recovery time and/or discomfort for the patient, as well as increase the duration and/or complexity of a surgical procedure for the practitioner. Further, the foregoing conventional implantation systems and methods may be insufficient for treatment of patients with unusual or complex spinal curvatures and maladies, which may occur in conditions such as e.g., spondylolisthesis, coronal plane deformity (such as scoliosis), sagittal plane deformity (such as alternation in segmental kyphosis or lordosis), axial translation, rotational deformity, etc.

Hence there is a salient need for alternative methods and devices for the alteration and/or correction of spinal curvature, which, inter alia, enable minimally invasive procedures (including percutaneous operations) for treatment of the aforementioned spinal conditions. Further, it is desirable that such alternative methods and devices be usable in combination with conventional implantation systems and methods.

SUMMARY

Improved devices, systems, and methods to alter vertebral alignment and/or to otherwise treat a target spinal segment are described herein.

In one aspect, an implant delivery apparatus is disclosed. In one embodiment, the apparatus comprises a distraction member configured for distraction of a disc space and an implant track configured for slidable delivery of a substantially linear implant to the distracted disc space.

In one variant, the distraction member comprises a non-detachable distraction mechanism configured to be reversibly actuated to increase a height thereof so as to enable (i) vertebral alignment or correction of e.g., spondylolisthesis, (ii) delivery of the implant to the disc space, and (iii) removal of the distraction member from the disc space after delivery of the implant. Further, the non-detachable distraction mechanism comprises an upper plate and lower plate, and the upper and lower plates are configured to be reversible reversibly movable between a closed (non-distracted) configuration and an open (distracted) configuration.

In one implementation, the upper and lower plates are configured to move along a vertical axis which is substantially perpendicular to a longitudinal axis of the implant track. Further, the upper and lower plates are configured to alter vertebral alignment in the coronal plane and reduce e.g., lateral spondylolisthesis.

In another implementation, the upper and lower plates are configured to move along a vertical axis which is substantially perpendicularly to a longitudinal axis of the implant track, as well as along a lateral axis which is substantially parallel to the longitudinal axis of the implant track. Further, the upper and lower plates are configured to increase a height of the vertebral disc space, as well as alter vertebral alignment in the sagittal plane and thereby reduce e.g., anterior or posterior spondylolisthesis.

In another variant, the distraction member comprises a detachable distraction mechanism configured to be actuated to increase a height thereof to enable (i) vertebral alignment and/or correction of e.g., spondylolisthesis, (ii) delivery of the implant to the disc space, and (iii) co-implantation of the distraction member within the disc space along with the implant (after withdrawal of the implant delivery instrument).

In another embodiment, the device comprises a distraction member configured for distraction of a disc space and an implant track configured for slidable delivery of a substantially curved implant to the distracted disc space.

In another aspect, a method of inserting an implantable device within an intervertebral space is disclosed. In one embodiment, the method includes (i) inserting a distraction member of an implant delivery apparatus into an intervertebral disc space, (ii) actuating the distraction mechanism to move the distraction mechanism into an open (distracted) position and to alter a position of a superior vertebral bone relative to an inferior vertebral bone, (iii) loading an implant onto an implant track of the implant delivery apparatus, and (iv) releasing a pusher device to slidably advance the implant down the implant track and into the intervertebral disc space.

In one variant, the method further includes moving the distraction member into a closed (non-distracted) configuration and withdrawing the distraction member and the implant track from the intervertebral disc space.

In another variant, the method further includes maintaining the distraction member in the distracted configuration, detaching the distraction member from implant track, and withdrawing the implant track from the intervertebral disc space.

In another aspect, an implant is disclosed. In one embodiment, the implant comprises a superior member, an inferior member, and at least one side wall connecting the superior and inferior members. Further, superior and inferior members and the at least one side wall define an interior cavity of the implant, which is configured to (i) receive and engage with an implant track of an implant delivery apparatus during implant delivery, and (ii) receive a bone forming material after implantation thereof in the disc space.

In one variant, the implant has a generally curved cuboid shape.

In another variant, the implant has a generally rectangular cuboid shape.

In yet another variant, the superior and inferior members each comprise an inclined surface such that the implant has a greater height one side of the implant relative to an opposing side of the implant, such that the implant has a generally tapered shape.

In another aspect, an implant delivery apparatus is disclosed. In one embodiment, the implant delivery apparatus includes an implant track that is continuous with a distraction member disposed at a distal end of the apparatus. The implant delivery apparatus enables distraction of the target intervertebral disc space and delivery of an implant using a single device.

In another aspect, a method for correction of spinal conditions is disclosed.

In a further aspect, a system for correction of spinal conditions is disclosed. In one embodiment, the system includes: (i) an implant delivery apparatus comprising a distraction member and an implant track, and (ii) an implant.

BRIEF DESCRIPTION OF THE DRAWINGS

FIGS. 1A-1C show diagrammatic representations of a spinal vertebral bone in multiple views.

FIGS. 2A and 2B illustrate a functional spinal unit (FSU), which includes two adjacent vertebrae and the intervertebral disc between them in multiple views.

FIG. 3 illustrates a top view of a schematic illustration of a vertebral bone.

FIGS. 6A and 6B illustrate views of a spinal segment showing resection of a portion of the spine.

FIG. 7A-7C respectively show top perspective, top plan and side elevation views of an exemplary implant delivery instrument according to one embodiment of the present disclosure.

FIGS. 8A and 8B show cross-sectional views of the exemplary implant delivery instrument of FIGS. 7A-7C.

FIGS. 9C-9F show side elevation views of the first embodiment of a distraction member of FIGS. 9A and 9B, illustrating exemplary movements thereof.

FIGS. 11A and 11B show side elevation views of the second embodiment of a distraction member of FIG. 10, illustrating exemplary movements thereof.

FIGS. 12A-12G respectively show front and side perspective views, as well as side elevation, front elevation, top plan, and rear elevation views of a first embodiment of an implant for use with the implant delivery instrument of FIGS. 7A-7C.

FIGS. 12H and 12I show front perspective views of the implant of FIGS. 12A-12G further including a movable member.

FIGS. 13-14C show top plan views illustrating loading and movement of the implant of FIGS. 12A-12G when utilized with the implant delivery instrument of FIGS. 7A-7C.

FIGS. 16A-16F show side and top views of a method of use of the implant delivery instrument of FIGS. 7A-7C having the first embodiment of a distraction member of FIGS. 9A and 9B for delivery of the implant of FIGS. 12A-12G.

FIGS. 17A-17D illustrate top, rear, first side and second side views of a target disc space having the implant of FIGS. 12A-12G implanted therein.

FIGS. 18A-18F show side and top views of a method of use of the implant delivery instrument of FIGS. 7A-7C having the second embodiment of a distraction member of FIGS. 10-11B for delivery of the implant of FIGS. 12A-12G.

FIGS. 19A and 19B show schematic side and front views of a target disc space having two implants implanted therein.

FIGS. 20A and 20B are respectively perspective and cross-sectional views of an exemplary pedicle screw assembly configured for use with the implants and implantation delivery devices disclosed herein.

FIGS. 20C-20E respectively show schematic top, rear and side views of a spinal segment having the pedicle screw assembly of FIGS. 20A and 20B and the implant of FIGS. 12A-12G implanted therein.

FIGS. 21A-21D respectively show front perspective, front elevation, top plan and side elevation views of an exemplary spinous process fixation device configured for use with the implants and implantation delivery devices disclosed herein.

FIGS. 21E and 21F respectively show schematic side and top views of a spinal segment having the spinous process fixation device of FIGS. 21A-21D and the implant of FIGS. 12A-12G implanted therein.

FIGS. 22A-22C respectively show top perspective, top plan and side elevation views of an exemplary implant delivery instrument according to another embodiment of the present disclosure.

FIGS. 22D and 22E show cross-sectional views of the exemplary implant delivery instrument of FIGS. FIG. 22A 22C.

FIGS. 23A-23D respectively show front elevation, side elevation, top plan and top perspective views of a first embodiment of an implant for use with the implant delivery instrument of FIGS. 22A-22C.

FIGS. 24A-24D show top plan views illustrating loading and movement of the implant of FIGS. 22A-22C when utilized with the implant delivery instrument of FIGS. 23A-23D.

FIGS. 24E and 24F show top views of a method of use of the implant delivery instrument of FIGS. 22A-22C for delivery of the implant of FIGS. 23A-23D.

FIGS. 25A-25D respectively show top plan, front elevation, side elevation and top perspective views of a second embodiment of an implant for use with the implant delivery instrument of FIGS. 22A-22C.

FIGS. 26A-26D show top views of a method of use of the implant delivery instrument of FIGS. 22A-22C for delivery of the implant of FIGS. 25A-25D.

Figures 4A, 4B:
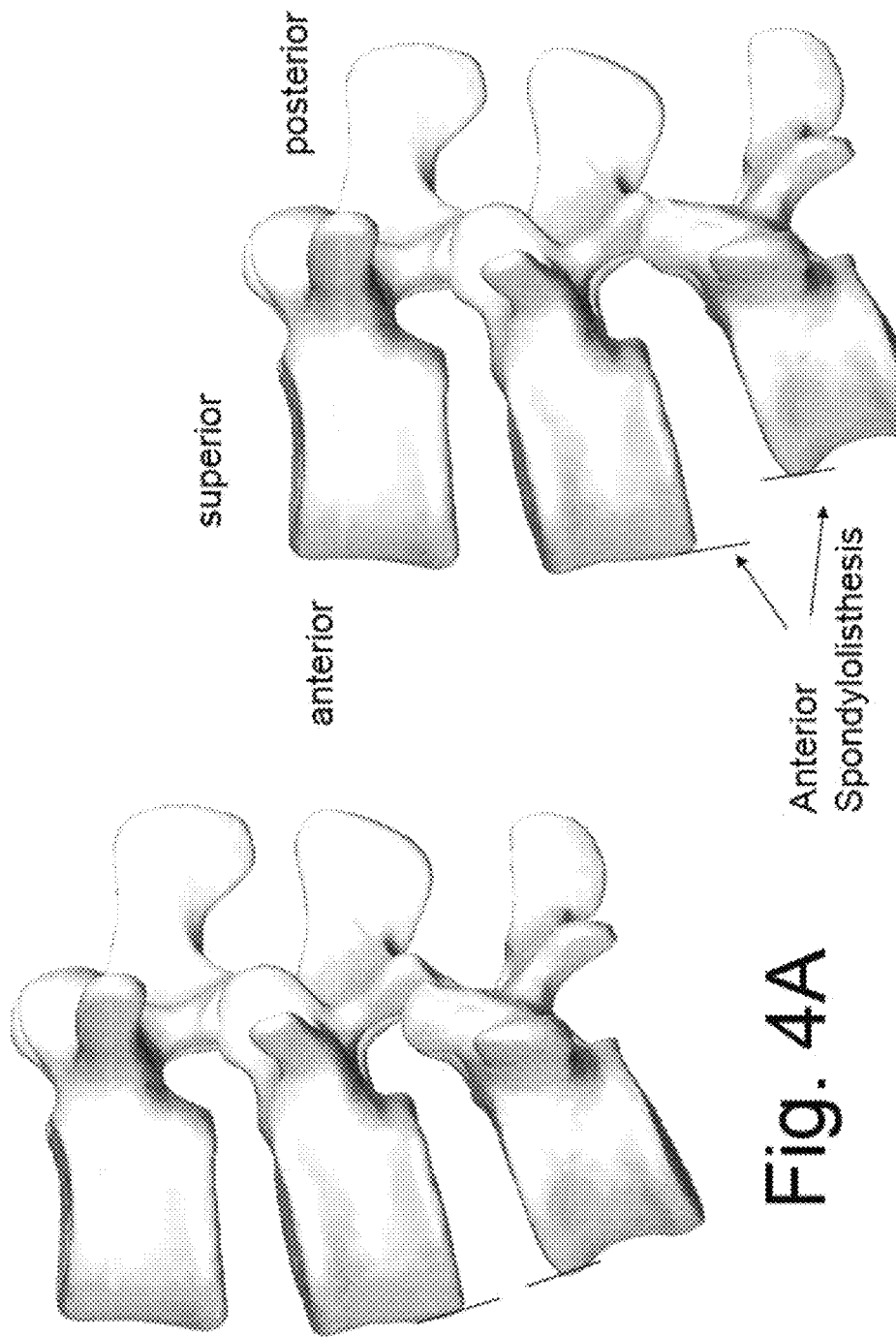
FIGS. 4A and 4B illustrate side views of a normally aligned spinal segment and a spinal segment having anterior spondylolisthesis, respectively.

All Figures © Copyright 2013-2017. Samy Abdou. All rights reserved.

DETAILED DESCRIPTION

In order to promote an understanding of the principals of the disclosure, reference is made to the drawings and the embodiments illustrated therein, and wherein like numerals refer to like parts throughout. Nevertheless, it will be understood that the drawings are illustrative and no limitation of the scope of the claims is thereby intended. Any such alterations and further modifications in the illustrated embodiments, and any such further applications of the principles of the disclosed devices as illustrated herein are contemplated as would normally occur to one of ordinary skill in the art.

Overview

In one aspect, improved devices, systems, and methods to alter vertebral alignment, or otherwise manipulate and fix a position of the vertebrae are described herein. Specifically, implantable devices and systems for implantation thereof (e.g., related components) and methods of use are disclosed herein.

It will be appreciated that in a variety of disorders, the vertebral bones of a human (or other vertebrate organism) may become mal-aligned and produce, among other conditions, translational, rotational and/or angulational deformities of the spinal column. The devices and methods disclosed herein can advantageously be used in the treatment of many spinal disorders, such as, inter alia, spondylolisthesis (anterior, posterior or lateral), coronal plane deformity (such as scoliosis), sagittal plane deformity (such as alternation in segmental kyphosis or lordosis), axial translation, rotational deformity, and the like.

In one example, spinal segment to be surgically treated using the methods and apparatus disclosed herein includes at least a superior vertebral bone, an immediately inferior vertebral bone, and the intervening intervertebral disc space.

A spinal segment comprised of two immediately adjacent vertebral bones and the intervertebral disc space disposed therebetween defines a "functional spinal unit" (FSU)—as described further below. An FSU to be surgically treated will be referred to as a target FSU and its intervertebral disc space as a target intervertebral disc space.

In one embodiment, an implant delivery apparatus includes a body, a handle extending from the body, an implant track disposed on distal side of the body, a distraction mechanism disposed at a distal end of the implant track, an implant pusher device disposed on operatively connected to the body. The implant delivery apparatus is configured to enable distraction of the target intervertebral disc space and delivery of an implant to the distracted disc space. The distraction mechanism is configured to move the vertebral bones of the target FSU into a desired configuration and correct alignment thereof. The implant track is configured to have an implant loaded thereon and slidably delivered to the distracted disc space utilizing the implant pusher. The implant includes a superior plate (configured to abut the superior vertebral bone), an inferior plate (configured to abut the inferior vertebral bone), and a side wall connecting the superior plate and the inferior plate. The superior plate, the inferior plate, and the side wall define a cavity which is configured to receive an outer aspect of the implant track. Further, protrusions may be disposed on the interior surfaces of the plates, which are configured to engage with grooves on the implant track. Alternatively or additionally, protrusions/ridges may be disposed on the exterior surface of the implant track, which are configured to engage with grooves on the interior surfaces of the implant.

In one variant, the distraction member is non-detachable and is configured to be removed from the target disc space after implantation of the implant. In another variant, the distraction member is detachable and is configured to be released from the implant track and implanted in the disc space along with the implant (having been advanced down the implant track and into the target disc space).

In one embodiment, a method of treatment includes entering the target intervertebral disc space and removing at least a portion of the viscoelastic material that comprises the natural nucleus pulposus within (at least a portion of) the intervertebral disc space. The target intervertebral disc space may be accessed using various surgical approaches (such as e.g., a direct anterior approach, an anterolateral approach, and/or a direct lateral approach, posterolateral approach, posterior approach, etc.), thereby creating one or more operative corridors at desired vertebral level(s) of the spinal column.

After removal of the viscoelastic material (and optional decortication of the bony surfaces adjacent to the evacuated disc space segment(s)), the method further includes inserting the distraction member into the target intervertebral disc space, and actuating the distraction member to alter alignment of the superior and inferior vertebral bones. Next, an implant is loaded onto the implant track and advanced down the track via release of the implant pusher, and the implant is positioned within the target intervertebral disc space. In one variant, the distraction member is removed from the disc space as the implant delivery instrument is withdrawn. In another variant, the method further includes detaching the distraction member from the implant track such that the distraction member is implanted into the disc space along with the implant.

Detailed Description of the Exemplary Embodiments

Exemplary embodiments of the apparatus and methods of the present disclosure are now described in detail.

It will be appreciated that while the exemplary embodiments are described with respect to human beings, various of the methods, apparatus and systems disclosed herein may be applied to other species having a spinal structure (i.e., vertebrates).

FIGS. 1A-1C show diagrammatic representations of a spinal vertebral bone 802 in multiple views. For clarity of illustration, the vertebral bone of FIGS. 1A-1C and those of other illustrations disclosed herein are represented schematically and it should be appreciated that actual vertebral bodies may include anatomical details that are not shown in these figures. Further, it is understood that the vertebral bones at a given level of the spinal column of a human or animal subject will contain anatomical features that may not be present at other levels of the same spinal column. The illustrated vertebral bones are intended to generically represent vertebral bones at any spinal level without limitation. It will be appreciated that the disclosed devices and methods may be employed at any applicable spinal level.

Additionally, the term "sagittal plane", as used herein, refers without limitation to the plane that splits the body into left and right segments. The terms "mid-sagittal plane" or "median plane", as used herein, refer to the plane that specifically splits the body into equal left and right halves. The term "coronal plane", as used herein, refers without limitation to the plane that divides the body into anterior (front) and posterior (back) segments. It will be appreciated that the coronal and sagittal planes are substantially perpendicular to one another.

As can be seen in FIGS. 1A-1C, the vertebral bone 802 contains an anteriorly-disposed vertebral body 804, a centrally-disposed spinal canal 806 and a posteriorly-placed lamina 808. The pedicle segments 810 of the vertebral bone 802 form the lateral aspects of the spinal canal 806 and connect the laminas 808 to the vertebral body 804. The spinal canal 806 contains neural structures such as the spinal cord and/or nerves. A midline protrusion termed the spinous process (SP) extends posteriorly from the medial aspect of laminas 808. A protrusion extends laterally from each side of the posterior aspect of the vertebral bone 802 and is termed the transverse process (TP). A right transverse process (RTP) extends to the right from the lateral aspect of the right pedicle. A left transverse process (LTP) extends to the left from the lateral aspect of the left pedicle. A superior protrusion extends above the lamina 808 on each side of the vertebral midline, and is termed the superior articulating process (SAP). An inferior protrusion extends inferiorly below the lamina 808 on each side of the vertebral midline, and is termed the inferior articulating process (IAP).

As a brief aside, it is noted that the posterior aspect of the pedicle 810 can be accessed at an indentation 811 in the vertebral bone 802 between the lateral aspect of the SAP and the medial aspect of the TP. In surgery, it can be common practice to anchor a bone fastener into the pedicle portion 810 of a vertebral bone 802 by inserting the fastener through indentation 811 and into the underlying pedicle 810 in a posterior to anterior direction.

FIGS. 2A and 2B illustrate a functional spinal unit (FSU), which includes two adjacent vertebrae and the intervertebral disc disposed therebetween. The intervertebral disc resides between the inferior surface of the upper vertebral body and the superior surface of the lower vertebral body, although it is not specifically shown in the figures. FIG. 2A shows the posterior surface of the adjacent vertebrae and the articulations between them. FIG. 2B shows an oblique view. The FSU contains three joints between the two vertebral bones, with the intervertebral disc comprising the anterior joint. The posterior joints include a facet joint 814 on each side of the midline, wherein each facet joint 814 is comprised of the articulation between the IAP of the superior vertebral bone and the SAP of the inferior bone.

These illustrations and definitions of anatomical structures are known to those of ordinary skill in the art. They are described in more detail in *Atlas of Human Anatomy*, by Frank Netter, third edition, Icon Learning Systems, Teterboro, N.J., which is incorporated herein by reference in its entirety. It should be appreciated that the directional language and terms regarding orientation such as upper, lower, upward, downward etc., are used throughout merely for convenience of description and are not limiting.

As shown in FIG. 3, the apophyseal ring is an outer rim segment of the vertebral body that is located on each of the superior and the inferior surfaces of a vertebral bone and comprise bony surfaces that abut the intervertebral discs. Further, the apophyseal ring to is circumferentially positioned and forms the most dense and strongest portion of the superior and inferior surfaces of said vertebral bone. The ring is comprised of dense bone that anchors the external fibers of the annulus fibrosis of the adjacent intervertebral disc. The apophyseal ring is discussed in greater detail in *The epiphyseal ring: a long forgotten anatomical structure with significant physiological function*. Dar G, et al. *Spine* (Phila Pa 1976). 2011 May 15; 36(11):850-6, which is incorporated herein by reference in its entirety.

In a healthy spine within normal physiological parameters (such as that shown in FIG. 4A), the two facet joints of a functional spinal unit (FSU) collectively function to prevent, inter alia, aberrant movement in the horizontal (i.e., axial) plane of the superior vertebral bone relative to the inferior vertebral bone. As a brief aside, it is noted that the horizontal plane of a human spine refers to a plane of the erect spine that is substantially parallel to a level floor on which the subject is standing.

However, with aging and spinal degeneration, displacement of the vertebral bones in the horizontal plane may occur, which is a condition termed spondylolisthesis. FIG. 4A illustrates three vertebral bones with relatively normal alignment, whereas FIG. 4B shows the anterior displacement of the middle bone relative to the inferior-most bone. As illustrated therein, the vertebral column of FIG. 4B may be characterized as having an anterior spondylolisthesis of the middle vertebral bone relative to the inferior-most vertebral bone. A spondylolisthesis can be anterior, as shown in FIG. 4B, posterior (where a superior vertebral bone of an FSU is posteriorly displaced in the horizontal plane relative to the inferior vertebral bone) or lateral. In general, anterior sponylolisthesis is more clinically relevant than posterior spondylolisthesis, and any of the foregoing types of sponylolisthesis can be further classified based on the extent of vertebral displacement. Characterization of spondylolisthesis is discussed in greater detail in *Principles and Practice of Spine Surgery* by Vaccaro, Bets, Zeidman; Mosby press, Philadelphia, Pa.; 2003, which is incorporated herein by reference in its entirety.

With degeneration of the spine, constriction of the spinal canal and impingement of the nerve elements contained therein frequently occurs, and is termed spinal stenosis. Spondylolisthesis can exacerbate the extent of nerve compression within the spinal canal as misalignment of bone within the horizontal plane will often further reduce the size of the spinal canal. Relief of the compressed nerves can be achieved by the surgical removal of the bone and ligamentous structures that constrict the spinal canal. Decompression of the spinal canal can, however, further weaken the facet joints and increase the possibility of additional aberrant vertebral movement. Therefore, conventional spinal decompression procedures may actually worsen the extent of spondylolisthesis or produce spondylolisthesis in an otherwise normally aligned FSU elsewhere in subject's spine. Accordingly, after decompression, surgeons will commonly fuse and immobilize the adjacent spinal bones in order to prevent the development of post-operative vertebral misalignment and/or spondylolisthesis.

Figure 5:
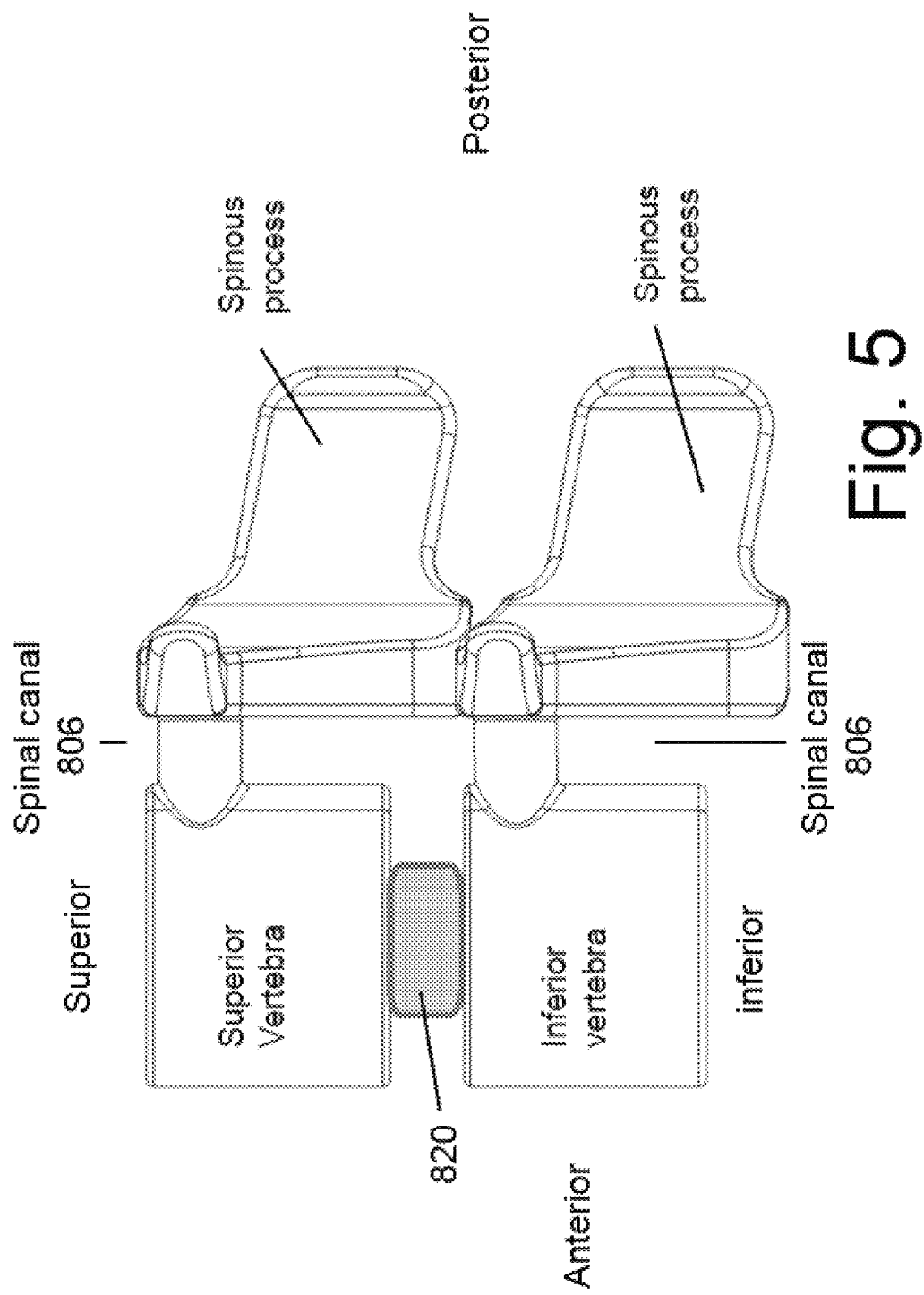
FIG. 5 illustrates schematic side view of a spinal segment having an exemplary implant inserted within a disc space thereof.

Regardless of the clinical reasoning or indication for fusion of the vertebral bones, many surgeons position an implant within the disc space that rests between the two vertebral bones which are to be fused. An example of a generic interbody implant 820 positioned within a disc space between superior and inferior vertebral bodies of an immobilized FSU is depicted in FIG. 5, where a side view of a schematic FSU is shown. Many embodiments of interbody implants are known in the art, such as those shown and described in U.S. Pat. Nos. 4,636,217; 5,015,247; 5,192,327; 5,443514; 5,749,916, 6,251,140; 6,342,074; 6,706,070; 6,767,367; 6,770,096; 6,852,127; 7,037,339; 7,227,477; 7,641,690, each of which is incorporated herein by reference in its entirety.

In general, an interbody implant is usually comprised of an outer superstructure manufactured from a synthetic biocompatible material (such as e.g., metal alloy, plastic material, ceramics, or the like), and an internal cavity contained therein. The internal cavity is configured to receive and house a bone forming material that may be inserted by the surgeon into the interbody implant at the time of implantation. Openings in the superstructure permit communication and fusion between the vertebral bone(s) outside of the device and the bone forming material contained within the cavity. In general, the superstructure separates and supports the vertebral bones that abut the implanted disc space. In this way, the device can be used to maintain the disc space height. The internal cavity contains the bone formation material that will form a fusion mass which will (over time) extend from the superior vertebral bone to the inferior vertebral bone. When the superstructure is manufactured from metallic alloy, it can be advantageously made of limited thickness thereby providing a larger internal cavity for containment of a greater volume of bone forming material. However, the metallic superstructure is generally X-ray opaque, thereby limiting the ability to follow bone healing in the post-operative period via X-ray imaging. In contrast, manufacture of the superstructure from plastic materials (such as PEEK or the like) or ceramic permits X-ray visualization of the healing bone within, but significantly limits the size of the internal cavity and the volume of bone forming material contained therein as the foregoing materials have a lower mechanical strength (relative to metallic materials) and require thicker walls to provide the necessary resistance to load, strain and/or stress on the implanted device.

In alternate embodiments, interbody implants may be manufactured without a dedicated internal cavity. In these latter embodiments, the outer surface of the implant may be at least partially comprised of a material capable of promoting osseointegration (e.g., direct bony ingrowth into the implant from the adjacent bone).

Considerable clinical experience has been gained by the implantation of the aforedescribed interbody implants via a posterior surgical corridor, and practitioners have become aware of the limitations and disadvantages associated therewith. For example, in a first limitation, the implants are generally large, having a width of at least 9 mm, and therefore require substantial bony resection of the posterior spinal elements for implantation. Specifically, implantation of such devices through a posterior surgical approach often involves removal of substantial portions of the facet joint at the implanted level. Facet joint resection can add time and complexity to the surgical work, as well as increased pain and/or recovery time for the patient. Further, in another limitation, facet joint resection can also significantly destabilize the implanted FSU so that pedicle screw fixation is needed to re-stabilize the spine. In other words, implantation of the interbody device may require a high degree of bony resection so as to require extensive supplemental fixation, which (again) adds time and complexity to the surgical process and can also increase pain and/or recovery time for the patient. In yet another limitation, given the proximity to nerve elements to the posterior surgical corridor, implant placement with limited facet resection requires a greater degree of nerve retraction and increases the risk of nerve injury.

Prior attempts to reduce the width of the interbody implant and avoid the foregoing limitations have yielded implants with a height to width ratio that is greater than one, however, these implants have an increased risk of roll-over and/or dislodging within the disc space.

The interbody implants and associated implantation devices and methods disclosed herein address the above identified issues with conventional spinal implants and techniques. The devices and methods are particularly advantageous for use in minimally invasive procedures—including percutaneous operations. Although specific examples are shown and described herein, it will be appreciated that the spinal implantation devices and methods of implantation of the present disclosure may be employed in a myriad of applicable interbody fusion procedures using a variety of surgical corridor/approaches and at various spinal segments and/or structures.

It is a purpose of the present disclosure to describe implantation devices and methods for the safe and reproducible placement of an interbody device into an intervertebral disc space. In one embodiment, the interbody device may be employed without other bone fixation implants (i.e., as a "stand alone" device). In another embodiment, the interbody device may be employed in conjunction with a spinous process fixation implant. In yet another embodiment, the interbody device may be used with screw fixation of the vertebral bones, such as, for example, pedicle screw assemblies or the like. In one implementation, a pedicle screw assembly is placed into an ipsilateral pedicle of each of the superior and inferior vertebral bones that abut the implanted disc space. The screw assemblies are joined by an interconnecting member, such as a rod, and the screw assembly and joined interconnecting member are used to rigidly fixate the vertebral bones to one another. The interbody device or the pedicle screw/rod assembly may be used on one side (i.e., unilateral) of the vertebral midline alone or, alternatively, on both sides (i.e., bilateral) of the vertebral midline, where the vertebral midline is substantially defined by the mid-sagittal plane that bisects the implanted disc space/vertebral bones into a right half and a left half. In still other embodiments, the interbody device may be used with one or more additional bone fixation implants.

In one embodiment, the disc space that is targeted for inter-body device implantation is identified using radiographic imagining imaging techniques (such as X-rays, CT, Mill and the like). A skin incision is made in the skin immediately posterior to the target disc space. The paraspinal muscles are retracted and a corridor is developed adjacent to the spinous process and the posterior aspect of the lamina. The lamina of each of the superior and inferior vertebrae that border the targeted disc space are identified—preferably by use of an imaging modality. Resection of the lamina posterior to the target disc space is performed, where at least a portion of the inferior aspect of the lamina of the superior vertebral bone (i.e., the vertebral bone that forms the superior border of the target disc space) is removed. FIG. 6A shows a schematic depiction of an exemplary resection of a segment 1152 of the inferior aspect of the lamina of the superior vertebral bone (when targeting the L4/5 disc space).

An additional resection of the lamina posterior to the target disc is then performed, where at least a portion of the superior aspect of the lamina of the inferior vertebral bone (i.e., the vertebral bone that forms the inferior border of the target disc space) is removed. The schematic depiction of FIG. 6A additionally shows an exemplary resection of a segment 1153 of the superior aspect of the lamina of the inferior vertebral bone. At least a portion of the ligament (i.e., the ligamentum flavum) that spans the region of lamina resection can also be removed such that the posterior aspect of thecal sac is exposed through a window W of FIG. 6B. While shown as being formed on only one side of the midline in FIG. 6A, alternatively the window W may be formed bilaterally (i.e., the window W may be formed on both sides of the vertebral midline, where the vertebral midline is defined by a sagittal plane that substantially extends through the spinous process and divides a vertebral bone into left and right halves).

The posterior aspect of the target disc space can then be exposed through a corridor that is lateral to thecal sac. The thecal sac may be retracted gently in the medial direction to enable identification of the posterior aspect of the target disc space. The disc space can then be entered and at least a segment of the disc material may be removed (i.e., discectomy). If necessary, a collapsed disc space having a small vertical height that is substantially below the normal value for that disc space level may be distracted to a desired (increased) height via sequential or iterative placement of shims or distractors within the disc space, where the disc space height is defined as the vertical distance from the superior disc space surface to the inferior disc space surface.

Additionally or alternatively, an implant placement instrument can be configured for distraction of the disc space. For example, the exemplary implant placement instruments disclosed herein have an intra-discal segment that is sized to be positioned within the disc space. The intra-discal segment includes opposing upper and lower plates or members, and the upper plate can be forcibly distracted away from the lower plate to enable the implant placement instrument to function as a distraction device. Accordingly, the vertebral bone superior to the target disc space and its immediately inferior vertebral bone can be forcibly moved away from one another, thereby increasing the vertical height of the target disc space.

Implant and Implant Placement Apparatus

One exemplary embodiment of an implant placement instrument 100 is shown in FIGS. 7A-11B. As depicted therein, the implant placement instrument 100 includes a body 105 and a handle 104 extended outwardly therefrom. An implant track 120 extends outwardly from an anterior surface of the body 105, and a distraction member extends outwardly from a distal end of the implant track 120.

As shown in FIGS. 7C and 9A-9F, in one embodiment, a distraction member 124 includes an upper plate 1242 and a lower plate 1244. The plates 1242 and 1244 are configured to be distracted apart so as to apply a distraction force onto the vertebral bones when the distraction member 124 is positioned within the intervertebral disc space. A distal end of each of the plates 1242 and 1244 comprises a generally continuously curved surface, such that each distal end has a generally quarter circle cross-section. A proximal end of each of the plates 1242 and 1244 also comprises a curved surface, although the proximal ends are of an irregular curvature which differs from the continuous curvature of the distal ends. In alternate implementations, the curvature of the proximal and distal ends may be identical (e.g., the proximal ends may comprise a continuously curved surface), or the proximal ends may have a non-curved surface (e.g., a squared surface, an inclined surface, etc.).

Figure 9A:
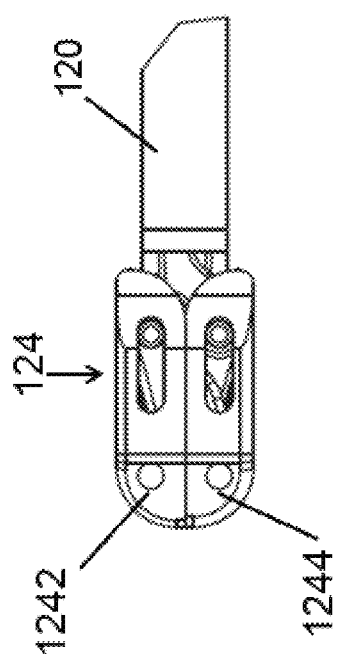
FIGS. 9A and 9B show side elevation views of a first embodiment of a distraction member for use with the implant delivery instrument of FIGS. 7A-7C.
Figure 9B:
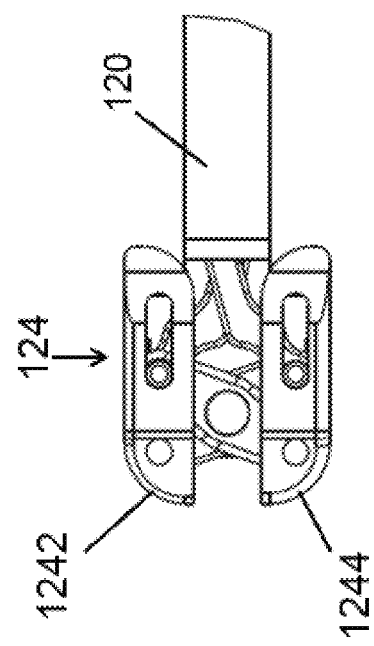

An exemplary closed (non-distracted) configuration of the distraction member 124 is shown in FIG. 9A, while an exemplary open (distracted) configuration is shown in FIG. 9B. As can be seen in FIG. 9A, in the closed configuration of the present embodiment, an interior surface of the upper plate 1242 is abutted to an interior surface of the lower plate 1244, and the continuously curved distal ends of the upper and lower plates 1242 and 1244 cooperatively form a generally half circle cross-section. Further, a height of the plates in the closed configuration is greater than a height of the implant track 120 (i.e., the exterior surfaces of the plates 1242 and 1244 respectively extend above and below a boundary of the implant track 120). The half circle cross-section of the distraction member in the closed configuration (forming curved, non-blunt end of the distraction member) may assist in enabling the distraction member to be pushed through tissues and/or a tissue corridor within the subject during insertion of the distraction member into the intervertebral disc space. As can be seen in FIG. 9B, in the open configuration, a space is disposed between the interior surface of the upper plate 1242 and the interior surface of the lower plate 1244, such that an overall height of the distraction member 124 is increased in the open configuration relative to the closed configuration. It is noted that while the plates 1242 and 1244 are movable relative to one another in the present embodiment, the upper and lower surfaces of the implant track 120 are not movable relative to each other (i.e., the upper and lower surfaces of the implant track are non-distractable) and remain stationary during distraction of the distraction member and delivery of the implant to the target disc space.

In the present embodiment, the distraction member 124 is non-detachable from the implant placement instrument 100. Accordingly, the distraction member is removed the target disc space at the conclusion of the procedure, and does not remain implanted therein. As shown in the illustrated embodiment, the plates 1242 and 1244 are joined and operable via crossed linkages (e.g., a scissor jack-like distraction mechanism), which are coupled to a distal end of implant track 120 and configured for reversible distraction of the distraction member 124. It is contemplated, however, that alternative or additional mechanisms for distraction may be incorporated into the distraction member 124. These alternative/additional distraction mechanisms may include, for example, wedges/inclines, pulleys, balloons, magnets, hydraulic drives, pistons or the like.

For example, in one alternate embodiment, the distraction member may comprise a worm screw drive or gear mechanism and an associated ridged track, which is configured to be turned (wound) via an attachable and/or insertable adjustment tool or the tool may be integrated into the implant placement instrument (see e.g., the distraction mechanism discussed below with reference to FIGS. 11A and 11B). The tool may be operated in a first rotational direction to increase a height of the distraction member, thereby increasing a distance between the superior and inferior members. Further, in some examples, the tool may be operated in a second rotational direction to decrease the height of the distraction member, and thereby decrease the distance between the upper and lower plates. Various exemplary mechanical (non-fluidic) mechanisms that can be adapted into the distraction member are shown and described in U.S. Pat. No. 7,909,870 and U.S. Patent Publication No. 2003/0163199, each of which is incorporated herein by reference in its entirety.

In another embodiment, the distraction member may include a balloon distraction mechanism made of either non-compliant or compliant material, which may be porous or non-porous, or may include a mesh material which may be coated or lined with a porous or non-porous material. The balloon may further include a port for coupling to a source of an inflation and/or expansion medium (e.g., a gas, a liquid, a semi-solid, a gel, a liquid that hardens into a solid material, etc.) for inflating and/or expanding the distraction mechanism. The devices can further include one or more anchoring or attachment features for fixing the balloon to one or both of the superior and inferior members. Actuation of such an embodiment of the distraction mechanism involves inflation of the balloon with the expansion medium, where the act of balloon inflation provides at least part of the force needed to produce the change in configuration of the distraction member (such as an increase in the height of the distraction member). An exemplary balloon driven distraction mechanism that can be adapted into the distraction member is shown and described in U.S. Pat. No. 8,123,807, which is incorporated herein by reference in its entirety.

In yet another embodiment, the distraction member can include a piston-based distraction mechanism. Specifically, a piston can be disposed within a cavity of one or both of the upper or lower plates. Note that in one implementation, the distraction member can include one or more apertures that allow filling and/or bleeding of the working fluid from the piston chamber. See also, e.g., U.S. Patent Application Publication No. 2007/0093901, which is incorporated herein by reference in its entirety, and describes the exemplary use of pistons in the manufacture of an expandable interbody implant, which may be integrated into the distraction member described above.

Turning now to FIGS. 9C-9F, exemplary movements and orientations of the plates 1242 and 1244 relative to each other during distraction of the distraction member 124 are illustrated. In one implementation, shown in FIGS. 9C and 9D, the plates 1242 and 1244 are configured to move both (i) vertically away from one another so as to cause vertebral distraction of the disc space generally along a longitudinal axis of the spine when in erect orientation, and (ii) along a direction E, which is substantially parallel to the longitudinal axis of the implant track 120. In the closed configuration (FIG. 9D) the plates 1242 and 1244 have a side-by-side arrangement where a longitudinal axis of each of the plates is substantially aligned with the longitudinal axis of the implant track 120. In the open configuration, the plates are separated by a space, and the lower plate 1244 is positioned forward of (or distal relative to) the upper plate 1242. The present implementation (illustrated in FIGS. 9C and 9D) enables the distraction member 124 to e.g., increase a height of the vertebral disc space, as well as alter vertebral alignment in the sagittal plane and thereby reduce anterior or posterior spondylolisthesis of the target FSU. It will be appreciated that the plates can be moved in one or both of the foregoing directions to varying degrees as necessary for adjustment of the target FSU.

In another implementation, FIGS. 9E and 9F illustrate that the plates 1242 and 1244 are configured for movement along direction F, which is substantially perpendicular to the longitudinal axis of the track 120. In the closed configuration (FIG. 9F), the plates are in a stacked arrangement, and an interior surface of the upper plate 1242 is abutted to an interior surface of the lower plate 1244. Further, the longitudinal axis of the upper plate 1242 is generally aligned with the longitudinal axis of the implant track 120, whereas the longitudinal axis of lower plate 1244 is parallel to and offset from the longitudinal axis of the implant track 120. In the open configuration (FIG. 9E), the plates have a space disposed therebetween, yet remain in a generally stacked arrangement. In this latter implementation, the distraction member 124 is configured to, e.g., alter vertebral alignment in the coronal plane and reduce lateral spondylolisthesis.

While the plates 1242 and 1244 of the distraction member 124 are shown as moving into a substantially parallel configuration relative to one another (i.e., in each of the foregoing implementations shown in FIGS. 9C-9F the longitudinal axis of the upper plate 1242 remains substantially parallel to the longitudinal axis of the lower plate 1244 in both the non-distracted and the distracted configurations), in alternate or additional implementations, the plates may be configured to move into non-parallel configuration in order to impart a desired anatomical relationship to the target FSU. For example, the distraction member can be configured such that a distance between the distal ends of the plates is greater than a distance between the proximal ends of the plates when the distraction member is in the open/distracted configuration. In this implementation, the distraction member can be used to not only re-align the vertebral bones in the various planes described but to also confer a greater lordosis (and/or kyphosis) to the disc space of the target FSU.

Figure 10:
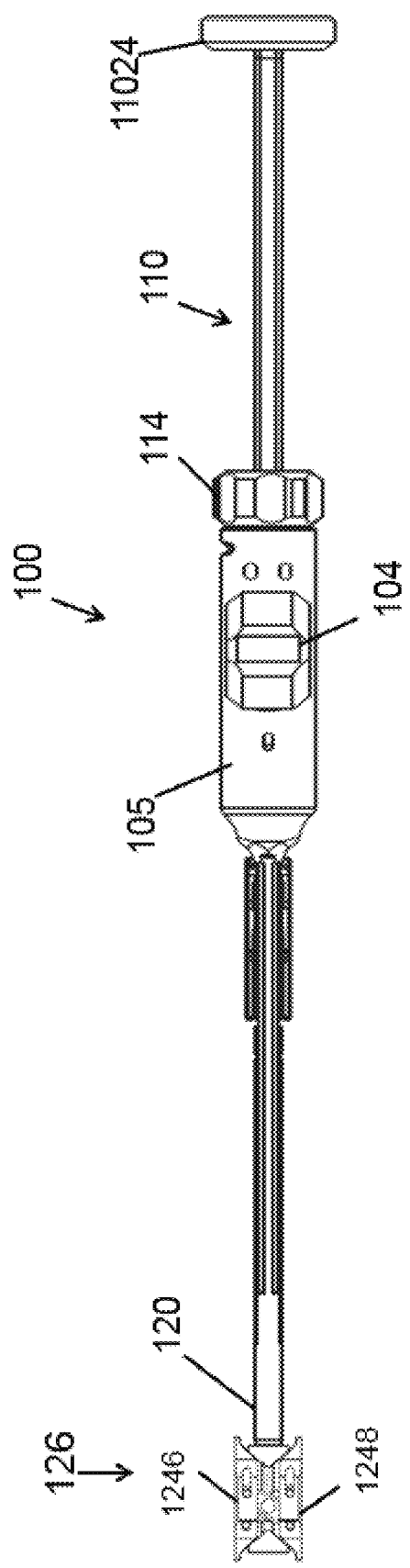
FIG. 10 shows a side elevation view of a second embodiment of a distraction member for use with the implant delivery instrument of FIGS. 7A-7C.

Turning now to FIGS. 10-11B, in an alternate embodiment, a detachable distraction member 126 includes an upper plate 1246 and a lower plate 1248. Similar to the plates 1242 and 1244 of the distraction member 124, the plates 1246 and 1248 are configured to be distracted apart so as to apply a distraction force onto the vertebral bones when the distraction member 126 is positioned within the intervertebral disc space. Different from the plates 1242 and 1244, each of the distal and proximal ends of the plates 1246 and 1248 comprises a generally inclined surface and have an overhang at a distal tip thereof. In alternate implementations, the proximal and distal ends comprise non-inclined surfaces (e.g., each having a squared surface, a continuously curved surface, an irregularly curved surface, etc.), or the proximal and distal ends may have different configurations (e.g., the proximal ends may comprise a continuously or irregularly curved surface, while the distal ends comprise the inclined surface).

An exemplary closed (non-distracted) configuration of the distraction member 126 is shown in FIG. 11A, while an exemplary open (distracted) configuration is shown in FIG. 11B. As can be seen in FIG. 11A, in the closed configuration, an interior surface of the upper plate 1246 is abutted to an interior surface of the lower plate 1248, and the plates have a generally stacked arrangement. Further, the inclined distal and proximal ends of the upper and lower plates cooperatively form a generally "V" shaped space therebetween, which overlaps with (aligns with) the implant track 120. The relatively small height the detachable distraction member in the closed configuration may assist in enabling the distraction member to be pushed through tissues and/or a tissue corridor within the subject during insertion thereof into the intervertebral disc space.

As depicted in FIG. 11B, in the open configuration, the upper and lower plates 1246 and 1248 have a space disposed therebetween, and remain in a generally stacked arrangement. Further, the upper and lower plates 1246 and 1248 form an "X"-like configuration.

The distraction member 126 is configured to be a separate, detachable member that may be uncoupled from the implant track 120 of the implant placement instrument 100 so as to enable implantation of the distraction member within the disc space in addition to an implant that is delivered by advancement along the implant track 120. After detachment from the implant placement instrument 100, the distraction member 126 is configured to be retained (or otherwise locked) in the distracted configuration. In the present embodiment, the plates 1246 and 1248 of the distraction member 126 are illustrated as being joined by linkages and driven by a screw 1250 (similar to a scissor jack-like distraction device with a worm screw drive). Specifically, the distraction member 126 comprises a worm screw drive or gear mechanism and an associated ridged track, which is configured to be turned (wound) via an adjustment tool integrated into the implant placement instrument. The tool may be operated in a first rotational direction to increase a height of the distraction member, thereby increasing a distance between the upper and lower plates. Further, the tool may be operated in a second rotational direction to decrease the height of the distraction member, and thereby decrease the distance between the upper and lower plates. While plates 1246 and 1248 are illustrated as being joined by linkages and driven by the screw 1250, it is contemplated that alterative distraction mechanisms may incorporated into the distraction member 126 (such as, e.g., wedges/inclines, pulleys, balloons, magnets, hydraulic drives, pistons or the like, specific examples of which are discussed above).

Further, while the plates 1246 and 1248 of distraction member 126 are shown as moving into a substantially parallel configuration relative to one another (i.e., in the foregoing implementation shown in FIGS. 11A-11B the longitudinal axis of the upper plate 1246 is substantially parallel to the longitudinal axis of the lower plate 1248 in both the non-distracted and the distracted configurations), in alternate or additional implementations, the plates may be configured to move into non-parallel configuration in order to impart a desired anatomical relationship to the target FSU. For example, the distraction member can be configured such that a distance between the distal ends of the plates is greater than a distance between the proximal ends of the plates when the distraction member is in the open/distracted configuration.

During use of the implant placement instrument 100, the operator may hold and manipulate the instrument using handle 104 for advancement of the distraction member 124 or 126 into the intervertebral disc space. If needed, a mallet, or the like, may be used to hammer against a proximal end 11024 of a proximal member 1102 in order to advance the distraction member 124 or 126 into the intervertebral disc space.

Figure 15:
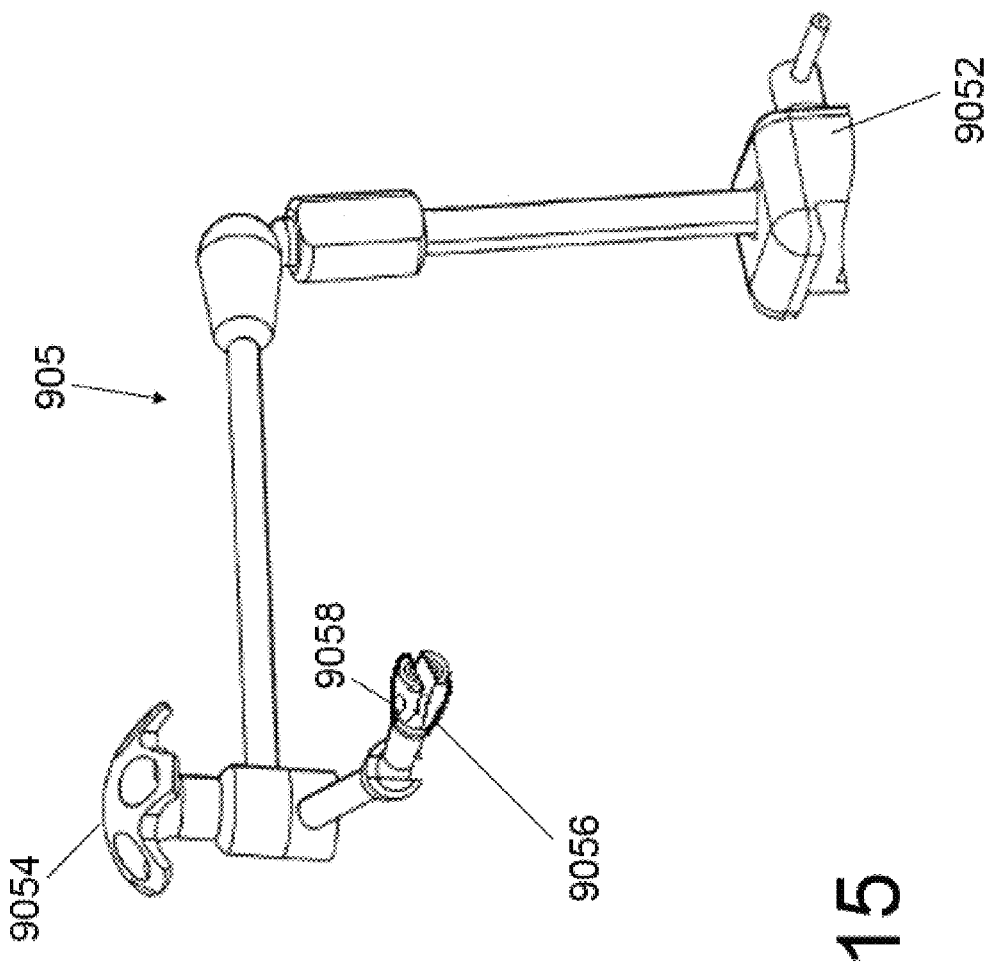
FIG. 15 illustrates a perspective view of an exemplary articulated frame configured for use with the implant delivery instruments disclosed herein.

Optionally, the implant placement instrument 100 may be stabilized via attachment to a fixation assembly that is anchored to a segment of the patient, such as, for example, a bony segment of the vertebral bone or another skeletal bone via a bone screw or the like. Additionally or alternatively, the implant placement instrument 100 may be stabilized via attachment to a fixation assembly that is anchored to the operating table on which the patient is positioned for surgery. An exemplary fixation assembly 905 is shown in FIG. 15 and is discussed elsewhere herein. The implant placement instrument 100 may also comprise a coupling region (for example, a coupling region 1046 of handle 104 shown in FIG. 7A) for attachment onto one or more of the fixation assemblies.

Once the distraction member 124 or 126 is positioned, a knob 114 is actuated so as to distract the intervertebral disc space and position the superior vertebral bone (i.e., the bone immediately above the target disc space) at a desired distance from and position relative to the inferior vertebral bone (i.e., the bone immediately below the target disc space). Specifically, in the embodiment shown in FIGS. 7A and 8B, the knob member 114 is disposed at a posterior surface of the body 105 of the implant placement instrument 100, and is configured to actuate the distraction member 124 or 126. For example, rotation of the knob member 114 in a first direction produces movement of the upper and lower plates away from one another towards the open (distracted) configuration (such as e.g., one of the configurations shown in FIG. 9B, 9C, 9E or 11B), whereas rotation in an opposite direction causes movement of the upper and lower plates towards one another and into the closed (non-distracted) configuration (such as e.g., one of the configurations shown in FIG. 9A, 9D, 9F or 11A). Alternatively, one of the plates may be movable and can be actuated via the knob, while the opposing plate is stationary. The knob 114 can be manually rotated by grasping the outer surface of the knob, or can be rotated by an instrument, such as, for example, a screw driver, a wrench, or the like that couples to a hex recess 1142 of the knob 114. In one exemplary implementation, a member 1102 attached at a posterior portion of the body 105 includes an aperture 11022 at a distal end portion 11024 which allows a screw driver to be advanced therethrough and into the recess 1142 of the knob 114 along trajectory D (see FIG. 7A).

After actuation of the knob 114 and distraction of the distraction member 124 or 126, an aperture 118 of the body 105 allows the operator to read a distance between a top surface of the upper plate 1242 and a bottom surface of the lower plate 1244. The reading can be used to select an appropriately sized implant to be advanced along the implant track 120 and into the distracted disc space, as will be discussed further below. The reading may be provided in a standard unit of measurement (such as millimeters, inches, etc.) or in selected letters and/or symbols that correspond to specific implant shapes and/or sizes. In the latter example, the implants usable with the implant placement instrument may be labeled with the corresponding letters and/or symbols.

One exemplary embodiment of an implant 205 configured for use with the implant placement instrument 100 is shown in FIGS. 12A-12G. As illustrated therein, the implant 205 includes a superior member 2051 and an inferior member 2052. An outer surface of the superior member 2051 is configured to abut an inferior surface of the vertebral bone immediately superior to the target disc space in which the implant 205 is positioned, while an outer surface of the inferior member 2052 is configured to abut a superior surface of the vertebral bone immediately inferior to the target disc space. The superior and inferior members 2051 and 2052 are connected by a side member (or side wall) 2053. The superior, inferior, and side members define an internal cavity 2055, which is disposed within the implant 205 and sized to receive at least a segment of the implant track 120 therein.

Although the implant 205 is depicted as having only one side member, it will be appreciated that in alternate embodiments, the implant may include one or more additional side members or partial side members. For example, the implant 205 can optionally include a movable side wall 20531, as depicted in FIGS. 12H and 12I. Specifically, the moveable side wall 20531 is moveable between a collapsed configuration (FIG. 12H) where the movable side wall 20531 is substantially flush with the side wall 2053, and an extended configuration (FIG. 12I) where the moveable side wall is disposed on an opposing lateral side of the implant 205 relative to the side wall 2053. The movable side wall 20531 may be comprised of a substantially elastic material. In one exemplary method of use, when loaded onto the implant track 120 the implant placement instrument 100, the movable side wall 20531 is compressed against the side member 2053 (in the collapsed configuration). When the insertion instrument 100 is removed from the disc space (after advancement of the implant into the disc space), the side wall is biased to the extended position. Stops (projections) on the top and bottom of the movable side wall may prevent the side wall from moving beyond the boundary of the implant (i.e., the projections are retained in the apertures in the superior and inferior members). It will be appreciated that the foregoing moveable side wall may enable (i) receipt of the exterior aspect of the implant track within the cavity and movement of the implant along with implant track in the collapsed configuration, (ii) added stability to the implant in the released configuration, and/or (iii) additional containment of bone graft material within the cavity.

As best illustrated in FIGS. 12D and 12F, each of the superior and inferior members 2051 and 2052 includes substantially linear lateral edges and a substantially pointed or angled edge at each of a distal end 2057 and a proximal end 2058 of the implant 205. In alternate embodiments, the superior and inferior members can include one or more curved surfaces (see e.g., implants 505 and 705 depicted in FIGS. 23A-23D and 25A-25D, respectively), and/or one or more of the distal and proximal ends can have a different configuration (e.g., curved, blunted, etc.).

Turning again to FIG. 12E, each of the superior and inferior members 2051 and 2052 has an inclined exterior surface. Specifically, at the distal end 2057, each of the superior and inferior members 2051 and 2052 has a greater height than at the proximal end 2058 thereof. The foregoing features give the implant 205 a generally rectangular cuboid and tapered shape. In alternate embodiments, the superior and inferior members can have an equal height at each of the distal and proximal ends (giving the implant a non-tapered shape), or one or more of the superior or inferior members can be inclined to a greater degree than the exemplary embodiment shown in FIG. 12E.

As discussed elsewhere herein, it is contemplated a variety of implants of different shapes and/or sizes may be manufactured or provided to be usable with the implant placement instrument, and the appropriately shaped/sized implant can be selected from a pre-fabricated set of implants (or manufactured) to be specific to the condition of the target FSU in order to correct curvature or otherwise stabilize the FSU. In one embodiment, the implant 205 may be manufactured in various sizes and provided with the implant placement instrument as a kit. For example, the kit can include two lordotic options, 0° (parallel) and 8° (lordotic), with heights ranging from 8 mm to 16 mm and from 10 mm to 16 mm, respectively. Each of the implants has a width of approximately 10 mm, and can have a length of 25 mm to 30 mm.

As an alternative, the method of implant placement may include, prior to the surgical procedure, selecting a height to which the disc space will be distracted at the time of surgery (i.e., selecting the height as part of a pre-operative planning procedure performed at a date earlier than that of the surgery date). After selecting the height, the implant can be manufactured, such as e.g., via additive or subtractive 3-D printing, to the selected height, as well as dimensioned and contoured to conform to the patient-specific anatomy of the subject into which the implant will be subsequently implanted at surgery. The method may also include the use of computer-assisted navigation and/or robotics in the placement of the implant during the surgical procedure. Further, more than one target FSU may be treated/implanted at surgery and each treated FSU may be implanted with more than one implant.

Returning to FIGS. 12A-12G, each of the superior and inferior members 2051 and 2052 includes surface features (e.g., indentations and protrusions, endplate engaging surfaces, and/or anti-migration teeth) which increase implant fixation and anchor the implant onto adjacent bone. Although not shown, the side member 2053 can additionally include similar surface fixation features. Further, the surfaces of the members 2051, 2052 and/or 2053 may be coated or manufactured with an osteo-conductive bioactive material (such as, e.g., demineralized bone matrix, hydroxyapatite, and the like) and/or an osteo-inductive bioactive material (such as, e.g., Transforming Growth Factor "TGF-B," Platelet-Derived Growth Factor "PDGF," Bone-Morphogenic Protein "BMP," and the like), which each promote bone formation. Furthermore, the surfaces of the implant 205 may be coated and/or manufactured with a textured or a porous ingrowth surface (such as, e.g., titanium wire mesh, plasma-sprayed titanium, tantalum, porous CoCr, and the like), provided with a bioactive coating (such as, e.g., a coating comprising tantalum, and/or helical rosette carbon nanotubes or other carbon nanotube-based coating) in order to promote bone in-growth and establish a mineralized connection between the bone and the implant.

Moreover, after implantation, the cavity 2055 may be filled with a bone forming material so as to enable a bony fusion that extends from the immediately superior vertebral bone, across the implant (via cavity 2055) and onto the immediately inferior vertebral bone. Each of surfaces 2051, 2052 and 2053 can include one or more apertures (such as, for example, an aperture 20515 within the superior surface 2051 shown in FIG. 12F) that allow direct communication between the cavity and the exterior of the implant. In this way, bone forming material placed into the cavity can form a bone bridge (i.e., fusion mass) across one or more of the apertures and fuse the superior and inferior vertebral bones to one another. Each of the aforedescribed features can reduce the likelihood of implant dislodgement from the implantation site within the disc space.

As can be seen in FIG. 13, once the distraction and/or positioning of the vertebral bones is performed and an appropriately sized/shaped implant has been selected, the implant 205 can be mounted onto an outer aspect of the implant track 120 for slidable delivery of the implant to the distracted disc space. Specifically, the implant 205 is mounted onto the implant track 120 along a direction L such that a pair of recesses 1202 and 1206 are aligned with and respectively receive complimentary protrusions of the implant. Accordingly, an upper surface of the implant track 120 engages with an interior surface of the superior member 2051, while a lower surface of the implant track 120 engages with an interior surface of the inferior member 2052.

As illustrated in 12A-12E and 12G, in one embodiment, a first pair of protrusions 2054 are disposed on an interior surface of each of the superior and inferior members 2051 and 2052 proximate to the proximal end 2058 of the implant 205, and are configured (sized and/or shaped) to be received within recesses 1202 and grooves 1204 (on opposing sides of the implant track 120) of the implant placement instrument 100. A second pair of protrusions 2056 are disposed on the interior surface of each of the superior and inferior members 2051 and 2052 at a central region of the implant 205, and are configured (sized and/or shaped) to be received within recesses 1206 and grooves 1208 (on opposing sides of the implant track 120) of the implant placement instrument 100. In one implementation, the protrusions have a head region that is greater in width/diameter than a stem region thereof (which may increase retainment of the implant to the implant track), or, in another implementation, the protrusions may be substantially cylindrical (which may increase ease of advancement of the implant along the implant track).

The protrusions are each (generally) disposed on the interior surfaces of the superior and inferior members on an opposing side of the implant 205 relative to the side member 2053. Accordingly, when the implant 205 is mounted onto the implant track 120, the side member 2053 is oriented away from the track. It is noted that, in the present embodiment, the protrusions 2054 are of different diameter, length/shape, and position within the cavity 2055 relative to the protrusions 2056, which thereby enables the first and second sets of protrusions to interact with and be slid within different (i.e., complimentarily configured) recesses and grooves when mounted onto and advanced down the implant track 120.

In alternate embodiments, the implant and the implant placement instrument can be configured with additional or fewer complimentary protrusions and grooves (such as e.g., having protrusions on an interior surface of only one of the superior and inferior members), and/or the protrusions can be of an identical or similar configuration (such as e.g., having two sets of protrusions of an equal diameter on each of the superior and inferior members). Further, in additional alternate embodiments, the interior surface of the side wall and an outer aspect of the implant track can be configured to have complimentary protrusions and grooves. Yet further, in additional alternate embodiments, the interior surfaces of the implant can include one or more grooves therein, which are configured to receive a rail or elongate projection on an exterior surface of the implant track. It will be appreciated that various combinations of the foregoing embodiments for engagement of the implant and the implant track are contemplated herein.

Figure 7A:
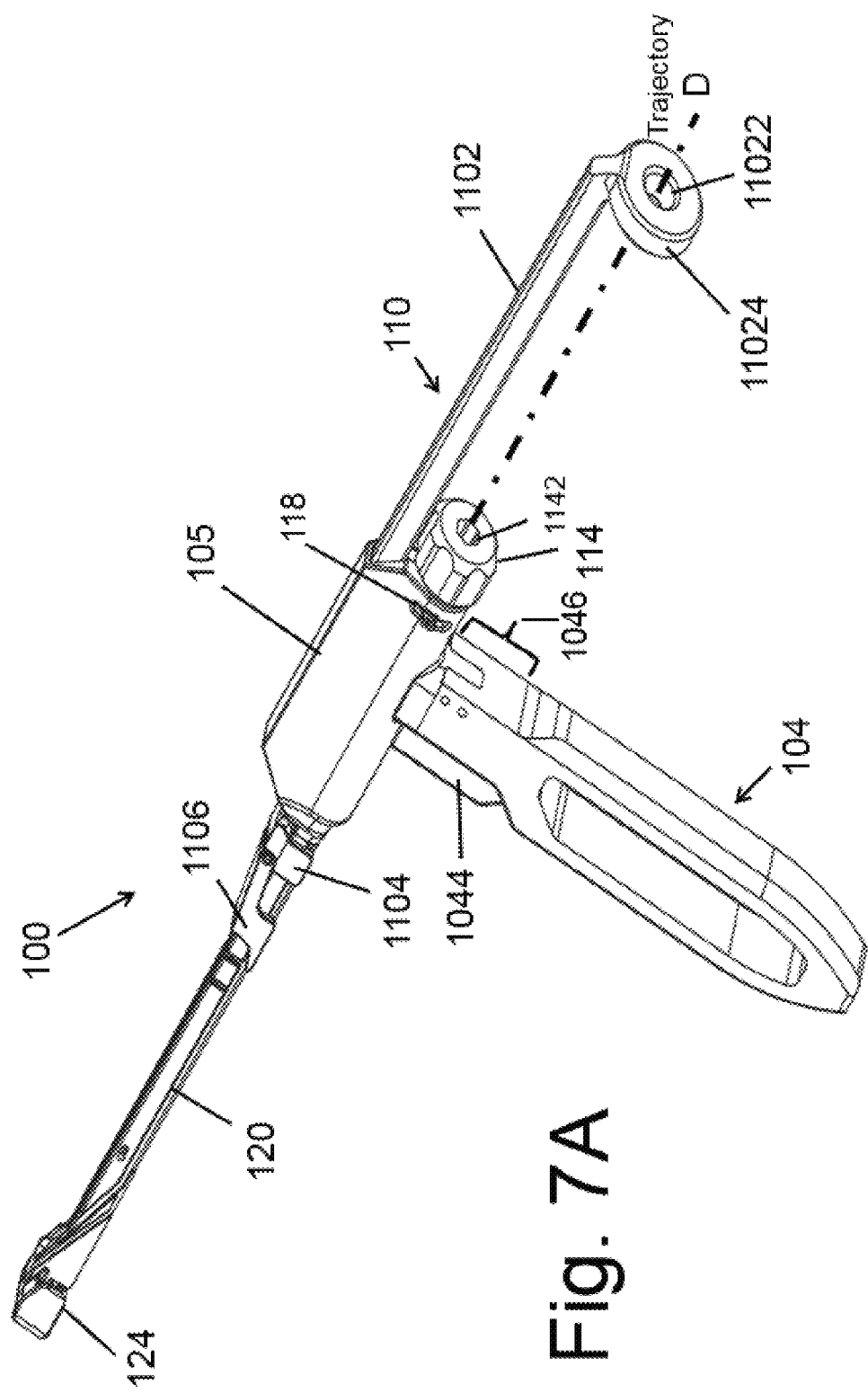
Figure 8A:
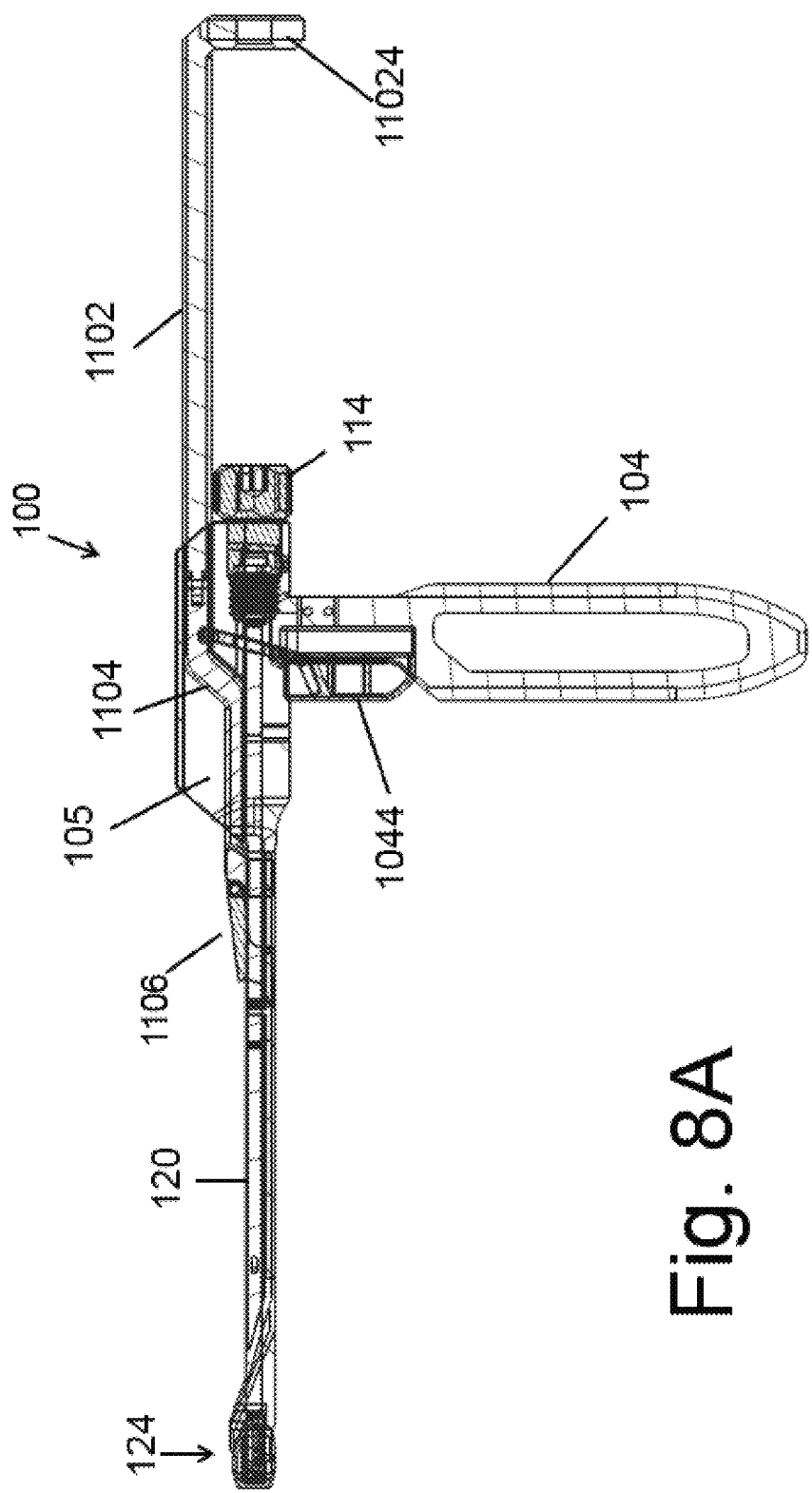

In order to enable the aforementioned mounting and sliding of the implant down the implant track, it is noted that the recesses 1202 are continuous with the grooves 1204, and the recesses 1206 are continuous with the grooves 1208 (on each side of the implant track 120). Thus, after the implant is mounted onto the implant track, a release member 1044 (FIG. 7A) on the handle 104 of the implant placement instrument 100 can be depressed to release an implant pusher 110. As shown in FIG. 7A, the implant pusher 110 includes the proximal member 1102, an intermediate member 1104, and a distal, rotatable member 1106. As can be seen in FIG. 8B, a bar 130 is coupled to the release member 1044 and is configured to enable actuation of the implant pusher 110 via the release member 1044. Specifically, when the release member 1044 is fully extended (i.e., when member 1044 is not depressed), one end of the bar 130 is positioned within a recess of the intermediate member 1104 so that the pusher 110 is immobilized relative to the body 105 and cannot be moved along the track 120. When the release member 1044 is depressed, the bar 130 is withdrawn from the recess within the intermediate member 1104 so that a force (such as, for example, a force exerted by a mallet, a manual force, a machine guided force, or a force from a spring loaded device) is applied to the proximal end 11024 to permit the (now-unconstrained) pusher 110 to advance along the implant track 120 and push the implant 205 towards the distraction member 124 or 126. Specifically, the implant 205 is engaged by the distal, rotatable member 1106 of the pusher 110 as it is advanced along the implant track 120. The implant 205 is retained onto the implant track 120 by the interaction of the protrusions 2054 and 2056 with the grooves 1204 and 1208 respectively. It is noted that the distal end 2057 is a leading edge or side of the implant, while the proximal end is a lagging edge or side of the implant when the implant 205 is advanced along the implant track 120.

Figure 16E:
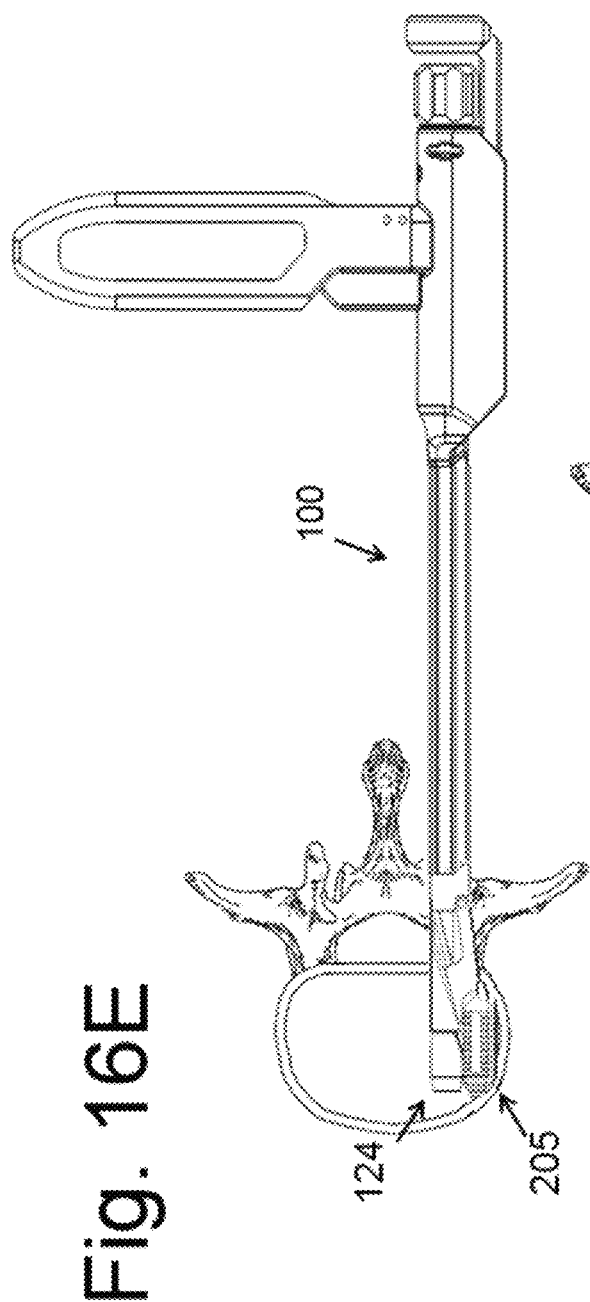

In the present embodiment, the implant is first advanced through a proximal region of the grooves along a linear pathway, and at the distal segment of the implant track the grooves include turns (curvatures or bends) so that the implant is ultimately positioned within the disc space at a lateral side of (and/or anterior to) the distraction member (as depicted in FIG. 16E and discussed below). FIGS. 14A-14C show step-wise movement of the implant 205 along the distal segment of the implant track 120. Specifically, the distal segment of the each of the grooves each 1204 and 1208 includes a bend, such that the terminal portion of each of the grooves is oblique or transverse relative to a longitudinal axis of the implant track 120. As the implant 205 is moved along terminal portion of the grooves 1204 and 1208 (via engagement with the distal, rotatable member 1106 of the implant pusher 110), the implant 205 moves laterally relative to the implant track 120 (i.e., onto a left side or a right side of the implant track), as well as forward toward the distal end of the implant track.

As can be seen in FIGS. 14A-14C, the distal, rotatable member 1106 of the implant pusher 110 includes (at a proximal end thereof) an arm 11061 rotatably connected to the intermediate member 1104 via a pin 11062, and (at a distal end thereof) an implant engagement portion comprising a protrusion 11063 and a shelf 11064. The protrusion 11063 is configured to engage the proximal end of the implant 205 at a side surface thereof in order to guide the implant through the bend at the terminal portion of the grooves 1204 and 1208 (FIG. 14A). Subsequently, the shelf 11064 is configured to engage an extended portion of the proximal end of the implant 205, and catch the extended portion on a raised lip of the shelf 11064. Such engagement enables further lateral (and forward) advancement of the implant 205, as well as rotation of the arm 11061 about an axis of the pin 11062 (FIGS. 14B and 14C), until the implant 205 is guided through an end of the grooves 1204 and 1208 (where the protrusions 2054 and 2056 disengage from the grooves 1204 and 1208, respectively) and is positioned adjacent to the distraction member 124 or 126.

While the longitudinal axis of implant track is aligned with the longitudinal axis of the distraction member in the present embodiments (as shown in e.g., FIG. 13), the latter may be alternatively offset from the longitudinal axis of the implant track. When the longitudinal axes of distraction member the implant track are offset relative to one another, the implant placement instrument may be configured, for example, so as advance the implant in a substantially linear trajectory along the implant track and into the target disc space (rather than including a curved trajectory at the distal end of the implant track).

Methods of Use

FIGS. 16A-17F illustrate exemplary methods for positioning a portion of the implant placement instrument within a target intervertebral disc space, mounting of the implant onto the implant track, advancement of the implant down the implant track and into the disc space, and removal of the implant placement instrument from the disc space.

Specifically, the disc space may be approached using any applicable corridor to the spine—such as, for example, via one or more of anterior, antero-lateral, lateral, postero-lateral and posterior tissue corridors. In one embodiment utilizing the postero-lateral and/or posterior approaches, for example, the paraspinal muscles are retracted after placement of a skin incision. A corridor is then developed to the postero-lateral and/or posterior aspect of the spinal column and at least a segment of the lamina and/or facet joint(s) can be removed. If necessary, a posterior aspect of thecal sac can be exposed. The posterior aspect of the target disc space is then exposed through a corridor that is lateral to thecal sac. The thecal sac is retracted gently in the medial direction, and the posterior aspect of the target disc space can be identified. The annulus fibrosis is incised and at least a segment of the native disc space is removed. After the preparation of the bony end plate, the target disc space is ready for advancement of an implant therein.

As discussed elsewhere herein, the implant placement instrument 100 may be hand held (using handle 104) during the procedure and/or the placement instrument may be anchored to a bony surface of the vertebral column. The placement instrument 100 may be additionally or alternatively attached to a coupler or segment of an articulating retention arm, which is anchored to the operating room table upon which the patient is positioned. Frame devices that anchor surgical instruments to the operating table are known in the art, and an exemplary articulating retention arm is show in FIG. 15. In the illustrated example, an articulated frame 905 has a member 9052 that reversibly attaches to the operating table onto which the patient is positioned. A member 9056 is adapted to reversibly and rigidly clamp onto (or otherwise couple with) a segment of the implant placement instrument 100 (such as, for example, a segment 1046 shown in FIG. 7A). A member 9054 is adapted to reversibly transition the frame 905 from a first state (i.e., a movable state where articulation of the frame segments is enabled) to a second state (i.e., a locked state where the frame segments are rigidly locked to one another). While the exemplary articulated frame 905 is illustrated, it is understood that other positioning or retaining devices may be alternatively (or additionally) used. Other exemplary positioning or retaining devices that can be used with the implant placement instruments described herein are disclosed in U.S. Pat. Nos. 4,254,763; 5,908,382; 6,302,843; 6,709,389; and 7,156,806, each of which is incorporated by reference herein in its entirety.

FIGS. 16A-16F illustrate a first exemplary embodiment of a method of use of the implant placement instrument 100. As depicted therein, the implant placement instrument 100 inserted into the target disc space via a posterior approach. As depicted in FIG. 16A (and discussed above with reference to FIGS. 7A-9F), after the distal end of the implant placement instrument is advanced into the target disc space, the knob 114 is actuated and the distraction member 124 is moved from the closed (non-distracted) configuration to the open (distracted) configuration in order to distract the disc space to a desired height and/or otherwise reposition the superior or inferior vertebral bones (such as, e.g., to correct anterior spondylisthesis as shown in the exemplary distracted configuration of FIG. 9C, or to correct lateral spondylolisthesis as shown in the exemplary distracted configuration of FIG. 9E).

After the desired height of the disc space and position of the superior or inferior vertebral bones is achieved, the implant size and/or shape may be selected based on the reading shown in the aperture 118. In alternate embodiments, the implant size and/or shape can be selected based on other criteria, such as, e.g., imaging of the target spinal segment.

Once the appropriate implant is selected (such as, e.g., implant 205 shown in FIGS. 12A-12G), it is mounted onto the implant track 120 as shown in FIG. 16C. The release member 1044 is then depressed and the implant pusher 110 is pushed forward (via, e.g., hammering with a mallet, manual movement, or machine guided movement, and/or a spring loaded device) such that the distal, rotatable member 1106 engages with the implant 205. The rotatable member 1106 advances the implant 205 along tract 120, as shown in FIG. 16D.

FIG. 16E illustrates delivery of the implant 205 into the disc space at a lateral position relative to the distraction member 124. In one embodiment of the method of implantation, the implant 205 is positioned to abut at least a portion of the inferior apophyseal ring of the superior vertebral bone and/or the superior apophyseal of the inferior vertebral bone. In an alternate embodiments, an implant can be positioned anterior to the distraction member or medial relative to the distraction member.

Figure 16F:
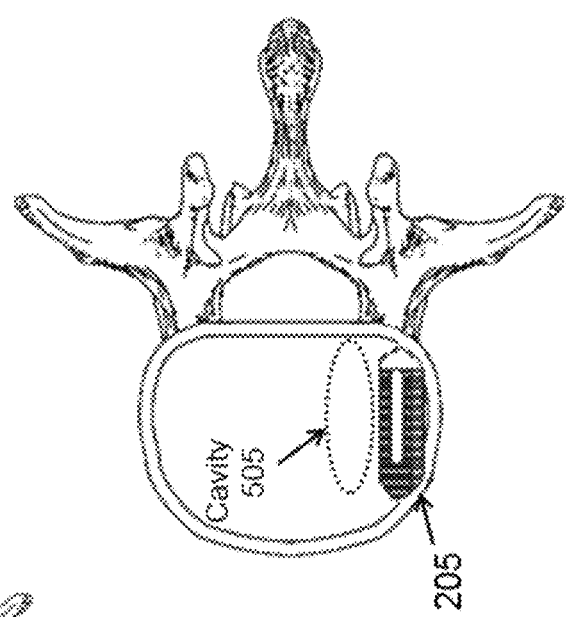

After the implant 205 is positioned within the target disc space, the knob 114 is actuated (e.g., actuated in a reverse direction) and the distraction member 124 is decreased in height to move the distraction member into the closed (non-distracted) configuration. The implant placement instrument 100 is then withdrawn from the disc space leaving the implant 205 positioned as shown in FIG. 16F.

FIGS. 17A-17D illustrate the implant 205 positioned within the disc space after the removal of the implant placement instrument 100 (the superior vertebral bone is not shown for diagrammatic simplicity).

In the embodiment of FIGS. 16A-16F, the distraction member 124 is a non-separable segment of the implant placement instrument 100 and is non-detachable therefrom. In other words, both of the distal end of the implant track and the distraction member are removed prior from the disc space prior to completion of the implantation procedure. Accordingly, after withdrawal of the placement instrument, a cavity 505 remains in the disc space at a location where the distraction member 124 had been positioned. Bone graft material may be packed into the cavity 2055 of the implant 205 and/or the cavity 505 (which is adjacent and medially disposed relative to the implant 205) so as to produce a bony fusion between the inferior surface of the superior vertebral bone and the superior vertebral surface of the inferior vertebral bone. It is noted that the bone graft material placed within the cavity 2055 may be in continuity with the bone graft placed within the cavity 505.

Figure 18E:
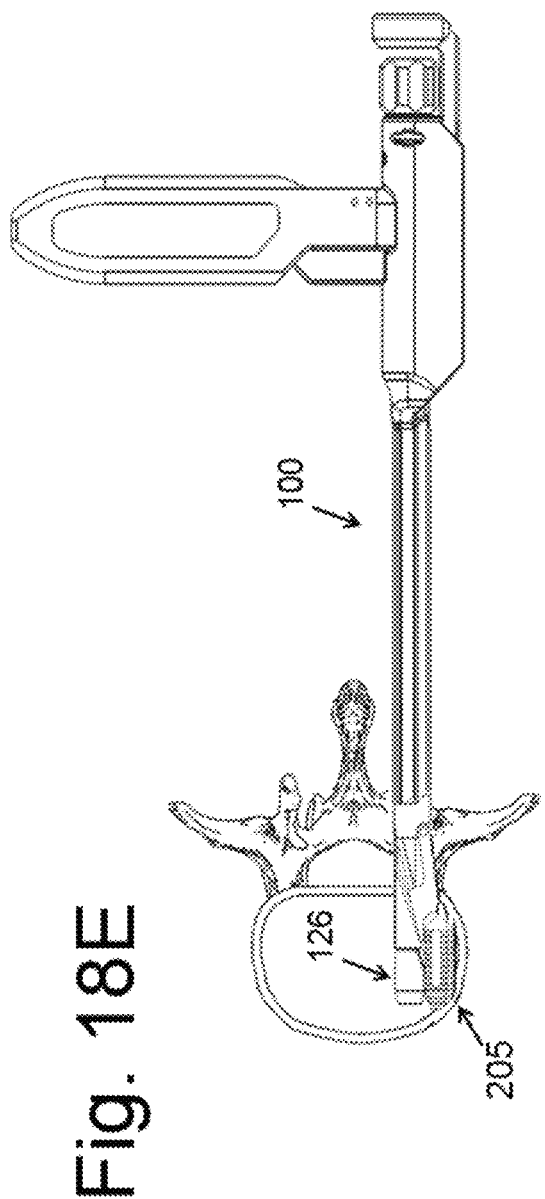

Turning now to FIGS. 18A-18F, another embodiment of a method of use of the devices disclosed herein is illustrated. First, the implant placement instrument 100 is inserted into the target disc space via a posterior approach. As depicted in FIG. 18A, after the distal end of the implant placement instrument is advanced into the target disc space, the knob 114 is actuated and the distraction member 126 is moved from the closed (non-distracted) configuration to the open (distracted) configuration in order to distract the disc space to a desired height and/or otherwise reposition the superior or inferior vertebral bones (such as, e.g., to correct lateral spondylolisthesis as shown in the exemplary distracted configuration of FIG. 11B). Similar to the method of use shown in FIGS. 16A-16F, after positioning of the implant placement instrument and distraction of the disc space (FIGS. 18A and 18B), the implant is selected (based on a size and/or configuration thereof) and mounted onto the implant track (FIG. 18C) and advanced along the track (FIG. 18D) and into the target disc space (FIG. 18E).

Different from the embodiment of FIGS. 16A-16F, in the present method, the distraction member 126 is a separate, detachable member that can be uncoupled from (reversibly attached to) the implant placement instrument 100 such that it remains in the disc space as an implant after the withdrawal of the implant placement instrument from the disc space. In other words, after the distraction member 126 is moved into the open (distracted) configuration and the implant 205 is positioned within the target disc space, the distraction member 126 is detached from the implant placement instrument 100 (via e.g., depression or actuation of a release member operatively coupled to the handle of the implant placement instrument 100) and the distraction member 126 retains its distracted height after the detachment. Specifically, once the desired distracted configuration is achieved, the distraction mechanism can be locked so as to make the configuration effectively permanent. Adhesives or yet other means for maintaining the desired position can be utilized as well.

Figure 18F:
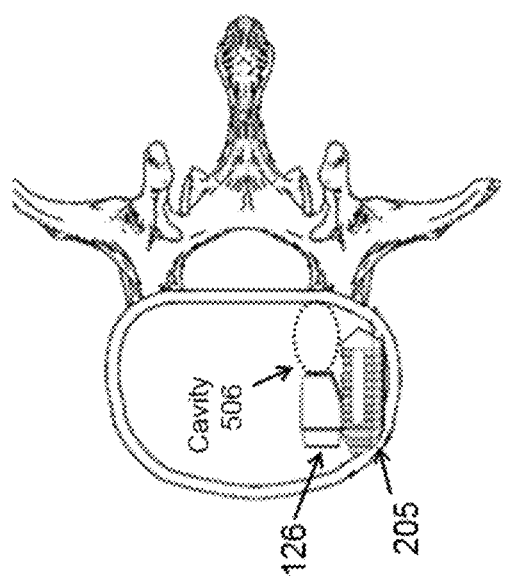

The implant placement instrument 100 is then removed from the disc space leaving the implant 205 and the detached distraction member 126—as shown in FIG. 18F. Bone graft material may be packed into the cavity 2055 of the implant 205 and/or the cavity 505 (which is adjacent and medially disposed relative to the implant 205, and adjacent to and posterior of the detached distraction member 126) so as to produce a bony fusion between the inferior surface of the superior vertebral bone and the superior surface of the inferior vertebral bone.

While implantation of only one implant (i.e., the implant 205) is shown in FIGS. 16E-17D, and implantation of only one implant (i.e., the implant 205) and one detached distraction member (i.e., the distraction member 126) is shown in FIGS. 18E-18F, it is contemplated that additional implants (having the same or a different configuration as the implant 205) and/or additional detached distraction members (having the same or a different configuration from the distraction member 126) can be implanted into a single target disc space in order to disperse the load and/or alter the alignment across the FSU.

For example, FIGS. 19A and 19B illustrate how use of multiple implants (and/or detached distraction mechanisms of different shapes and/or sizes) can be used to alter the vertebral alignment within the vertebral column. Specifically, an implant (or detached distraction mechanism) may comprise a greater height at its anterior edge than at its posterior edge, as shown in FIG. 19A, so that a lordosis curve between the superior and inferior vertebral bones that abut the target disc space is altered (i.e., use of the implants or detached distraction mechanisms to a greater or lesser lordosis—or even leave the lordosis unchanged). Further, the implants (or detached distraction mechanisms) can be placed at opposing lateral sides of the target disc space so as to further alter the alignment of the implanted FSU. FIG. 19B illustrates that a first implant (or detached distraction mechanism) of a given height may be positioned at a first lateral side segment of the target disc space, and a second implant (or detached distraction mechanism) of a different height may be positioned at an opposing second lateral side segment of the target space, thereby altering the vertebral alignment in the coronal plane of the spinal column. In this way, this implant arrangement may be used in the treatment of spinal misalignment conditions such as, for example, scoliosis.

Additional Spinal Stabilization Devices and Techniques

One or more supplemental fixation devices and/or methods may be utilized with the foregoing apparatus and methods in order to rigidly immobilize the superior and inferior vertebral bones of the target FSU (having the implant 204 and/or the distraction member 206 implanted therein). In one example, pedicle screw immobilization can be employed by the placement of one or more bone screw assemblies into the posterior aspect of the ipsilateral pedicle of each of the superior and inferior vertebral bones (e.g., a screw my enter each of the bones in proximity to position 811 shown in FIGS. 1A-1C).

An exemplary pedicle screw assembly 34 is shown in FIGS. 20A and 20B. As depicted therein, the pedicle screw assembly 34 includes: a housing body 341 having a cavity 340 configured to receive an inter-connecting member (such as a rod), a set screw 342 that threadedly couples within a top portion of the cavity 340, a thrust washer 344 seated within a bottom portion of the cavity 340 (proximate to an anchor member-receiving portion 3413 of the housing body 341), and a bone anchor member including a head 346 and a threaded 348 configured for insertion into bone. In the assembly 34, the head 346 of the bone anchor member is seated within the anchor member-receiving portion 3413 and the threaded shank 348 of the bone anchor member extends out of an aperture that is positioned within the bottom of the anchor member-receiving portion 3413. It will be appreciated that the terms "above" and "below" are relative and depend on the orientation of the assembly 34. As used herein, the assembly 34 is oriented with the set screw 342 at the superior aspect of the assembly and the threaded shank 348 at the inferior aspect of the assembly. Thus, the set screw is located "above" the bone anchor member and the cavity which receives the inter-connecting member receiving is disposed therebetween.

During use thereof (as shown in FIGS. 20C-20E), a connecting member 350 (such as a rod) is used to connect two or more of the assemblies 34, such as, e.g., connecting a first assembly 34 anchored into a superior vertebral bone and a second assembly 34 anchored into an inferior vertebral bone, the superior and inferior vertebral bones having one or more of the implants 205 (depicted in FIG. 20E) and/or the detached distraction members 126 implanted (not specifically depicted) therebetween. Each of the opposing ends of the connecting member 350 is received within the cavity 340 of one of the assemblies 34. Threaded engagement of the set screw 342 with the top portion of the cavity 340, the connecting member is movable within the cavity 340 relative to the housing body 341 and the head portion 346. Further, the head portion 346 can rotate within the anchor member-receiving portion 3413 such that a longitudinal axis of threaded shank 348 can assume different orientations and angles relative to a longitudinal axis of the housing body 341. With advancement of set screw 342, a compressive force is produced between the inter-connecting member 350 (contained within the inter-connecting member receiving portion 340) and the anchor member-receiving portion 3413 such that the interconnecting member 350, the head portion 346 and the housing 341 are immobilized relative to one another. In this way, the two assemblies are rigidly interconnected by the interconnecting member, and the procedure may optionally be repeated on the contra-lateral (opposing) side. Exemplary embodiments of pedicle screw fixation of adjacent vertebral bones (for use the methods and apparatus described herein) are disclosed in U.S. Pat. No. RE37665 and U.S. Patent Publication No. 2006/0084981, each of which is incorporated herein by reference in its entirety.

As an alternative (or in addition) to pedicle screw fixation, a spinous process fixation implant may be used for supplemental FSU stabilization. An exemplary spinous process fixation device 605 is illustrated in FIGS. 21A-21F. Specifically, the fixation device 605 includes a first member 610 and an opposing second member 612, which are configured to be adjoined via an interconnecting member 615 and attached onto opposing (contra-lateral) spinous processes of two adjacent vertebral bones. As depicted in FIGS. 21E and 21F, the spinous processes are forcibly captured between the first and second members 610 and 612. The interconnecting member 615 is then tightened or otherwise locked relative to the members 610 and 612, and prevents the members 610 and 612 from moving away from one another. A plurality of projections 617 on an interior surface of each of the members 610 and 612 penetrate the spinous processes and increase bone fixation onto the bone for the fixation device 605. In the present embodiment, two implants 205 interbody are implanted bilaterally within the target disc space. In the axial plane (FIG. 21F), the implants 205 provide two anterior column supports while the spinous process fixation device 605 provides posterior midline support. In the lateral view (FIG. 21E), the implants 205 form an anterior abutment surface and the spinous process fixation device 605 forms posterior abutment surface. Thus, the combined use of the implants and the spinous process fixation device forms a balanced three-point support of the vertebral bones. Additionally, bone graft material may be placed between the spinous process and/or lamina of the superior and inferior vertebral bones after appropriate decortication of the bone at the intended graft recipient site, and/or one or more detached distraction members may be implanted within the disc space.

Alternate Configurations

It is further contemplated that, in alternate embodiments, the distraction member and/or the implant track could be configured to include a curvilinear segment. In such embodiments, an implant may follow a trajectory down the implant track that is at least partially curvilinear (and may have a segment of defined a specified curvature), or the implant trajectory may also (or instead) comprise a segment that at least partially follows a non-linear path around the distraction member.

Other alternate embodiments are shown in FIGS. 22A-26D. As depicted therein, an implant placement instrument 400 includes a body 405 and a handle 404 extended outwardly therefrom. An implant track 420 extends outwardly from an anterior surface of the body 405, and a distraction member 424 extends outwardly from a distal end of the implant track 420.

Although not specifically shown, it will be appreciated that the distraction member 424 may have a similar configuration and method of operation/use to those discussed above with reference to distraction members 124 and 126. For example, the distraction member 424 can include upper and lower plates that are (reversibly) moveable from a (closed) non-distracted configuration to an open (distracted) configuration via actuation of a knob 414, which can be manually rotated by grasping the outer surface of the knob, or can be rotated by an instrument, such as, for example, a screw driver, a wrench, or the like that couples to a hex recess 4142 of the knob 414. In one exemplary implementation, a member 4102 attached at a posterior portion of the body 405 includes an aperture 41022 at a distal end portion 41024 configured to enable a screw driver to be advanced therethrough and into the recess 4142 of the knob 414. After movement into the distracted configuration, an aperture 418 of the body 405 allows the operator to read a distance between the upper and lower plates for selection of an appropriately sized implant to be advanced along the implant track 420 and into the distracted disc space. In one implementation, the distraction member 424 is non-detachable and is configured for removal from the disc space after delivery of the implant thereto. In another implementation, the distraction member 424 is detachable and is configured to be implanted within the disc space after delivery of the implant thereto.

A first exemplary embodiment of an implant 505 configured for use with the implant placement instrument 400 is shown in FIGS. 23A-23D. As illustrated therein, the implant 505 includes a superior member 5051 and an inferior member 5052. An outer surface of the superior member 5051 is configured to abut an inferior surface of the vertebral bone immediately superior to the target disc space in which the implant 505 is positioned, while an outer surface of the inferior member 5052 is configured to abut a superior surface of the vertebral bone immediately inferior to the target disc space. The superior and inferior members 5051 and 5052 are connected by a side member (or side wall) 5053. In alternate embodiments, one more additional or partial side walls may additionally be included in the implant (such as e.g., a flexible/movable side wall). As best illustrated in FIGS. 23A and 23B, the superior, inferior, and side members define an internal cavity 5055, which is disposed within the implant 505 and sized to receive at least a segment of the implant track 520 therein.

Different from the implant 205 show in FIGS. 12A-12G, each of the superior and inferior members 5051 and 5052 includes substantially continuously curved lateral edges and a substantially linear edge at each of a distal end 5057 and a proximal end 5058 of the implant 505. More specifically, a first lateral side 50571 of the implant 505 (at a closed side of the cavity 5055) has a convex curvature, while a second lateral side 50581 thereof (at an open side of the cavity 5055) has a concave curvature. As can be seen in FIG. 23A, each of the superior and inferior members 5051 and 5052 has an inclined exterior surface. Specifically, at the first lateral side 50571, each of the superior and inferior members 5051 and 5052 has a greater height than at the second lateral side 50581 thereof. The foregoing features give the implant 505 a generally curved cuboid shape with tapered exterior surfaces inclined from the concave side to the convex side thereof.

In alternate embodiments, the superior and inferior members can have an equal height at each of the distal and proximal ends (giving the implant a non-tapered shape), or one or more of the superior or inferior surfaces can be inclined to a greater degree than the exemplary embodiment shown in FIG. 23A. Further, in other alternate embodiments the superior and inferior members can curved to a greater or lesser degree. One such alternate embodiment, a second exemplary embodiment of an implant 705 configured for use with the implant placement instrument 400, is illustrated in FIGS. 25A-25D. As can be seen therein, the implant 705 has a similar shape to implant 505, however, each of the superior and inferior members 7051 and 7052 includes a convex curvature a first lateral side 70571 of the implant 705 (at a closed side of a cavity 7055 which is closed by a side wall 7053) and a concave curvature a second lateral side 70581 thereof (at an open side of the cavity 5055), which each have a lesser degree of curvature as compared to the corresponding structures of the implant 505. Further, at each of a distal end 7057 and a proximal end 7058 of the implant 705, the implant includes curved edge (rather than a linear edge as in the implant 505).

As discussed elsewhere herein, it is contemplated a variety of implants of different shapes and/or sizes may be manufactured or provided to be usable with the implant placement instrument, and the appropriately shaped/sized implant can be selected from a pre-fabricated set of implants to be specific to the condition of the target FSU in order to correct curvature or otherwise stabilize the FSU. Alternatively, a pre-operative planning procedure may be carried out to select dimensions and/or configurations for one or more implants specific to the anatomy of the patient, and the one or more implants can be manufactured (such as e.g., via subtractive or additive 3-D printing) for later implantation thereof.

In the present embodiment, each of the superior and inferior members 5051 and 5052 of the implant 505 and the superior and inferior members 7051 and 7052 of the implant 705 includes surface features (indentations and protrusions) which increase implant fixation and anchor the implant onto adjacent bone. Although not shown, the side members 5053 and 7053 can additionally include similar surface fixation features. Further, the surfaces of the superior, inferior, and/or side members may be coated or manufactured with an osteo-conductive bioactive material (such as, e.g., demineralized bone matrix, hydroxyapatite, and the like) and/or an osteo-inductive bioactive material (such as, e.g., Transforming Growth Factor "TGF-B," Platelet-Derived Growth Factor "PDGF," Bone-Morphogenic Protein "BMP," and the like), which each promote bone formation. Still further, the surfaces of the implants may be coated and/or manufactured with a textured or a porous ingrowth surface (such as, e.g., titanium wire mesh, plasma-sprayed titanium, tantalum, porous CoCr, and the like), provided with a bioactive coating (such as, e.g., a coating comprising tantalum, and/or helical rosette carbon nanotubes or other carbon nanotube-based coating) in order to promote bone in-growth and establish a mineralized connection between the bone and the implant.

Moreover, after implantation, the cavity 5055 and 7055 may be filled with a bone forming material so as to enable a bony fusion that extends from the immediately superior vertebral bone, across the implant (via cavity 2055) and onto the immediately inferior vertebral bone. Each of the superior, inferior and/or side members can include one or more apertures (such as, for example, an aperture 50515 of the implant 505 and apertures 70515 of the implant 705 shown in e.g., FIGS. 23C and 25D, respectively) that allow direct communication between the cavity and the exterior of the implant. In this way, bone forming material placed into the cavity can form a bone bridge (i.e., fusion mass) across one or more of the apertures and fuse the superior and inferior vertebral bones to one another. Each of the aforedescribed features can reduce the likelihood of implant dislodgement from the implantation site within the disc space.

Turning to FIG. 24A, once the distraction and/or positioning of the vertebral bones is performed and an appropriately sized/shaped implant has been selected, the implant 505 can be mounted onto an outer aspect of the implant track 420 for slidable delivery to the distracted disc space. Specifically, the implant 505 can be mounted onto the implant track 420 along a direction M such that a recess 4202 is aligned with receives complimentary protrusions on the interior surfaces of the implant. Specifically, as illustrated in FIGS. 23A, 23B and 23D, a first pair of protrusions 5054 are disposed on an interior surface of each of the superior and inferior members 2051 and 2052 proximate to the proximal end 2058 of the implant 505, and a second pair of protrusions 5056 are disposed on an interior surface of each of the superior and inferior members 5051 and 5052 proximate to the proximal end 5058 of the implant 505. The protrusions 5054 and 5056 are configured (sized and/or shaped) to be received within recesses 4202 (and grooves 4204 (on opposing sides of the implant track 120).

Each of the protrusions 5054 and 5056 is disposed on an opposing lateral side of the implant relative to the side wall 5053 (i.e., at the second lateral side 50581). Accordingly, when the implant 505 is mounted onto the implant track 420, the side member 5053 is oriented away from the track. It is noted that, in the present embodiment, the protrusions 5054 are of a similar diameter and length/shape to the protrusions 5056. In alternate embodiments, the implant and the implant placement instrument can be configured with additional or fewer complimentary protrusions and grooves, and/or the protrusions can be of different sizes, lengths, shapes or other configurations. Further, the implant placement instrument can include an offset, additional grooves configured to receive one of the pairs of protrusions (similar to the configuration shown in the implant placement instrument 100).

Figure 22D:
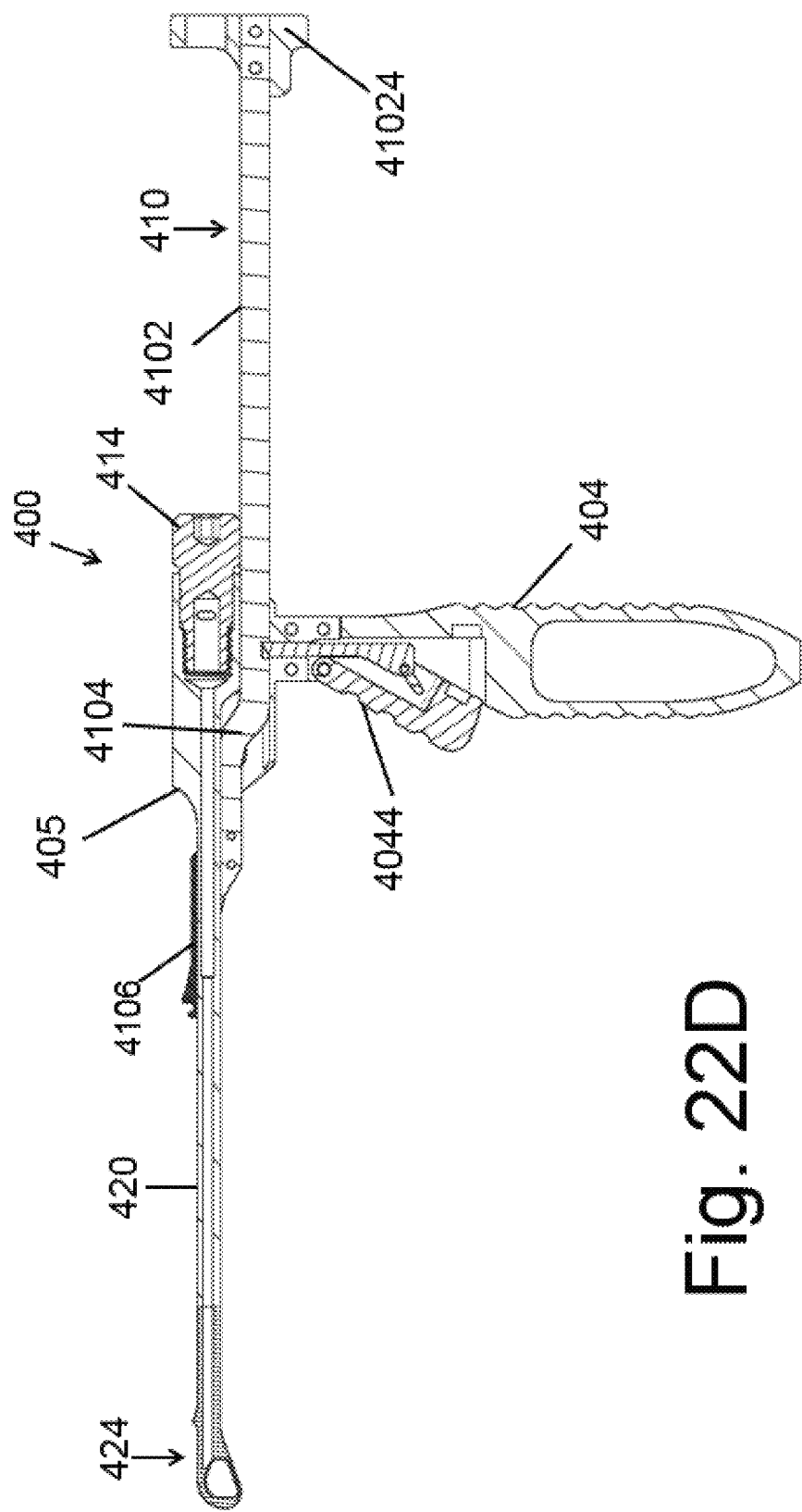

In order to enable the aforementioned mounting and sliding of the implant down the implant track, it is noted that the recesses 4202 are continuous with the grooves 4204 (on each side of the implant track 420). Thus, after the implant is mounted onto the implant track, a release member 4044 (FIG. 22A) on the handle 404 of the implant placement instrument 400 can be depressed to release an implant pusher 410. As shown in FIGS. 22A and 22D, the implant pusher 410 includes the proximal member 4102, an intermediate member 4104, and a distal member 4106. As can be seen in FIGS. 22D and 22E, a bar 430 is coupled to the release member 4044 and is configured to enable actuation of the implant pusher 410 via the release member 4044. Specifically, when the release member 4044 is fully extended (i.e., when member 1044 is not depressed), one end of the bar 430 is positioned within a recess of the intermediate member 4104 so that the pusher 410 is immobilized relative to the body 405 and cannot be moved along the implant track 420. When the release member 4044 is depressed, the bar 430 is withdrawn from the recess within the intermediate member 4104 so that a force (such as, for example, a force exerted by a mallet, a manual force, a machine guided force, or a force from a spring loaded device) is applied to the proximal end 41024 will permit the (now-unconstrained) pusher 410 to advance along the implant track 420 and push the implant 505 towards the distraction member 424. Specifically, the implant 505 is engaged by the distal member 4106 of the pusher 410 as it is advanced along the implant track 420. The implant 505 is retained onto the implant track 420 by the interaction of the protrusions 5054 and 5056 with the grooves 4204.

In the present embodiment, the implant is first advanced through a proximal region of the grooves along a substantially linear pathway (which can be coincident with or parallel to a longitudinal axis of the implant track), and at the distal segment of the implant track the grooves include turns (curvatures or bends) so that the implant is ultimately positioned within the disc space with the distal end 5057

(i.e., a leading edge of the implant) anterior of the distraction member 424. FIGS. 24B-24C show step-wise movement of the implant 505 along the distal segment of the implant track 420. Specifically, the distal segment of the each of the grooves each 1204 and 1208 includes a bend, such that the terminal portion of each of the grooves is oblique relative to a longitudinal axis of the implant track 420. As the implant 505 is moved along terminal portion of the grooves 4204 (via engagement with the distal member 4106 of the implant pusher 410), the implant 505 moves laterally relative to the implant track 420 (as well as forward toward the distal end of the implant track).

As can be seen in FIGS. 24A-24D, the distal member 4106 of the implant pusher 410 includes (at a proximal end thereof) includes a blunted end that engages with the proximal end 5058 of the implant 505. The distal member 4106 further comprises a hooked protrusion 41061 (FIG. 24A) that is configured to reversibly latch or otherwise reversibly couple with the proximal end 5058 of the implant 505. The engagement between the hooked protrusion and the implant enables an operator or surgeon performing the procedure to optionally back the implant out (reverse movement along the implant track) if necessary. (Although not specifically shown, a similar hooked protrusion can be incorporated into the implant placement instrument 100 to enable reverse movement of the implant.)

During forward movement of the implant 505 along the distal segment of the implant track 420, the engagement of the blunted end of the distal member 4106 with the implant 505 enables concurrent forward and lateral advancement of the implant 505. Specifically, the concave curvature of the second lateral side 50581 is guided around a curved exterior surface of the distraction member 424, until the implant 505 is pushed through an end of the grooves 4204 (where the grooves 4204 disengage from the protrusions 5054) and the implant is positioned adjacent anterior to and lateral of the distraction member 424. It will be appreciated that the foregoing description can be similarly applied to use of the implant 705 with the implant placement instrument 400.

FIGS. 24E-24F and 26A-26D illustrate additional exemplary embodiments of methods of use of the devices disclosed herein. Specifically, FIGS. 24E and 24F depict the implant placement instrument 400 inserted into the target disc space via a postero-lateral approach for delivery of the implant 505 (having a greater degree of curvature than the implant 705). The postero-lateral approach enables sufficient space within the target FSU for the insertion of the implant 505 into the disc space and guidance around the curved exterior surface of the distraction member. After release from the implant placement instrument, the implant 505 is positioned proximate to the anterior portion of the disc space.

As depicted in FIGS. 26A-26D, the implant placement instrument 400 is inserted into the target disc space via a posterior approach for delivery of the implant 705 (having a lesser degree of curvature than the implant 505). The posterior approach enables sufficient space within the target FSU for the insertion of the implant 705 into the disc space and guidance around the curved exterior surface of the distraction member. After release from the implant placement instrument, the implant 705 is positioned proximate to the anterior portion of the disc space. In alternate embodiments, the implant placement instrument may be inserted along a posetero-lateral approach for delivery of the implant 705 to the disc space, and/or the implant can be positioned laterally, medially, or at another desired position within the disc space.

It will be appreciated that the methods of use discussed in detail above with reference to FIGS. 16A-18F are applicable to methods of using the implant placement instrument 400 with either of the implants 505 or 705.

It will be further appreciated that the disclosed device embodiments or any of their components can be made of any biologically adaptable or compatible materials. Materials considered acceptable for biological implantation are well known and include, but are not limited to, stainless steel, titanium, tantalum, combination metallic alloys, various plastics (such as PEEK and the like), resins, ceramics, biologically absorbable materials and the like. The system or any of its components can alternatively or additionally be entirely or partially made of a shape memory material or other deformable material. Any components may be also coated/made with osteo-conductive (such as demineralized bone matrix, hydroxyapatite, and the like) and/or osteo-inductive (such as Transforming Growth Factor "TGF-B," Platelet-Derived Growth Factor "PDGF," Bone-Morphogenic Protein "BMP," and the like) bio-active materials that promote bone formation.

Further, any surface may be made with a porous ingrowth surface (such as, for example, porous titanium, titanium wire mesh, plasma-sprayed titanium, tantalum, porous CoCr, and the like), provided with a bioactive coating, made using tantalum, and/or helical rosette carbon nanotubes (or other carbon nanotube-based coating) in order to promote bone in-growth or establish a mineralized connection between the bone and the implant, and reduce the likelihood of implant loosening. The system or any of its components may be made by additive or subtractive manufacturing, such as, for example, 3D-printing.

While this specification contains certain specific features and attributes, these should not be construed as limitations on the scope of what is claimed or of what may be claimed, but rather as descriptions of features specific to particular embodiments. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a sub-combination or a variation of a sub-combination. Similarly, while operations are depicted in the drawings in a particular order, this should not be understood as requiring that such operations be performed in the particular order shown or in sequential order, or that all illustrated operations be performed, to achieve desirable results. Only a few examples and implementations are disclosed. Variations, modifications and enhancements to the described examples and implementations and other implementations may be made based on what is disclosed.

It will also be recognized that while certain aspects of the disclosure are described in terms of a specific sequence of steps of a method, these descriptions are only illustrative of the broader methods of the disclosure, and may be modified as required by the particular application. Certain steps may be rendered unnecessary or optional under certain circumstances. Additionally, certain steps or functionality may be added to the disclosed embodiments, or the order of performance of two or more steps permuted. All such variations are considered to be encompassed within the disclosure disclosed and claimed herein.

What is claimed is:

1. A surgical apparatus for use in an implantation procedure performed on a functional spinal unit of a subject, the functional spinal unit comprising a superior vertebral bone, an inferior vertebral bone, and an intervertebral disc space disposed between the superior vertebral bone and the inferior vertebral bone, the surgical apparatus comprising:

an implant comprising:
a superior member, an exterior surface of the superior member configured to abut an inferior surface of the superior vertebral bone;
an inferior member, an exterior surface of the inferior member configured to abut a superior surface of the inferior vertebral bone;
a first side wall connecting the superior member and the inferior member; and
an internal cavity, at least a portion the internal cavity bordered by the superior member, the inferior member, and the first side wall; and an implant placement apparatus configured for use with the implant, the implant placement apparatus comprising:
a handle assembly comprising a body, the body extending from a front surface to an opposing back surface;
an implant track comprising an upper surface, a lower surface, a distal end, and a proximal end, each of the upper surface and the lower surface extending from the distal end to the proximal end along a first longitudinal axis of the implant track, the proximal end disposed at the front surface of the body, the implant track configured to guide delivery of the implant to the intervertebral disc space;
a distraction assembly disposed at the distal end of the implant track and extended outwardly therefrom, the distraction assembly comprising a first plate and a second plate, the first plate movable relative to the second plate, wherein the distraction assembly is configured to enable transition of the first plate and the second plate from a non-distracted configuration to a distracted configuration; and
an implant pusher member movably coupled to the body of the handle assembly, the implant pusher member configured to advance the implant along at least a portion of the implant track and onto an implantation site;
wherein at least a portion of the upper surface of the implant track is configured to engage with at least a portion of an interior surface of the superior member of the implant, and at least a portion of the lower surface of the implant track is configured to engage with at least a portion of an interior surface of the inferior member of the implant; and
wherein the implant and the implant placement apparatus are configured such that at least a portion of the implant track is seated within the internal cavity of the implant when the at least portion of the upper surface is engaged with the at least portion of the interior surface of the superior member and the at least portion of the lower surface is engaged with the at least portion of the interior surface of the inferior member.

2. The surgical apparatus of claim 1, wherein the distraction assembly is further configured to enable reversible transition of the first plate and the second plate between the distracted configuration and the non-distracted configuration.

3. The surgical apparatus of claim 1, wherein the implant placement apparatus further comprises an actuator operatively coupled to the distraction assembly, the actuator configured to cause the transition of the first plate and the second plate from the non-distracted configuration to the distracted configuration upon actuation of the actuator, the distracted configuration comprising a distance between the first plate and the second plate in at least one plane being increased relative to the non-distracted configuration.

4. The surgical apparatus of claim 1, wherein the upper surface of the implant track is non-movable relative to the lower surface, the upper surface of the implant track configured to remain stationary relative to the lower surface throughout the transition of the first plate and the second plate from the non-distracted configuration to the distracted configuration and the delivery of the implant to the intervertebral disc space.

5. The surgical apparatus of claim 1, wherein the body of the handle assembly comprises a first bore extending from the front surface to the back surface along a second longitudinal axis, the first bore configured to seat at least a portion of the implant pusher member and enable movement of the implant pusher member therein.

6. The surgical apparatus of claim 1, wherein the implant placement apparatus further comprises a display disposed on an outer surface thereof, the display configured to provide a reading corresponding to a distance between a first reference point on the first plate and a second reference point on the second plate of the distraction assembly when in the distracted configuration.

7. The surgical apparatus of claim 6, wherein the reading provided by the display is configured to correspond to a vertical distance between the exterior surface of the superior member and the exterior surface of the inferior member of the implant.

8. The surgical apparatus of claim 1, wherein one or more of the interior surface of the superior member or the interior surface of the inferior member of the implant each comprises one or more engagement features configured to engage with one or more complimentary features on a corresponding one of the upper surface or the lower surface of the implant track.

9. The surgical apparatus of claim 8, wherein the one or more engagement features comprise one or more protrusions and the one or more complimentary features comprise one or more grooves are each configured to receive corresponding ones of the one or more protrusions and enable slidable advancement therethrough.

10. The surgical apparatus of claim 8, wherein the one or more engagement features comprise one or more grooves, and the one or more complimentary features comprise one or more ridges each configured to be received within a corresponding one of the one or more grooves and enable slidable advancement over the one or more grooves.

11. The surgical apparatus of claim 1, wherein the implant track further comprises a first segment and a second segment, the second segment more proximal to the distal end than the first segment, the first segment configured to enable advancement of the implant along a first trajectory that is at least one of along or parallel to the first longitudinal axis, and wherein the second segment is configured to enable advancement of the implant along a second trajectory, the second trajectory comprising a non-linear trajectory.

12. The surgical apparatus of claim 11, wherein the implant further comprises a leading side during the advancement of the implant along the at least portion of the implant track and onto the implantation site, the leading side configured to be (i) oriented toward the distraction assembly when the implant is loaded on the implant track, and (ii) positioned anterior of the distraction assembly after advancement to the distal end of the implant track.

13. The surgical apparatus of claim 1, wherein the implant track further comprises a first segment and a second segment, the first segment configured to enable advancement of the implant along a first trajectory that is at least one of coincident with or parallel to the first longitudinal axis, the second segment configured to enable advancement of the implant along a second trajectory that is oblique relative to the first longitudinal axis.

14. The surgical apparatus of claim 11, wherein the implant further comprises a leading side during the advancement of the implant along the at least portion of the implant track and onto the implantation site, the leading side configured to be (i) oriented toward the distraction assembly when the implant is loaded on the implant track, and (ii) positioned onto one of a right side or a left side of the distraction assembly after advancement to the distal end of the implant track.

15. The surgical apparatus of claim 1, wherein the implant placement apparatus further comprises an actuator operatively coupled to the implant pusher member, the actuator configured to cause the transition of the implant pusher member from an immobilized state to a movable state, a distal segment of the implant pusher member configured to engage with a lagging side of the implant when the implant is loaded on the implant track and the implant pusher member is in the movable state, the lagging side of the implant oriented towards the body of the handle assembly when the implant is loaded on the implant track.

16. The surgical apparatus of claim 1, wherein the implant further comprises a second side wall, the second side wall configured to be movable between a collapsed configuration and an expanded configuration, the second side wall being disposed proximate to the first side wall in the collapsed configuration, the second side wall being disposed on an opposing side of the implant relative to the first side wall in the expanded configuration.

17. A method of treating a functional spinal unit of a subject utilizing a surgical apparatus, the functional spinal unit comprising a superior vertebral bone, an inferior vertebral bone, and an intervertebral disc space disposed between the superior vertebral bone and the inferior vertebral bone, the surgical apparatus comprising an implant and an implant placement apparatus, the method comprising:
forming a tissue corridor in tissues of the subject, the tissue corridor extending to the intervertebral disc space;
utilizing a handle assembly of the implant placement apparatus to manipulate the implant placement apparatus and insert at least a distal end of an implant track and a distraction member through the tissue corridor, the distraction member disposed at the distal end of the implant track and extending outwardly therefrom, the implant track extending from an anterior surface of the handle assembly along a first longitudinal axis;
positioning the distraction member within the intervertebral disc space such that an upper plate of the distraction member abuts an inferior surface of the superior vertebral bone and a lower plate of the distraction member abuts a superior surface of the inferior vertebral bone;
actuating the distraction member, the actuating causing (i) transition of the distraction member from a non-distracted configuration to a distracted configuration, and (ii) increase of a distance between the superior vertebral bone and the inferior vertebral bone in at least one plane;
loading an implant onto the implant track, the implant comprising a superior member, an inferior member, at least one side wall connecting the superior member and the inferior member, an internal cavity, and at least one interior surface of the implant comprising an engagement feature configured to engage with a complimentary feature on an outer surface of the implant track, the loading comprising engaging the engagement feature with the complimentary engagement feature and receiving at least a portion of the implant track within the internal cavity of the implant;
utilizing an implant pusher member of the implant placement apparatus to advance the implant down a first segment of the implant track along a first trajectory that is at least one of coincident with or parallel to the first longitudinal axis of the implant track;
utilizing the implant pusher member to advance the implant down a second segment of the implant track along a second trajectory that is at least one of oblique or curved relative to the first longitudinal axis of the implant track; and
disengaging the engagement feature from the complimentary engagement feature and depositing the implant one or more of lateral or anterior relative to the distraction member within the intervertebral disc space.

18. The method of claim 17, further comprising:
after the depositing of the implant, causing transition of the distraction member from the distracted configuration to the non-distracted configuration; and
withdrawing the distraction member and the distal end of the implant track from the intervertebral disc space and the tissue corridor.

19. The method of claim 17, further comprising:
after the depositing of the implant, releasing the distraction member from the distal end of the implant track, and maintaining the distraction member in the distracted configuration; and
withdrawing the distal end of the implant track from the tissue corridor such that the distraction member remains implanted within the intervertebral disc space.

20. A surgical apparatus configured for implantation of an implant within a functional spinal unit of a subject, the implant comprising: a superior member, an inferior member, at least one side wall connecting the superior member and the inferior member, and an internal cavity, the functional spinal unit comprising: a superior vertebral bone, an inferior vertebral bone, and an intervertebral disc space disposed between the superior vertebral bone and the inferior vertebral bone, the surgical apparatus comprising:
a handle assembly comprising a body, the body extending from a front surface to an opposing back surface, a first bore disposed within the body and extending from the front surface to the back surface along a first longitudinal axis;
an implant track comprising an upper surface, a lower surface, a distal end, and a proximal end, each of the upper surface and the lower surface extending from the distal end to the proximal end along a second longitudinal axis of the implant track, the proximal end disposed at the front surface of the body, the implant track configured to guide delivery of the implant to the intervertebral disc space;
a distraction assembly disposed at the distal end of the implant track and extended outwardly therefrom, the distraction assembly comprising a first plate and a second plate, the first plate movable relative to the second plate, the distraction assembly configured to enable transition of the first plate and the second plate from a non-distracted configuration to a distracted configuration; and an implant pusher member movably coupled to the body of the handle assembly, the implant pusher member configured to (i) be seated within the first bore, and (ii) transition from an immobilized state to a movable state;

wherein the surgical apparatus is configured such that, when the implant is loaded onto the implant track, (i) at least a portion of the upper surface of the implant track is configured to engage with at least a portion of an interior surface of the superior member of the implant, (ii) at least a portion of the lower surface of the implant track is configured to engage with at least a portion of an interior surface of the inferior member of the implant, and (iii) at least a portion of the implant track is seated within the internal cavity of the implant; and wherein, when the implant pusher member is in the movable state and the implant is loaded onto the implant track, the implant pusher member and the implant track are configured to (i) advance the implant down a first segment of the implant track along a first trajectory that is at least one of coincident with or parallel to the second longitudinal axis of the implant track, (ii) advance the implant down a second segment of the implant track along a second trajectory that is at least one of oblique or curved relative to the second longitudinal axis of the implant track, and (iii) deposit the implant in a position that is one or more of lateral or anterior relative to the distraction assembly.

* * * * *